US010010636B2

(12) United States Patent
Henniges et al.

(10) Patent No.: US 10,010,636 B2
(45) Date of Patent: Jul. 3, 2018

(54) STERILIZATION CONTAINER CAPABLE OF PROVIDING AN INDICATION REGARDING WHETHER OR NOT SURGICAL INSTRUMENTS STERILIZED IN THE CONTAINER WERE PROPERLY STERILIZED

(71) Applicant: Stryker Corporation, Kalamazoo, MI (US)

(72) Inventors: Bruce Henniges, Galesburg, MI (US); Robert W. Childers, Trinity, FL (US); Erik Vaclav Chmelar, Midland, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 14/849,157

(22) Filed: Sep. 9, 2015

(65) Prior Publication Data
US 2015/0374868 A1    Dec. 31, 2015

Related U.S. Application Data

(63) Continuation of application No. PCT/US2014/024799, filed on Mar. 12, 2014.
(Continued)

(51) Int. Cl.
*A61L 2/08*    (2006.01)
*A61L 2/00*    (2006.01)
(Continued)

(52) U.S. Cl.
CPC .................. *A61L 2/24* (2013.01); *A61L 2/07* (2013.01); *A61L 2/208* (2013.01); *A61L 2/28* (2013.01); *A61L 2202/24* (2013.01)

(58) Field of Classification Search
CPC ................. A61L 2/00; A61L 2/26; A61L 2/28
(Continued)

(56) References Cited

U.S. PATENT DOCUMENTS 6,234,310 B1    5/2001 Goldhaber
6,428,746 B1    8/2002 Muscarella et al.
(Continued)

FOREIGN PATENT DOCUMENTS

CN    1701820 A    11/2005
JP    2002515970 A    5/2002
(Continued)

OTHER PUBLICATIONS

Brochure "3M Comply SteriGage Chemical Integrators", Aug. 2008.
(Continued)

*Primary Examiner* — Monzer R Chorbaji
(74) *Attorney, Agent, or Firm* — Howard & Howard Attorneys PLLC

(57) ABSTRACT

A sterilization container for sterilizing at least one surgical instrument. The container includes at least one sensor for measuring an environmental characteristic of the container during the sterilization of the instrument. The measure of the environmental characteristic is supplied to a processor. The processor compares the measurement of the container environment to a validated measurement for the sterilization process. If the measured environmental characteristic is at least equal to the validated sterilization process measurement, the processor presents an indication that the surgical instruments was properly sterilized.

22 Claims, 65 Drawing Sheets

Related U.S. Application Data

(60) Provisional application No. 61/779,956, filed on Mar. 13, 2013.

(51) Int. Cl.
*G05B 1/00* (2006.01)
*A61L 2/24* (2006.01)
*A61L 2/20* (2006.01)
*A61L 2/07* (2006.01)
*A61L 2/28* (2006.01)

(58) Field of Classification Search
USPC .............. 422/3, 38, 50, 83, 105, 119, 26, 28
See application file for complete search history.

(56) References Cited

U.S. PATENT DOCUMENTS

| | | | |
|---|---|---|---|
| 6,884,392 B2 | 4/2005 | Malkin et al. | |
| 7,122,150 B2 | 10/2006 | Gonzalez et al. | |
| 7,138,087 B1* | 11/2006 | Malkin | A61B 1/123 422/26 |
| 7,575,716 B2 | 8/2009 | Wu et al. | |
| 2005/0265889 A1 | 12/2005 | Wu et al. | |
| 2007/0102045 A1 | 5/2007 | Patzek | |

FOREIGN PATENT DOCUMENTS

| | | |
|---|---|---|
| JP | 2005514170 A | 5/2005 |
| WO | 9719709 A1 | 6/1997 |
| WO | 00/09743 A1 | 2/2000 |
| WO | 2004/043499 A2 | 5/2004 |

OTHER PUBLICATIONS

PCT "International Search Report and Written Opinion" for PCT/US2014/024799, Jul. 2014.
3M, "3M Comply SteriGage Chemical Integrators for All Steam Sterilization Cycles", Aug. 2008, 4 pages.
English language abstract for CN 1701820 extracted from espacenet.com database dated Nov. 15, 2017, 1 page.
English language abstract for JP 2002-515970 extracted from espacenet.com database dated Apr. 28, 2018, 1 page.
English language abstract for JP 2005-514170 extracted from espacenet.com database dated Apr. 28, 2018, 1 page.

* cited by examiner

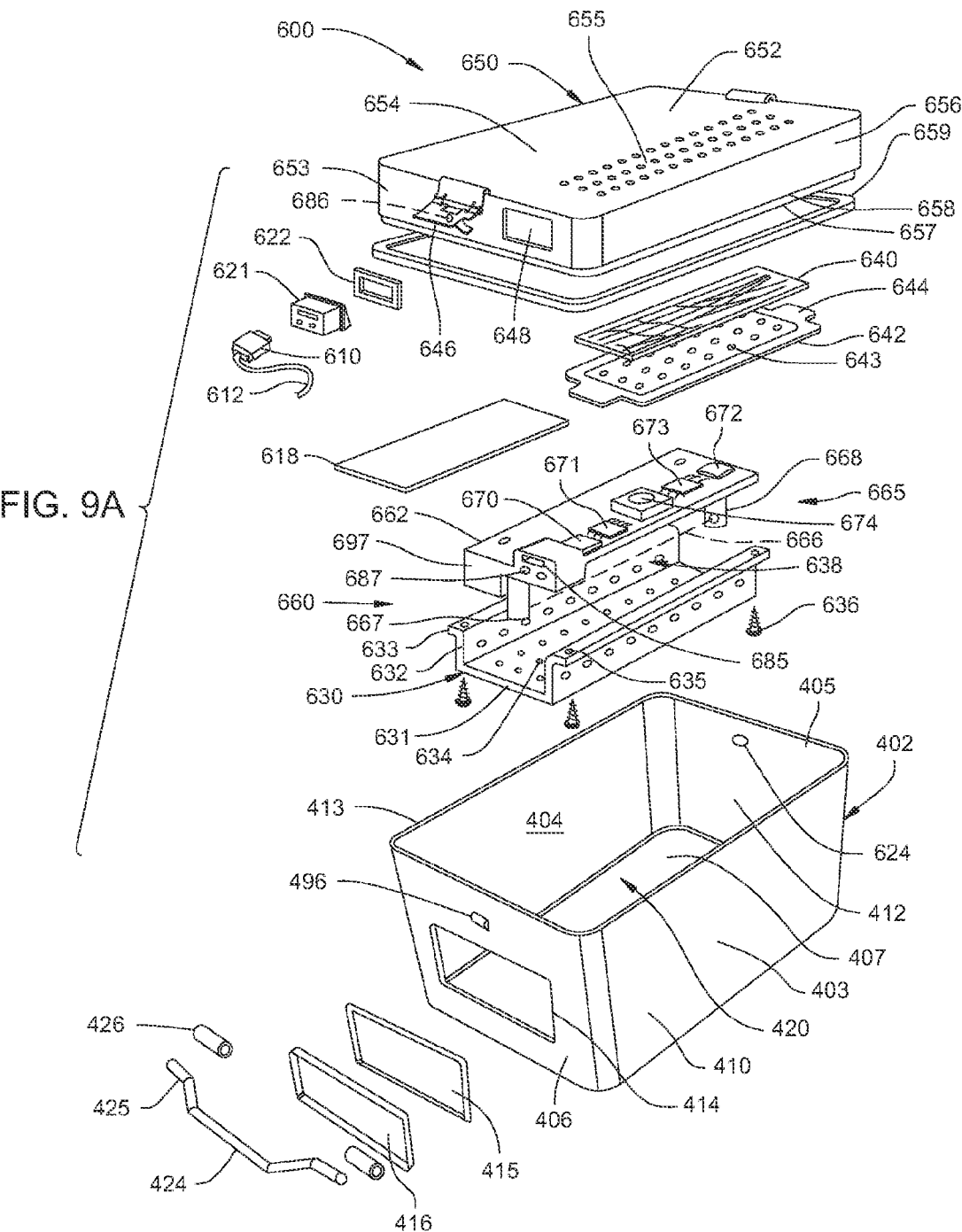

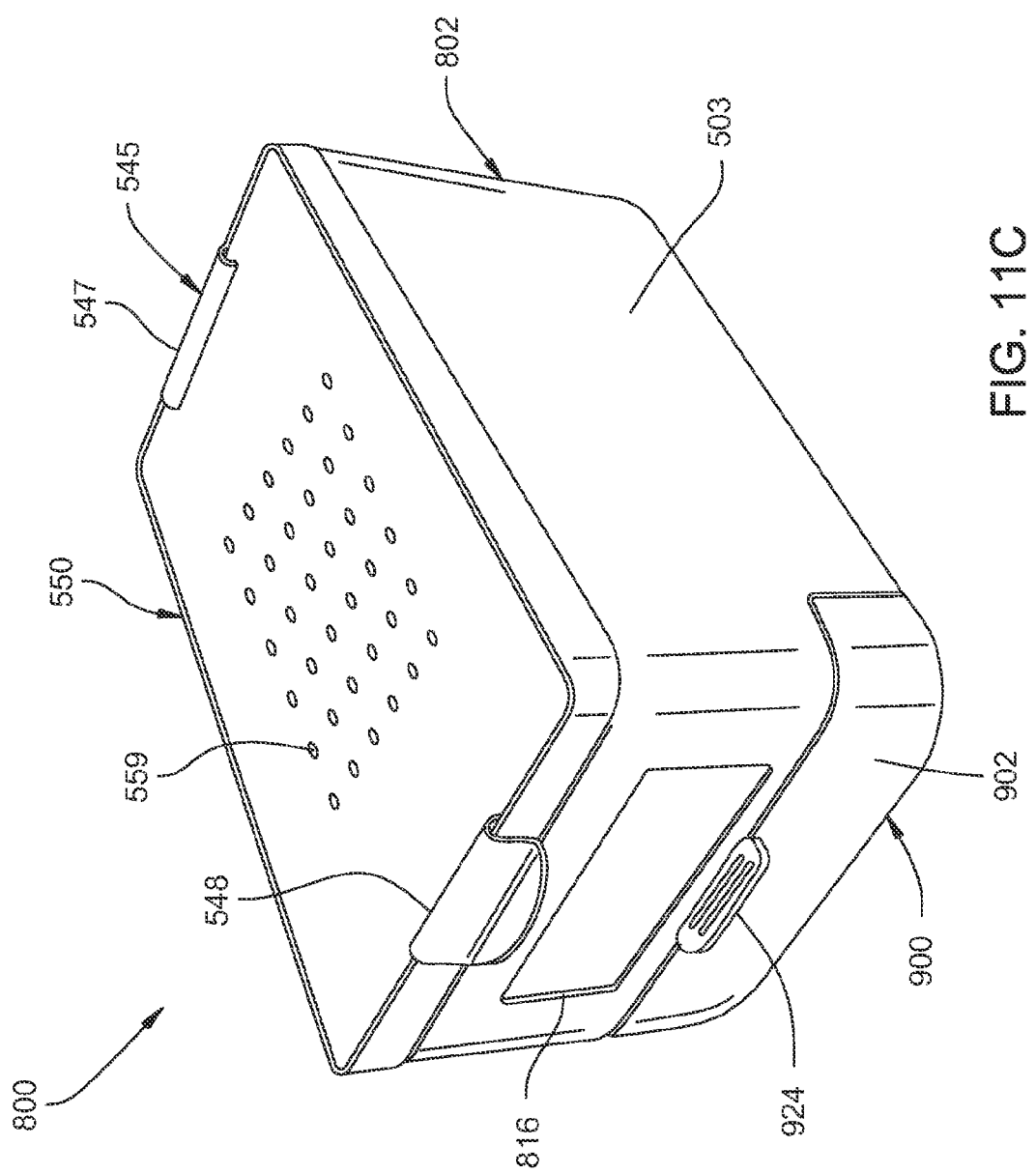

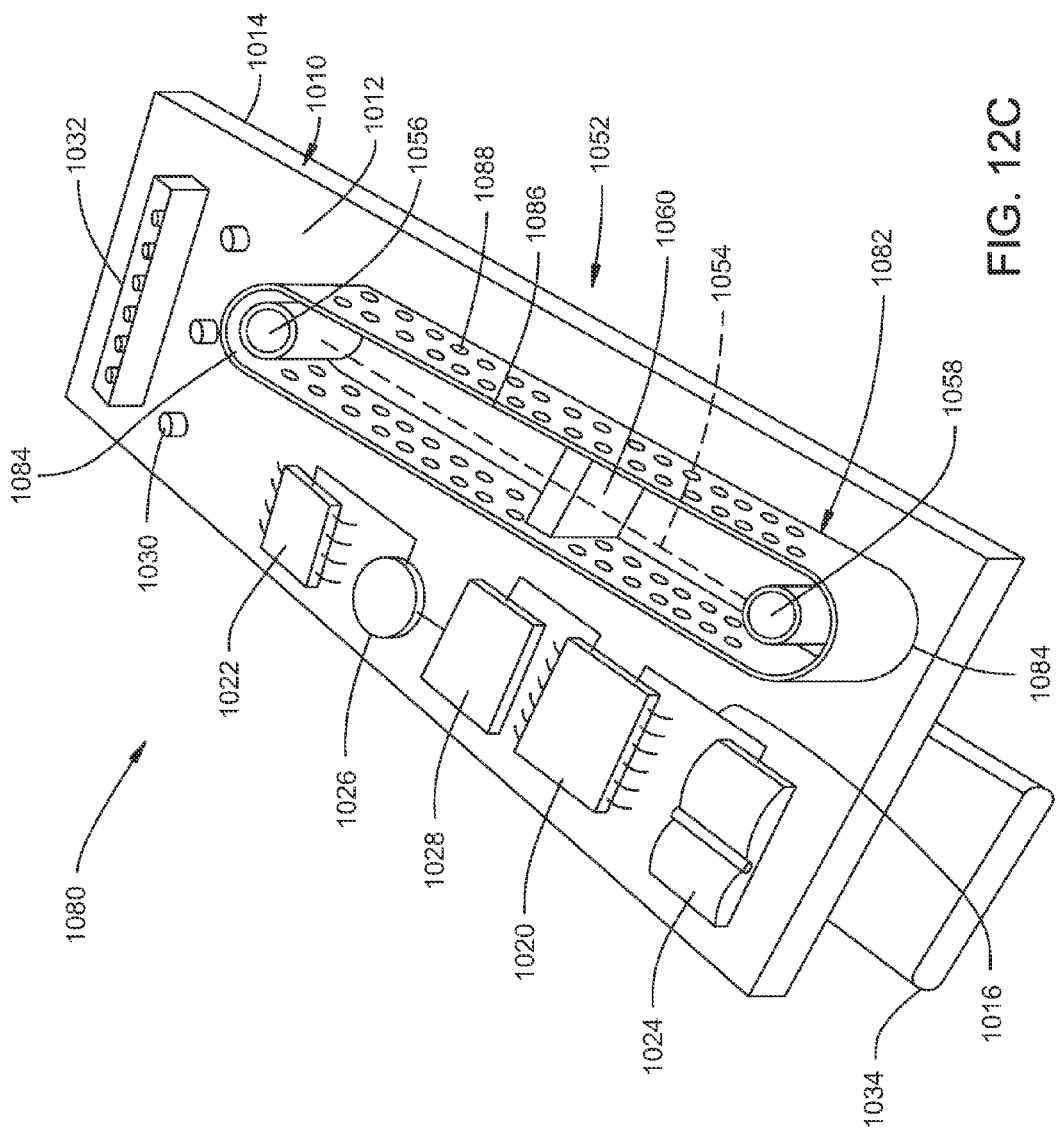

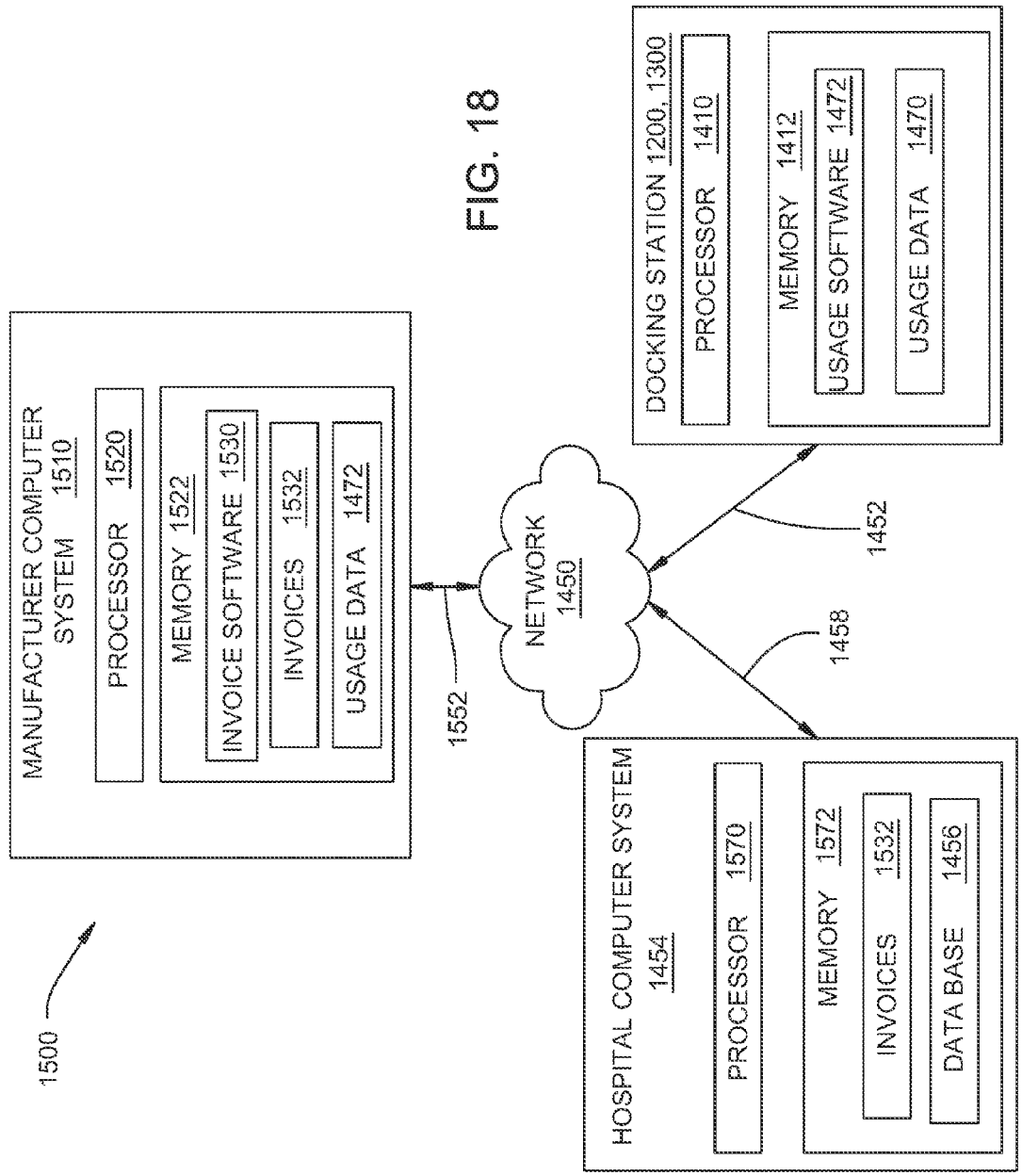

| | Content Identification ID 1610 | | Container ID 1605 | | Nominal Process Parameters | |
|---|---|---|---|---|---|---|
| ID Number | Surgical Instruments and Tools 180 | Rack 160 or 720 | Container Type | Microbial Barrier | Saturated Steam | Drying (min) |
| 1610-1 | Instruments, Utensils-System7 Handpieces and Attachments 180-1 | Insert Tray Stryker7102-450-010 | Stryker7102-450-040 | KC100 | 270F-for 4 minutes | 20 to 30 |
| 1610-1 | Instruments, Utensils-System7 Handpieces and Attachments 180-1 | Insert Tray Stryker7102-450-010 | Stryker7102-550-040 | Aesculap US994 | - | - |
| 1610-1 | Instruments, Utensils-System7 Handpiece and Attachments 180-1 | Insert Tray Stryker7102-450-010 | Stryker7102-550-040 | Aesculap US090 | 270F for 4 minutes | 20 to 30 |
| 1610-1 | Instruments, Utensils-System7 Handpiece and Attachments 180-1 | Stryker7102-450-010 | Stryker7102-450-040 | KC100 | 275F for 3 minutes | 16 |
| 1610-1 | Instruments, Utensils-System7 Handpiece and Attachments 180-1 | Stryker7102-450-010 | Stryker7102-450-040 | KC100 | - | - |
| 1610-1 | Instruments, Utensils-System7 Handpiece and Attachments 180-1 | Stryker7102-450-010 | Stryker7102-550-040 | Aesculap US090 | 275F for 3 minutes | 16 |
| 1610-3 | StrykerBatteries 180-3 | N/A | Rigid Container | Aesculap US994 | - | - |
| 1610-3 | StrykerBatteries 180-3 | Aesculap BasketJP224R | Aesculap | KC100 | - | - |
| 1610-4 | Flexible Bronchoscope 11001Bn1 180-4 | Mfgr Product Code | Perforated Case Wrap | | - | - |

FIG. 19A-1

| VSPM1150-Steam | | Nominal Process Parameters | | VSPM1150-HPV | | Sensor Module Usage Data | | |
|---|---|---|---|---|---|---|---|---|
| PreVac Saturated Stream Sterilization | Drying (min) | Sterrad 100NX | Aeration (min) | Sterrad100NX | Aeration (min) | DD:MM:YYHH:MM.SS | Content ID | Sensor Module |
| VSPM1150-S-1 3:55 at ≥ 270°F Saturated Steam | 20 at ≤ 15 in HG | | | | | 3/6/2013 11:03:00 3/4/2013 10:04:00 | CID1610-1 | Stryker SM00001S |
| - | - | Standard Cycle | 8 | VSPM1150-H-1, 22°C, Pinj ≤ 0.5 Torr Area* ≥ 2500 mg·s/L vp ≥ 300 Torr | 8 at ≤ 5 Torr | 3/7/2013 11:41:00 3/6/2013 11:43:00 3/4/2013 10:44:00 | CID1610-1 | Stryker SM00001H |
| T ≤ 3:55 at ≥ 270°F Saturated Steam | 20 at ≤ 15 in HG | - | - | - | - | 3/6/2013 12:43:00 3/4/2013 11:44:00 | CID1610-1 | Stryker SM00002S |
| T ≥ 2:54 at ≥ 275°F Saturated Steam | 20 at ≤ 15 in HG | Standard Cycle | 8 | VSPM1150-H-1, 22°C, Pinj ≤ 0.5 Torr Area* ≥ 2500 mg·s/L vp ≥ 300 Torr | 8 at ≤ 5 Torr | 3/6/2013 01:43:00 3/4/2013 12:44:00 | CID1610-1 | Stryker SM00003S |
| - | - | - | - | - | - | 3/6/2013 11:43:00 3/4/2013 10:44:00 | CID1610-1 | Stryker SM00002H |
| T ≥ 2:54 at ≥ 275°F Saturated Steam | 20 at ≤ 15 in HG | Express Cycle | 8 | VSPM1150-H-1, 22°C, Pinj ≤ 0.5 Torr Area* ≥ 2000 mg·s/L vp ≥ 300 Torr | 4 at ≤ 5 Torr | 3/6/2013 11:43:00 3/4/2013 10:44:00 | CID1610-1 | Stryker SM00004S |
| - | - | Express Cycle | 8 | VSPM1150-H-1, 22°C, Pinj ≤ 0.5 Torr Area* ≥ 2000 mg·s/L vp ≥ 300 Torr | 4 at ≤ 5 Torr | 3/6/2013 11:43:00 3/4/2013 10:44:00 | CID1610-3 | Stryker SM00003H |
| - | - | - | - | VSPM1150-H-1, 22°C, Pinj ≤ 0.5 Torr Area* ≥ 2000 mg·s/L vp ≥ 300 Torr | 4 at ≤ 5 Torr | 3/6/2013 12:43:00 3/4/2013 11:44:00 | CID1610-3 | Stryker SM00004H |
| - | - | Flex Cycle | 5 | VSPM1150-H-1, 22°C, Pinj ≤ 0.5 Torr Area* ≥ 2000 mg·s/L vp ≥ 300 Torr | 5 at ≤ 5 Torr | 3/6/2013 01:43:00 3/4/2013 12:44:00 | CID1610-4 | Stryker SM00005H |

FIG. 19A-2

| The Equipment in CID1160-1 must fit in the insert tray slots and includes up to 16 lb of saws/handpieces, colletts, keys and attachments. ||||
|---|---|---|---|
| Part No | Description | | Weight (lb) |
| 7209-000 | Precision Saw | | 2.290 |
| 7208-000 | Sagittal Saw | | 2.190 |
| 7207-000 | Sternum Saw | | 2.000 |
| 7206-000 | Reciprocating Saw | | 1.900 |
| 7205-000 | Dual Trigger Rotary Handpiece | | 2.182 |
| 7203-000 | Single Trigger Rotary Handpiece | | 2.112 |
| 4300-034 | Sabo Saw | | 1.400 |
| 6203-110 | Small Synthes Quick Connect | | 0.232 |
| 6203-113 | Hudson Attachment | | 0.288 |
| 6203-131 | 1/4" Stryker Adj. Keyed Chuck | | 0.316 |
| 6203-132 | 5/32" Stryker Adj. Keyed Chuck | | 0.166 |
| 6203-133 | 1/4" Stryker Adj. Keyless Chuck | | 0.496 |
| 6203-134 | 1/8" Stryker Adj. Keyless Chuck | | 0.272 |
| 6203-135 | Hudson Modified Trinkle Attachment | | 0.260 |
| 6203-160 | Trinkle Attachment | | 0.264 |
| 6203-210 | Synthes Reaming Attachment (Large) | | 0.238 |
| 6203-215 | Synthes DHS Reaming Attachment | | 0.294 |
| 6203-026 | Dual Trigger 0.7-1.8 mm Wire Collet | | 0.444 |
| 6203-126 | Dual Trigger 2.0 -3.2 mm Pin Collet | | 0.444 |
| 6203-226 | Dual Trigger 3.0-4.2 mm Pin Collet | | 0.442 |
| 6203-036 | Single Trigger 0.7-1.8 mm Wire Collet | | 0.448 |
| 6203-136 | Single Trigger 2.0-3.2 mm Pin Collet | | 0.446 |
| 6203-236 | Single Trigger 3.0-4.2 mm Pin Collet | | 0.446 |
| 7102-453-010 | Sternum/Sabo Insert Tray | | 1.710 |
| 1331-314-009 | 1/4" Thumb Key(MIM) | | 0.092 |
| 1331-001-009 | 1/4" Thumb Key | | 0.094 |

FIG. 19B

| The equipment in CID 1160-3 Includes up to 8 of the following batteries ||
|---|---|
| 4112-000 | CD II Small Battery |
| 4115-000 | CD II Large Battery |
| 6212-000 | System6 Small Battery |
| 6215-000 | System6 Large Battery |
| 7212-000 | SmartLife Battery |
| 7215-000 | SmartLife Battery |

Fig. 19C

| The Equipment in CID 1160-4 includes one Karl Storz Flexible Bronchoscope 11001 Bn1 |
|---|

Fig. 19D

| The Equipment in CID1160-5 includes one Stryker 502-719-030 C-Mount 1.9 mm x 58 mm 30 degrees |
|---|

Fig. 19E

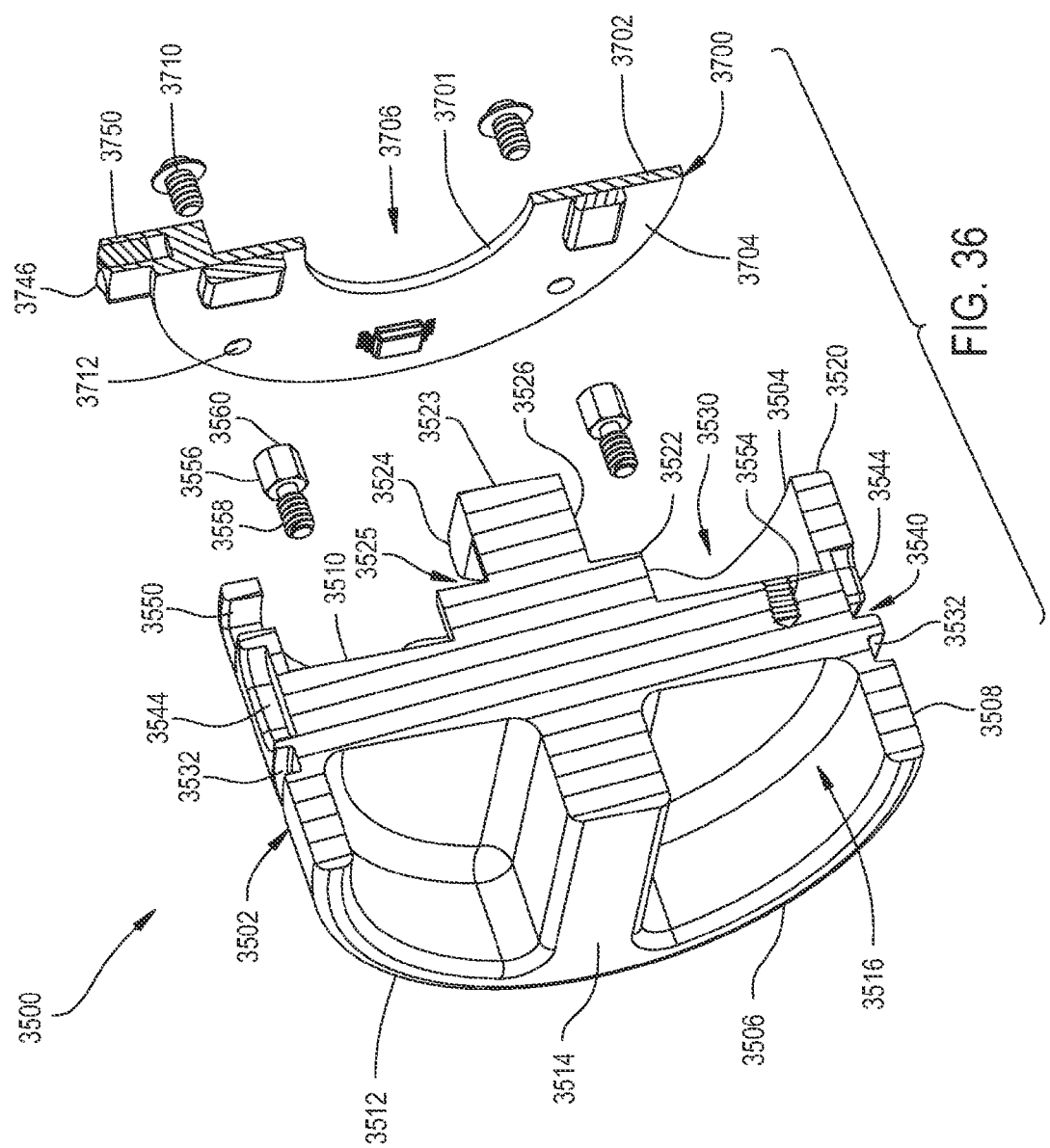

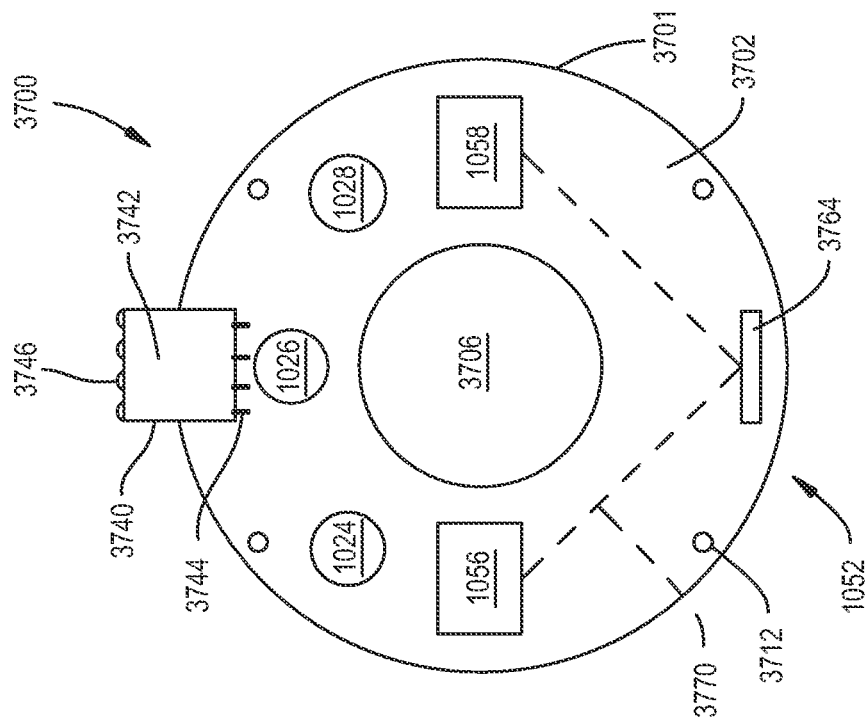
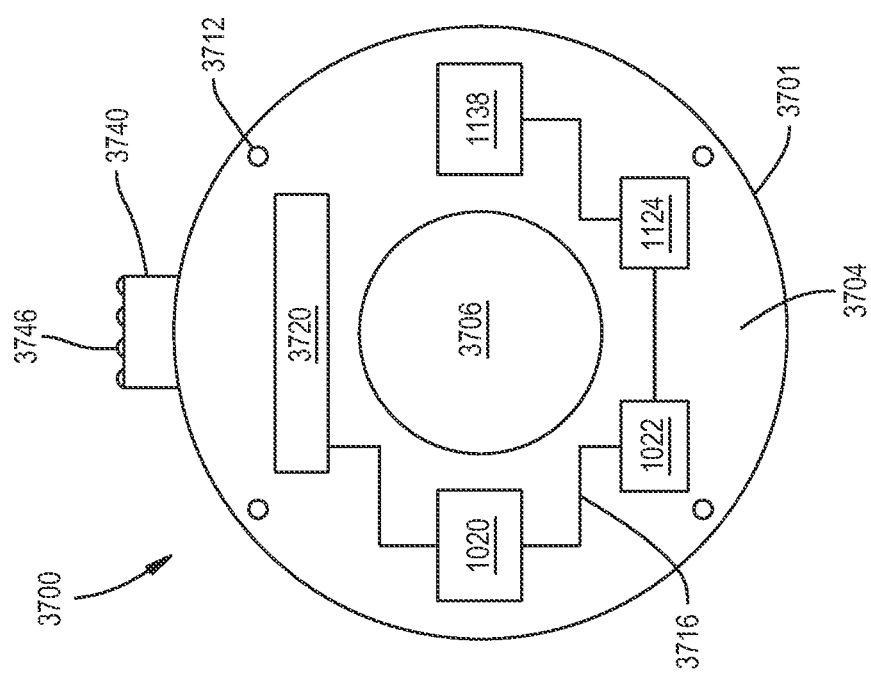
FIG. 37B
FIG. 37A

STERILIZATION CONTAINER CAPABLE OF PROVIDING AN INDICATION REGARDING WHETHER OR NOT SURGICAL INSTRUMENTS STERILIZED IN THE CONTAINER WERE PROPERLY STERILIZED

RELATIONSHIP TO EARLIER FILED APPLICATION

This application is a continuation of PCT App. No. PCT/US2014/024799 filed 12 Mar. 2014. PCT App. No. PCT/US2014/024799 is a non-provisional application based on U.S. Prov. Pat. App. No. 61/779,956 filed 13 Mar. 2013. The contents of the priority applications are incorporated herein by reference.

FIELD OF THE INVENTION

This invention relates generally to sterilization systems for surgical instruments. More particularly, this invention relates to a container and electronic sensor module for monitoring and verifying appropriate sterilization measurements have been met during a sterilization process and a method for using an electronic sensor module for determining if surgical instruments within the container have been properly exposed to a set of required process measurements during a sterilization process cycle.

BACKGROUND OF THE INVENTION

Sterilization of instruments and equipment used in medical and surgical procedures is important to prevent post-surgical infections in patients. Hospitals and medical facilities utilize a variety of cleaning and sterilization techniques and methods to re-process soiled or previously used surgical instruments. A hospital or medical center typically includes a sterile processing department that handles the cleaning and sterilization of medical instruments of the facility.

The sterile processing department commonly has several sections including a cleaning section, a sterilization section and a sterile storage section. Surgical equipment used during medical procedures return from the operating room to the cleaning section. In the cleaning section, the surgical instruments are cleaned of any visible liquid or solid medical waste and processed through a manual or an automated washing process. The automated washer uses high pressure streams of water and detergent to remove debris and residue from instrument surfaces. The washer exposes surgical instruments to high temperature water and sometimes damaging chemicals for a period of time. Some surgical instruments are not amenable to processing through the automated washer and are required to be manually washed.

After washing, the surgical instruments undergo a functional equipment inspection to check for broken parts or defects in the surgical equipment. Defective parts are repaired or replaced. Next, the individual surgical instruments are prepared for sterilization by placement of the surgical instruments in containers. Some surgical instruments are required to have a certain geometrical orientation during the sterilization process so that sterilant may effectively enter, contact and leave the surgical equipment during processing. The instruments can be grouped together by procedure to form a surgical tool set.

To preserve the sterility of the surgical instruments during handling and storage after sterilization, surgical instruments are typically placed into various container systems that form a sterile barrier around the instruments. Given that this barrier is intended to prevent ambient microbial organisms from adhering to the sterilized instruments these barriers are sometimes referred to as microbial barriers or SBSs (sterile barrier systems). One popular container system in use today is one that is constructed with two types of materials, one material being a "rigid" impermeable material and the other material that is a microbial filter. The microbial filter is constructed to allow the sterilizing agent, typically a vapor or gas, to penetrate during sterilization but prevents micro-organisms such as mycobacterium, vegetative bacteria, viruses, fungi, and bacterial spores from entering the container. Another container system is formed by using a perforated "rigid" material such as aluminum or stainless steel and the entire perforated container is wrapped with a microbial filter like material. The perforated "rigid" material provides structure to transport, handle and stack the containers of surgical instruments, but by itself does not prevent micro-organisms from entering the container. The sterile barrier material protects the surgical instruments from contamination during post sterilization handling and storage. The outer sterile wrap can be a spun polypropylene wrap and is permeable to sterilizing fluids or gases while forming a microbial barrier. When a container system is not used, individual surgical instruments can be packed in a flexible envelope material such as Tyvek typically constructed of a semi-permeable Tyvek on one side to allow the sterilizing agent to ingress and egress, and a non-permeable Mylar on the other side that allows the contents to be viewed To visually verify that containers of surgical instruments have been exposed to sterilizing agents, chemical indicators may be added to the inside and/or the outside of the sterile barrier system prior to undergoing the sterilization process. Chemical indicators are specifically designed for the type of sterilizing agent, gas or vapor used. The Class I Chemical Indicator is a chemical indicator system recognized by the FDA and JCAHO for use in hospitals in the United States. European regulatory agencies currently recognize proof of exposure chemical indicators, which provide parametric release, as well as Class I chemical indicators. A Class I chemical indicator provides a visual indication that it has been exposed to a sterilization agent, but does not indicate the level of exposure or amount of time of exposure. External chemical indicators are typically used so the hospital sterile processing department personnel can determine where the individual containers of equipment are in the workflow within the department and the internal chemical indicators are used to indicate to the hospital personnel setting up for a surgical procedure that the equipment inside of the sterile barrier has been exposed to a sterilization agent. If the external chemical indicator does not indicate exposure to the sterilization agent within the Sterile Processing Department, the surgical tool set must be processed to insure sterility. If the internal chemical indicator does not indicate exposure to the sterilization agent when the container is opened, the container and equipment must be returned to the Sterile Processing Department for reprocessing, typically beginning with the cleaning process. Determining that a container of surgical equipment has not been exposed to a sterilizing agent, while preparing for a surgical procedure is disruptive to the efficiency of the operating room and requires that another set of surgical equipment be located and properly set ultimately causing schedule delays and/or other adverse disruptions. Various types of chemical indicators have been developed including tapes, paper strips and catalytically activated systems. Tapes, labels, and paper strips are printed with an ink that changes color when exposed to a specific sterilization agent or chemical. Integrating or wicking paper is made with an ink or chemical at one end that melts and wicks along the paper over time under the desired process values. A color bar reaches an acceptable area if the process values are met. The chemical indicators are different for the various types of sterilization modalities, and thus the chemical indicator visual changes are not the same across sterilization methods. Sometimes the color change indicating exposure to one modality, e.g. steam autoclave, is opposite the color change for a different sterilizing modality, e.g. hydrogen peroxide sterilization. This causes confusion for the health care workers when reading and interpreting the various chemical indicator color changes.

Once the surgical instruments are fully packed and ready for sterilization, the surgical tool sets are processed through a sterilization process to destroy microorganisms. Various sterilization methods and agents have been used to sterilize surgical instruments.

Saturated Steam heat is one sterilant that is used to destroy microorganisms. Pressures higher than atmospheric pressure are necessary to increase the temperature of the steam for destruction of microorganisms that pose a greater challenge to kill. The saturated steam at a required temperature and time must penetrate and reach every surface of the items to be sterilized. A sterilization chamber contains the articles to be sterilized. When steam initially enters the sterilizer chamber under pressure, it condenses upon contact with cold items. This condensation liberates heat, simultaneously heating and wetting items in the load. The entire load must be exposed to moist heat for a minimum time and at a minimum defined temperature in order to affect sterilization. For example, one type of surgical tool set may require 34 minutes at 270 degrees Fahrenheit to destroy the microorganisms and another 20 minutes of evacuation to dry the instruments within the sterile barrier so that condensation does not accumulate within the sterile barrier. A minimum temperature-time and steam concentration relationship is required to be maintained throughout all portions within the sterile barrier and across the sterilizer chamber load to complete sterilization. The time, temperature and steam concentration to destroy micro-organisms depends upon many factors. For example the size, surface area, thermal mass, orientations and depths of internal cavities of the contents of the load within the sterile barrier as well as the steam penetration properties of the sterile barrier used can affect the reliability to destroy micro-organisms. After the steam cycle has been completed, the water condensate must be evaporated to dry contents of the load to maintain sterility. A vacuum can be drawn on the chamber to assist in the evaporation of any remaining water. The normative reference commonly used to determine appropriate sterilization exposure times are listed in Table 5 which is taken directly from ANSI/AAMI ST79: 2010/A2: 2011 "Comprehensive Guide to Steam Sterilization and Sterility Assurance in Health Care Facilities, Amendment 2".

TABLE 5

| Minimum cycle times for dynamic-air-removal steam sterilization cycles | | | |
|---|---|---|---|
| Item | Exposure time at 132° C. (270° F.) | Exposure time at 135° C. (275° F.) | Drying times |
| Wrapped instruments | 4 minutes | | 20 to 30 minutes |
| | | 3 minutes | 16 minutes |
| Textile packs | 4 minutes | | 5 to 20 minutes |
| | | 3 minutes | 3 minutes |
| Wrapped utensils | 4 minutes | | 20 minutes |
| | | 3 minutes | 16 minutes |
| Unwrapped nonporous items (e.g., instruments) | 3 minutes | 3 minutes | NA |
| unwrapped nonporous and porous item in mixed load | 4 minutes | 3 minutes | NA |

NOTE-
This table represents the variation in sterilizer manufacturers' recommendations for exposure at different temperatures. For a specific sterilizer, consult only that manufacturers recommendations.

Some surgical equipment such as gastroscopes and endoscopes are sensitive to the steam and high temperatures required by steam sterilization. Hydrogen peroxide vapor is another agent used to sterilize surgical instruments. Hydrogen peroxide is vaporized externally from the sterilization chamber in a defined reaction chamber. The vaporized hydrogen peroxide is introduced into the sterilization chamber, at which point it contacts the sterile barrier and passes through the barrier to contact the contents of the container to be sterilized. The hydrogen peroxide vapor is introduced into a sterilization chamber containing the articles to be sterilized. Hydrogen peroxide sterilizers today typically operate at much lower temperatures than steam sterilizers with maximum temperatures being around 122 degrees Fahrenheit for a hydrogen peroxide sterilizer. A minimum hydrogen peroxide concentration, pressure changing "pulse cycle", and temperature relationships over time are required to be maintained throughout all portions of the load to complete sterilization. After the hydrogen peroxide vapor cycle has been completed, the chamber is purged of residual and condensed hydrogen peroxide. RF energy may be used to energize the residual hydrogen peroxide vapor during this aeration phase creating a plasma that facilitates the aeration process. Some older plasma systems utilized RF energy during the sterilant exposure phase with the expectation that the plasma phase would be more effective at killing microorganisms than the vapor phase. Residual hydrogen peroxide is required to be removed from the surgical instruments and packaging prior to use in order to prevent burns and injury to healthcare workers and patients.

Other liquid and gaseous agents can also be used to sterilize surgical instruments such as ethylene oxide gas, formaldehyde gas and ozone gas. These sterilizing agents use "low temperature" sterilization conditions as do the Hydrogen Peroxide sterilizers described above allowing their use on sensitive medical equipment as an alternate to potentially damaging high temperature steam sterilization.

Unfortunately, these gases are somewhat higher in toxicity and/or are difficult to control during the sterilization process so they do not enjoy wide-spread use throughout hospital systems.

Regulations within the medical device industry require the Original Equipment Manufacturer (OEM) to provide instructions to the Hospitals and Health care providers on proper use and maintenance of reusable medical equipment. The OEM can be the designer, manufacturer or distributor of reusable medical equipment. Within the category of reusable medical equipment, certain equipment and instruments can become contaminated by biological material from the patient like bodily fluids, mucus and tissue during use so that it must be cleaned and/or sterilized before being used again. Certain reusable medical equipment such as Colonoscopes cannot be sterilized using the equipment in a hospital central processing department. Based on the risks versus benefits analysis sterilization can be replaced by high level disinfection for these devices. The generally accepted definition of a sterilization process is, "the reduction of $10^6$ organisms down to zero", and high level disinfection process is, "the reduction of $10^3$ organisms down to zero". Sterilization is defined as the Sterility Assurance Level (SAL) which utilizes the, "overkill method", to show a 12 log reduction of the most challenging organism to the method of sterilization being employed. A 12 log reduction means that there is a one in one million probability of a single viable organism surviving the sterilization process. Disinfection is defined in three categories; High Level Disinfection (HLD): Many or all pathogenic microorganisms with the exception of bacterial spores, Intermediate Level Disinfection (ILD): May be cidal for mycobacterium, vegetative bacteria, most viruses, and most fungi; but does not necessarily kill bacterial spores, and Low Level Disinfection (LLD): Kill most vegetative bacteria, some fungi, and some viruses. The OEM is responsible to provide proper cleaning and sterilization (or disinfection) instructions to the Health Care users. The OEM is not allowed to randomly select cleaning and sterilization techniques prior to selling new reusable medical equipment, they are required to validate the cleaning and sterilization processes. For steam sterilization validations OEMs can use the American National Standard ANSI/AAMI ST79 in the United States and ISO 17665-1 in other countries. These mentioned standards are incorporated by reference to this patent application. These standards include sterilization (or disinfection) validation testing protocols for the OEMs regarding the cleaning and sterilization methods so that Health Care facilities do not have to individually validate these methods using their sterilization equipment for each medical device they purchase. Even though these standards are accepted throughout the medical device industry by the Healthcare Regulatory agencies and the Healthcare providers, there is potential for human error, uncontrollable variability and sterilizing system equipment problems that enter into the Healthcare delivery system which may cause inconsistencies in the sterilization or disinfection results for reusable medical equipment. Examples: the OEM validates a new set of equipment per the governing standards. The governing standards require that organism X be used to inoculate the new set of equipment for a given sterilization agent. The OEM follows the governing protocols and validates the new equipment to a 10E-6 Sterility Assurance Level (SAL) using these nominal steam process values in a small chamber steam autoclave able to hold only one set of equipment (e.g. 14"×14"×24" chamber). The OEMs instructions resulting from the SAL validation could be as follows: Wrapped using 500 grade wrap, Dynamic air removal (pre-vac)cycle, Sterilization temp 132° Celcius, Exposure time 4 minutes, Dry time 30 minutes. The hospital sets up the sterile barrier system and follows all instructions, but instead of a single container autoclave, they have a large steam autoclave where the chamber can hold 40 sterile barrier system containers and a wheeled shelving rack where they roll the loaded rack into the autoclave. Uncontrolled variable: The OEM validated their equipment in an ambient temperature of 25° C. (pre-sterilized equipment started at 25° C.) and the hospital stores their pre-sterilized equipment in a conditioned environment at 20° C. Thermodynamically, the lower starting temperature and a significantly larger total chamber load at the hospital reduces the actual exposure steam/temperature duration below the validated level for proper organism destruction. Human error: the Hospital followed all instructions properly, but a heavy medical instrument that did not have a container was included inside the sterile barrier system. This caused a reduction of the temperature build up of all equipment inside the sterile barrier system. Sterilization equipment problem example: a power spike advances the sterilizer by 1 minute thus shortening the actual exposure duration by that amount. Similar examples can be established for other sterilization processes such as Hydrogen peroxide sterilization processes and methods. Another factor that can cause problems with the sterilization of medical devices is where a mixed load of equipment is sterilized together in a single process. The mixed load in this example is medical equipment that has the same sterilization time duration, but different dry times across the various containers which are sterilized together. If this occurs, there could be some residual moisture retained in the equipment that requires a longer drying time. This residual moisture can wick out. This wicking out results in a water stain forming on the SBS wrap used on a perforated container, but the water stain is not discovered until the operating room personnel are preparing the equipment for the next surgical procedure. Once the operating room personnel notice the water stain during set-up, they have to return all of the equipment for reprocessing to the sterile processing department. The SBS materials are not designed to maintain their anti-microbial properties if they become wet. Since it is not known when or how it became wet, the entire group of equipment becomes suspect due to the water stain and thus must be reprocessed. These are some examples of problems that desire a better system and solution so that healthcare delivery is efficient and safe.

Further, the current practice is to, as part of the process of sterilizing a surgical instrument, perform a test to verify that the sterilizer in which the instrument is sterilized is properly functioning. This test is performed with a biological indicator. A biological indicator includes known number and type of microorganisms that have an appreciable resistance to the mode of sterilization being practiced.

The biological indicator is placed in a tray or container and is processed through a specific sterilization process. The biological indicator can be placed within a sterile barrier and wrap prior to processing such that its exposure to the sterilant is similar to a surgical tool set. Many biological indicators used today are self contained. The self contained biological indicators have a housing sealed to a microbial barrier material that allows a path for the sterilizing agent to penetrate and reach the biological agent, but not allow other micro-organisms to enter. These biological indicators do not require a container or wrap during use.

Therefore, there are typically different biological indicators for each sterilization process modality used in a sterile processing department. This requires the sterile processing department to be trained to properly execute the biological indicator tests for every sterilizer and sterilizing modality within the department. For example if a hospital has both autoclave steam and hydrogen peroxide equipment, the sterile processing department has to purchase and maintain both types of biological indicators and be trained to properly process the biological indicators. Also, the different manufacturers of hydrogen peroxide equipment typically each require a specific biological indicator be used in this test. So if a sterile processing department has two hydrogen peroxide systems, each made by a different manufacturer, the sterile processing department needs to become proficient at operating two biological indicator tests, one for each system. Bacterial spores have been used as biological indicators. The biological indicator is sealed or enclosed in a protective package. After exposure to the sterilization process, the biological indicator is placed in a growth medium and cultivated for a period of time, after which they are read by department personnel. For example, steam autoclave biological indicators use *Geobacillus stearothermophilus* at a $10^6$ population and are incubated for a minimum of 24 hours in a growth medium. For Hydrogen Peroxide sterilization agents, a *Geobacillus stearothermophilus* at a $10^6$ population is used and incubated in a growth medium at a specific temperature for 24 hours. Subsequent growth of the biological agent indicates a failure of the sterilization process and subsequent no growth of the biological agent microorganisms under suitable conditions indicates the proper operation of the sterilization process for that particular cycle. Because the biological agent used in biological indicators are more resistant to their specific sterilization agents than common microorganisms potentially found on surgical instruments, the demonstration that the biological indicator has been inactivated provides assurance that other microorganisms, including potential pathogens in the load, have also been destroyed.

For Hydrogen peroxide sterilizers, a typical sterile processing department runs a biological indicator test every 24 hours as a check on the proper operation of the equipment. The biological indicator test is typically run by itself or with the first lot of medical equipment processed through the sterilizer machine for the day. A biological indicator test can take up to 24 hours to complete. Consequently, subsequent loads of surgical instruments and tools are quarantined for the time period required to complete the biological indicator test so as to verify that the sterilizer is properly functioning.

Many sterilization processes take less than an hour to perform. However, owing to the need to verify that the sterilizer is properly functioning, an instrument can be quarantined for up to the additional 24 hours required to obtain the results of the biological indicator test. This means that at a hospital, at any given moment in time, a significant number of the hospital's surgical instruments may be in quarantine. This requires the hospital to have a large inventory of surgical instruments so that, at any given instant, a sufficient number of instruments are sterilized and ready for use. Requiring the hospital to maintain this large inventory of instruments can add to the cost of maintaining the hospital.

If the biological indicator test fails, all of the lots of surgical equipment processed in the sterilizer machine, since the last passed biological indicator test, are potentially non-sterile. This equipment is then reprocessed again through the cleaning and sterilization process.

If first biological indicator test indicates the sterilizer is operating properly, it is assumed that the sterilizer has sterilized the instruments placed in the sterilizer up until the execution of the next biological indicator test. This assumption is made even though there is a possibility that between the two consecutive tests, the sterilizer may start to malfunction. The fact that the sterilizer may have started malfunctioning is not known until the results of the second biological indicator tests are read. In the interim, however, the equipment sterilized between the first and second tests may have been released from quarantine and used in a procedure. This means the equipment used on a patient may be a piece of equipment that was not properly sterilized.

Further, having to execute a biological indicator test requires resources include the time of hospital personnel.

The current processes for determining the proper operation of the various sterilizing equipment's sterilization processes and the use of microbial barriers for subsequent storage have many problems that add time and expense to the entire sterilization process. The use of microbial barriers and wraps to encase surgical instruments adds expense in the purchase of the materials and time for department personnel to wrap and create the sterile barrier containing the surgical instruments. The use of microbial barriers also increases the difficulty of the sterilant to enter the wrapped package and complete sterilization, particularly for low vapor pressure sterilants such as hydrogen peroxide vapor. Variations in sterile barrier materials and how they are applied will introduce variation in the sterilant concentration within the wrapped package. Variations in the mass, materials of construction, and surface area of the instrument load can also introduce variation in the sterilant concentration within the wrapped package.

The use of chemical indicators adds expense in the purchase of the chemical indicators and the time for department personnel to place and read the chemical indictors. The use of biological indicators adds expense in the purchase of the biological indicators and the time for department personnel to place, incubate and subsequently read the results of the biological indictor.

If either of the chemical or biological indicator tests fail, all of the unused lots of surgical equipment processed in the sterilizer machine, since the last acceptable test, must be reprocessed again through the cleaning and sterilization process, adding time, expense and increasing the inventory of surgical instruments required. As discussed above, there is a possibility that instruments that may not have been sterilized were used on patients. If this event occurs appropriate action may need to be taken. In addition, if the sterilizer has an equipment or process problem during one biological incubation period, this problem may not be detectable until the reading at the end of the subsequent biological indicator (BI) incubation period (by reading a failed biological indicator in the subsequent test). This allows the possibility of releasing medical equipment from quarantine from the time the problem occurs (during the first incubation period) until the time of the failed BI test.

Another problem with the current processes for determining the validity of a sterilization process is that many of the steps in the process depend upon human action and judgment and as such are prone to human error. Human error can occur by incorrect orientation and placement of surgical instruments in racks and containers. Human error can occur by placing items so that they block the flow of sterilant into the container and adversely affect sterilization efficacy of the items therein. Human error can occur by placing too many instruments within the container adversely affecting sterilization efficacy. Human error can occur by stacking containers on top of one another so that the sterilant is not able to flow freely into all of them. Human error can occur by incorrectly operating the sterilization machine. Human error can occur by incorrect placement and reading of chemical indicators. Human error can occur by incorrect placement, incubation, and reading of biological indicators.

SUMMARY OF THE INVENTION

This invention is directed to a new and useful system and method for determining if surgical instruments have completed a sterilization process cycle and have met a set of required process measurements during the sterilization process cycle. The system includes a container defined by several panels. The panels define a cavity within the container and an opening into the container. The container receives surgical instruments that may be within a removable insert tray into the cavity. A cover is coupled to the container and is movable between an open position and a closed position. A sensor module is mounted to the container. The sensor module includes one or more sensors. The sensors are configured to and positioned to monitor at least one characteristic of the environment inside the container. The sensor module includes a processor with instructions regarding how to interpret the environmental s obtained from the sensors.

The container of instruments is placed within a sterilization chamber, the chamber door is closed and a sterilization cycle performed. The sensors monitor the changes in the characteristics of the container environment as a result of the sterilization cycle. The processor compares the environmental measurements taken by the sensors within previously validated sterilization process measurements. These validated sterilization process measurements are measurements of the container environment taken during previous sterilization processes in which subsequent testing has shown were successful.

If the evaluation of the environment measurements indicates that the environment within the container was sufficient to affect success sterilization of the instruments, the processor indicates that the surgical instruments were successfully sterilized. Alternatively, the evaluation may indicate the container environment was not an environment in which it can be certain that the instruments in the container were sterilized. If this is the result of evaluation, the processor presents an indication that the instruments were not properly sterilized.

A benefit of this system is that soon after the sterilization process is performed, an indication is provided regarding whether or not the instruments were exposed to a process in which they were properly sterilized.

BRIEF DESCRIPTION OF THE DRAWINGS

The invention is pointed out with particularity in the claims. The above and further features and advantages of the invention are understood by the following Detailed Description taken in conjunction with the accompanying drawings in which:

FIG. 9A is an exploded top perspective view of yet another container for sterilization of medical/surgical instruments having sensors mounted in the cover in accordance with one embodiment;

FIG. 11C is an assembled top perspective view of the container of FIG. 11A;

FIG. 12C is a top perspective view of a sensor printed circuit board for sensing hydrogen peroxide concentration and other environmental characteristics in accordance with one embodiment;

FIG. 18 is a diagrammatic view of a networked computer system for tracking container usage and billing in accordance with one embodiment;

FIGS. 19A-1 and 19A-2, when placed side-to-side, collectively form a table of equipment to be sterilized; validated sterilization process measurements for the equipment; sensor module usage data; sterilizer process nominal parameters; and container identification data;

FIGS. 19B-19E are lists of equipment that can be sterilized based on specific content identifiers and the weights of at least some of the equipment;

FIG. 36 is an enlarged cross sectional view of the removable sensor module;

FIG. 37A is a rear view of the removable sensor module printed circuit board;

FIG. 37B is a front view of the removable sensor module printed circuit board;

DETAILED DESCRIPTION

I. Overview

Figure 1:
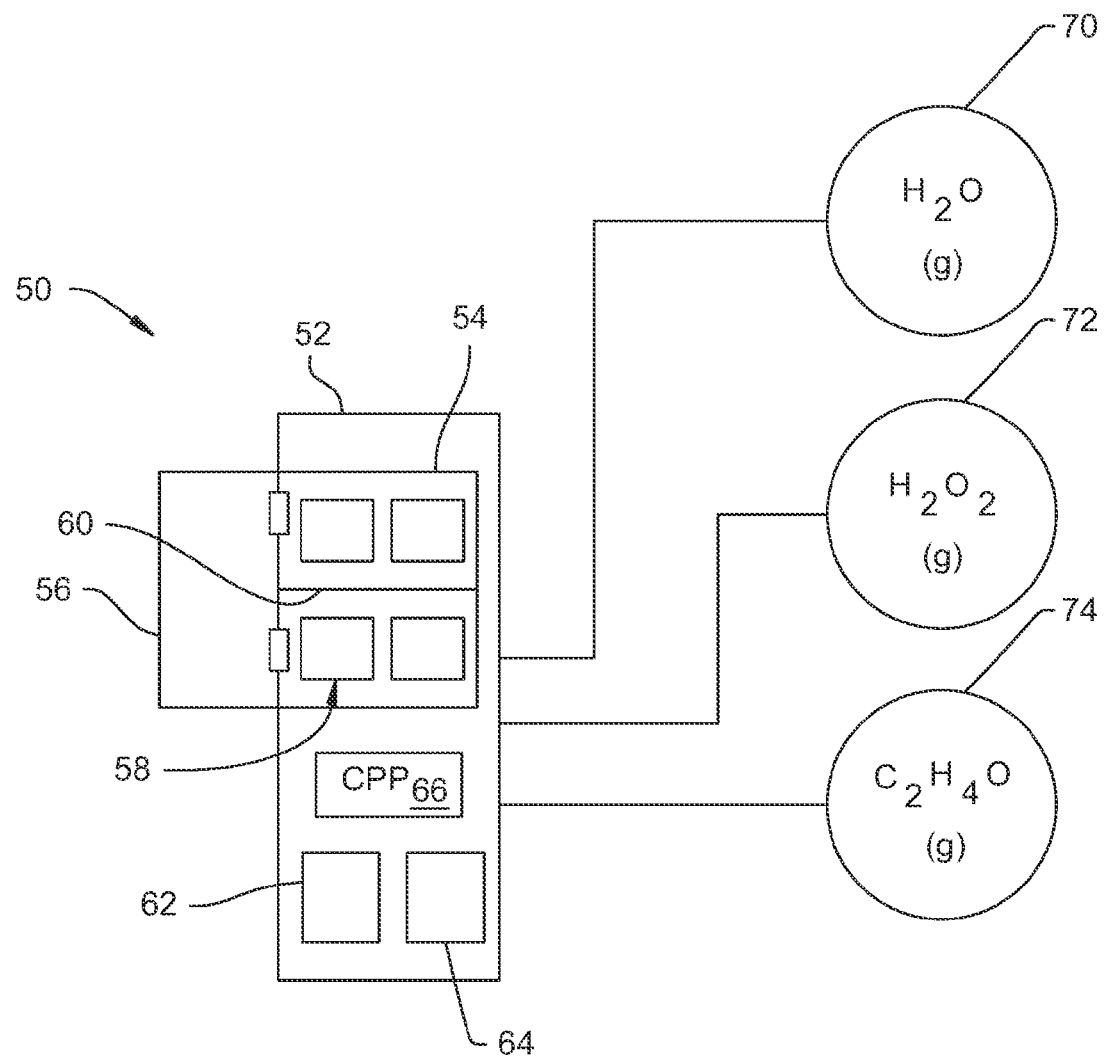
FIG. 1 is a diagrammatic view of a sterilization chamber used for sterilization of medical/surgical instruments.

FIG. 1 illustrates a sterilization apparatus 50 used for sterilizing medical and surgical instruments. Sterilization apparatus 50 comprises a sterilization chamber 52 that holds one or more sterilization containers 58. Each container 58 can hold one or more surgical instruments that are desired to be sterilized. Sterilization chamber 52 includes a containment vessel 54 that can be sealed after door 56 is closed. Containment vessel 54 has one or more shelves 60. Containers 58 are arranged on shelves 60.

Sterilization chamber 52 further includes a vacuum pump 64. Vacuum pump 62 can decrease the pressure within containment vessel 54 to below atmospheric pressure. A sterilization agent or sterilant is injected into containment vessel 54. Various sterilants can be used including gaseous water vapor or steam ($H_2O$) 70, hydrogen peroxide gas ($H_2O_2$) 74 or gaseous ethylene oxide ($C_2H_4O$) 74. At least one of the sterilization agents are introduced into containment vessel 54 during a sterilization cycle.

During a sterilization cycle, the sterilant is required to come into contact with the all of the surgical instruments with the containment vessel 54 at a required concentration for a required time to affect sterilization of the surgical instruments. After the sterilization cycle has been completed, the sterilization chamber must be purged of any residual or condensed sterilant. The removal rate of sterilant from the chamber is increased by the use of vacuum pump 64. Drawing a vacuum within containment vessel 54 causes any condensed sterilant to evaporate into a gaseous state and be removed.

Sterilization chamber 52 is operated using a set of chamber process parameters (CPP) 66. CPP 66 are the environmental operating conditions generated within containment vessel 54 by sterilization apparatus 50. In one example embodiment, CPP 66 includes temperature, pressure, humidity, hydrogen peroxide vapor and time.

II. First Container Embodiment

Figure 2:
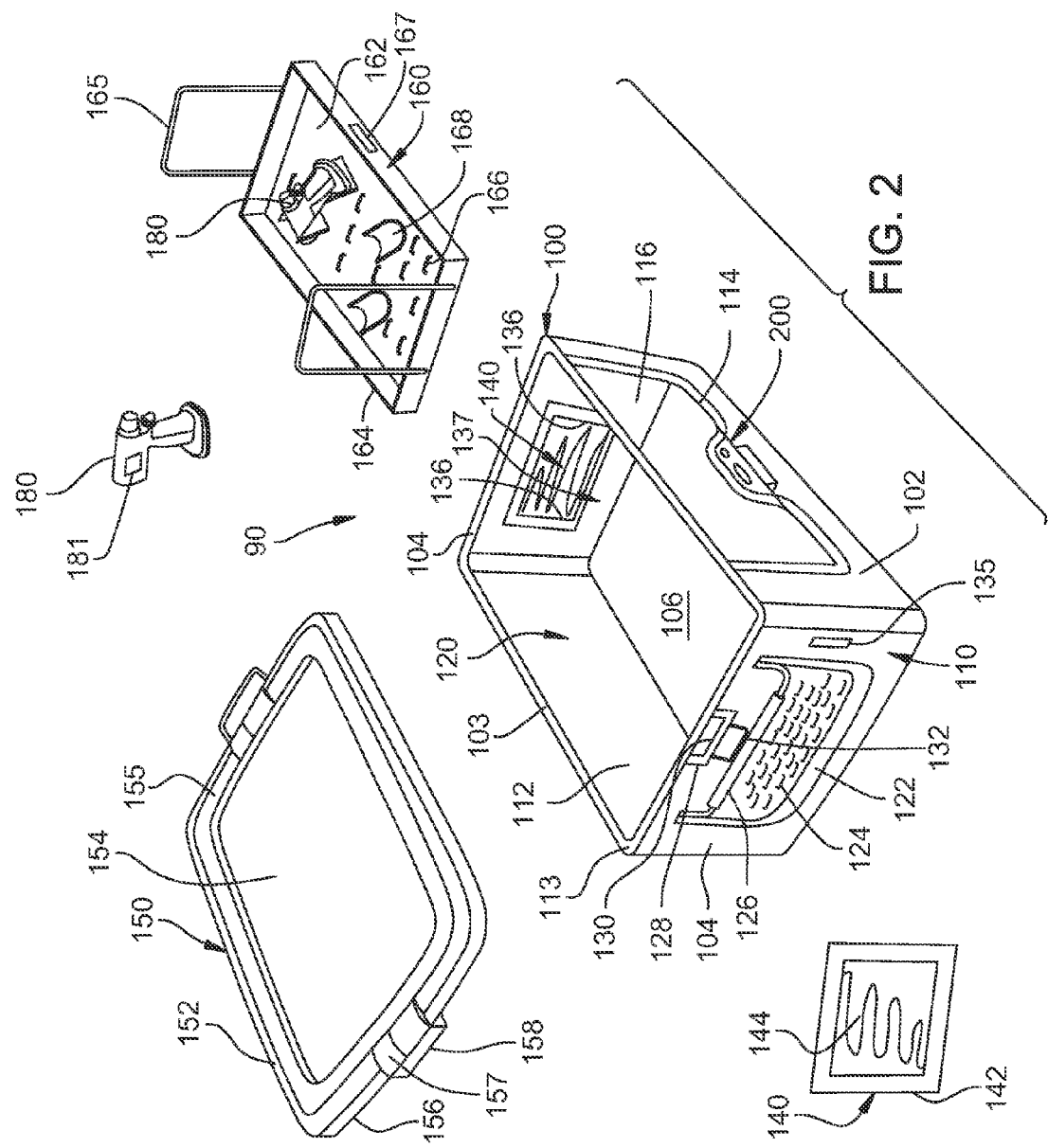
FIG. 2 is a top perspective view of a container used for sterilization of medical/surgical instruments of this invention showing the container separated from the cover and an instrument rack in accordance with one embodiment.

Turning to FIG. 2, a container assembly 90 of a first embodiment of this invention is illustrated. Container assembly 90 includes a container 100 that is generally rectangular in shape and is defined by an opposed spaced apart planar front panel 102, a planar rear panel 103 and a pair of opposed spaced apart planar side panels 104. Panels 102 and 103 are oriented orthogonal to panels 104. A planar bottom panel 106 is perpendicular to panels 102, 103 and 104 and forms the bottom of container 100. An interior cavity 120 is defined by panels 102, 103, 104 and 106 within container 100. Container 100 has outer surfaces 110, inner surfaces 112 and an upper peripheral rim 113. Container 100 can be formed from materials such as stamped or deep drawn aluminum, stainless steel, plastic or other suitable materials.

Front panel 102 has a window or opening 114 defined therein. Opening 114 is covered by a panel 116 formed from a material that is transparent such as acrylic or glass. Transparent panel 116 allows a user to visually see the contents of container 100. Panel 116 is sealed to the adjacent panel 102. Panel 116 is located on front panel 102, but may be located on back panel 103 or side panels 104.

Each of side panels 104 has a recessed portion 122 defined in outer surface 110 that extends from just above bottom panel 106 to just below rim 113. A series of holes 124 are defined through recessed portion 122 and extend into cavity 120. A pivoting handle 126 is attached to each side panel 104 and extends across the width of recessed portion 122. Handle 126 pivots between a stored position where handle 126 is adjacent recessed portion 122 (shown in FIG. 2) and a carrying position where handle 126 extends perpendicular to side panel 104. Handle 126 allows a user to grasp and lift container 100.

A pivoting latch 128 is attached to each side panel 104 below rim 113 by a hinge 130. Latch 128 has a U-shaped bail portion 132 that mates with a portion of cover 150. Latch 128 allows a user to releasably lock cover 150 to container 100. A pair of spaced apart L-shaped side rails 136 are mounted to inner surface 112 on opposite sides of recessed portion 122 and extend perpendicular away from inner surface 112 towards cavity 120. An L-shaped bottom rail 137 is mounted between the ends of rails 136 at the bottom of recessed portion 122. A bar code or RFID tag 135 (FIG. 3) is mounted to outer surface 110 of side panel 104. Bar code or RFID tag 135 can contain information about container assembly 90 such as the type of container or the contents of container 100.

Filter assemblies 140 are mounted in cavity 120 adjacent inner surfaces 112 of side panels 104. Each filter assembly 140 is supported and retained by L-shaped rails 136 and 137. Filter assembly 140 covers holes 124. Filter assembly 140 is generally square in shape and has a square frame 142 and a filter material 144 mounted within frame 142. Filter material 144 is a microbial barrier material that is permeable to sterilant. Here "sterilant" is understood to be a gas, vapor or aerosol that has ability to render biological contaminates including microorganisms innocuous. Filter material 144 allows sterilant to pass from the outside of container 100 through holes 124, through filter material 144 and into interior cavity 120 where the sterilant can contact the surgical instruments 180. Filter material 144 also forms a microbial barrier preventing microorganisms from entering into container 100 after container 100 has been processed through a sterilization process.

Filter assembly 140 is placed by a user inserting and sliding frame 142 along side rails 136 until frame 142 abuts bottom rail 137. Rails 136 and 137 are dimensioned to force filter assembly 140 to be compressed against the inner surface 112 of side panel 104 when inserted into rails 136 and 137. Rails 136, 137 and frame 142 are dimensioned such that when filter assembly 142 is mounted in container 100, a seal is formed between the outer periphery of frame 142 and inner surface 112. Filter assembly 140 is sealingly mounted to the inner surface 112 of container 90 to form a continuous microbial barrier with the adjacent panel inner surface 112.

Cover 150 is used to cover and enclose container 100. Cover 150 includes a generally rectangular shaped frame 152 that surrounds a transparent window panel 154. Cover 150 has a top surface 155 and a bottom surface 156. Frame 152 can be formed from materials such as stamped aluminum or other suitable materials. Transparent panel 154 formed from a material that is transparent such as acrylic or glass. Transparent panel 154 allows a user to visually see the contents of container 100. A pair of blocks 157 are mounted to opposite sides of frame 152. Each block 157 has defined therein a linear groove 158 that extends the length of block 157. Bail portion 132 of latch 128 mates with groove 158 in order to retain cover 150 to container 100. Bail portion 132 is placed into groove 158 and latch 128 is pivoted downward to a locked position where cover 150 is removable and sealingly locked to container 100. An elastomeric seal (not shown) is mounted to the cover frame 152. When the cover 150 is installed on container 100, the elastomeric seal prevents micro-organisms from entering the interior of the cover and container 100 by sealing the gap between the cover and upper peripheral rim 113 of container 100, thus completing an enclosure to keep micro-organisms from entering the interior where the surgical instruments 180 are located.

A rack or insert tray 160 is used to hold medical/surgical instruments 180 within container 100 during sterile processing. Rack 160 includes a generally rectangular shaped base 162 with four walls 164 that extend perpendicularly upward from base 162. A pair of spaced apart handles 165 are mounted to opposing walls 164 allowing a user to lift rack 180. Apertures 166 are defined in base 162. Several support members 168 extend upwardly from base 162.

Medical/surgical instruments 180 rest on and are supported by support members 168. Support members 168 are dimensioned and shaped so that medical/surgical instruments 180 are retained in a preferred orientation for sterile processing.

In one embodiment, medical/surgical instruments 180 can be manual instruments such as scalpels, forceps and osteotomes. In another embodiment, medical/surgical instruments 180 can be powered instruments such as rotary handpieces, drills, or endoscopes. Reusable medical/surgical instruments require cleaning and sterilization prior to re-use to destroy microorganisms that may be present. Medical/surgical instruments 180 with dead end lumens need to be oriented with the lumen horizontal or pointing downward during automated washing and sterile processing such that liquids do not accumulate in the lumen and so that sterilant can enter and exit from the lumen.

An electronic sensor assembly or module 200 is mounted to front panel 102 below window 114. Electronic sensor module 200 contains electronic components and sensors that measure environmental conditions in container 100. These components also determine if required conditions have been met to insure sterility of the contents of container 100. Electronic sensor assembly 200 can be mounted to other container panels such as back panel 103 side panel 104 or cover 150.

Figure 3:
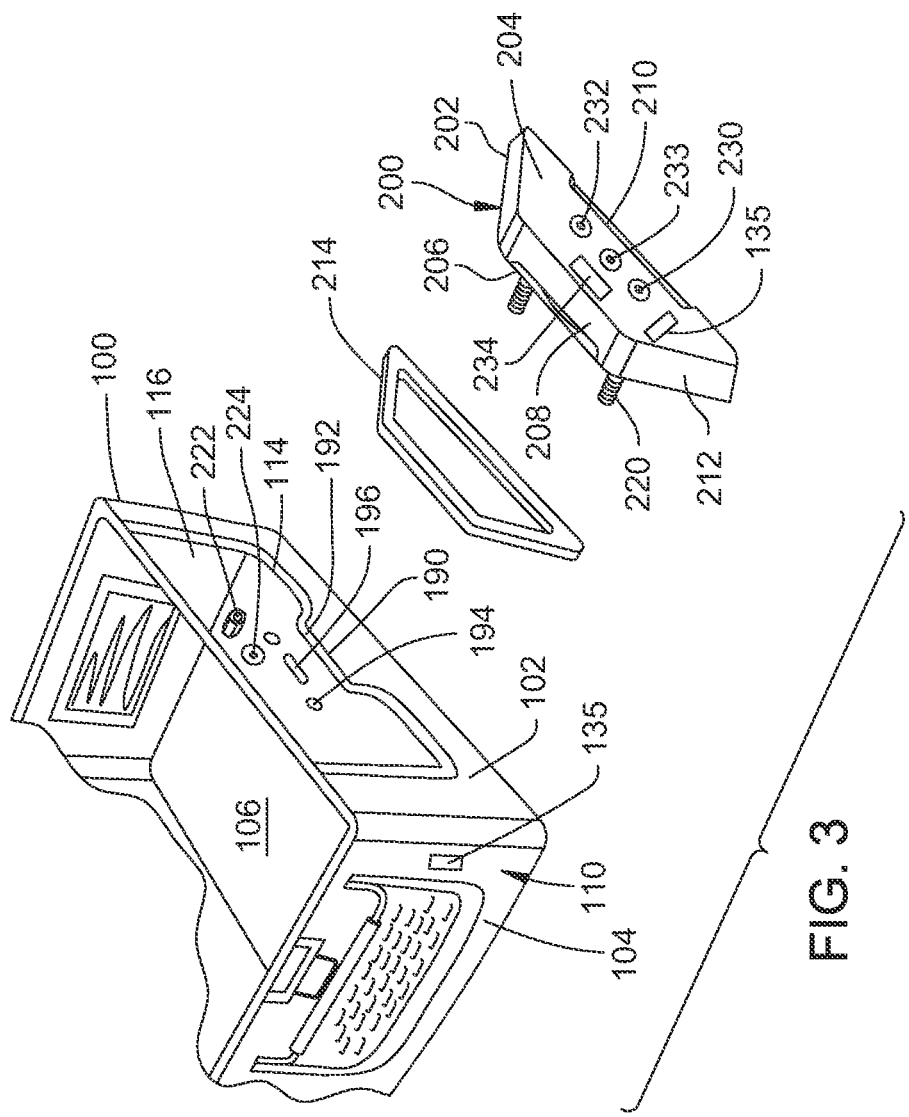
FIG. 3 is an enlarged perspective view of the container of FIG. 2 illustrating the electronic sensor module separated from the container in accordance with one embodiment.

With reference to FIG. 3, further details of container 100 and electronic sensor module 200 are illustrated. Container 100 further comprises a raised section 190 that extends upwardly from the base of window 114. Ramp sections 192 extend between the base of window 114 and raised section 190. A pair of spaced apart holes 194 are defined in panel 116. An opening 196 is defined in transparent panel 116 above raised section 190 and between holes 194.

Electronic sensor module 200 includes a generally trapezoidal shaped housing 202 that has a front side 204, rear side 206, top side 208, bottom side 210 and angled sides 212. Housing 202 can be formed from any suitable material such as injection molded plastic, aluminum or stainless steel. A pair of threaded studs 220 extend perpendicularly away from rear side 206.

Electronic sensor module 200 is mounted to container 100 by placing housing 202 above raised section 190 and inserting studs 220 through holes 194. Washers 224 are placed over studs 220 and fasteners 224 such as a nut are threaded onto studs 220 securing electronic module 200 to container 100. Gasket, seals or a curable sealing material 214 are used between sensor module 200 and container 100 to prevent micro-organisms from entering the interior of the container through mounting holes 194 or opening 196. In this position rear side 206 of electronic module 200 abuts transparent panel 116 and extends over opening 196. Electronic module 200 can be retrofitted to various existing types of containers by modifying the existing containers to include holes 194 and opening 196.

A green light emitting diode (LED) 230, a red LED 232 and a yellow LED 233 are mounted within housing 202 and are visible through an opening in front side 204. In another embodiment, LEDs are replaced with another visual type of indicator pane or display. These alternate embodiments provide a visual status of the equipment load, the sensor modules or other items that are helpful visual indicators to the operators using these systems during disinfection or sterilization processes. A display 234 such as a liquid crystal display is mounted within housing 202 above LEDs 230-233 and is visible through an opening in front side 204. LEDs 230-233 and LCD 234 provide visual information to personnel using container 100.

A bar code, UPC code or RFID tag 135 is mounted to front side 124. Bar code or RFID tag 135 can contain information about electronic module 200 such as the type of electronic module and/or the contents of container 100. Bar code or RFID tag 135 can be optionally located on other exterior panels of container 100 or on sensor module 200.

Figure 4:
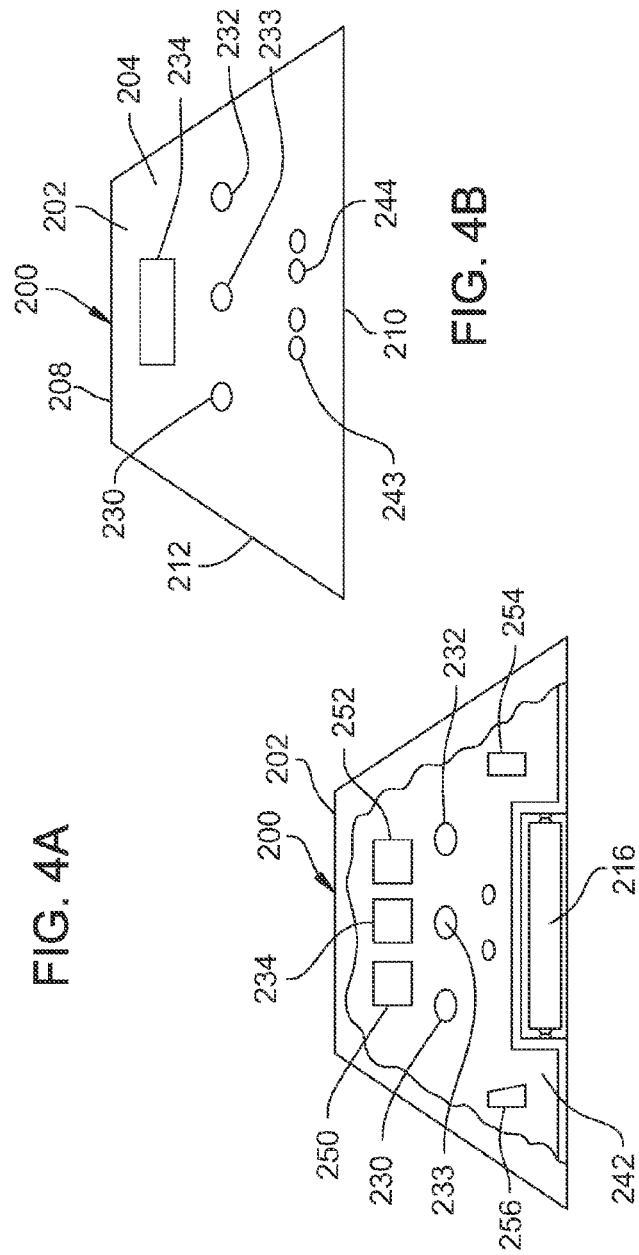
FIG. 4A is a rear view of the electronic sensor module in accordance with one embodiment.
FIG. 4B is a front view of the electronic sensor module.
FIG. 4C is a front cut-away view of the electronic sensor module.
FIG. 4D is a bottom view of the module of FIG. 4A.

Referring to FIGS. 4A, 4B and 4C, further details of electronic sensor module 200 are illustrated. A battery compartment 215 is located on rear side 206. Battery compartment 215 contains a battery 216 that is mounted between terminals 217 and 218. A cover 219 is snap fit to housing 202 covering battery compartment 215. Battery 216 provides power to electronic module 200. Connector terminals 243 and 244 are used to connect to devices external to electronic module 200. For example, connector terminals 244 are connected with battery 216 and can be connected to a source of power in order to recharge battery 216. Connector terminals 243 can be used to transmit and receive data between electronic module 200 and an external device.

An opening 226 is located in the back side 206 of housing 202. Several sensors 240 are coupled to a printed circuit board 242 that is mounted within housing 202. Sensors 240 are visible or exposed through opening 226. Sensors 240 measure environmental characteristics such as temperature, pressure, humidity and chemical concentration levels. When housing 202 is mounted to container 100, sensors 240 are positioned over opening 196 such that sensors 240 are exposed to the environmental conditions within interior cavity 120. In one embodiment, sensors 240 can extend through opening 196 into interior cavity 120.

Other electronic components are mounted to printed circuit board 242 as seen in FIG. 4C to allow electronic module to monitor the characteristics of the environment in container 100. A processor 250 and memory 252 are mounted to printed circuit board 242. A wireless module 254 and passive components 256 are mounted to printed circuit board 242. Wireless module 254 allows electronic module 200 to communicate with other external devices. These devices include transceiver heads and computer systems. In one embodiment, wireless module 254 can transmit and receive data and instructions from other external computer systems and networks.

A green light emitting diode (LED) 230, a red LED 232 and a yellow LED 233 are mounted to printed circuit board 242. Alternately, these three LEDs can be replaced by a multi-colored LED assembly to produce one or more distinctively different colors. These distinctively different colors provide information to the user as to the status of the container. For example red LED 232 can indicate the container of equipment is non-sterile. The yellow LED 233 can indicate the container of equipment is ready to be sterilized. The green LED 230 can indicate the container of equipment has been properly sterilized. A display 234 such as a liquid crystal display can be mounted to printed circuit board 242.

LEDs 230, 232, 233 and LCD 234 provide visual information to personnel using container 100.

III. Second Container Embodiment

Figure 5:
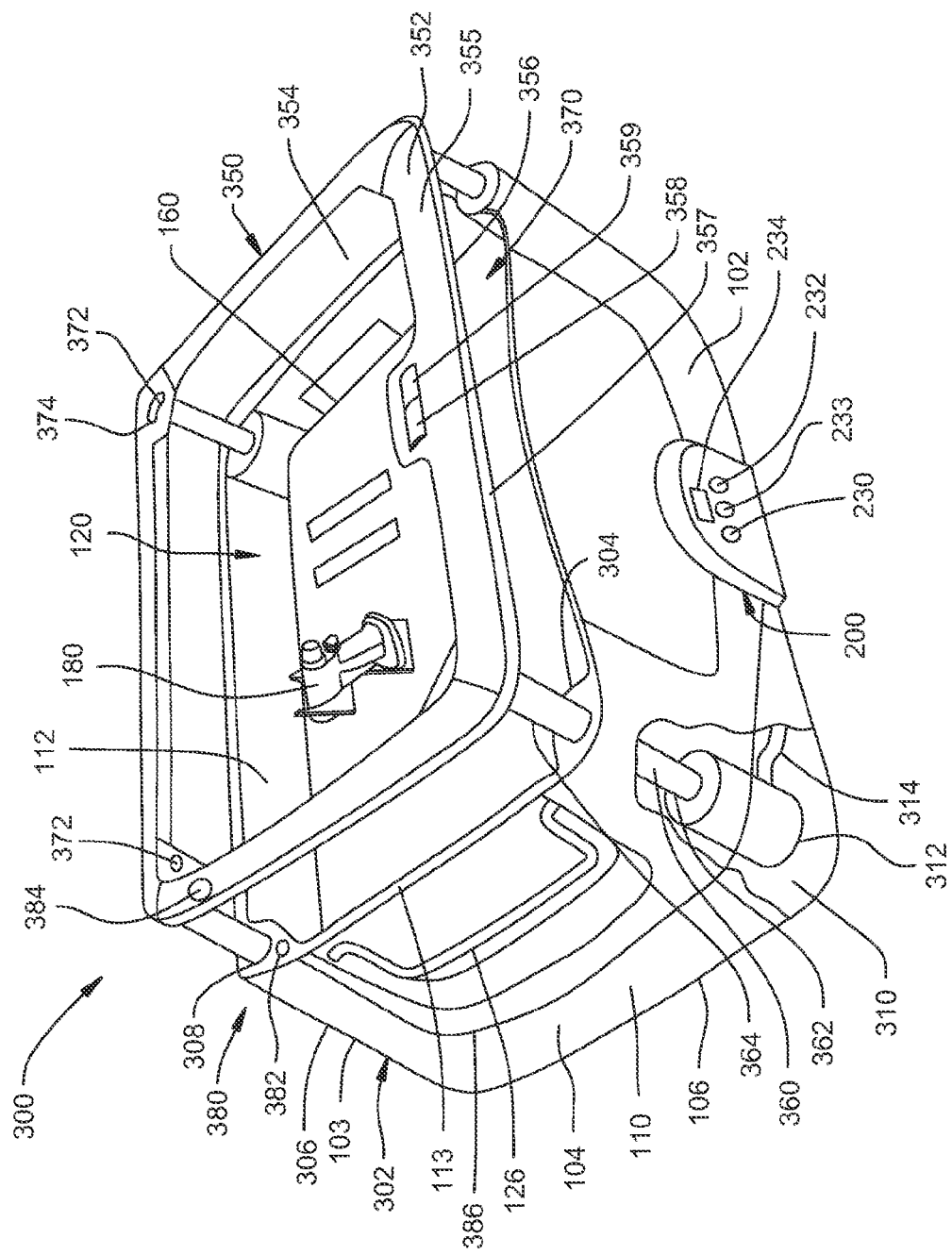
FIG. 5 is a top perspective view of an automatic closing container used for sterilization of medical/surgical instruments with the cover in an open position in accordance with one embodiment.

FIG. 5 illustrates a container assembly 300 of a second embodiment of the present invention. In FIG. 5, common reference numbers to like items in FIG. 2 have been given the same reference number. Container assembly 300 includes a container 302 that is generally rectangular in shape. Container 302 is similar to container 100; however, some features of container 100 have been omitted and other features have been added. For example, container 302 does not include any holes 124 or a filter assembly 140.

Electronic module 200 is mounted to front panel 102. Electronic sensor module 200 contains electronic components and sensors that measure environmental characteristics within container 302 and determine if required conditions have been met to insure sterility of the contents of container 302.

Container 302 further includes four rounded shoulders 304. Each of shoulders 304 is located at an interior corner 306 of container 302 and extends along the length of corner 306 between bottom panel 106 and rim 113. A bore 308 is defined in each shoulder 304 and extends into an internal compartment 310. A linear actuator 312 is mounted in each of compartments 310. Each linear actuator 312 is in communication with electronic module 200 through an electrical cable 314.

A cover 350 is used to cover and enclose container 302. Cover 350 includes a generally rectangular shaped frame 352 that surrounds a transparent window panel 354. Cover 350 has a top surface 355 and a bottom surface 356. An elastomeric gasket 357 is mounted to bottom surface 356 and makes a seal when mated with rim 113 when cover 350 is in a closed position. Control buttons 358 and 359 are mounted to the front top surface of frame 352 and are in communication with electronic module 200 through wireless communication means (not shown). Control button 358 closes cover 350 and control button 359 opens cover 350.

Four rods 360 are coupled between cover 350 and linear actuators 312. Rods 360 have a proximal end 362 and a distal end 364. Proximal end 362 is located in compartment 310 and connected to linear actuator 312. Rod 360 extends through bore 308 terminating at distal end 364. Distal end 364 is removably coupled to frame 352. Electronic module 200 triggers linear actuator 312 to move rods 360 and cover 350 in a linear direction toward and away from container 302.

Cover 350 can be attached and detached from rods 360 in order to facilitate loading and unloading of container 302. Four quick release pin 372 are inserted through apertures 374 located in each interior corner of frame 352. Quick release pin 372 mates with a bore (not shown) in the distal end 364 of rod 360 in order to retain frame 352 to distal end 364. Each quick release pin 372 has one or more ball bearings (not shown) that are biased outwardly by an internal spring. When all four quick release pins 372 are removed, cover 350 can be removed from rods 360 allowing access to interior cavity 120. Medical personal can manually place tray 160 and surgical instruments to be sterilized into cavity 120.

In an open position, as shown in FIG. 5, cover 350 is supported by rods 360 and is spaced apart from rim 113. A gap or opening 370 is formed between frame 352 and rim 113. In the open position, sterilant can enter into and exit from interior cavity 120 through opening 370 during sterile processing.

Figure 6:
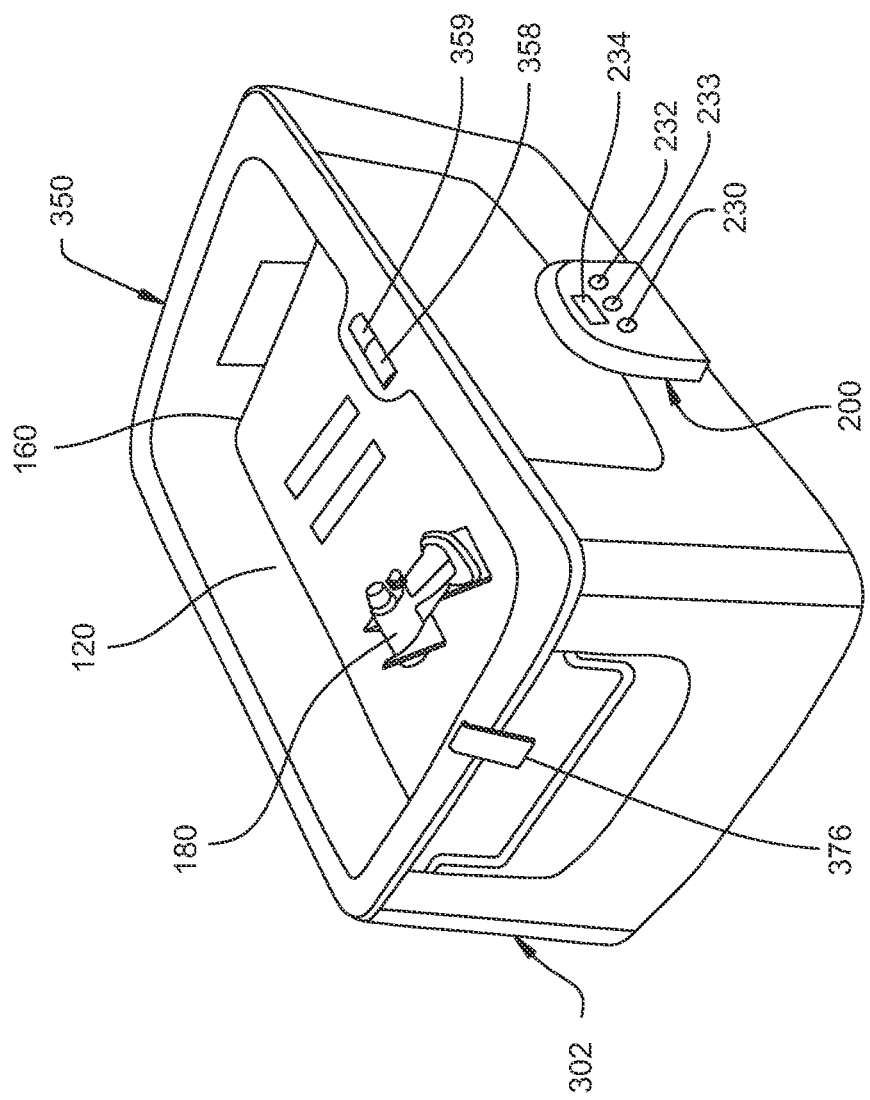
FIG. 6 is a top perspective view of the automatic closing container of FIG. 5 with the cover in a closed position.

Turning to FIG. 6, cover 350 is shown in a closed position sealing container 302 and the contents of container 302 (i.e. rack 160 and surgical instruments 180). After electronic module 200 determines that the operating conditions within container 302 during sterile processing were sufficient to meet or exceed a required set of operating conditions, electronic module 200 directs linear actuators 312 to close cover 350 and turns on green LED 230. The closing and sealing of cover 350 and an "on" green LED 230 indicates the contents of the container were properly sterilized and the container properly sealed. A continuously "on" green LED 230 can alternately be a flashing "on" green LED 230 so that the discharge rate of the battery can be slowed in order to extend battery life.

In the closed position, gasket 357 is held against rim 113 forming a seal between frame 352 and container 302. The sealed container allows sterile instruments within the container to be removed from the sterilizer 50 while maintaining a sterile environment within container 302 after processing. When surgical instruments 180 within closed container 302 are required for a surgical procedure, a user depresses open button 359 which causes electronic sensor module 200 to direct actuators 312 to move cover 350 to the open position. The user then manually removes quick release pins 372 and cover 350 allowing access to interior cavity 120 for removal of the sterilized surgical instruments 180.

After cover 350 is opened, the environment within container assembly 300 may no longer be sterile. When electronic sensor module 200 opens cover 350, electronic sensor module also turns off green LED 230 and turns on red LED 232. The illumination of red LED 232 indicates to a user that the container seal has been broken. Inferentially this is an indication that the contents of the container are no longer sterile. If cover 350 is opened and then closed, red LED 232 will remain lit informing a user that the contents of the container are no longer sterile.

Container assembly 300 further optionally includes one or more tamper seals 376 (FIG. 6) in addition to tamper sensors 380 (FIG. 5). Tamper seals 376 and tamper sensors 380 are used to indicate if container assembly 300 has been opened during storage causing the sterility of the contents of container assembly 300 to be compromised. Tamper seal 376 is a tape or seal that is mounted between container 302 and cover 350. Removal or opening of cover 350 causes tamper seal 376 to be broken indicating to a user the sterility of the contents of container assembly 300 have been compromised.

Returning to FIG. 5, tamper sensor 380 may comprise a Hall effect sensor 382 and a magnet 384. Hall effect sensor 382 is mounted to the top of shoulder 304 adjacent to bore 308. Magnet 384 is mounted to the bottom side of frame 352. Hall effect sensor is in communication with electronic module 200 through a cable 386 mounted within container 302. When cover 350 is in the closed position, magnet 384 is juxtaposed to Hall effect sensor 382. Hall effect sensor 382 senses the magnetic field generated by magnet 384 and sends an electrical signal indicating the presence of magnet 384 to electronic sensor module 200. Electronic module 200 can keep green LED 230 illuminated indicating to a user that the contents of container assembly 300 are sterile. When cover 350 is moved away from container 302, breaking the sterile barrier created by the container assembly 300, Hall effect sensor 382 sends an electrical signal to electronic module 200 indicating a reduced magnetic field generated by magnet 384. Electronic module then turns off green LED 230 and turns on red LED 232. The illumination of red LED 232 indicates to a user that the contents of container assembly 300 are no longer sterile. In order to extend the battery charge of battery 216, LEDs can flash providing indications to the user as described above.

IV. Third Container Embodiment

Referring to FIGS. 7A-7D, a container assembly 400 of a third embodiment of the present invention is shown. With specific reference to FIG. 7A, container assembly 400 comprises a container 402 that is generally rectangular in shape and is defined by a planar front panel 403, an opposed planar rear panel 404 and a pair of opposed spaced apart planar side panels 405 and 406. Panels 403 and 404 are oriented orthogonal to panels 405 and 406. A planar bottom panel 407 is mounted perpendicular to panels 403-406 and forms the bottom of container 402. An interior cavity 420 is defined within container 402. Container 402 has outer surfaces 410 and inner surfaces 412. An upper peripheral rim 413 is defined by the upper edges of panels 403-406. Container 402 can be formed from materials such as stamped aluminum or other suitable materials.

Side panel 406 has an opening 414 that is covered by a panel 416 that is transparent to visible light but is opaque to infrared (IR) and/or ultraviolet (UV) light frequencies. Panel 416 prevents external or internal UV and/or IR light from passing through panel 416. Transparent panel 416 allows a user to visually see the contents within container 402. An elastomeric gasket 415 seals panel 416 to side panel 406. Gasket 415 and panel 416 are attached to side panel 406 using an adhesive.

Another opening 418 is defined in side panel 406 extending from just above bottom panel 406 to below opening 414. Opening 418 is smaller than opening 414. Opening 418 is dimensioned to receive a window 421. Window 421 can be either transparent or opaque and can be formed from a plastic material. A gasket or hermetic seal 422 seals window 421 to side panel 406. Gasket 422 and panel 421 are attached to side panel 406 using an adhesive.

A pivoting handle 426 is attached to each of side panels 405 and 406. Handle 426 has ends 425 that are retained to side panels 405 and 406 by circular shaped bands 426. Two bands 426 are rigidly attached and sealed to side panel 405. Two bands 426 are rigidly attached and sealed to side panel 406. Ends 425 are received by bands 426 and can rotate within bands 426. Handles 424 pivot between a stored position where handles 424 are adjacent side panels 405, 406 and a carrying position where handles 424 extend perpendicular to side panels 405, 406. Side panels 405, 406 further include a pair of opposed L-shaped steps 496 that are mounted to opposite ends of container 402. More particularly, steps 496 extend generally perpendicularly away from opposed portions of flange 453 and are angled slightly downwardly. Steps 496 are used in conjunction with locking lid latch 446, mounted to the cover 450 to secure cover 450 to container 402. Locking lid latch 446 is rotated by a user downwardly over steps 496 to a locked position where cover 450 is retained to and locked to container 402 while compressing cover gasket 456 between cover 450 and container 402. This compression inhibits the entry of microbes into the container.

Figure 7A:
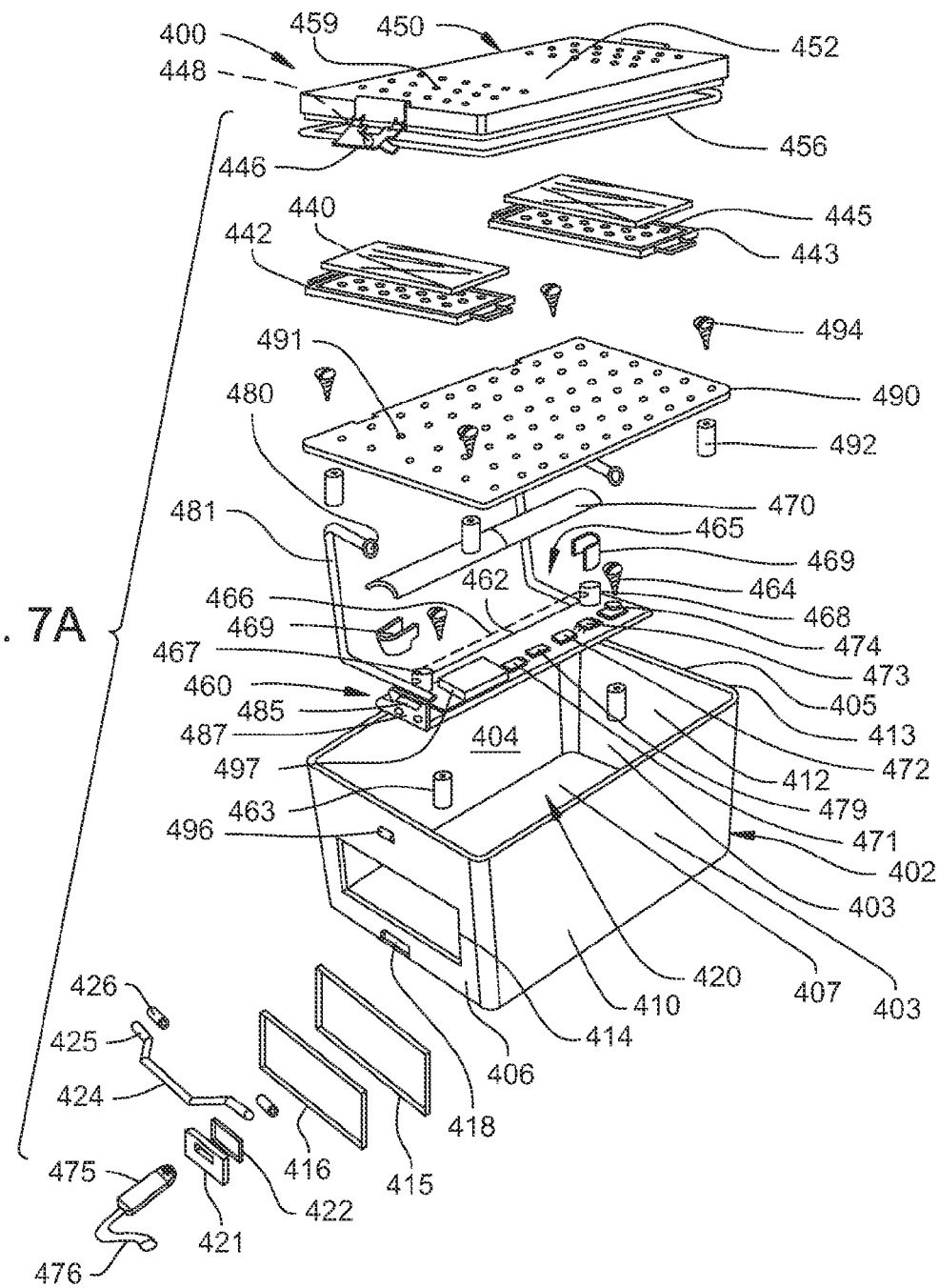
FIG. 7A is an exploded top perspective view of another container for sterilization of medical/surgical instruments having a false bottom in accordance with one embodiment.
Figure 7B:
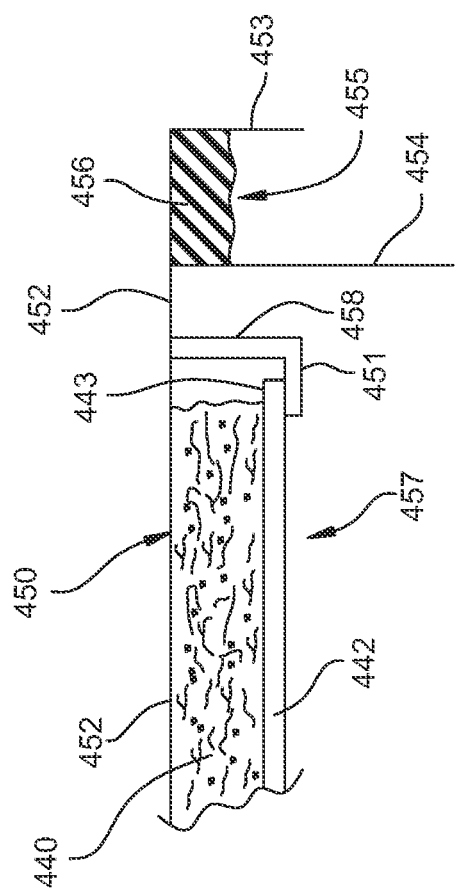
FIG. 7B is an enlarged partial cross-sectional view of the cover of FIG. 7A.

With additional reference to FIG. 7B, a cover 450 is used to cover and enclose container 402. Cover 450 includes a generally rectangular shaped panel 452. Cover 450 can be formed from materials such as stamped aluminum or other suitable materials. Two arrays of holes 459 are defined in and extend through panel 452. Holes 459 are located toward each of the ends of panel 452. Holes 459 allow sterilant to enter and leave container 402 during sterilization processing. An outer peripheral flange 453 extends downwardly from the outer edges of panel 452. A rectangular interior wall 454 extends downwardly from panel 452 and is spaced inwardly from flange 453 along the entire length of flange 453. Flange 453 and wall 454 define a U-shaped groove 455 there between. An elastomeric gasket 456 is mounted in groove 455. Cover 450 fits over panels 403, 404, 405 and 406 such that rim 413 rests between flange 453 and wall 454 and is in contact with gasket 456. Gasket 456 forms a seal between cover 450 and container 402. Wall 454 further defines an interior recess 457 below panel 452. A pair of spaced apart opposed L-shaped rails 458 extend perpendicularly away from the bottom surface of panel 452 into recess 457. The terminal lips 451 of L-shaped rails 458 face each other.

Two filters 440 are mounted in recess 457. Each filter 440 is supported by a filter support member 442. Filter support member 442 has outwardly extending shoulders 443 that extend from each end of filter support member 442. Shoulders 443 are retained by terminal lips 451 of rails 458. Filter support member 442 further includes an array of apertures 445. Filters 440 cover holes 459. Filter 440 and filter clip 442 are generally rectangular in shape.

Filter 440 and filter support member 442 are formed from a flexible material such that filter 440 and filter support member 442 can be bent to allow shoulders 443 to slide under the terminal lips 451. Alternatively, filter 440 can be placed by a user onto filter support 442 and the combination is inserted along rails 458. Rails 458 are dimensioned so that as filter 440 and clip 442 are inserted into rails 458, filter 440 is compressed or squeezed against the inner surface of cover 450.

Filter 440 is formed from a microbial barrier material that is permeable to sterilant. Filter 440 allows sterilant to pass from the outside of cover 450, through holes 459, through filter 440, through apertures 445 and into interior cavity 420 where the sterilant contacts surgical instruments. Filter 440 also forms a microbial barrier preventing microorganisms from entering into container assembly 400 after container assembly 400 has been processed through a sterilization process.

A locking lid latch 446 is attached to each of end of cover 450. One end of locking lid latch 446 is rotatable attached to each cover end. Locking lid latch 446 can be rotated up and down. When locking lid latch 446 is rotated downward and engaged with L-shaped steps 496, the cover 450 is removable locked to container 402. Magnets 448 are mounted to an interior facing surface of locking lid latch 446 and work with hall effect sensor 480 as described later.

An electronic sensor assembly or module 460 is mounted within container 402. Electronic sensor module 460 contains electronic components and sensors that measure the characteristics of the environment within container 402 during sterilization processing and determine if required conditions have been met to insure sterility of the contents of container 402.

With reference to FIG. 7A, electronic sensor module 460 has a rectangular shaped printed circuit board (PCB) 462. PCB 462 contains printed circuit lines (not shown) that electrically connect the components of electronic module 460. PCB 462 is mounted above and spaced from bottom panel 407 by two or more insulated spacers or standoffs 463. Fasteners 464 such as screws retain PCB 462 and standoffs 463 to bottom panel 407.

Sensors are mounted to PCB 462 to monitor one or more characteristics of the environment inside container 402. These sensors including a sensor 472 that monitors the concentration of water vapor. This is sometimes referred to as a humidity or steam sensor. A sensor 473 monitors the fluid (gas) pressure inside the container. A sensor 474 monitors the temperature within the container. There is also a processor 479 and a memory 471. Also, mounted to the top side of PCB 462 is an optical sensor 465 that senses the amount of infrared (IR) or ultraviolet (UV) light transmitted through an optical path length 466 within container 402. In one embodiment, optical sensor 465 detects concentrations of hydrogen peroxide gas ($H_2O_2$). In another embodiment, optical sensor 465 detects concentrations of ethylene oxide gas ($C_2H_4O$). In another embodiment, optical sensor 465 detects concentrations of water or water vapor ($H_2O$). In another embodiment, optical sensor 465 detects both hydrogen peroxide vapor ($H_2O_2$) and water vapor ($H_2O$).

Optical sensor 465 includes an IR or UV source or emitter 467 and an IR or UV receiver or detector 468 mounted to the top side of PCB 462. Light filters (not shown) can be mounted around IR detector 468 and/or light source 467 to remove any undesired wavelengths. Because hydrogen peroxide gas absorbs infrared light at a wavelength of 2.93 microns, the amount of light at that frequency transmitted through a known path length 466 containing hydrogen peroxide gas is proportional to the concentration of the hydrogen peroxide gas. Hydrogen peroxide gas also absorbs ultraviolet light at wavelengths near 240 nanometers. The absorption of light through a gas is described by the Beer-Lambert law.

Semi-circular light concentrators 469 are mounted to PCB 462. One light concentrator 469 is positioned around emitter 467 and another light concentrator is positioned around detector 468. Light concentrators 469 reflect light rays that are not coaxial to detector 468. An elongated light shield 470 is mounted over optical path length 466 and emitter 467, detector 468 and both light concentrators 469. Light shield 470 is attached to PCB 462. Light shield 470 prevents stray light rays from leaving optical sensor 465 and entering interior cavity 420. Light concentrators 469 and shield 470 are formed from a material that is light reflective such as polished stainless steel. Light concentrators 469 and light shield 470 can work together to reflect emissions from emitter 467 and concentrate those emissions to increase the energy detected by detector 468.

A battery 497 is mounted to PCB 462 and supplies power to the components of electronic module 460. Battery 497 can be formed from one or more battery cells to form a battery pack depending on the voltage and power requirements of electronic sensor module 460. In one embodiment, battery 497 is a rechargeable battery. In another embodiment, battery 497 is replaced with a new battery after being discharged. Light emitting diodes (LED) 487 such as green, red and yellow LEDS are mounted to PCB 462. LEDS 487 provide visual information to personnel using container assembly 400.

Figure 7C:
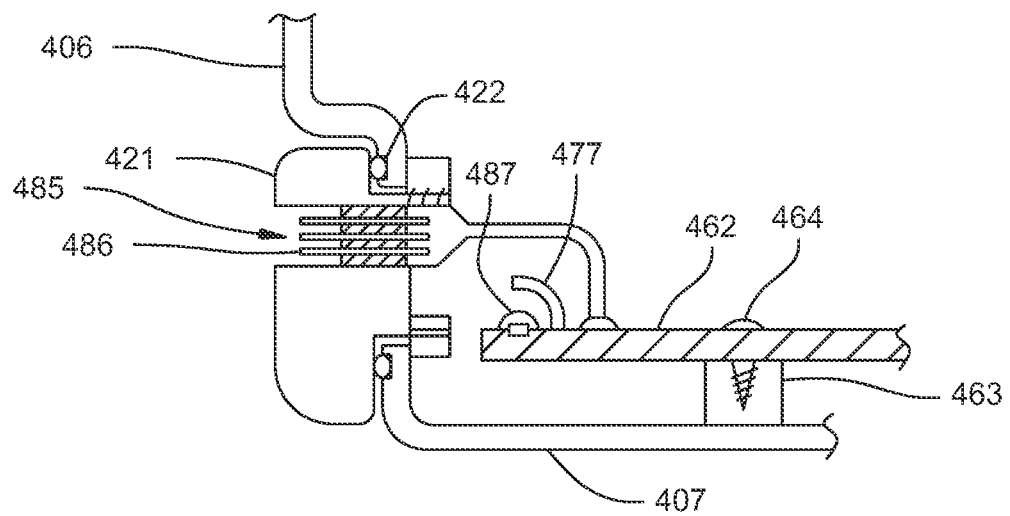
FIG. 7C is an enlarged cross-sectional view of one side wall embodiment of the container of FIG. 7A illustrating details of a hermetic connector and internal light emitting diodes.

FIG. 7C illustrates additional components contained within window 421. Window 421 in FIG. 7C is formed from a transparent material such as plastic. A hermetically sealed connector 485 is mounted within window 421 and contains several terminals 486 that extend through connector 485 and are electrically connected to PCB 462. Hermetic connector 485 is connected with an external connector 475 and cable 476 (FIG. 7A) in order to transmit and receive data from container assembly 400. LEDS 487 on PCB 462 are viewed by a user through window 421. A light shield 477 blocks light generated by LEDS 487 from reaching optical sensor 465.

Figure 7D:
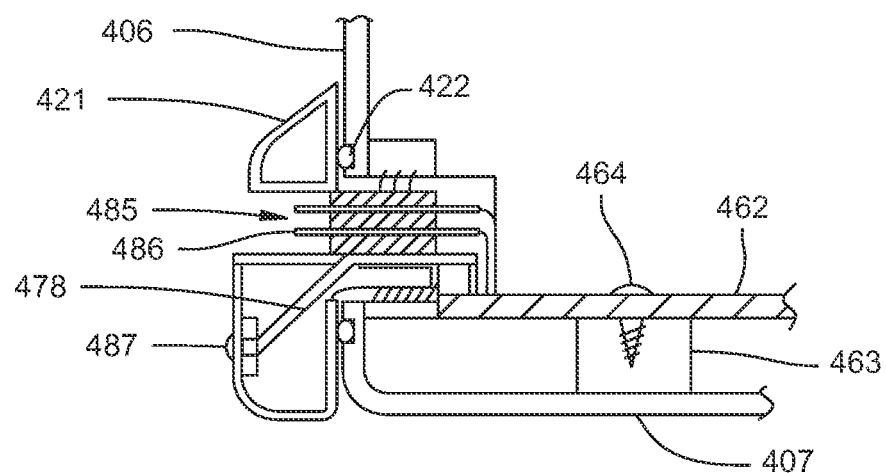
FIG. 7D is an enlarged cross-sectional view of another side wall embodiment of the container of FIG. 7A illustrating details of a hermetic connector and external light emitting diodes.

FIG. 7D illustrates another embodiment of components contained within window 421. Window 421 in FIG. 7D is formed from an opaque material such as plastic. A hermetically sealed connector 485 is mounted within window 421 and contains several terminals 486 that extend through connector 865 and are electrically connected to PCB 462. Hermetic connector 485 is connected with an external connector 475 and cable 476 (FIG. 7A) in order to transmit and receive data from container assembly 400. In the embodiment of FIG. 7D, LEDS 487 are not mounted to PCB 462. LEDS 487 are mounted to the outside of window 421 and are connected to PCB 462 by wires or terminals 478 that extend through window 421. Window 412 is sealingly mounted to container wall 406 with a seal, gasket or curable sealing material 422.

Returning to FIG. 7A, a hall effect sensor 480 is mounted to the interior surface 412 of side wall 406 below rim 413 and another hall effect sensor 480 is mounted to the interior surface 412 of side wall 405 below rim 413. Hall effect sensors 480 are connected to PCB 462 by wires 481. When cover 450 is placed over container 402, magnets 448 are juxtaposed to Hall effect sensors 480. The Hall effect sensors 480 sense the magnetic field generated by magnets 448 and output an electrical signal indicating the presence of a detected magnetic field. When latch 446 is opened to remove cover 450 from container 402, Hall effect sensors 480 sense the absence of a magnetic field and output an electrical signal indicating no detected magnetic field. Electronic sensor module 460 can use signals from hall effect sensor 480 to monitor if latches 446 have been properly maintained or tampered with after sterilization. Alternately, a mechanical item like a one way locking zip strip (not shown) that prevents locking lid latch 446 from decoupling from L-shaped step 496 can serve as a way to visually indicate that the locking lid latch 446 has been maintained in the correct position. These mechanical one way locking zip strips are typically broken and removed so the locking lid latch 446 can be unlatched from L-shaped step 496.

A false bottom plate 490 is mounted over electronic module 460 and bottom panel 407. False bottom plate 490 is rectangular in shape and has a series of holes 491 extending through plate 490. False bottom plate 490 is supported above electronic module 460 by standoffs 492. Standoffs 492 rest on bottom panel 407. Fasteners 494 retain plate 490 to bottom panel 407. Fasteners 494 such as screws extend through false bottom plate 490, standoffs 492 and are threaded into bottom panel 407. Holes 491 allow sterilant to flow under false bottom plate 490 and into electronic sensor module 460. This allows the sensors in the module to take measurements of the characteristics of the environment internal to container 400.

During use, a rack or tray 160 (FIG. 2) containing medical/surgical instruments 180 (FIG. 2) in a desired orientation to be sterilized can be placed within container 402. Rack 160 is placed and rests on plate 490. Electronic module and sensors 460 are hidden under plate 490. After tray 160 is placed within container 402, cover 450 is placed over container 402 and locking lid latches 496 are moved to the locked position, locking and sealing the cover 450 to container 402. A connector 475 and cable 476 are attached to connector 485 and memory 471 is programmed with validated sterilization process measurement (VSPM). After programming, container assembly 400 is ready for processing through a sterilization process cycle.

V. Fourth Container Embodiment

Figure 8:
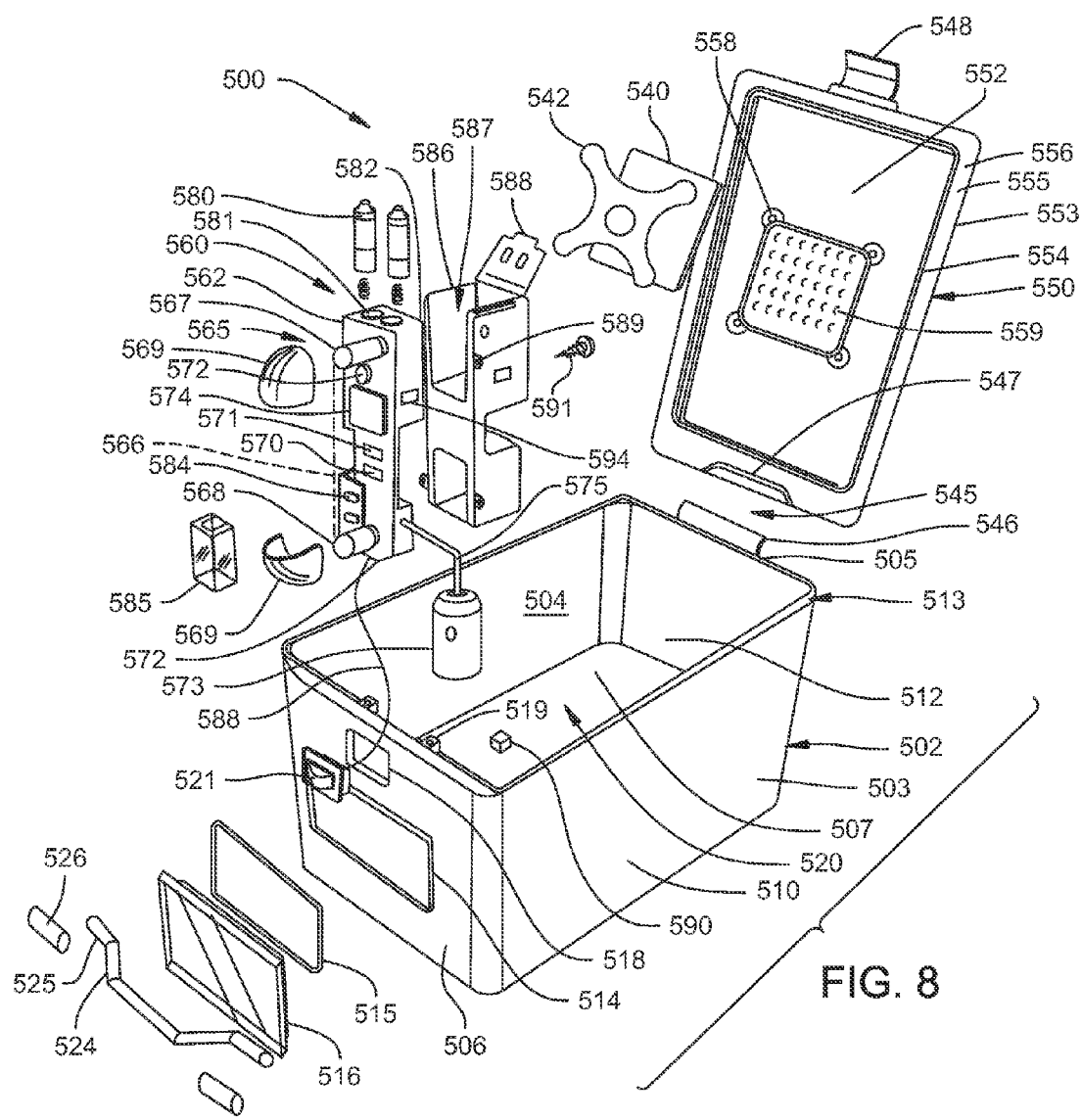
FIG. 8 is an exploded top perspective view of an additional container for sterilization of medical/surgical instruments having a false side in accordance with one embodiment.

FIG. 8 depicts a container assembly 500 of a fourth embodiment of the present invention. Container assembly 500 comprises a container 502 that is generally rectangular in shape and is defined by a planar front panel 503, an opposed planar rear panel 504 and a pair of opposed spaced apart planar side panels 505 and 506. Panels 503 and 504 are oriented orthogonal to panels 505 and 506. A planar bottom panel 507 is mounted perpendicular to panels 503, 504, 505 and 506 and forms the bottom of container 502. An interior cavity 520 is defined within container 502. Container 502 has outer surfaces 510 and inner surfaces 512. An upper peripheral rim 513 is defined by the upper edges of panels 503-506. Container 502 can be formed from materials such as stamped aluminum or other suitable materials.

Side panel 506 has a rectangular shaped opening 514 that is covered by a panel 516 that is transparent to visible light but is opaque to IR and/or UV light frequencies. Panel 516 prevents IR and/or UV light internal or external to container 502 from passing through panel 516. Transparent panel 516 allows a user to visually see the contents within container 502. An elastomeric gasket 515 seals panel 516 to side panel 506. Gasket 515 and panel 516 are attached to side panel 506 using an adhesive or suitable mechanical fasteners (not shown). Another rectangular shaped opening 518 is defined in side panel 506 above opening 514 and below rim 513. Opening 518 is dimensioned to receive a hermetically sealed switch 521. Several mounting blocks 519 are attached to the interior surface 512 of panel 506 and extending into cavity 520. Two mounting blocks 519 are positioned below rim 513 and two mounting blocks 519 are positioned at the bottom of panel 506.

A pivoting handle 524 is attached to each of side panels 505 and 506. Handle 524 has ends 525 that are retained on side panels 505 and 506 by circular shaped bands 526. Two bands 526 are welded to side panel 505 and two bands 526 are welded to side panel 506. Ends 525 are received by bands 526 and can rotate within bands 526. Handles 524 pivot between a stored position where handles 524 are adjacent side panels 505, 506 and a carrying position where handles 524 extend perpendicular to side panels 505, 506.

Cover 550 is used to cover and enclose container 502. Cover 550 includes a generally rectangular shaped panel 552. Cover 550 can be formed from materials such as stamped aluminum or other suitable materials. An array of holes 559 are defined in and extend through panel 552. Holes 559 allow sterilant to enter and leave container 502 during sterilization processing. An outer peripheral flange 553 extends downwardly from the outer edges of panel 552. An inner wall 554 extends downwardly from panel 552 and is spaced inwardly from flange 553. Flange 553 and flange 554 define a U-shaped groove 555 there between. An elastomeric gasket 556 is mounted in groove 555. Cover 550 fits over panels 503-506 such that rim 513 rests between flanges 553 and wall 554 and is in contact with gasket 556. Gasket 556 forms a seal between cover 550 and container 502. Four generally C-shaped retainer clips 558 extend downward from the bottom surface of panel 552. Clips 558 are positioned toward the center of panel 552 around the outermost holes 559.

A onetime use or multi-use filter 540 is mounted over holes 559. Filter 540 is supported by a filter support member 542. Filter support member 542 is retained to panel 552 by retainer clips 558. Filter support member 542 is formed from a flexible material such that the ends of support member 542 can be bent under retainer clips 558 in order to retain filter 540 and support member 542 to retainer clips 558. Filter 540 covers holes 559. Support member 542 and retainer clips 558 compress filter 540 against the bottom side of panel 552 over holes 559. Filter 540 is formed from a microbial barrier material that is permeable to sterilant. Filter 540 allows sterilant to pass from the outside of container 502 through holes 559, through filter 540 and into interior cavity 520 where the sterilant contacts surgical instruments. Filter 540 also forms a microbial barrier preventing microorganisms from entering into container assembly 500 after container assembly 500 has been processed through a sterilization process.

Container assembly 500 further comprises a lift off hinge 545. Lift off hinge 545 has a C-shaped flange 546 extending away from rim 513 of side panel 505 and another C-shaped flange 547 extending away from one end of cover 550. Flanges 546 and 547 mate with each other to form hinge 545. Flanges 546 and 547 are dimensioned such that when cover 550 is rotated with flanges 546 and 547 in engagement with each other toward a closed position, one end of cover 550 is retained to container 502.

A pivoting latch lock 548 is mounted to the other end of cover 550. Latch lock 548 is rotated by a user downwardly over switch 521 to a locked position where cover 550 is retained to and locked to container 502. The movement of latch lock 548 against switch 521 toggles switch 521 from an open circuit to a closed circuit. Container assembly 500 is unlocked and opened by a user moving latch lock 548 away from switch 521 and rotating cover 550 about hinge 545. The movement of latch lock 548 away from switch 521 toggles switch 521 from a closed circuit to an open circuit.

An electronic sensor assembly or module 560 is mounted within container 502. Electronic module 560 contains electronic components and sensors that measure the characteristics of the environment within container 502 during sterilization processing and determine if required conditions have been met to insure sterility of the contents of container 502.

Electronic sensor module 560 has a rectangular shaped printed circuit board (PCB) 562. PCB 562 contains printed circuit lines (not shown) that electrically connected the components of electronic sensor module 560. Various electronic components and sensors are mounted to PCB 562 to allow electronic module 560 to monitor the environment inside container 502. A processor 570, memory 571 water vapor or steam sensor 572 and isolated temperature sensor 574 are mounted to a top side of PCB 562. A diaphragm type pressure sensor 573 and/or a capacitance manometer are mounted within interior cavity 520 and is connected to PCB 562 via a cable 575.

Also, mounted to PCB 562 is an optical sensor 565 that senses the amount of IR or UV light transmitted through an optical path length 566 within container 502. In one embodiment, optical sensor 565 detects concentrations of hydrogen peroxide gas ($H_2O_2$). In another embodiment, optical sensor 565 detects concentrations of water ($H_2O$).

Optical sensor 565 includes a light source or emitter 567 and light receiver or detector 568 mounted to PCB 562. Light filters (not shown) can be mounted around detector 568 to remove any undesired wavelengths. Semi-circular light concentrators 569 are mounted to PCB 562. These concentrators can have parabolic, elliptical, or other shapes that concentrate the light on the photo detector that faces the emitter 567. One light concentrator 569 is positioned around emitter 567 and another IR light concentrator is positioned around detector 568.

Replaceable and/or rechargeable batteries 580 are received within openings 581 of a battery compartment 582. Battery compartment 582 is mounted to a backside of PCB 562. Batteries 580 supply power to the components of electronic module 560 through printed circuit lines (not shown) within PCB 562. Batteries 580 can be individual cells or packaged together into a battery pack arrangement.

Light emitting diodes (LEDS) 584 such as green, red and yellow LEDS are mounted to the top side of PCB 562. A transparent cover 585 is mounted to PCB 562 over LEDS 584. LEDS 584 are viewed by a user through cover 585 and window 516. LEDS 584 provide visual information to personnel using container assembly 500. A connector 594 is mounted to PCB 562 and extends through a bottom portion of battery compartment 582. Connector 594 is used to connect to an external connector and cable in order for electronic sensor module 560 to transmit and receive data or instructions from external systems and devices.

Battery compartment 582 and a portion of PCB 562 are contained within an insulative housing 586. Housing 586 is formed from an insulating material such as plastic. Housing 586 is generally rectangular in shape includes an interior chamber 587 and a cover 588. Mounting flanges 589 extend perpendicularly away from housing 586 and parallel to side panel 506. Battery compartment 582 and a portion of PCB 562 are mounted within chamber 587. Cover 588 is rotated to a closed position over battery compartment 582. Switch 521 is also in communication with PCB 562 through a wire 588.

Housing 586 is mounted to the interior surface 512 of panel 506. Housing 586 is spaced from bottom panel 507 by an insulated spacer or standoff 590. Fasteners 591 such as screws extend through mounting flanges 589 and are threaded into mounting blocks 519.

During use, a rack or tray 160 (FIG. 2) containing medical/surgical instruments 180 (FIG. 2) in a desired orientation to be sterilized are placed within container 502. Rack 160 is placed onto and rests on bottom panel 507.

An external cable (not shown) is attached to connector 594 in order to store in memory 571 a validated sterilization process measurement (VSPM). After instruments are placed in container 502, cover 550 is placed over container 502 engaging hinge 545 and latch lock 548 is moved into engagement with switch 521 to a locked position, locking the cover 550 to container 502. Container assembly 500 is now ready for processing through a sterilization process cycle.

VI. Fifth Container Embodiment

Referring to FIG. 9A, a container assembly 600 of a fifth embodiment of the present invention is shown. Container assembly 600 includes a version of container 402. The version of container 402 of FIG. 9A is the same as the previously described container 402 of FIG. 7A except that opening 418 is not present. Also magnets 624 are mounted to interior facing vertical side surfaces of side panels 405 and 406 slightly below rim 413.

Figure 9B:
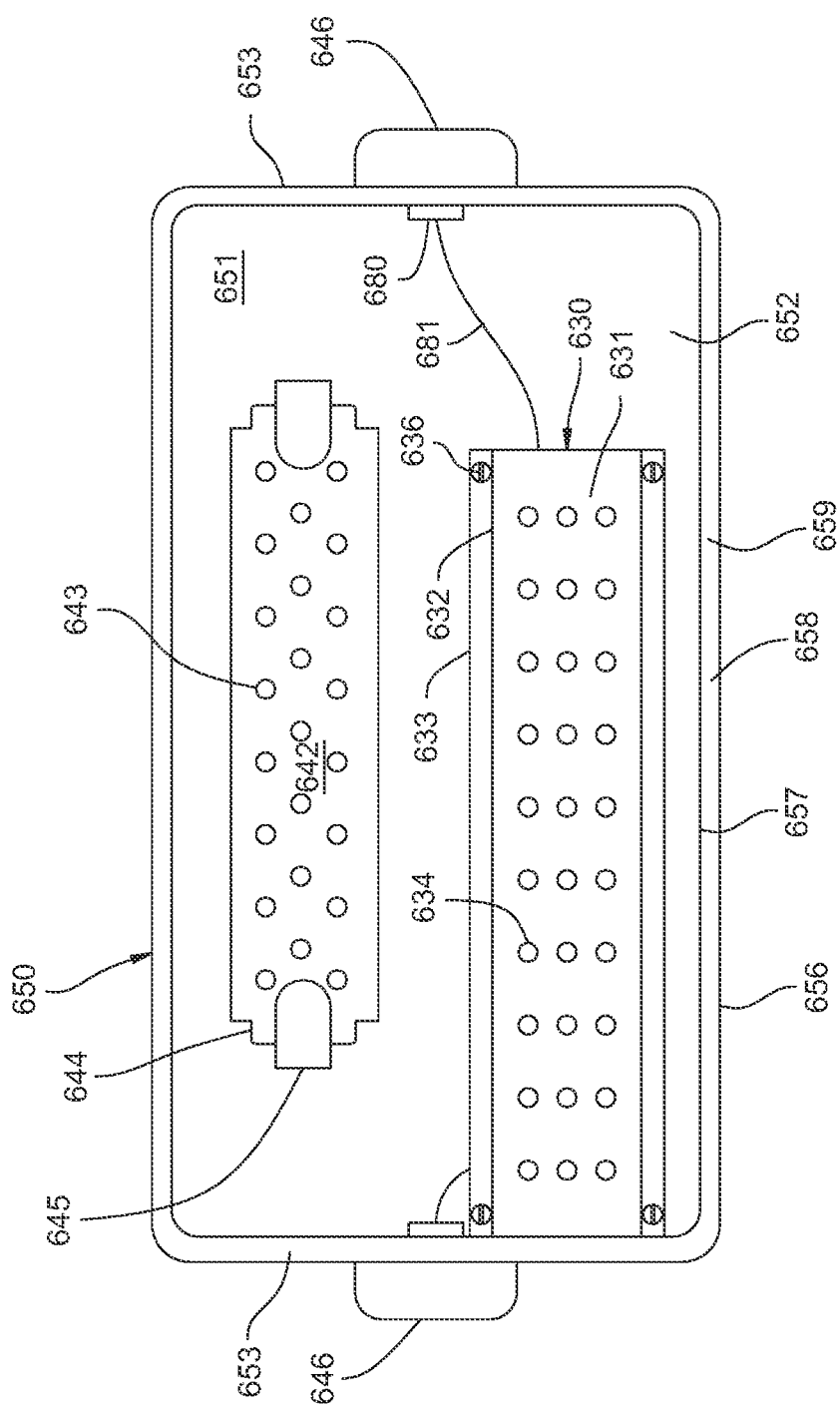
FIG. 9B is a bottom view of the cover of FIG. 9A.

With additional reference to FIG. 9B, cover 650 is used to cover and enclose container 402. Cover 650 includes a generally rectangular shaped panel 652. Cover 650 can be formed from materials such as stamped aluminum or other suitable materials. Cover 650 has an inner surface 651, an outer surface 654 and opposed ends 653. An array of holes 655 are defined in and extend through panel 652. Holes 655 allow sterilant to enter and leave container 402 during sterilization processing. An outer peripheral wall 656 extends downwardly from the outer edges of panel 652. Another rectangular wall 657 extends downwardly from panel 652 and is spaced inwardly from wall 656 along the entire length of wall 656. Walls 656 and 657 define a U-shaped groove 658 there between. An elastomeric gasket 659 is mounted in groove 658.

Cover 650 fits over panels 403, 404, 405 and 406 such that rim 413 rests between walls 656 and 657 and is in contact with an elastomeric gasket 659. Gasket 659 forms a seal between cover 650 and container 402.

Cover 650 further includes an opening 648 defined in one end 653. Opening 648 is dimensioned to receive a window 621. Window 461 is transparent and formed from a plastic material. A hermetic seal 622 seals window 621 to end 653. Window 621 and hermetic seal 622 are attached to end 653 using an adhesive.

Side panels 405, 406 further include a pair of opposed L-shaped steps 496 that are mounted to opposite ends of container 402. More particularly, steps 496 extend generally perpendicularly away from side panels 405, 406 and are angled slightly downwardly with an upwardly arc shape. Steps 496 are used in conjunction with locking lid latch 646, mounted to the cover 650 to secure cover 650 to container 402. Locking lid latch 646 is rotated by a user downwardly over steps 496 to a locked position where cover 650 is retained to and locked to container 402 while compressing cover gasket 659 between cover 650 and container 402 creating a seal. A locking lid latch 646 is attached to each of end of cover 650. One end of locking lid latch 646 is rotatable attached to each cover end. Locking lid latch 646 can be rotated up and down. When locking lid latch 646 is rotated downward and engaged with L-shaped steps 496, the cover 650 is locked to container 402. Magnets 686 are mounted to an interior facing surface of locking lid latch 646 and work with hall effect sensor 680 as described later.

A single or multi-use filter 640 is mounted to the bottom surface 651 of cover 650 over holes 655. Filter 640 is supported by a filter support member 642 that extends the length of filter 640. Filter support member 642 includes an array of apertures 643 and an opposed pair of shoulders 644 that extend away from ends of filter support member 642. A pair of spaced apart C-shaped clips 645 (FIG. 9B) extend away from bottom surface 651. When filter 640 and filter support member 642 are mounted to the bottom side 651 of cover 650, a portion of clips 645 extend over shoulders 644 of filter support member 642 thereby retaining filter 640 to cover 650. Filter 640 covers holes 655. Filter support holds the filter 640 to the cover so that all material entering through holes 655 must pass through the filter.

Filter 640 and filter support member 642 are formed from a flexible material such that filter 640 and filter support member 642 can be bent to allow shoulders 644 to slide under clips 644. Filter 640 is formed from a microbial barrier material that is permeable to sterilant. Filter 640 allows sterilant to pass from the outside of cover 650, through holes 655, through filter 640, apertures 643 and into interior cavity 420 where the sterilant contacts surgical instruments. Filter 640 also forms a microbial barrier preventing microorganisms from entering into container assembly 600 after container assembly 600 has been processed through a sterilization process.

Cover 650 further includes a housing 630. Housing 630 has a generally rectangular shape with a U-shaped cross section. Housing 630 can be formed from materials such as stamped aluminum or other suitable materials. Housing 630 comprises a bottom wall 631 and side walls 632. Side walls 632 are spaced apart by bottom wall 631 and are oriented perpendicular to bottom wall 631. Flanges 633 extend perpendicularly away from a distal end of each side wall 632. Mounting holes 635 extend through flanges 633 at opposite ends of housing 630. Bottom wall 631 and side walls 632 define a cavity or enclosure 638 within housing 630. An array of holes 634 are defined in bottom wall 631 and side walls 632. Holes 634 allow sterilant to enter and leave cavity 638. Housing 630 is mounted to the inner surface 651 of panel 652 adjacent end 653 and spaced slightly from wall 657 using fasteners 636 such as screws. Fasteners 636 extend through mounting holes 635 and are threaded into inner surface 651.

An electronic sensor assembly or module 660 is mounted within housing 630 that is retained to cover 650. Electronic sensor module 660 as well as the below described modules 760 and 850 contains components that perform the same general functions as module 560.

With reference to FIG. 9A, electronic sensor module 660 has a rectangular shaped printed circuit board (PCB) 662. PCB 662 contains printed circuit lines (not shown) that electrically connect the components of electronic module 660. PCB 662 is mounted and contained within housing cavity 638. An insulated spacer 618 is mounted over PCB 662 and is located between cover inner surface 651 and PCB 662.

Various electronic components and sensors are mounted to PCB 662 to allow electronic sensor module 660 to monitor operating conditions within container 402. A processor 670, memory 671, humidity or steam sensor 672, pressure sensor 673 and isolated temperature sensor 674 are mounted to a top side of PCB 662. Mounted to a bottom side of PCB 662 is an optical sensor 665 that senses the amount of IR and/or UV light transmitted through an optical path length 666 within cavity 638. In one embodiment, optical sensor 665 detects concentrations of hydrogen peroxide gas ($H_2O_2$).

Optical sensor 665 includes a light source or emitter 667 and a light receiver or detector 668 mounted to the bottom side of PCB 662. Light emitter 667 generates either IR or UV light. Light filters (not shown) can be mounted around emitter 667 or detector 668 to remove any undesired wavelengths.

A rechargeable battery 697 is mounted to the bottom side of PCB 662 and supplies power to the components of electronic module 660 through printed circuit lines (not shown) within PCB 662. Light emitting diodes (LED) 687 such as green, red and yellow LEDS are mounted to one end of PCB 662. LEDS 687 provide visual information to personnel using container assembly 600. LEDS 687 within cover 650 are viewed by a user through window 621.

A hermetic connector 685 is mounted within window 621 and extends between the outside of cover 650 to inside cover 650. Hermetic connector 685 contains several terminals that are electrically connected to PCB 662. Hermetic connector 685 can be connected with an external connector 610 and cable 612 in order to transmit and receive data from container assembly 600. Hermetic connector 685 allows communication with electronic sensor module 660 when container assembly 600 is in a sealed state.

With additional reference to FIG. 9B, Hall effect sensors 680 are mounted to an interior portion of wall 657 at each of ends 653. Hall effect sensors 680 are connected to PCB 662 by wires 681. When cover 650 is placed over container 402, magnets 624 are juxtaposed to Hall effect sensors 680. The Hall effect sensors 680 sense the magnetic field generated by magnets 624 and output an electrical signal to processor 670 indicating the presence of a detected magnetic field. When cover 650 is removed from container 402, Hall effect sensors 680 sense the absence of a magnetic field and output an electrical signal to processor 670 indicating no detected magnetic field.

During use, a rack or tray 160 (FIG. 2) containing medical/surgical instruments 180 (FIG. 2) in a desired orientation to be sterilized are placed within container 402. Rack 160 is placed and rests on bottom panel 407. After tray 160 is placed within container 402, cover 650 is placed over container 402 and locking lid latches 496 are moved to the locked position over steps 646, locking the cover 650 to container 402. External connector 610 and cable 612 are attached to hermetic connector 685 and memory 671 is loaded with validated sterilization process measurement (VSPM). After programming, container assembly 600 is ready for processing through a sterilization process cycle.

VII. Sixth Container Embodiment

Figure 10:
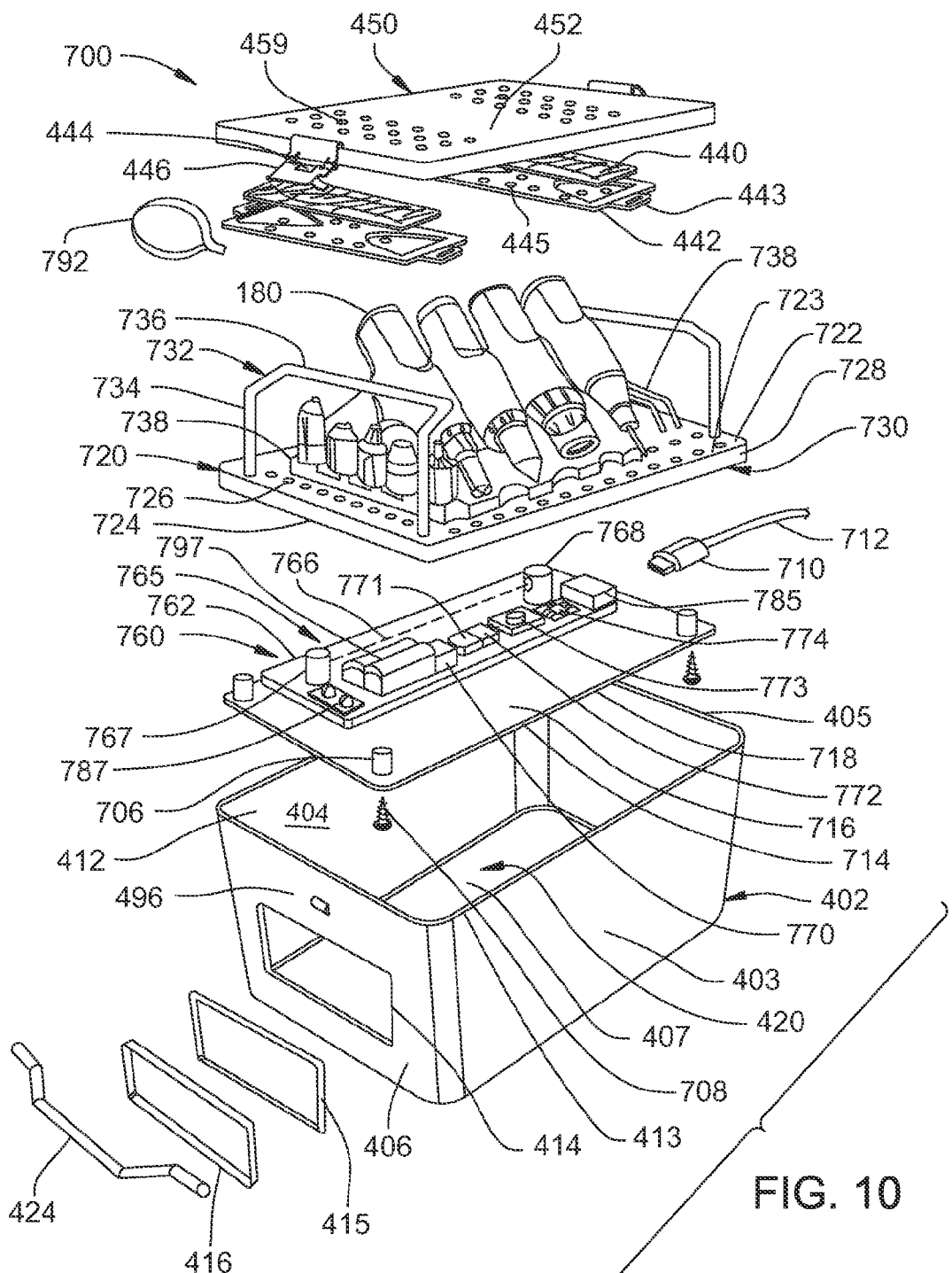
FIG. 10 is an exploded top perspective view of one more container for sterilization of medical/surgical instruments having sensors mounted to a tray or rack in accordance with one embodiment.

Referring to FIG. 10, a container assembly 700 of a sixth embodiment of the present invention is shown. Container assembly 700 comprises a container 402. Container 402, filters 440 and cover 450 of FIG. 10 are the same as the previously described container 402, filters 440 and cover 450 of FIG. 7A except that opening 418 has been omitted from container 402.

Container assembly 700 includes a rack or tray 720 that contains an electronic sensor assembly or module 760. Tray 720 can be formed from suitable materials such as stainless steel or aluminum. Tray 720 comprises a generally planar rectangular shaped base 722 that is perforated with an array of holes 726. Base 722 has an upper surface 723 and a bottom surface 724. A peripheral flange 728 extends perpendicularly downward from the edges of base 722 and encircles base 722. Flange 728 and base 722 define a cavity 730 under base 722. Holes 726 allow sterilant to enter and leave cavity 730.

Tray 720 is used to hold medical/surgical instruments 180 within container 402 during sterile processing. Tray 720 includes a pair of spaced apart handles 732 that are mounted to opposite ends of base 722. Handles 732 allow a user to grasp and lift tray 720. Handles 732 include a pair of vertical rods 734 attached to base 722 and a horizontal grasping bar 736 that extends between rods 734.

Several support members 738 are mounted to and extend upwardly from base 722. Medical/surgical instruments 180 rest on and are supported by support members 738. Support members 738 are dimensioned and shaped so that medical/surgical instruments 180 are held and retained in a preferred orientation for sterile processing. It is important for some medical/surgical instruments 180 to be oriented in certain geometric orientations during sterile processing such that sterilant can readily enter and exit from the surgical instruments.

A bottom plate 714 is mounted to the bottom surface 724 of base 722 enclosing cavity 730. Plate 714 has a top surface 716 and a bottom surface 718. Four spacers or standoffs 706 are located at the corners of plate 714. Spacers 706 position plate 714 a fixed distance from base 722. Fasteners 708 such as screws extend through the corners of plate 714, spacers 706 and are threaded into base 722 thereby retaining plate 714 to base 722.

An electronic sensor module 760 is mounted within cavity 730. More specifically, module 760 is mounted to the top side 716 of plate 714.

Electronic sensor module 760 has a rectangular shaped printed circuit board (PCB) 762. PCB 762 contains printed circuit lines (not shown) that electrically connect the components of electronic module 760. PCB 762 is mounted to side 716 of plate 714.

Various electronic components and sensors are mounted to PCB 762 to allow electronic module 760 to monitor operating conditions within container 402. A processor 770, memory 771 humidity or steam sensor 772, pressure sensor 773 and isolated temperature sensor 774 are mounted to a top side of PCB 762.

Also, mounted to the top side of PCB 762 is an optical sensor 765 that senses the amount of IR and/or UV light transmitted through an optical path length 766 within cavity 730. In one embodiment, optical sensor 765 detects concentrations of hydrogen peroxide gas ($H_2O_2$).

Optical sensor 765 includes a light source or emitter 767 and a light receiver or detector 768 mounted to the top side of PCB 762. Light source 767 generates IR or UV light. Light filters (not shown) can be mounted around detector 768 to remove any undesired wavelengths.

A replaceable or rechargeable battery 797 is mounted to the top side of PCB 762 and supplies power to the components of electronic module 760 through printed circuit lines (not shown) within PCB 762. Light emitting diodes (LEDS) 787 such as green, red and yellow LEDS are mounted to one end of PCB 762. LEDS 787 provide visual information to personnel using container assembly 700. When tray 720 is located within container 402, LEDS 787 are visible by a user through transparent panel 416.

A connector 785 is mounted to the other end of PCB 762. Connector 785 can be attached to an external connector 710 and cable 712 in order to transmit and receive data from electronic module 760. Connector 785 is used to load memory 771 with a validated sterilization process measurement (VSPM).

Tray 720 is programmed with VSPM. External connector 710 is attached to connector 785. The VSPM are downloaded to memory 771 from an external source. Because each tray 720 is designed to accommodate specific medical/surgical instruments 180, tray 720 only needs to be programmed with VSPM once. VSPM are stored within memory 771 for use during subsequent sterilization processing cycles.

Tray 720 containing medical/surgical instruments 180 in a desired orientation to be sterilized are placed within container 402. Tray 720 is placed and rests on bottom panel 407. After tray 720 is placed within container 402, cover 450 is placed over container 402 and locking lid latches 446 are moved to the locked position over steps 496, locking and sealing the cover 450 to container 402.

A lockout tag or breakable seal 792 is attached between locking lid latch 496 and steps 446. Ends of tag 792 extend through an opening 444 in steps 446 and through latch 496 and are mated to form a continuous loop. Tag 792 indicates to a user if any tampering has occurred within container assembly 700 or if the sterile barrier within container assembly 700 has been compromised after sterile processing. Tag 792 is only useable once and is cut in order to gain access to the contents of container assembly 700. After lockout tag 792 is attached, container assembly 700 is ready for processing through a sterilization process cycle.

VIII. Seventh Container Embodiment

Figure 11A:
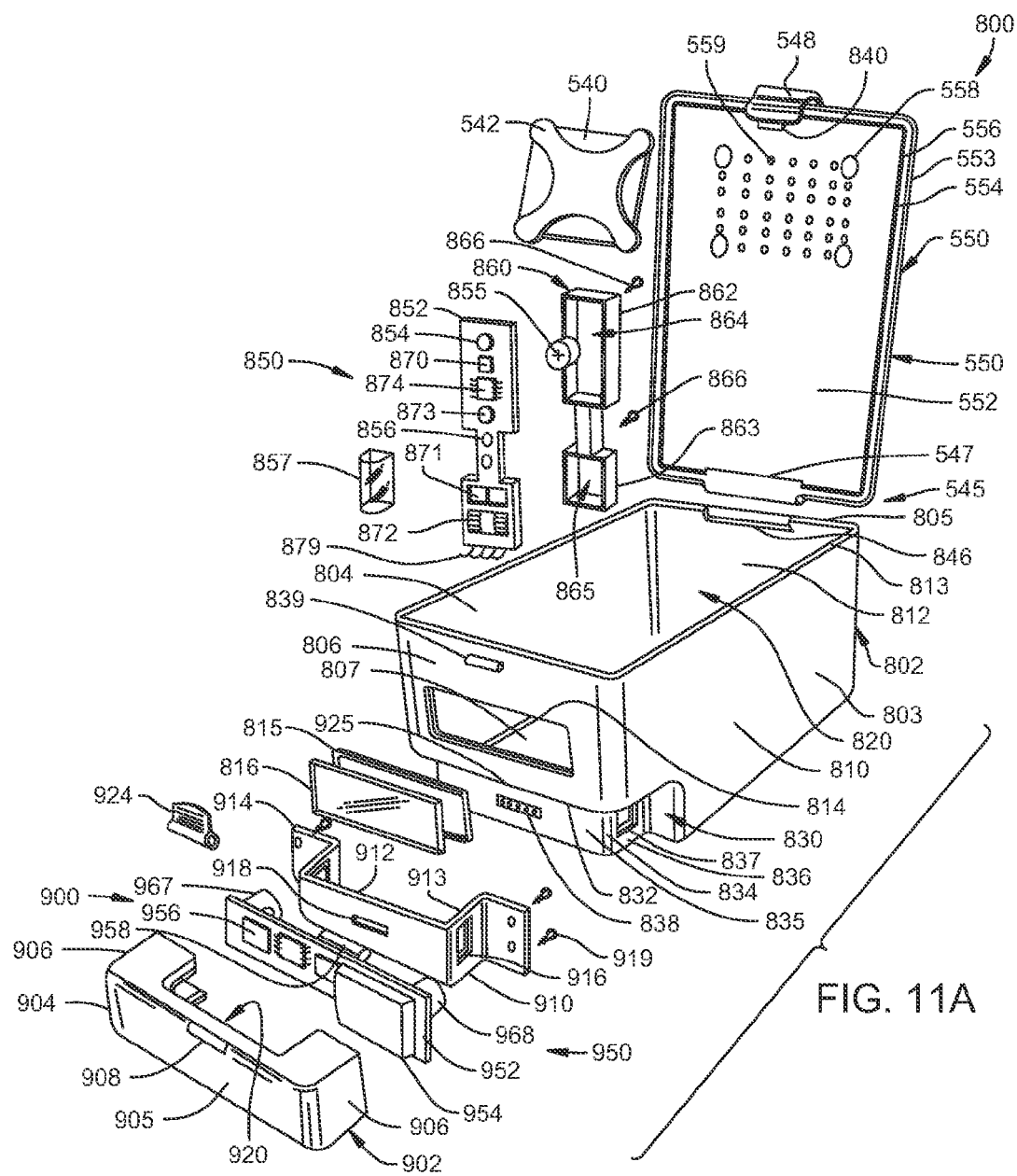
FIG. 11A is an exploded top perspective view of one more container for sterilization of medical/surgical instruments having a removable optical sensor module in accordance with one embodiment.

Referring to FIG. 11A, a container assembly 800 of a seventh embodiment of the present invention is shown. Container assembly 800 comprises a container 802 that is generally rectangular in shape and is defined by a planar front panel 803, an opposed planar rear panel 804 and a pair of opposed spaced apart planar side panels 805 and 806. Panels 803 and 804 are oriented orthogonal to panels 805 and 806. A planar bottom panel 807 is mounted perpendicular to panels 803, 804, 805 and 806 and forms the bottom of container 802. An interior cavity 820 is defined within container 802. Container 802 has outer surfaces 810 and inner surfaces 812. An upper peripheral rim 813 is defined by the upper edges of panels 803-806. Container 802 can be formed from materials such as stamped aluminum or other suitable materials.

Side panel 806 has an opening 814 that is covered by a panel 816 that is transparent to visible light but is opaque to IR and UV light frequencies. Panel 816 prevents IR and UV light from entering into interior cavity 820. Transparent panel 816 allows a user to visually see contents within container 802. An elastomeric gasket 815 seals panel 816 to the outside surface of side panel 806. Gasket 815 and panel 816 are attached to side panel 806 using an adhesive.

Container 802 further includes a generally U-shaped cutout 830 that is located at the bottom of side panel 806 below opening 814. Cutout 830 is defined by a horizontal shelf 832 that extends perpendicularly from side panel 806 into cavity 820 and a U-shaped wall 834 that extends perpendicularly downward from shelf 832 and terminates at bottom panel 807. U-shaped wall 834 has a center section 835 and two diametrically opposed outer sections 836.

Diametrically opposed windows 837 are defined in each of outer sections 836. Windows 837 are separated from each other by a portion of interior cavity 820. Windows 837 are formed from a transparent material such as plastic and are attached to outer sections 836 by an adhesive.

A hermetic connector 838 is mounted toward the center of center section 835. Hermetic connector 838 contains several terminals that extend through side panel 838 into interior cavity 820. Hermetic connector 838 allows communication with electronic components within container 802. A latch lock receiver 839 is mounted toward the center of side panel 806 below rim 813.

Cover 550 is generally the same as previously described in FIG. 8, except that a magnet 840 has been added to an interior face of pivoting latch lock 548. Holes 559 allow sterilant to enter and leave container 802 during sterilization processing. Gasket 556 forms a seal between cover 550 and container 802. Disposable filter 540 is mounted over holes 559. Filter 540 is supported by a filter support member 542. Filter support member is retained to panel 552 by retainer clips 558. Filter 540 covers holes 559.

Support member 542 and retainer clips 558 compress filter 540 against the bottom side of panel 552 over holes 559. Filter 540 is formed from a microbial barrier material that is permeable to sterilant. Filter 540 allows sterilant to pass from the outside of cover 550 through holes 559, through filter 540 and into interior cavity 820 where the sterilant can contact surgical instruments. Filter 540 also forms a microbial barrier preventing microorganisms from entering into container assembly 800 after container assembly 800 has been processed through a sterilization process.

Container assembly 800 further comprises a lift off hinge 545. Lift off hinge 545 has a C-shaped flange 846 extending from rim 813 of side panel 805 and another C-shaped flange 547 extending from one end of cover 550. Flanges 846 and 547 mate with each other to form hinge 545. Flanges 846 and 547 are dimensioned such that when cover 550 is rotated with flanges 846 and 547 in engagement with each other toward a closed position, one end of cover 550 is retained to container 802.

A pivoting latch lock 548 is mounted to the other end of cover 550. Latch lock 548 can be rotated by a user downwardly to a position where latch lock 548 mates with latch lock receiver 839 as shown in FIG. 11C. When latch lock 548 is fully engaged with latch lock receiver 839, cover 550 is sealingly locked to container 802. Cover 550 is removed from container 802 by unlatching latch lock 548 from latch lock receiver 839.

A fixed sensor module 850 is mounted within container 502. The electronic components of fixed sensor module 850 use a relatively low amount of power.

Fixed sensor module 850 has a rectangular shaped printed circuit board (PCB) 852. PCB 852 contains printed circuit lines (not shown) that electrically connect the components of electronic sensor module 850. A Hall effect sensor 854, processor 870, memory 871, humidity or steam sensor 872, pressure sensor 873 and isolated temperature sensor 874 are mounted to a front side of PCB 852.

A replaceable and/or rechargeable battery 855 is mounted to a rear side of PCB 852. In one embodiment, because the components mounted to PCB 852 consume a relatively small amount of power, battery 855 is watch battery. Battery 855 supplies power to the components of electronic sensor module 850.

Light emitting diodes (LEDS) 856 such as green, red and yellow LEDS are mounted to the front side of PCB 852. A transparent cover 857 is mounted to PCB 852 over LEDS 856. LEDS 856 within container 802 are viewed by a user through cover 857 and transparent panel 816. LEDS 856 provide visual information to personnel using container assembly 800.

PCB 852 is mounted and contained within an enclosure 860. Enclosure 860 is formed from an electrically insulating material such as plastic. Enclosure 860 has two generally rectangular shaped sections, an upper section 862 and a lower section 863. Upper section 862 defines a receptacle 864 and lower section 863 defines a receptacle 865. PCB 852 is mounted to enclosure 860 such that end sections of PCB 852 are contained within receptacles 864 and 865.

Enclosure 860 with PCB 852 is mounted within interior cavity 820. Enclosure 860 rests on shelf 832 and is attached to the interior surface 812 of panel 806. Fasteners 866 such as screws attach enclosure 860 to interior surface 512. PCB 852 is further attached to and in communication with hermetic connector 838 via terminals 879 that extend from PCB 852 and connect with hermetic connector 838.

A removable optical sensor assembly or module 900 is connectable and removable from container 502. Removable optical sensor module 900 contains electronic components that consume relatively larger amounts of power than the electronic components of fixed sensor module 850. The electronic components used in removable optical sensor module 900 are also higher in cost than the electronic components used in fixed sensor module 850. Removable optical sensor module 900 measures one or more characteristics of the environment within container 802 during sterilization processing.

Figure 11B:
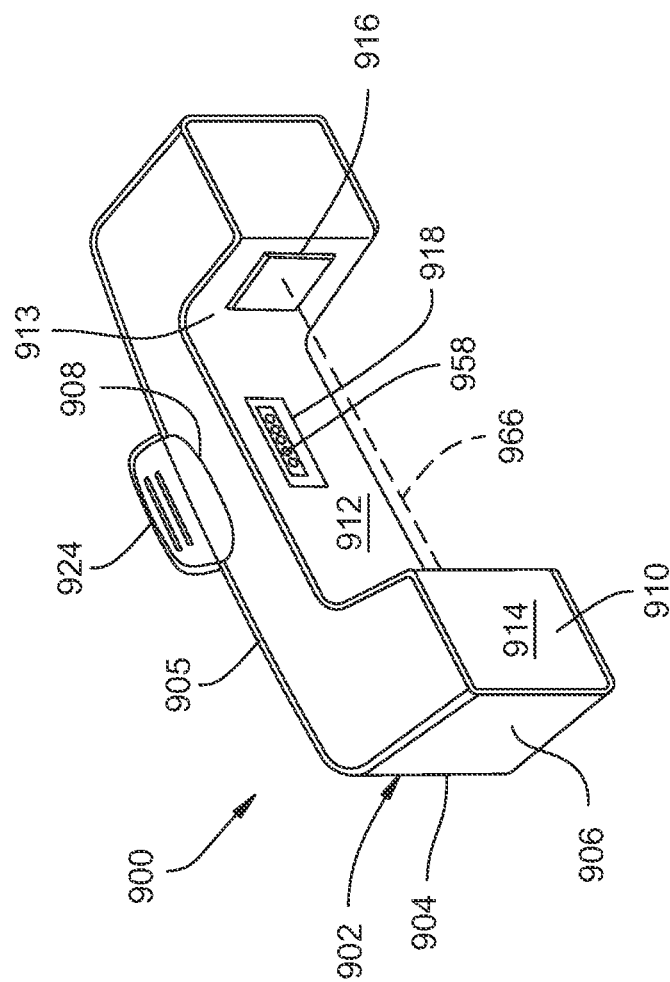
FIG. 11B is an assembled top perspective view of the removable optical sensor module of FIG. 11A.

With reference to FIGS. 11A, 11B and 11C removable optical sensor module 900 comprises a generally U-shaped housing 902 and at least one optical sensor 950. Housing 902 is formed from an electrically insulating material such as plastic. Housing 902 includes a generally U-shaped outer wall 904 and a U-shaped inner wall 910. A hollow cavity 920 is defined between outer wall 904 and inner wall 910. Outer wall 904 has a center section 905 and end sections 906 that extend perpendicularly away from opposite ends of center section 905. A rectangular shaped opening 908 is defined toward the top of center section 905.

Inner wall 910 has a center section 912 and end sections 913 that extend perpendicularly away from opposite ends of center section 912. A step 914 extends perpendicularly away from a distal end of each end section 913. Steps 914 are parallel to center section 912. A rectangular shaped transparent window 916 is located in each of outer sections 913. Windows 916 are diametrically opposed to each other. A connector passage 918 is defined in center section 912. Connector passage 918 allows a connector attached to sensor 950 to extend through passage 918. Fasteners 919 such as screws are used to retain inner wall 910 to outer wall 904.

Optical sensor module 900 is mounted in and received by cutout 830 of container 802 as shown in FIG. 11C. A retaining clip 924 is mounted in opening 908. When optical sensor module 900 is placed and slid in a horizontal direction into cutout 830, retaining clip 924 engages and mates with a retaining tab 925 on container 802. Retaining tab 925 extends downwardly from the bottom of shelf 832 towards cutout 830. Retaining clip 924 and tab 925 retain optical sensor module 900 to container 802. Optical sensor module 900 is removed from container 802 by a user pulling retaining clip 924 away from side panel 806 thereby releasing retaining clip 924 from engagement with retaining tab 925. Optical sensor module 900 can then be slid in a horizontal direction away from side panel 806.

Optical sensor 950 is mounted to housing 902 within cavity 920. Optical sensor 950 is mounted between outer wall 904 and inner wall 910. Optical sensor 950 senses the amount of IR or UV light transmitted through an optical path length 966 (FIG. 11B) within container 802. Optical sensor 950 detects concentrations of gases such as hydrogen peroxide gas ($H_2O_2$) or ethylene oxide gas ($C_2H_4O$).

Optical sensor 950 has a printed circuit board (PCB) 952. An IR and/or UV light source or emitter 967 and a light receiver or detector 968 is mounted to one side of PCB 952. Light filters (not shown) can be mounted around light source 968 to remove any undesired wavelengths.

A connector 958 is mounted to one side of PCB 952. Connector 958 extends through connector passage 918 (FIG. 11B). Connector 958 mates with connector 838 of container 802 when housing 902 is inserted into cutout 830 and attached to container 802. When attached, connectors 958 and 838 allow for communication to occur between optical sensor 950 and fixed sensor module 850. In an optional embodiment, optical sensor 950 includes a wireless transceiver that communicates with another wireless transceiver within fixed sensor module 850.

A battery 954 is mounted to a second side of PCB 952 to supply power to the optical sensor 950. Battery 954 is rechargeable through connector 958. Signal conditioning and communication devices 956 are also mounted to a second side of PCB 952. Signal conditioning and communication devices 956 include logic circuits, amplifiers, filters and input/output interfaces to condition and transmit electrical signals between emitter 967, receiver 968 and fixed sensor module 850.

When optical sensor module 900 is attached to container 902, light generated by emitter 967 is transmitted through a first window 916, a second window 837, along optical path length 966 within interior cavity 920, through a third window 837, a fourth window 916 and is received by detector 967. The windows are transparent to the wavelengths/wavelengths of the photonic energy that is transmitted through the windows.

Detector 967 generates an electrical signal that is proportional to the amount of IR or UV light received which is proportional to the concentration of sterilant within container 802. The electrical signal is conditioned by signal conditioning and communication devices 956 and transmitted through connectors 958 and 838 to processor 870 for use in determining the sterility of the contents of container assembly 800.

During use, a rack or tray 160 (FIG. 2) containing medical/surgical instruments 180 (FIG. 2) in a desired orientation to be sterilized are placed within container 802. Rack 160 is placed onto and rests on bottom panel 807.

An external cable and connector (not shown) are attached to connector 838 in order to load memory 871 with validated sterilization process measurement (VSPM). After tray 160 is placed within container 802, cover 550 is placed over container 802, engaging hinge 545 and latch lock 548 is moved into engagement with latch lock receiver 839 to a locked position, locking cover 550 to container 802. Container assembly 800 is now ready for processing through a sterilization cycle.

Removable optical sensor module 900 is attachable and detachable from container 802 and has several advantages. Because removable optical sensor module 900 contains higher cost electronic sensor components that may consume larger amounts of power, it is desirable to recharge and re-use a relatively small number of removable optical sensor modules 900 with a relatively large number of containers 802 that contain fixed sensor modules 850 in order to reduce the overall cost of the sterilization system. Splitting the sterilization sensor electronics into two separate assemblies 850 and 950 allows for the use of a lower number of removable optical sensor modules.

IX. Electronic Sensor Printed Circuit Boards

Figure 12A:
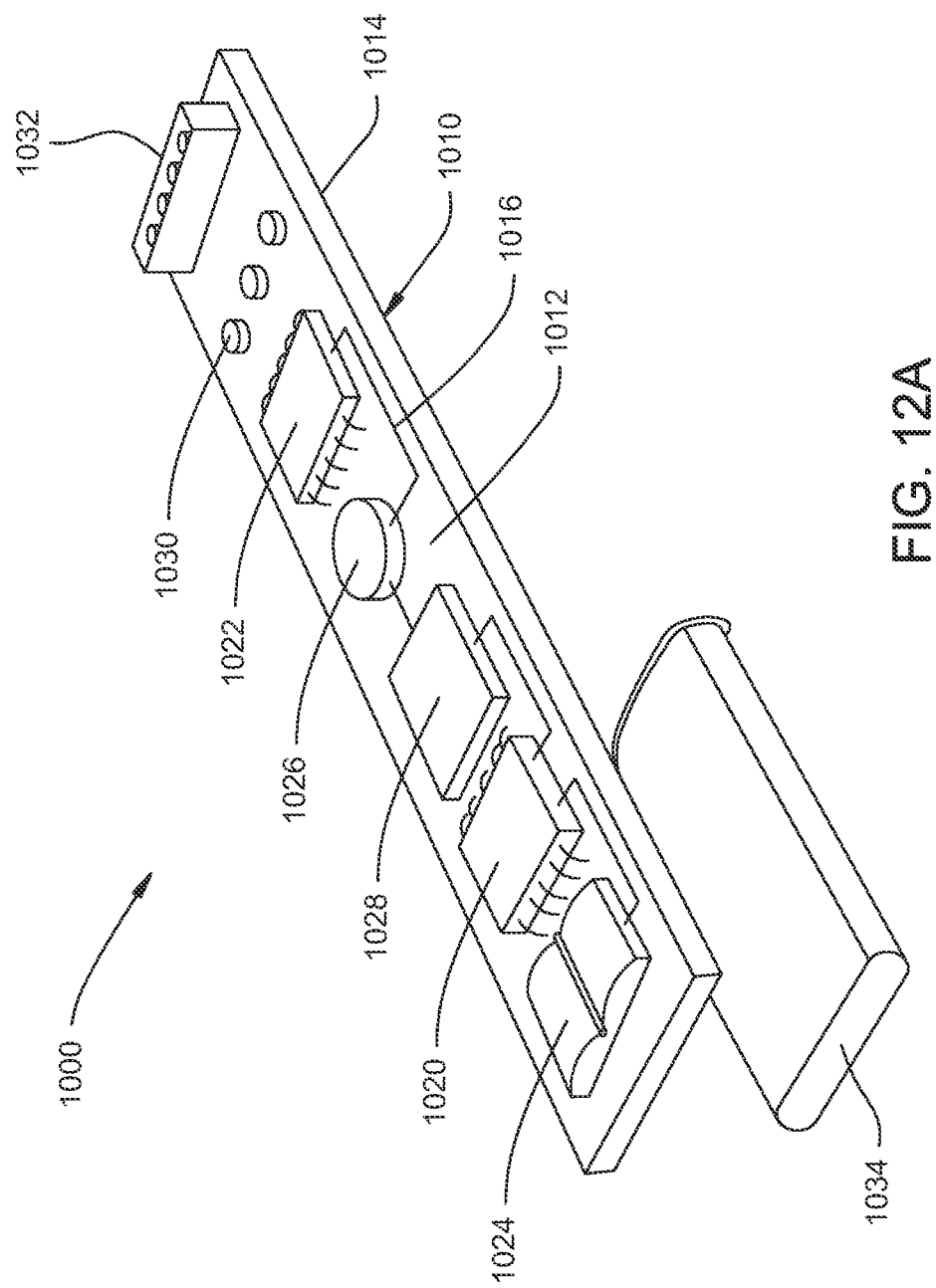
FIG. 12A is a top perspective view of a sensor printed circuit board for sensing steam concentration and other characteristics of the environment in the container in accordance with one embodiment.
Figure 12B:
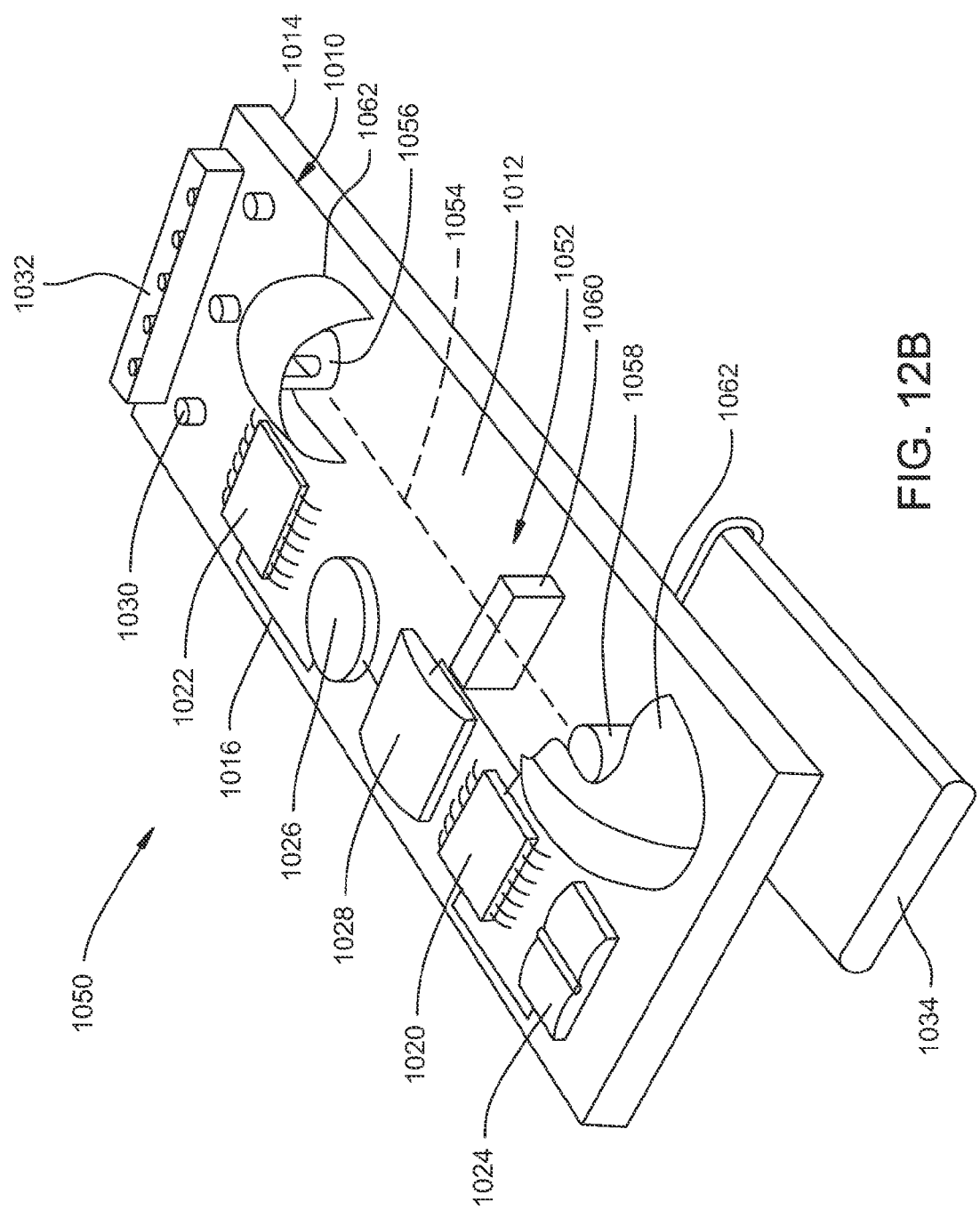
FIG. 12B is a top perspective view of another sensor printed circuit board for sensing hydrogen peroxide concentration and other environmental characteristics in accordance with one embodiment.

FIGS. 12A, 12B and 12C, illustrate further details of the design of sensor modules, 200, 460, 560, 660 and 760. With specific reference to FIG. 12A, a steam sensing module 1000 is shown. Steam sensing module is specialized for monitoring and recording steam sterilization process measurements. Steam sensing module 1000 comprises a generally rectangular shaped multi-layer printed circuit board (PCB) 1010 that has a top side 1012 and a bottom side 1014. Printed circuit lines 1016 are patterned on each side and layer of PCB 1010 in order to electrically connect the components of steam sensing module 1000.

A processor 1020 and memory 1022 are mounted to top side 1012. A humidity or water vapor sensor 1024 is mounted to top side 1012. Humidity or water vapor sensor 1024 can be a hygrometer type humidity sensor or a capacitive humidity sensor. Humidity sensor 1024 outputs an electrical signal (voltage) that is proportional to the concentration of water vapor surrounding steam sensing module 1000. In another embodiment, water vapor sensor is a optical sensor with an emitter and detector that operates at a specific wavelength to monitor and read the water vapor concentration surrounding the optical sensor. Water vapor optical sensor operation is not described in detail here, but operates at a different wavelength as the optical sensor 1052 for Hydrogen Peroxide vapor as describe later.

Pressure sensor 1026 is mounted to top side 1012. Pressure sensor 1026 can be a semi-conductor piezoresistive strain gauge that uses the piezoresistive effect of bonded or formed strain gauges to detect strain due to applied pressure. Pressure sensor 1026 uses strain gauges connected to form a Wheatstone bridge circuit that maximizes the electrical output and reduces sensitivity to errors. Pressure sensor 1026 measures a absolute pressure in atmospheres (atm) or bars. Pressure sensor 1026 outputs an electrical signal (voltage) that is proportional to the absolute pressure surrounding steam sensing module 1000.

Temperature sensor 1028 is mounted to top side 1012. The structure of temperature sensor 1028 is not part of the present invention. Temperature sensor 1028 outputs an electrical signal (typically a voltage) that is proportional to the temperature surrounding steam sensor module 1000. Temperature sensor 1028 is mounted and located in an isolated manner such that thermal characteristics of the mounting method maximizes the ability of the sensor to measure the temperature of the environment with minimal interference from the mount and mounting location.

Light emitting diodes (LEDS) 1030 such as green, red and yellow LEDS are mounted to top side 1012. A connector 1032 is mounted to top side 1012. Connector 1032 is used to connect to an external connector and cable in order for processor 1020 to transmit and receive data from external systems and devices. A replaceable and/or rechargeable battery or battery pack 1034 is mounted to bottom side 1014. Battery 1034 supplies power to the components of steam sensing module 1000. Processor 1020 and memory 1022 are in communication with each other. Processor 1020 is further in communication with each of sensors 1024, 1026, 1028, LEDS 1030, connector 1032 and battery 1034.

Turning to FIG. 12B, a hydrogen peroxide sensing module 1050 is shown. Hydrogen peroxide sensing module 1050 is used when hydrogen peroxide is used to sterilize the instruments. Hydrogen peroxide sensing module 1050 contains the same sensors and components previously described for steam sensing module 1000. In addition, hydrogen peroxide sensing module 1050 further includes one or more optical sensor 1052 that senses the amount of IR and/or UV light transmitted through an optical path length 1054.

The one or more optical sensor 1052 includes an IR or UV light source or emitter 1056. The emitter 1056 may be a bulb or an LED. Sensor 1052 also includes a detector 1058 capable of output a signal proportional to the intensity of the wavelength of light emitted by emitter 1055. The sensor 1052 is mounted to top side 1012. Light filter 1060 is mounted towards detector 1058 to remove any undesired wavelengths. Semi-circular light concentrators 1062 are mounted to top side 1012. One light concentrator 1062 is positioned around emitter 1054 and another light concentrator 1062 is positioned around detector 1058. Light concentrators 1062 reflect light rays that are not coaxial to detector 1058. Light concentrators 1062 are formed from a material that efficiently reflects emitter 1054 energy towards detector 1058 such as polished stainless steel. Processor 1020 is further in communication with emitter 1056 and detector 1058.

Optical sensor 1052 is configured to detect hydrogen peroxide ($H_2O_2$) vapor. Because hydrogen peroxide vapor absorbs infrared light at a wavelength of 2.93 microns and UV light at a wavelength of 240 nanometers, the amount of light transmitted through a known path length (1054) of hydrogen peroxide vapor is proportional to the concentration of the hydrogen peroxide vapor. A higher concentration of hydrogen peroxide gas results in less light reaching detector 1058. A lower concentration of hydrogen peroxide gas results in more light reaching detector 1058. In one embodiment, optical sensor is capable to measure the concentration of hydrogen peroxide from 0.05 mg/l up to 25 mg/L concentration typically used for sterilization.

The transmittance of light through a gas is described by the Beer-Lambert law. The Beer-Lambert law states that there is a logarithmic dependence between the transmission T, of light through a substance and the product of the absorption coefficient of the substance, α, and the distance the light travels through the material (i.e., the path length), l. The absorption coefficient can, in turn, be written as a product of either a molar absorptive (extinction coefficient) of the absorber, ε, and the molar concentration c of absorbing species in the material, or an absorption cross section, σ, and the (number) density N of absorbers. For hydrogen peroxide gas, $$T = \frac{I}{I_0} = e^{-\alpha' l} = e^{-\sigma l N}$$

where $I_0$ and I are, respectively, the intensity of the light transmitted in the absence of the light absorbing gas and the transmitted light, respectively; σ is the hydrogen peroxide molar absorption coefficient and N is the hydrogen peroxide concentration. Light detector 1058 outputs an electrical signal (voltage) that is proportional to the concentration of hydrogen peroxide gas surrounding hydrogen peroxide sensing module 1050.

FIG. 12C illustrates another embodiment of a hydrogen peroxide sensing module 1080. Hydrogen peroxide sensing module 1080 contains the same sensors and components previously described for hydrogen peroxide sensing module 1050 except light concentrators 1062 have been replaced with a different type of light concentrator. An oval shaped light concentrator assembly 1082 is mounted to the top side 1012 of PCB 1010.

Light concentrator assembly 1082 includes a pair of arc or U-shaped light concentrators 1084 and a pair of elongated parallel light shields 1086. One light concentrator 1084 surrounds emitter 1056 and another light concentrator 1084 surrounds detector 1058. Light shields 1086 extend between light concentrators 1084 and are parallel to and spaced apart from light path 1054. An array of holes 1088 are defined in light shields 1086. Holes 1088 allow hydrogen peroxide gas to circulate along light path 1054. Light concentrators 1084 and light shields 1086 are formed from a material that is reflective of emitter energy such as polished stainless steel. In one embodiment, one sensor module combines sensors and electronic components from both steam sensor module 1000 and hydrogen peroxide sensor module 1050 so that one sensor module can be used to monitor and record in both steam and hydrogen peroxide sterilization processes. When combining steam sensor module and hydrogen peroxide sensor module into one sensor module, all components and sensors from both sensor module 1000 and 1050 can incorporated into one sensor module system as described above or the redundant components can be eliminated saving cost and reducing the size of the combined sensor module.

X. Electrical Schematic

Figure 13:
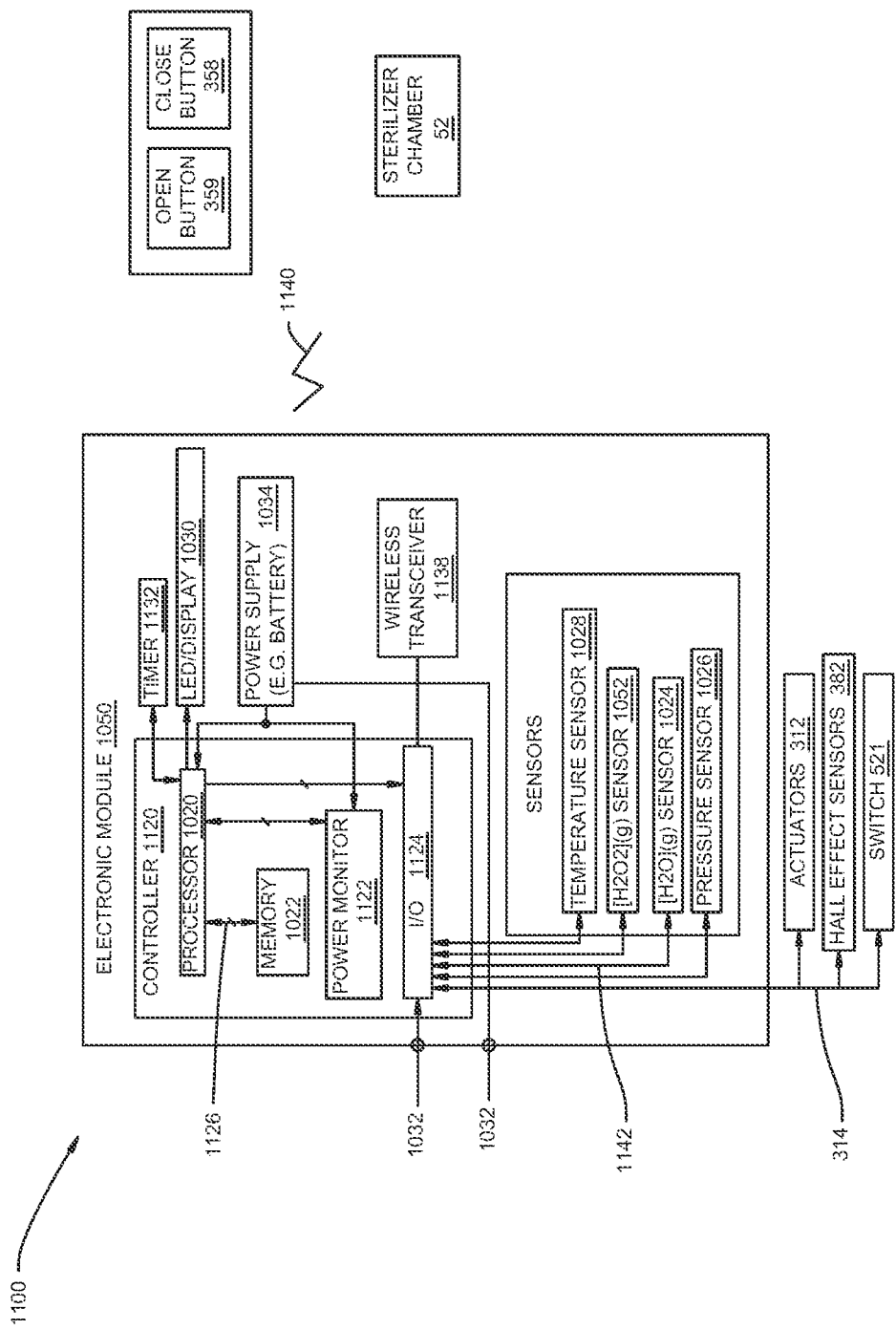
FIG. 13 is an electrical block diagram of the electronic sensor module in accordance with one embodiment.

Turning to FIG. 13, a block diagram 1100 of an example electronic sensor module is shown. The schematic of FIG. 13 is intended to illustrate features of electronic sensor modules, 200, 460, 560, 660, 760, 1000, 1050 and 1080. FIG. 13 will generally be described with reference to electronic sensor module 1050.

Electronic sensor module 1050 includes a controller 1120. Controller 1120 comprises a processor 1020, memory 1022, power monitor 1122 and input/output interface 1124. Processor 1020 is in communication with memory 1022, power monitor 1122 and input/output interface 1124 via one or more communication buses 1126.

Processor 1020 is a suitable microprocessor, field programmable gate array or an application specific integrated circuit. One or more sets of instructions or software are stored on a machine-readable medium or memory 1022 that embodies any one or more of the methods or functions described herein. Memory 1022 is a random access memory (RAM) or a nonvolatile random access memory such as NAND flash memory or any other suitable memory. Processor 1020 can also contain memory that at least partially stores programs within processor 1020 during execution thereof. Memory 1022 stores software or programs that at least partially control the operation of container assemblies 90, 300, 400, 500, 600, 700 and 800.

The term "memory or machine-readable medium" shall also be taken to include any medium that is capable of storing, encoding or carrying out a set of instructions for execution by the processor and that cause the processor to perform any one or more of the methodologies shown in the various embodiments of the present invention. Machine-readable medium or memory shall accordingly be taken to include, but not be limited to, solid-state memories, optical and magnetic media, and carrier wave signals.

Power monitor 1122 regulates and controls the power from power supply 1034. Input/output interface 1124 provides the required timing, signal levels and protocols to allow processor 1020 to communicate with components external to controller 1120.

Electronic sensor module 1050 further includes a timer 1132, LEDS/display 1030, power supply 1034, wireless transceiver 1138 and one or more sensors. Timer 1132 provides clock signals and a real time clock to processor 1020. Timer 1132 may also include additional time information like date and time of day information to processor 1020. LEDS/display 1030 provide visual information to a user. Power supply 1034 supplies power to electronic sensor module 1050. Power supply 1034 is a battery or other suitable power source.

I/O interface 1124 is in communication with connector 1032 and wireless transceiver 1138. Wireless transceiver 1138 includes a wireless transmitter and receiver that can transmit and receive wireless signals 1140 containing data and instructions between electronic sensor module 1050 and other components and devices. In one embodiment, electronic sensor module 1050 is in wireless communication with sterilization chamber 52 (FIG. 1). In another embodiment, electronic sensor module 1050 is in wireless communication with open 359 and close 358 buttons (FIG. 5). In another embodiment, electronic sensor module 1050 is in wireless communication with a docking station as will be described later.

Processor 1020 is further in communication with the sensors of electronic sensor module 1050 through I/O interface 1124. In one embodiment, the sensors are mounted within a common enclosure to electronic sensor module 1050. In another embodiment, the sensors are located remote from electronic sensor module 1050 and are in communication with electronic sensor module 1050 through a signal cable or through wireless communication means.

Humidity or water vapor sensor 1024, pressure sensor 1026, temperature sensor 1028 and hydrogen peroxide gas sensor 1052 are all in communication with I/O interface 1124 via one or more communication busses 1142. Actuators 312 (FIG. 5), Hall effect sensors 382 (FIG. 5) and switch 521

(FIG. 8) are also in communication with I/O interface 1124 via one or more external cables 314 (FIG. 5), 588 (FIG. 8). Processor 1020 via I/O interface 1124 receives data from the sensors that indicate environmental characteristics within a container undergoing sterilization processing.

Figure 14:
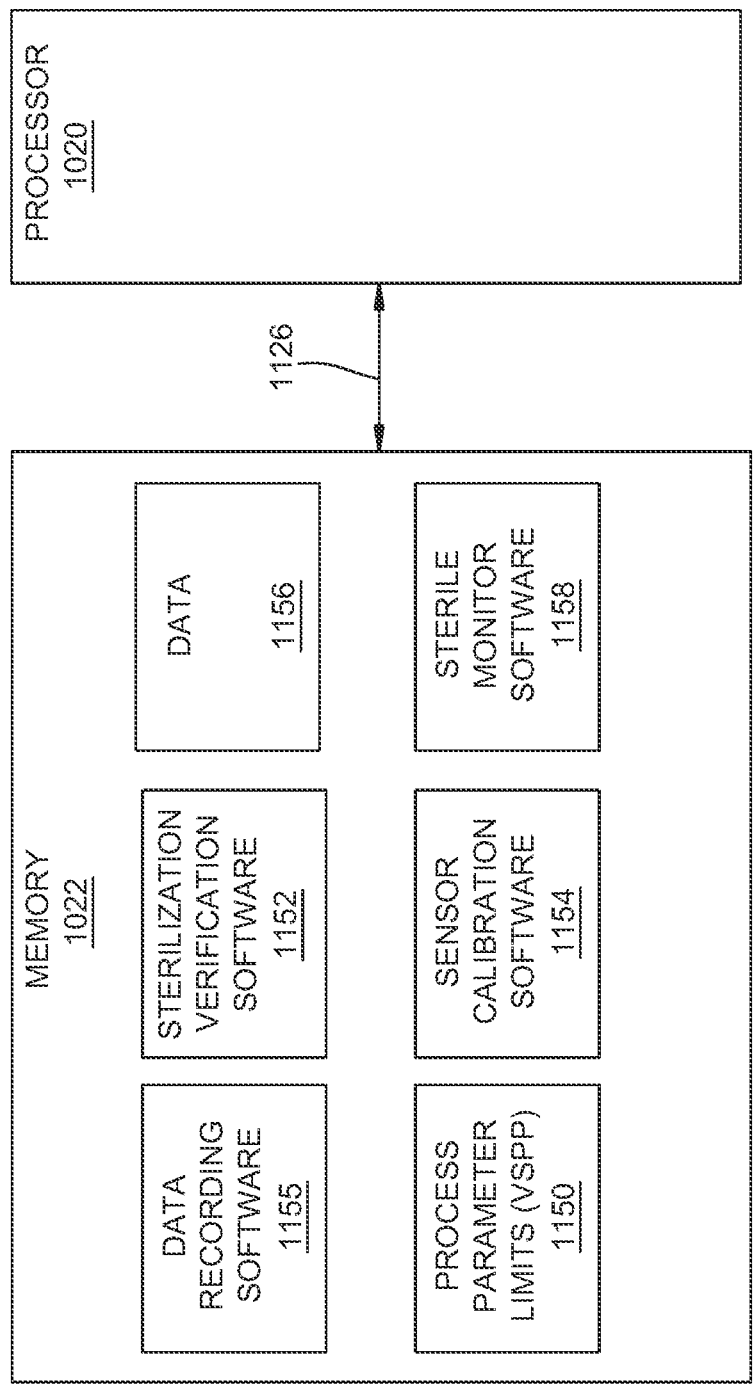
FIG. 14 is a block diagram of software programs or sets of instructions stored by a memory or machine readable medium in accordance with one embodiment.

FIGS. 13 and 14 and the accompanying discussion are intended to provide a general description of an exemplary controller or processor adapted to implement the described embodiments. While embodiments will be described in the general context of instructions residing on memory stored within a controller, those skilled in the art will recognize that embodiments may be implemented in a combination of program modules running in an operating system. Generally, program modules include routines, programs, components, and data structures, which perform particular tasks or implement particular abstract data types.

With reference to FIG. 14, details of the contents of memory 1022 are illustrated. Memory 1022 can store a variety of data, sets of instructions, software, firmware, programs or utilities for execution by processor 1020 and that cause processor 1020 to perform any one or more of the methods herein described. Memory 1022 comprises validated sterilization process measurements (VSPM) 1150, sterilization verification software 1152, sensor calibration software 1154, data recording software 1155, data 1156 and sterile monitor software 1158.

Validated sterilization process measurements (VSPM) 1150, are measurements, minimum values or limits that when met within a container, during a sterilization process, insure sterilization of the equipment load. Sterilization verification software 1152 uses VSPM 1150 to determine if the environment within a container meets the VSPM measurements, minimum values or VSPM limits.

Sensor calibration software 1154 is used during a sensor calibration process to calibrate the sensors. Sensor calibration software 1154 is used to calibrate or verify accuracy of the sensors prior to the sensors being used to monitor the sterilization process measurements within the container. Sensor calibration can be done in conjunction with the docking station 1300 in FIG. 16 or sensor calibration software can be used to calibrate the sensors independent of the docking station 1300.

By way of example, sensor calibration software 1154 calibrates the sensors that measure the environmental characteristic by measuring the extent to which a specific wavelength of light is absorbed. One such sensor is the vaporized hydrogen peroxide sensor. Specifically this calibration is performed when chamber is close to a perfect vacuum, for example approximately 0.2 Torr. At this time there is virtually no gas (vapor) in the chamber. When the chamber, and the container environment is in this state, there is, by no extension essentially no absorption of the emitted light. Data recording software 1155 records the measurement, the signal from the sensor detector when the container is in this state as the signal level indicating that the container is gas free. The subsequent signals representative of the measured gas are compared to this base signal. Based on this comparison and constants developed based on the Beer-Lambert law, the concentration of the measured gas is calculated.

XI. Docking Station

Figure 15:
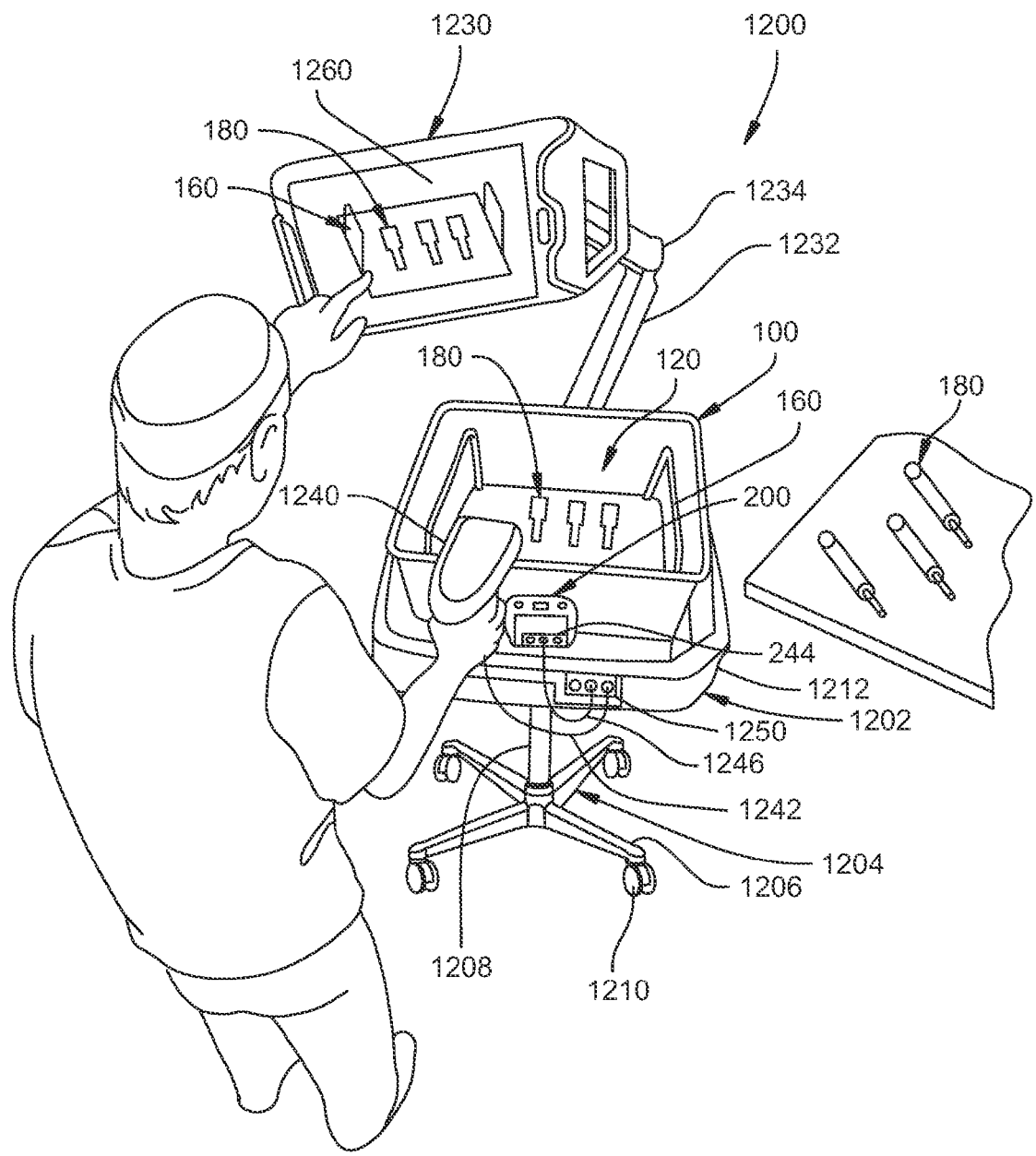
FIG. 15 is a perspective view of a docking station for use with a container in accordance with one embodiment.

FIG. 15 illustrates one embodiment of a docking station 1200 used in conjunction with container assemblies 90, 300, 400, 500, 600, 700 and 800. Docking station 1200 is used during the loading of surgical instruments into the containers and to recharge batteries of container embodiments described herein. With reference to FIG. 15, docking station 1200 comprises a frame 1202 and a display 1230. Frame 1202 includes a base 1204 that has four legs 1206 spaced apart from each other by ninety degrees and a support member 1208. Legs 1206 extend outwardly from the bottom of support member 1208. Wheels 1210 are mounted to the distal ends of legs 1206 to allow docking station 1200 to be moved within a medical facility.

A shelf or container holder 1212 is mounted to the upper end of support member 1208. A container, for example, container 100 of FIG. 2 rests on and is supported by shelf 1212. Display 1230 is mounted to base 1202 by an articulated arm 1232 that has one or more pivoting joints 1234. Arm 1232 can be moved to several different angles and positions by a user by moving and rotating pivoting joints 1234. Arm 1232 allows display 1230 to be positioned for optimal viewing by medical personnel.

Docking station 1200 further includes a handheld reader 1240 and connector plugs 1250. Handheld reader 1240 is in communication with connector plugs 1250 via a cable 1242. Handheld reader 1240 can be either a bar code scanner or an RFID reader. In one embodiment, handheld reader 1240 is a bar code scanner that can scan bar codes 135, 235 (FIG. 3) located on container assemblies 90-800. The bar code reader is also used to read bar codes on the instrument trays or racks 160 and 720 that may be placed in the containers. In another embodiment, handheld reader 1240 is an RFID reader that can read RFID tags 135, 235 (FIG. 3) located on container assemblies 90-800. Handheld reader 1240 transmits scanned data to docking station 1200. Handheld reader 1240 is used to obtain data and information about the containers and/or their contents. This read data can be processed by the docking station to provide information back to the user. For example, the docking station can produce an image of the equipment set and equipment rack to be loaded into the container. The docking station can provide instructions on what to load, what orientation to load and how to complete the sterile barrier of the container.

As discussed above, each instrument tray or rack is designed to hold a specific set of instruments. A set of validated sterilization process measurements are known for the particular rack/tray and associated instruments. The hand held reader retrieves from the tray or rack the data identifying the tray or rack Based on these tray or rack identifying data, the docking station retrieves the VSPM data from the docking station memory. These data are loaded into the sensor module memory for the set of instruments to be sterilized. The read data can also be used with other asset tracking systems and workflow tracking systems within the hospital to track the location and contents of the container assemblies.

Connector plugs 1250 are mounted to a proximal section of shelf 1212. Connector plugs 1250 are used to connect devices to docking station 1200 using cables and connectors. Container 100 with electronic sensor module 200 is connected to docking station 1200 through cable 1246. One end of cable 1246 is connected to connector 244 and the other end of cable 1246 is connected to one plug of connector plugs 1250. Cable 1246 is used to recharge batteries of electronic sensor module 200 and to transmit and receive data between electronic module 200 and docking station 1200. For example, validated sterilization process measurements can be transmitted from docking station 1200 via cable 1246 and stored in electronic sensor module 200. In another embodiment, docking station 1200 can communicate by wireless means with electronic sensor module 200.

Display 1230 is in communication with a controller 1402 (FIG. 17) that is internal to docking station 1230. Display 1230 is a touch screen display such as a liquid crystal, LED or plasma display that allows a user to provide input to the docking station. Other input devices such as a keyboard can be connected to docking station 1200. Controller 1402 can show various pictures or screens 1260 on display 1230. For example, in FIG. 15, screen 1260 displays surgical instruments 180 to be placed by a user into tray 160 of container 100. Screen 1260 illustrates to the user the type of, the name of or number of instruments 180 to be placed on tray 160 and the correct location and orientation of each instrument 180 on tray 160. In FIG. 15, the surgical instruments 180 shown are powered surgical drills or handpieces.

In one embodiment, handheld reader 1240 reads bar codes on surgical instruments 180 to be sterilized. Handheld reader transmits the bar code information via cable 1242 to controller 1402. Controller 1402 can search a database of tray configurations and display a screen 1260 to a user identifying the correct tray 160 to be used with the identified surgical instruments 180 and the number, location and orientation of the identified surgical instruments 180 to be placed in tray 160. The combination of surgical instruments, instrument rack 160 and other items that were validated together comprise the equipment load inside of the sterile barrier. This equipment load is described in FIG. 19 as content ID 1610. The user can populate the tray 160 with the correct surgical instruments 180 in the correct position for sterilization while viewing screen 1260. Screen 1260 assists in preventing the placement of incorrect surgical instruments 180 with an incorrect tray 160. Screen 1260 also assists in preventing a user from incorrectly orientating the surgical instruments 180 in tray 160.

Figure 16:
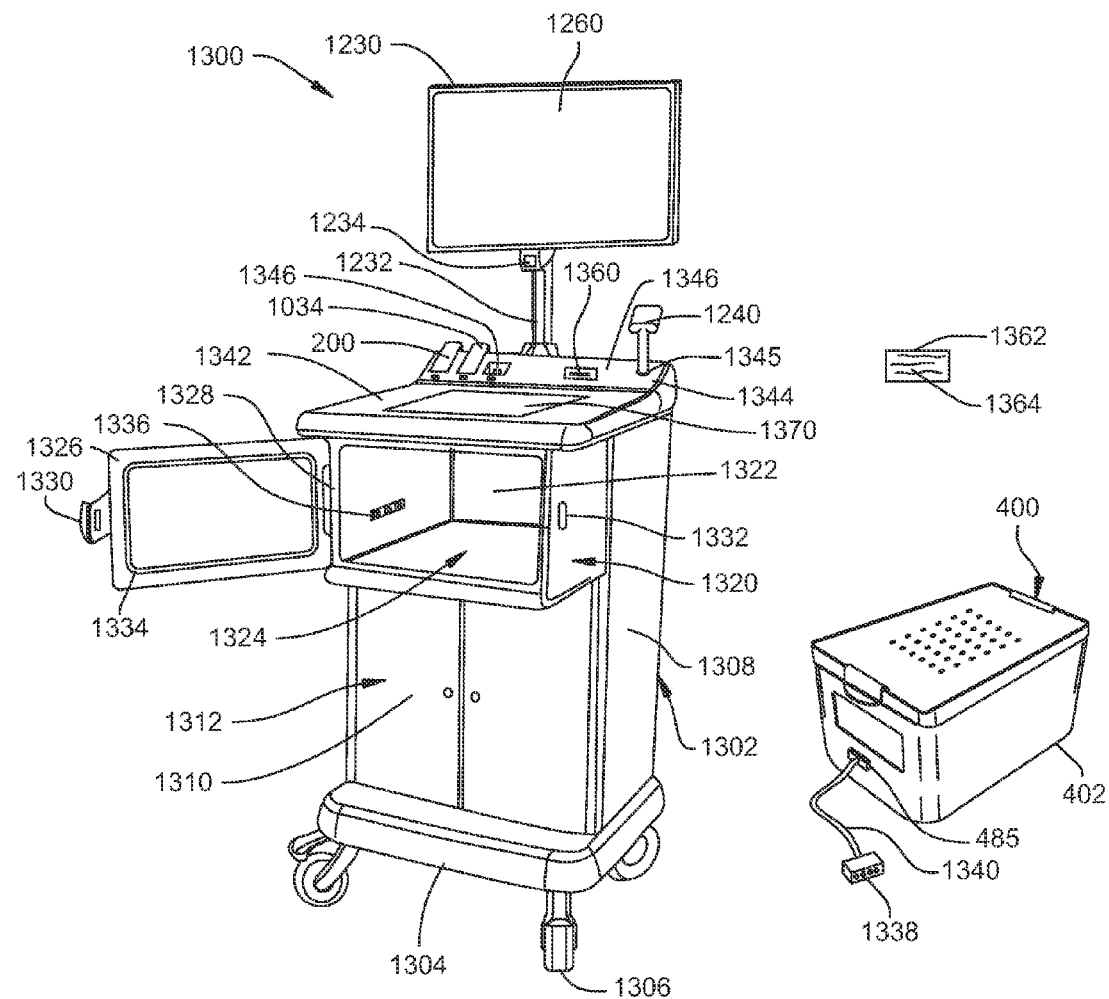
FIG. 16 is a perspective view of another docking station that includes sensor calibration for use with a container in accordance with one embodiment.

Referring to FIG. 16, another embodiment of a docking station 1300 is shown. Docking station 1300 is used in conjunction with container assemblies 90, 300, 400, 500, 600, 700 and 800. Docking station 1300 is used during the loading of surgical instruments into the containers, to calibrate sensors and to recharge batteries. Docking station 1300 comprises a frame 1302 and a display 1230. Frame 1302 includes a generally rectangular base 1304 that has four wheels 1306 mounted to the corners of base 1304.

Panels 1308 cover the sides and rear of frame 1302. A pair of doors 1310 are mounted to the front of frame 1302 allowing access to an interior compartment 1312 of frame 1302. A rectangular shaped calibration chamber 1320 is mounted to the upper half of frame 1302 above doors 1310. Calibration chamber 1320 has a proxil end that extends over doors 1310 and a distal end that abuts rear panel 1308. Calibration chamber 1320 has interior side, top, bottom and rear panels or walls 1322. Panels 1322 define an interior cavity 1324. Calibration chamber 1320 holds a container assembly such as container assembly 400 during a calibration process to calibrate the sensors contained within container assembly 400.

A door 1326 is mounted to the front of calibration chamber 1320 by a hinge 1328. Door 1326 is moved to open and close calibration chamber 1320. Door lock 1330 mates with a lock receptacle 1332 to keep door 1326 in a closed position. An elastomeric gasket 1334 is mounted around a peripheral edge of door 1326 and forms a seal when door 1326 is closed.

A connector 1336 is mounted to a side interior wall 1322. Connector 1336 is mated with a connector mating portion 1338 and cable 1340 when container assembly 400 is placed in interior cavity 1324. The other end of cable 1340 is connectable to connector 485 mounted to container 402. Connectors 485, 1336, 1338 and cable 485 allow docking station 1300 to communicate with electronic sensor module 460 (FIG. 7A) within container 402 during a calibration process. While connector 1336 is shown in FIG. 16 as being connected to container assembly 400, any of container assemblies 90, 400, 500, 600 700 and 800 can be connected to connector 1336 and calibrated using calibration chamber 1320.

A planar shelf 1342 is mounted over the top of calibration chamber 1320 and has an angled portion 1344. A user can place a container on shelf 1342. Handheld reader 1240 is stored in a holder 1345 in angled portion 1344 when not in use.

Several charging receptacles 1346 are mounted to angled portion 1344. Charging receptacles 1346 are shaped to receive electronic sensor modules 200 (FIG. 1) that have been removed from their respective container in order to recharge batteries within electronic sensor module 200. Charging receptacles 1346 are also able to receive removable battery packs such as batteries 1034 (FIG. 12B) for recharging. Charging receptacles 1346 contain terminals (not shown) that are connected to a battery charger internal to docking station 1300.

Display 1230 is mounted to frame 1302 by an articulated arm 1232 that has one or more pivoting joints 1234. Arm 1232 is moved to several different angles and positions by a user by moving and rotating pivoting joints 1234. Arm 1232 allows display 1230 to be positioned for optimal viewing by medical personnel. Display 1230 can show screens 1260 as previously described in conjunction with FIG. 15.

Figure 17:
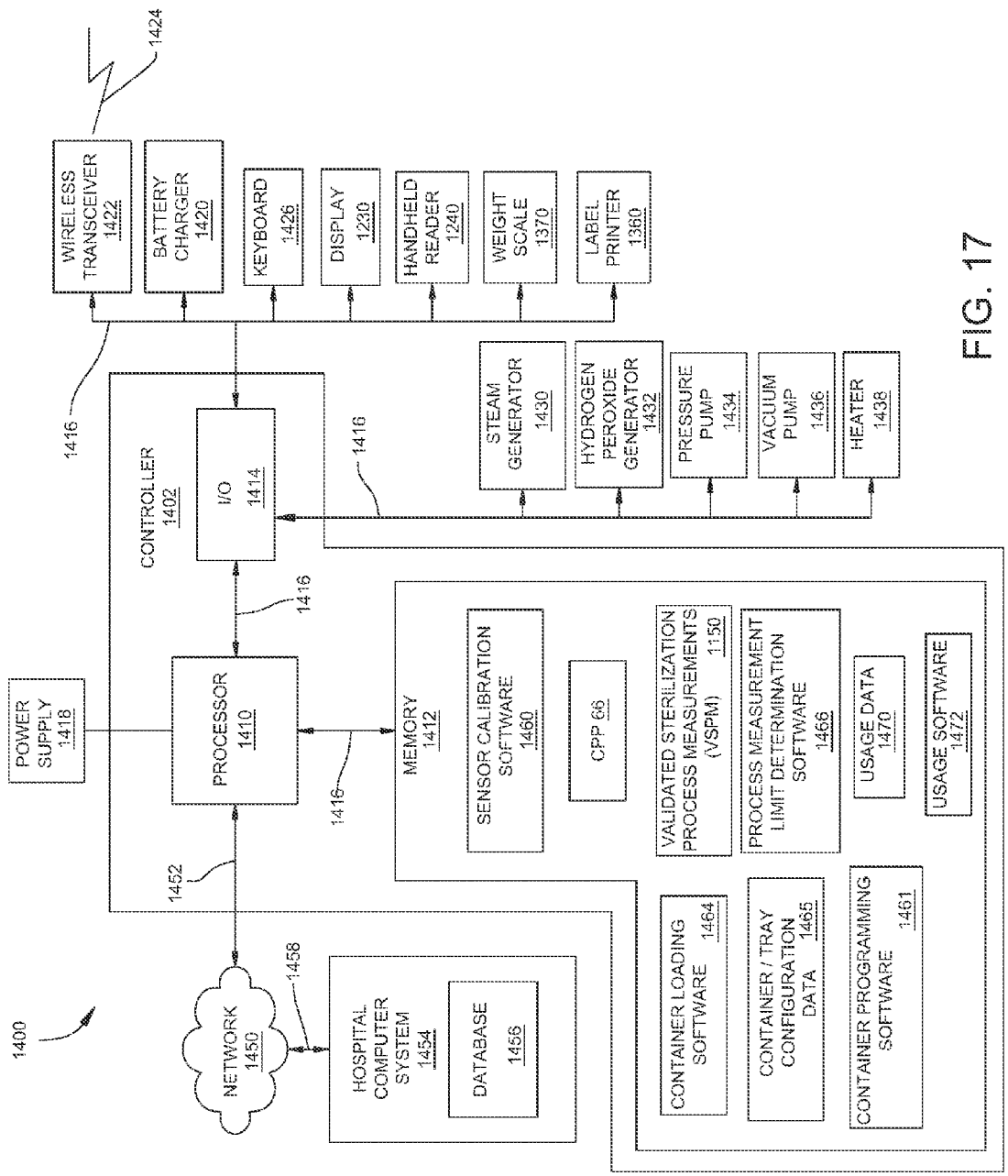
FIG. 17 is a block diagram of the controller of the docking stations of FIGS. 16 and 17.

Turning now to FIG. 17, an electrical block diagram 1400 of docking stations 1200 and/or 1300 is depicted. A docking station controller 1402 controls the operation of docking stations 1200 and 1300. Docking station controller 1402 comprises a processor 1410, memory 1412 and input/output interface 1414. Processor 1410 is in communication with memory 1412 and input/output (I/O) interface 1414 through one or more communication buses 1416. The components of controller 1402 are mounted to a printed circuit board (not shown).

Processor 1410 is a suitable microprocessor, field programmable gate array or an application specific integrated circuit. One or more sets of instructions or software are stored on a machine-readable medium or memory 1412 that embodies any one or more of the methods or functions described herein. Memory 1412 is a random access memory (RAM) or a nonvolatile random access memory such as NAND flash memory or any other suitable memory. Processor 1410 can also contain memory that least partially stores programs within processor 1410 during execution thereof. Memory 1412 stores software or programs that control the operation of docking stations 1200 and 1300.

Power supply 1418 supplies power to the components of controller 1402 and other components of docking stations 1200 and 1300. Power supply 1418 is connected to a utility power source. I/O interface 1414 provides the required timing, signal levels and protocols to communicate with components internal and external to controller 1402.

I/O interface 1414 is in communication with battery charger 1420 and wireless transceiver 1422. Battery charger 1420 is used to recharge the batteries contained within the electronic sensor modules connected to the docking station. Wireless transceiver 1422 includes a wireless transmitter and receiver that can transmit and receive data and instructions via a wireless signal 1424. In one embodiment, docking stations 1200 and/or 1300 communicate with container assemblies 90-800 using wireless signal 1424.

I/O interface 1414 is also in communication with other external components such as a keyboard 1426, display 1230 and handheld reader 1240. Keyboard 1426 is used to input information to docking stations 1200 and 1300. Processor 1410 transmits video display data such as screens 1260 to be shown on display 1230. Handheld reader 1240 transmits data to processor 1410.

I/O interface 1414 is further in communication with several components used during a calibration procedure with docking station 1300. I/O interface is in communication with a steam generator 1430, hydrogen peroxide generator 1432, pressure pump 1434, vacuum pump 1436 and heater 1438 via communication bus 1416. All of the calibration components are mounted within interior compartment 1312 (FIG. 16) below calibration chamber 1320 (FIG. 16).

Steam generator 1430 is connected by piping to calibration chamber 1320. Steam generator 1430 is used to generate a known concentration of steam within calibration chamber 1320 during a calibration procedure. Hydrogen peroxide generator 1432 is connected by piping to calibration chamber 1320. Hydrogen peroxide generator 1432 is used to generate a known concentration of hydrogen peroxide within calibration chamber 1320 during a calibration procedure. Pressure pump 1434 is connected by piping to calibration chamber 1320. Pressure pump 1434 is used to generate a known pressure level within calibration chamber 1320 during a calibration procedure.

Vacuum pump 1436 is connected by piping to calibration chamber 1320. Vacuum pump 1436 is used to generate a known vacuum level within calibration chamber 1320 during a calibration procedure. Heaters 1438 are mounted to the outer surfaces of interior walls 1322 (FIG. 16) of calibration chamber 1320. Heaters 1438 are used to generate a known temperature within calibration chamber 1320 during a calibration procedure. Processor 1410 controls the operation of steam generator 1430, hydrogen peroxide generator 1432, pressure pump 1434, vacuum pump 1436 and heater 1438 during a calibration procedure.

Processor 1410 is in communication with a network 1450 via a network communication fabric 1452. In one embodiment, network 1450 is in communication with a medical facility or hospital data processing system or computer system 1454 via network communication fabric 1458. Docking stations 1200 and 1300 can transmit and receive information from computer system 1454. For example, hospital computer system 1454 can maintain a database 1456 of surgical instruments and tools used within the medical facility. Docking stations 1200 and 1300 can transmit information regarding the number and type of sterile or non-sterile surgical instruments contained in a container to hospital computer system 1454 in order to update database 1456. Data transmitted and received between the various computer systems and data sources may be encrypted for security purposes to prevent unauthorized access or tampering.

Memory 1412 can store a variety of data, sets of instructions, software, programs or utilities for execution by processor 1410 and that cause processor 1410 to perform any one or more of the methods herein described. Items stored in memory 1412 may be encrypted prior to storage for security purposes.

Memory 1412 comprises nominal chamber processing parameters (CPP) 66, sensor calibration software 1460, container programming software 1461, container loading software 1464, container configuration data 1465, equipment load data, validated sterilization process measurements (VSPM) 1150, process measurement limit determination software 1466, usage data 1470 and usage software 1472.

CPP 66 are the nominal processing settings used by health care workers to program CPP 66 to the nominal sterilization process for sterilization chamber 52 to control the sterilization process cycle. Sensor calibration software 1460 is used by docking station 1300 during the calibration of the sensors associated with a respective container. Sensor calibration software 1460 at least partially controls the operation of steam generator 1430, hydrogen peroxide generator 1432, pressure pump 1434, vacuum pump 1436 and heater 1438 during a calibration procedure.

Container programming software 1461 is used to load container memory 1022 with VSPM 1150. Container loading software 1464 is used with container/tray configuration data 1465 to verify that the correct surgical instruments are loaded into the proper tray and container.

VSPM 1150 are the values of sterilization process measurements associated with an equipment load, that when met within a container for an equipment load, insure sterilization of the container contents. Container and tray configurations 1464 are a database of container types, tray and rack types if needed and surgical instruments that detail the tray to be used with specific surgical instruments and the placement and orientation of the surgical instruments within the tray. VSPM 1150 is correlated to the surgical equipment load using methods described herein. Container loading software extracts the surgical equipment load configuration to aid the health care worker when they are loading and preparing a container for sterilization. Container loading software can also facilitate data inputs to record who is preparing the container, when they are preparing the container, what is loadento the container and other pertinent information that are required by regulations or are good business practices for recording, tracking or improving the quality of the container loading process. The container and tray configurations data can be written text, images of instrument racks, instrument configurations and/or instrument orientations or a combination of both text and images.

Process measurement limit determination software 1466 is used to determine and generate the values for VSPM 1150 data. Typically, process measurement limit determination software 1466 will be used by the OEM of the instrument set to establish and correlate VSPM data of the equipment combination to the sterilization validation. Hospitals or users of the VSPM data would not typically use process measurements limit determination software 1466. Hospitals could use the process measurements limit determination software 1466 if they want to validate and correlate a surgical equipment load that is different than what was provided by the OEM. Usage data 1470 contains data tracking the number of sterilization processing cycles undergone by each of the respective containers or tracks the number of hours that each of the respective containers are in use. Usage software 1472 is a software program that monitors the number of sterilization processing cycles undergone by each of the respective containers or tracks the number of hours that each of the respective containers are in use and generates usage data 1470. Usage data can be used for billing, sterile processing or workflow status, calibration status or for preventative maintenance of electronic sensor modules or containers.

In some versions of the invention the hand held reader is used to identify which specific instruments are placed in a container. After a sterilization cycle, the sterilization process measurements recorded by the sensor module for the container is matched with the data identifying the instruments in the container. Thus a log is maintained for each instrument of the number of sterilization processes to which the instrument was exposed and the environmental measurements made during the process. These data may also be used for inventory and billing control.

XII. Computerized Method of Tracking Container Usage and Billing on Fee Per Use Basis With reference to FIG. 18, a diagrammatic view of a networked computer system 1500 for tracking container usage and billing is shown. Networked computer system 1500 comprises one of docking stations 1200, 1300, a manufacturer computer system 1510 and a hospital computer system 1454 that are all interconnected by a communication network 1450 and in communication with each other. Communication network 1450 can encompass a variety of networks such as the internet, local area networks, wide area networks or wireless communication networks.

Manufacturer computer system 1510 and hospital computer system 1454 include any type of computing device or machine that is capable of receiving, storing and running a software product including not only computer systems and servers, but also devices such as routers and switches, mainframe computers and terminals. The operation of manufacturer computer system 1510 and hospital computer system 1454 will be described in the general context of instructions residing on hardware within a server computer. Those skilled in the art will recognize that embodiments may be implemented in a combination of program modules running in an operating system. Program modules include software, routines, programs, components, and data structures, which perform particular tasks or implement particular data types. The invention may also be practiced in distributed computing environments where tasks are performed by remote processing devices that are linked through a communications network. In a distributed computing environment, software program modules may be located in both local and remote memory storage devices.

Manufacturer computer system 1510 is in communication with network 1450 via communication fabric 1552. Manufacturer computer system 1510 includes a processor 1520 and memory 1522. Memory 1512 can store a variety of data, sets of instructions, software, programs or utilities for execution by processor 1520. Memory 1522 comprises invoice software 1530, invoices 1532 and usage data 1472. Usage data 1472 can include hospital account information like hospital name, account number, billing interval, contract pricing and other pertinent information to properly track equipment usage and billing.

Docking station 1200, 1300 transmits usage data 1472 to manufacturer computer system 1510. Invoice software 1530 when executed by processor 1520 generates invoices 1532 based on usage data 1472 received from docking station 1200, 1300. Processor 1520 stores the invoices in memory 1532 and transmits the invoices 1532 to hospital computer system 1454.

Hospital computer system 1510 is in communication with network 1450 via communication fabric 1458. Hospital computer system 1454 includes a processor 1570 and memory 1572. Memory 1572 can store a variety of data, sets of instructions, software, programs or utilities for execution by processor 1570. Memory 1572 comprises invoices 1532 received from manufacturer computer system 1510 and database 1456.

Networked computer system 1500 is used in conjunction with a business model where docking stations 1200, 1300 and containers 90-800 are leased or rented to a medical facility or hospital. The medical facility or hospital pays for using the docking stations and containers on a fee per use basis. In one embodiment, docking station 1200, 1300 tracks the frequency of use of containers 90-800 during sterilization processing and generates usage data 1472 that is transmitted to manufacturer computer system 1510. Manufacturer computer system 1510 generates invoices 1532 based on the amount of use of containers 90-800 and transmits the invoices to hospital computer system 1454 where the invoices are processed for payment.

XIII. Validated Sterilization Process Measurements (VSPM)

FIGS. 19A-1 and 19A-2 when placed side-to-side form a table of validated sterilization process measurements (VSPM) 1150. VSPM 1150 are stored in memory 1412, memory 1522 or memory 1572 (FIG. 17). In some embodiments VSPM 1150 are stored in sensor module memory 1022. VSPM 1150 data in other embodiments are stored in memory 1412, or memory 1522 or memory 1572 in a secure manner so that the correlated or associated VSPM data is not modified after the validation and correlation process described herein. VSPM 1150 data are determined during a validation and correlation process as described in detail later. Generally, the validation and correlation process is used to correlate or associate sterilization process measurements, as measured by sensors within containers during the sterilization validation process to a desired microorganism killing result for a given set of surgical equipment or equipment load. The data measured and recorded by the electronic sensor system during the validation is then used to establish VSPM measurements, thresholds or VSPM limits data sets. After the VSPM data sets are validated and correlated, these VSPM data sets are used to compare sterilization process measurements at health care facilities, as monitored by sensors within container assemblies, to determine if the process measurements for the equipment load meet, exceed or are within the VSPM data set. This comparison method is considered a verification method that can be used with suitable sensor systems and container assemblies each time Healthcare personnel sterilize surgical equipment loads or sets using the methods and systems described herein. The VSPM data in one embodiment are time based sterilization process measurements or limits that, based on the validation and correlation method, that when achieved during a sterilization processes for the associated set of surgical equipment, confirm that the sterilization process measurements were verified thus assuring the same results achieved during the validation process, namely the same level of sterilization or disinfection of the equipment load. VSPM 1150 include one or more data sets (VSPM 1150-Steam1, VSPM-1150-HPV) associated with content identifier (ID) 1610. Content identifier 1610 identifies the surgical equipment load inside the sterile barrier or container. Content ID 1610 describes the surgical instruments, surgical tools 180 (FIG. 2), and instrument racks 160, 720 within the container or sterile barrier, often called the surgical equipment load, that are correlated or associated with validated sterilization process measurements (VSPM) data sets. For example content CID 1160-3 can identify a Stryker batteries surgical equipment load consisting of rechargeable batteries for rotary surgical handpieces 180. CID 1160-3 can be written, electronic or both types of text, images or photographs that describe the composition of the equipment load associated with VSPM data. For example, content identifier can include surgical equipment types, part numbers, serial numbers, quantities and other unique equipment load identifiers that were validated together during a sterilization validation and correlation process. In one embodiment, content identifier 1610 can be electronic photographs taken of the equipment load during the sterilization validation process using methods in FIGS. 22-24. In another embodiment, content identifier 1610 may include a listing of the tray or rack identifier model number for instrument rack (160, 720) that was used during a sterilization validation process as well as a listing of all of the equipment contained therein. For example equipment content identifier CID-1610-1 includes the instruments and utensils 180-1 listed in FIG. 19(*a*) and the instrument rack (160, 720) identified as Stryker 7102-450-010. For Tray or rack 720 identification is important because it orients the cannulas within the rotary surgical handpieces in a generally downward orientation to facilitate air removal and water drainage thereby facilitating sterilization.

VSPM 1150 further includes one or more data sets of validated sterilization process measurements, when one or more sterilization process validations were performed and associated with a content identifier 1610 or equipment load. For example one data set (VSPM-1150-S-1) for a validated steam sterilization process, can contain water vapor measurements, temperature measurements and time limit and absolute pressure measurements and time limit for a content identifier CID 1610-1. In another embodiment, another data set (VSPM-1150-H-1) for a Hydrogen Peroxide sterilization process can consist of temperature limits, pressure limits, water vapor concentration and the area under the time based hydrogen peroxide vapor concentration curve associated with the same content identifier CID 1160-1. For steam sterilization, the temperature is the threshold or minimum temperature held for a minimum period of time that the interior environment and instrument load within container assemblies 90-4600 are required to experience during a sterilization process in order to insure VSPM data measurements are met. For example, the validated sterilization process measurements for container No 7102-450-040 when rack No. 7102-450-010 is contained in the first row of the table of FIGS. 19A-1 and 19A-2. More particularly these data are the VSPM data for when the rack and the instruments disposed on the rack (collectively the load) are subjected to a steam sterilization process. AS specified by the table cell the instruments on the rack considered to be sterilized if the interior of the container is subjected to saturated steam at a minimum temperature of 270° F. and that temperature is maintained for at least 3 minutes 55 seconds.

The temperature of saturated steam can be calculated from the pressure measurements and compared against the temperature measurements to verify that the steam is saturated. This comparison of the measured steam temperature to the calculated saturation temperature can also be used to verify that air is not present in sufficient quantity to adversely affect sterilization efficacy.

The validated sterilization process measurements data 1150 may have thresholds or limits that the individual measurements must simultaneously stay within as a function of time or across the same time interval. For the example just provided, the temperature, absolute pressure and saturation level of steam may have limits established for the 3 minute 55 second time period. Alternately, these measured process measurements may have specific limits that vary as a function of time. For example, the first 2 minutes of a steam sterilization cycle, the temperature may have a minimum threshold of 131° C. and above and for the next 2 minutes the temperature may have a different threshold of 133° C. and above. When the instrument set is designed and validated for more than one type of sterilization cycle, the VSPM can include more than one type of VSPM data set. If the OEM designs and validates its equipment to be sterilized with both steam and hydrogen peroxide sterilization process, the VSPM table contains VSPM data for both sterilization process. In the table of FIGS. 19A-1 and 19A-2, the VSPM data for the separate sterilization processes are shown in separate columns. In this table, the VSPM measurements for a steam sterilization process is shown in the first row. Row two contains the VSPM data for the same load if the instruments are to be subjected to a vaporized hydrogen peroxide sterilization process. The table has both VSPM data sets, one set of data for steam sterilization (VSPM-1150-S-1) and one set of data for hydrogen peroxide sterilization (VSPM-1150-H-2) with the same content CID 1610-1. More specifically, content CID 1610-1 can be associated with Temperature, absolute pressure and steam saturation VSPM 1150-S-1 data set for steam sterilization and Temperature, absolute pressure, hydrogen peroxide concentration and water concentration VSPM 1150-H-1 data set for hydrogen peroxide sterilization. This provides the capability for the VSPM data sets to be added for a given equipment load or content ID to include additional VSPM data for specific sterilization modalities after they have been validated and correlated as described herein. The sensor modules can be designed for use in a single sterilization modality and denoted by SM0000XS for steam or SM0000XH for hydrogen peroxide where 0000X identifies the type of sensor module. In another embodiment, the sensor modules can also be designed for use in more than one sterilization modality. For example sensor module denoted by SM0000XSH can be used in both steam sterilization and hydrogen peroxide sterilization modalities where 0000X is the serial number assigned to the sensor module. FIG. 19 is arranged with a unique sensor module in a row. A sensor module could be used with any compatible Content ID 1610. For example, Stryker Sensor Module SM00001S could be used with Content Identification CID 1610-1, CID 1610-2 or CID 1610-5.

For some sterilization processes, the validated sterilization process measurements are measurements that are generated over time. In the simplest form, these measurements are measurements that indicate the environment inside the container had a minimal concentration of a particular sterilant for a defined minimum period of time. One simple example are a set of measurements that indicate the container environment contained saturated steam for a period of at least 5 minutes.

A more complex set of measurements are used to generate the area under a curve. The X-axis against which this curve is plotted is time; the Y-axis is the concentration of the sterilant. Typically the time is in seconds and the concentration mg/l. Thus for one set of instruments in a container the validated sterilization process may be a process where the area under this curve is a vaporized hydrogen peroxide concentration of 5000 (mg/l)(sec.) This means that for a first sterilization cycle the validated sterilization process measurements are satisfied if a concentration of 25 mg/l of vaporized hydrogen peroxide is measured for at least 200 seconds. For a second sterilization cycle the validated sterilization process measurements are satisfied if a concentration of 20 mg/l of vaporized hydrogen peroxide is measured for at least 100 second. It should of course further be appreciated that the area under this curve is typically for a minimal concentration of sterilant. Thus, in the example above, time periods in which the container environment has a concentration of vaporized hydrogen peroxide less than 18 mg/l are not integrated into the targeted measurement.

The area under the time based hydrogen peroxide concentration curve is the threshold or minimum (mg/liter)(sec) of hydrogen peroxide to which the interior of one of the containers is exposed to insure that the contents of the container are sterilized. For example, the interior of container Stryker 7102-450-040 is required to be exposed to a minimum of 2500 mg-s/l of hydrogen peroxide during a sterilization process cycle when equipment of content ID CID 1610-1 is present as set forth in the line 2 of FIG. 19A. If the water vapor content is low compared to what it could have been at 100% saturation at any time during the exposure, the effective concentration can be reduced at that time when it is added into the area under the time based concentration curve. For example, the effective concentration can be halved when the concentration of water vapor is less than 80% of the saturation concentration. The saturation concentration of water vapor depends upon both vapor temperature and the concentration of hydrogen peroxide vapor that is present.

Additional information in other embodiments described in FIG. 19A may be optionally associated with either CID 1610 or VSPM 1150 data sets or both. For example, Container ID 1605 identifies and describes the specific type of container 90-4600 that was previously subjected to a sterilization validation process. When the sterilization process results are known to or are suspected to be affected by the type of container or the type of sterile barrier used for an equipment load, container ID may be associated with either content ID or VSPM data sets or both. If the type of container or sterile barrier used during a sterilization process is known to not affect sterilization results, container ID may not be associated with content ID or VSPM data sets. The later embodiment allows the sterile barrier or container type used for sterilization at health care facilities to change for an equipment load without changing the sterilization results as long as the process measurements are properly verified to comply with VSPM 1150 using sensor modules and methods described herein. For example, a container identified identifies a specific container serial number provided by an OEM or within the medical facility. The container ID can identify and translate to the container type, sterile barrier used, the electronic sensor module 200, 460, 560, 660, 760, 1000, 1050, 1080 type or sensor module configuration. Other data associated with content ID 1610 or VSPM 1150 data or both listed in FIG. 19 can be useful, but not necessary when using different embodiments of this invention. For example, Nominal process parameters can be output by the docking station so the sterilizer operator can set the nominal process parameters for programming the sterilizer. These nominal process parameters in this example would be greater than or equal to the nominal process parameters used during the validation and correlation of VSPM 1150 data to content ID 1610. In other embodiments, data table may further include sensor module usage. The total number of sterilization cycles can be obtained from the sensor module usage data and can be used for business purposes like automated invoicing, preventative maintenance and for periodic replacement of container and sensor components. The dates, content identifiers, container identifiers for the sterilized loads are used by the central processing department for inventory tracking, billing and control purposes.

During loading and programming of a container using a docking station, at least a portion of VSPM 1150 are transmitted from the docking station to the electronic sensor module and are stored in module memory 1022 (FIG. 14). For example, if the container is being loaded and programmed with content ID 1610-1 and tray ID Stryker 7102-450-010, only the VSPM 1150-S-1 associated with content ID 1610-1 and associated sterilization process are transmitted from memory 1412 to memory 1022.

XIV. Automatic Closing Container Vent

Figure 20A:
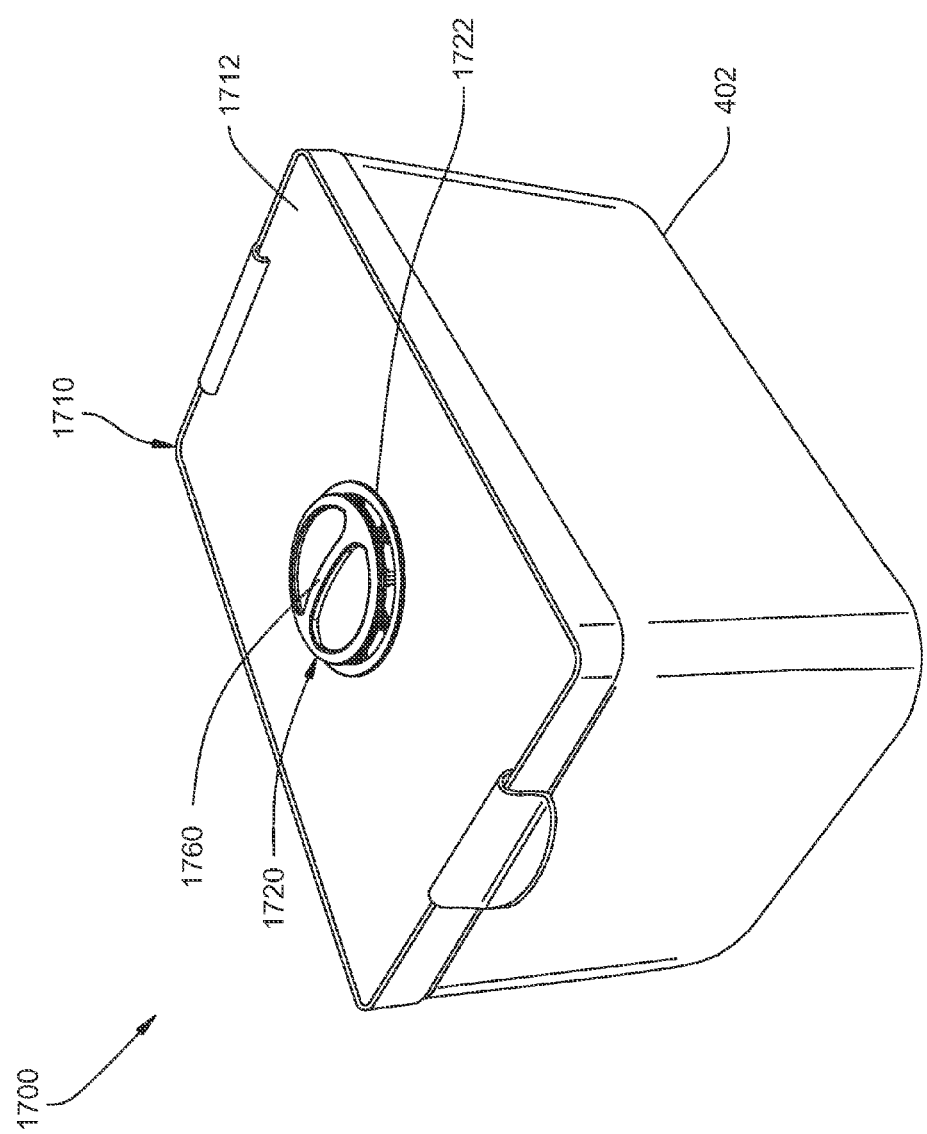
FIG. 20A is a perspective view of an automatic closing lid cap mounted to a container cover in accordance with one embodiment.
Figure 20B:
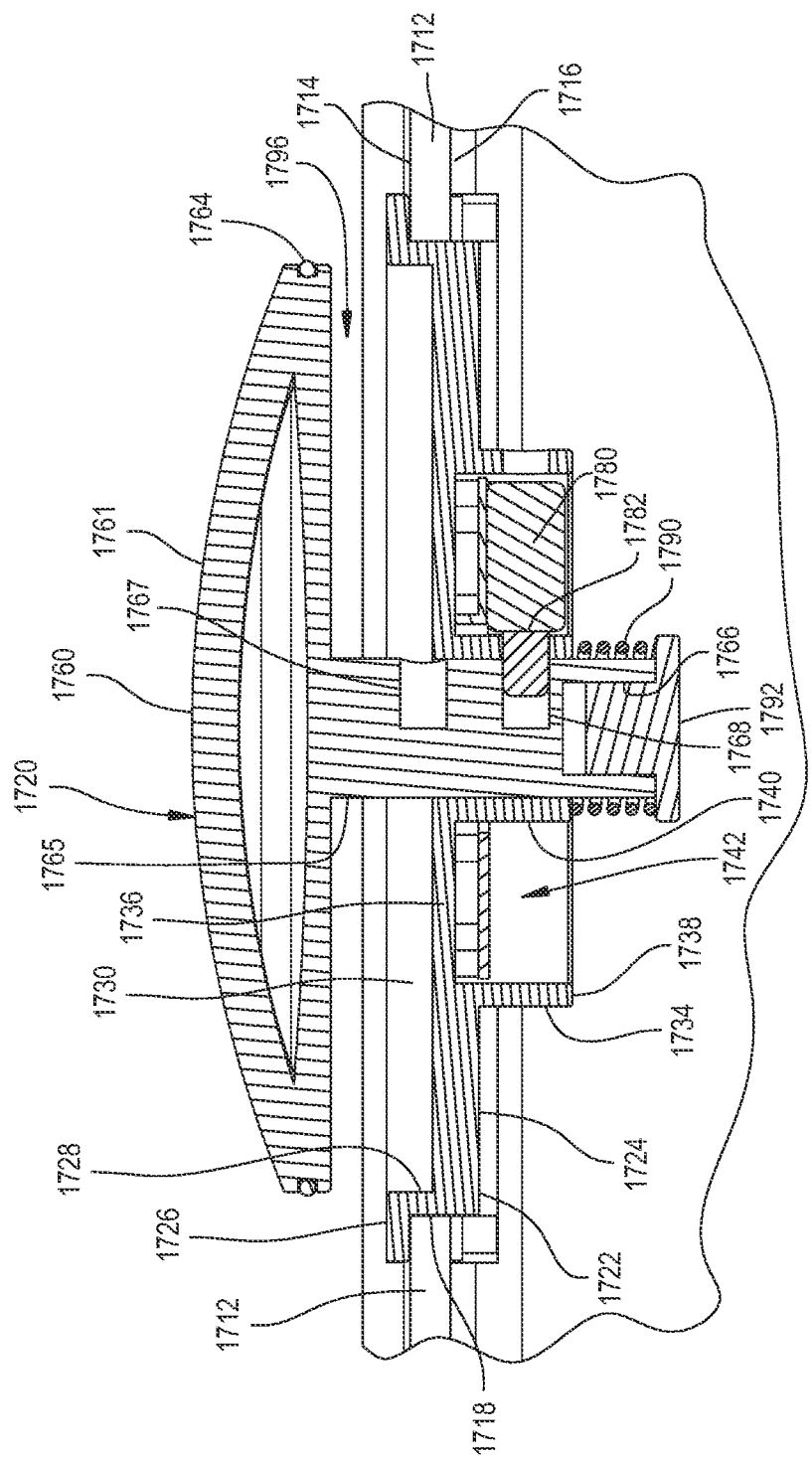
FIG. 20B is a cross-sectional view of the automatic closing lid cap of FIG. 20A.
Figure 20C:
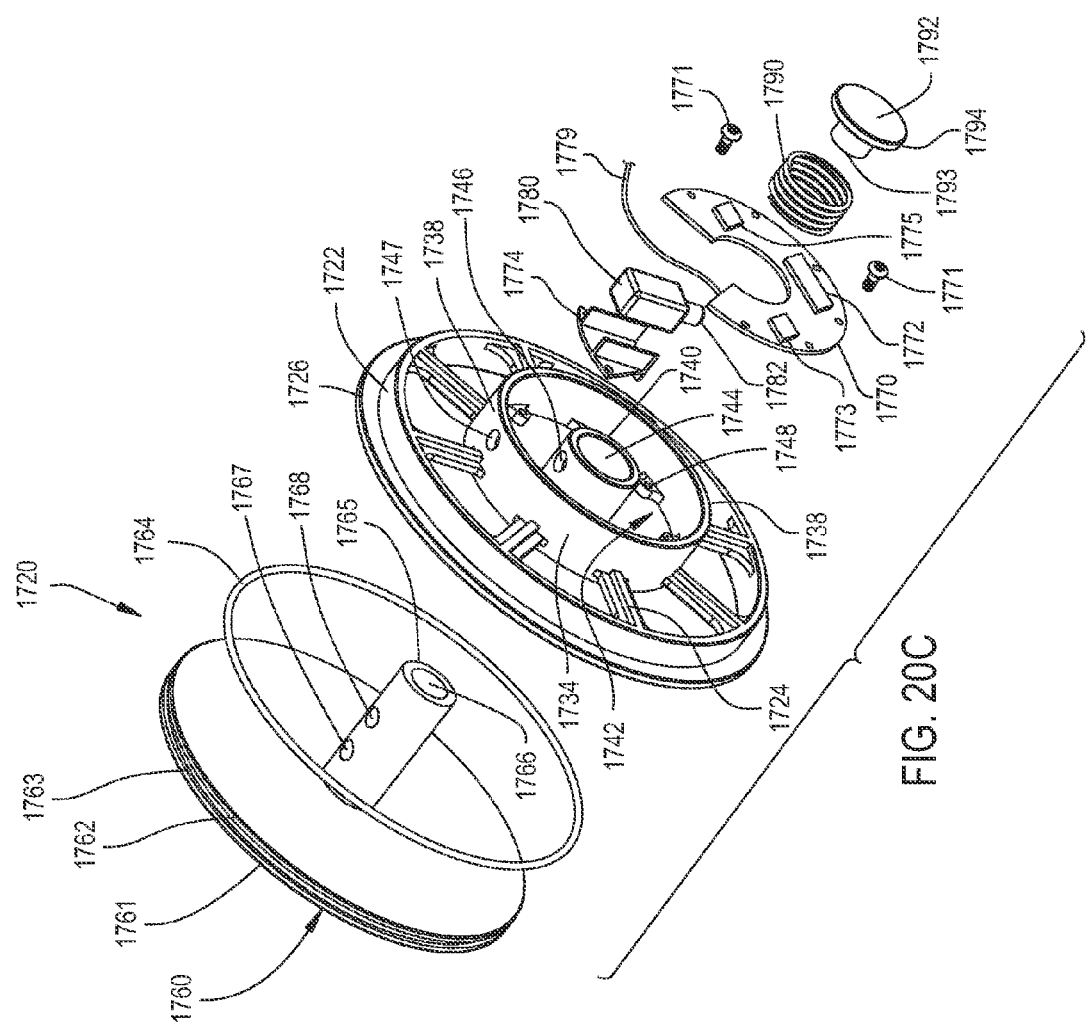
FIG. 20C is an exploded perspective view of the automatic closing lid cap of FIG. 20A.

FIGS. 20A-20C illustrate a container assembly 1700 having an automatic closing lip cap assembly 1720 that is mounted to a container cover 1710. Container assembly 1700 can retrofit an existing sterilization container into a container that automatically closes after receiving a closing signal from an electronic sensor module. Automatic closing container vent, when positioned in an open state during a sterilization process, allows unrestricted passage of sterilization agents into the container providing easier access to the contents of the container to affect sterilization.

Container assembly 1700 is employed when the efficiency of the sterilizing process is reduced or rendered ineffective as a result of the presence of a filter over the through openings in the container. One reason a filter may have this affect on the sterilizing process is because owing to the composition of the filter and the composition of the sterilant, the presence of the filter inhibits the flow of sterilant through the filter. The presence of a filter may adversely also affect sterilization is because, the sterilant when exposed to the material forming the filter, undergoes a chemical reaction that reduces the efficacy of the sterilant.

Thus, to avoid these undesirable effects of the presence of a filter container assembly 1700 typically does not include a filter. The vent is open and flow through the vent is unrestricted at least for the time period the container and the contents therein are undergoing a sterilization cycle.

Container cover 1710 is generally similar to cover 450 of FIG. 7A; however cover 1710 does not have any holes 459 or filter assemblies 440. Cover 1710 has a planar top panel 1712. Top panel 1712 has an upper surface 1714 and a bottom surface 1716. A circular central opening 1718 is defined in top panel 1712. Cover 1710 is placed over container 402 in order to enclose container 402.

Container cover 1710 and container vent assembly 1720 can be retrofitted to any the previously described containers 100, 402, 502 and 802 in order to provide the containers with a cover that automatically closes after the completion of a sterilization process cycle. While container vent assembly 1720 is shown mounted to cover 1710, container vent assembly 1720 alternatively can be mounted to any of the side panels of container 402. By relocation the container vent to a different panel it may allow steriliant to enter and exit more efficiently to affect sterilization of the contents of the container. Also, more than one container vent 1720 positioned on one or more panels may be used on a single container.

Automatic closing container vent assembly 1720 is mounted to top panel 1712. More specifically, container vent assembly 1720 is received by opening 1718. Container vent assembly 1720 comprises a circular carriage 1722, cap 1760, circuit board 1770 and linear solenoid 1780. Carriage 1722 includes an outer ring 1728 connected to a central drum 1734 by cross members 1724. Outer ring 1728 is perpendicular to cross members 1724. A peripheral rim 1726 extends perpendicularly away from and surrounds ring 1728. A recess 1730 is defined between ring 1728 and cross members 1724. Carriage 1722 and container vent 1760 are formed from injection molded plastic.

Carriage 1722 is mounted in opening 1718. Rim 1726 rests on top surface 1714 supporting carriage 1722. The outer surface of ring 1728 abuts the annular portion of panel 1712 defined by opening 1718. In one embodiment, carriage 1722 is press fit into opening 1718. In another embodiment, carriage 1722 is sealingly affixed to panel 1712 using an adhesive or sealed mechanical fasteners.

Central drum 1734 is cylindrical in shape and has a base 1736. An outer wall 1738 and an inner hub 1740 extend perpendicularly away from base 1736. Base 1736, outer wall 1738 and inner hub 1740 define a groove 1742 therein. A central bore 1744 extends entirely through base 1736 and inner hub 1740. Another bore 1746 extends perpendicularly through inner hub 1740 approximately midway along the length of inner hub 1740. Bore 1746 extends between groove 1742 and bore 1744. Several mounting bosses 1748 are affixed to base 1736 adjacent wall 1738. Mounting bosses 1748 extend perpendicularly away from base 1736 into groove 1742. Mounting bosses 1748 are used to attach circuit board 1770 to carriage 1722.

Cap 1760 includes a circular disc 1761 that is attached to a cylindrical shaft 1765. Disc 1761 has an outer annular side 1762. An annular groove 1763 is defined in side 1762. Groove 1763 is dimensioned to receive a circular elastomeric O-ring 1764. Cylindrical shaft 1765 extends perpendicularly away from the bottom side of disc 1761. Shaft 1765 has a central bore 1766 that extends partially into shaft 1765 parallel to the axis of shaft 1765. Shaft 1765 also has two bores 1767 and 1768 that extend partially into shaft 1765 perpendicular to the axis of shaft 1765. Bores 1767 and 1768 have a length that is approximately one half the diameter of shaft 1765. Bore 1767 is spaced from the bottom side of disc 1761 and bore 1768 is spaced from the terminal end of central bore 1766.

A printed circuit board 1770 is affixed in groove 1742 by fasteners 1771. Groove 1742 is dimensioned to receive printed circuit board 1770. Fasteners 1771 extend through circuit board 1770 and are threaded into mounting bosses 1748. Several electrical components are mounted to circuit board 1770. A battery 1772, wireless transceiver 1773, solenoid housing 1774 and solenoid driver 1775 are mounted to circuit board 1770. Linear solenoid 1780 is mounted in and held by solenoid housing 1774. Battery 1772 is either a rechargeable or replaceable battery or supplies power to the components of circuit board 1770. Printed circuit board 1770 is in communication with one of electronic sensor modules 200, 460, 560, 660, 760 and 850. In one embodiment, wireless transceiver 1773 receives wireless communications from one of the electronic sensor modules 200-850. In another embodiment, an electrical cable 1779 is connected between circuit board 1770 and one of the electronic sensor modules 200-850. Solenoid driver 1775 is in communication with linear solenoid 1780 and causes linear solenoid 1780 to move an attached rod 1782. Rod 1782 is linearly movable between an extended position and a retracted position.

A coil spring 1790 surrounds shaft 1765. A spring retainer 1792 is mounted over coil spring 1790 and includes a boss 1793 that extends into bore 1766. Spring retainer 1792 retains coil spring 1790 to shaft 1765. Spring retainer 1792 has an annular lip 1794 that extends over and abuts a distal end of spring 1790. The proximal end of spring 1790 abuts the terminal end of inner hub 1740. Spring retainer 1792 is either press fit into bore 1766 or is affixed in bore 1766 using an adhesive. Coil spring 1790 biases container vent 1760 to move towards carriage 1722. In an open position, as shown in FIG. 20B, a passage 1996 is formed between carriage 1722 and the bottom of disc 1761.

Container vent 1760 is retained in the open position, by solenoid rod 1782 extending through inner hub bore 1746 and into container vent bore 1768. In this position, coil spring 1790 is compressed. Container vent 1760 is opened from a closed position in a two step process. First, a user uses an input device to trigger the retraction of solenoid rod 1782 out of bore 1767 by solenoid 1780. In one embodiment, the input device is the touch screen 1230 (FIG. 15) of docking station 1200. Second, the user manually grasps container vent 1760 and pulls upwardly on container vent 1760 moving container vent 1760 away from carriage 1722. Solenoid rod 1782 is outwardly biased by a spring (not shown) such that when container vent bore 1768 moves into axial alignment with inner hub bore 1746, rod 1782 automatically extends into container vent bore 1768 thereby holding container vent 1760 in the open position.

During use, lip cap assembly 1720 and container cover 1710 are part of the container assembly that undergoes a sterilization process cycle in a sterilization chamber. After electronic sensor module 200-850 determines that the environment within container 402 during sterile processing were sufficient to meet or exceed a required set of environmental characteristics (VSPM 1150) to insure sterility of the surgical instruments being sterilized, sensor module 200-850 transmits an electrical signal via wireless transceiver 1773 or electrical cable 1779 to solenoid driver 1775 instructing solenoid driver 1772 to close container vent 1760.

Solenoid driver 1775 causes solenoid 1780 to retract solenoid rod 1782. When rod 1782 moves out of engagement with bore 1768, spring 1790 biases container vent 1760 to move into recess 1730 thereby closing passage 1796. The travel of container vent 1760 is limited by the abutment of the bottom of disc 1761 against cross members 1724. At the same time, O-ring 1764 is compressed between the disc outer side 1762 and the inner surface of ring 1728 forming a seal.

In one embodiment, when container vent bore 1767 moves into axial alignment with inner hub bore 1746, rod 1782 automatically extends into container vent bore 1767 thereby holding container vent 1760 in the closed position. In another embodiment, after container vent 1760 is closed, sensor module 200-850 transmits an electrical signal via wireless transceiver 1773 or electrical cable 1779 to solenoid driver 1775 instructing solenoid driver 1772 to cause solenoid 1780 to extend solenoid rod 1782. In the extended position, the distal end of rod 1782 is received by and engaged with bore 1767, thereby locking container vent 1760 to carriage 1722.

The use of automatic closing container assembly 1700 and automatic closing lip cap assembly 1720 allows existing containers to be retrofitted with an automatic closing device that eliminates the need for filters or filter assemblies. When passage 1796 is open, sterilant is able to readily enter and permeate container 402 without interference.

After the container and its contents are subjected to the phase or phases of a sterilization cycle in which sterilant is introduced into the container, passage 1796 is held open for an additional time period. This is to allow residual sterilant that may be in the container to evaporate and vent from the container. A benefit of allowing this venting of the sterilant is that, if the sterilant is potentially hazardous to tissue, the likelihood of residual sterilant contacting a patient or hospital personnel is substantially eliminated.

In some versions of the invention the processor integral with the sensor module closes cap 1760 over passage 1796 when the sensor measurements indicate that the container environment has been at a select temperature or pressure for a select period of time. In other versions of the invention the processor closes the cap when the sensor measurements indicate that the container has been cycled through a set number of pressure set points.

Figure 21:
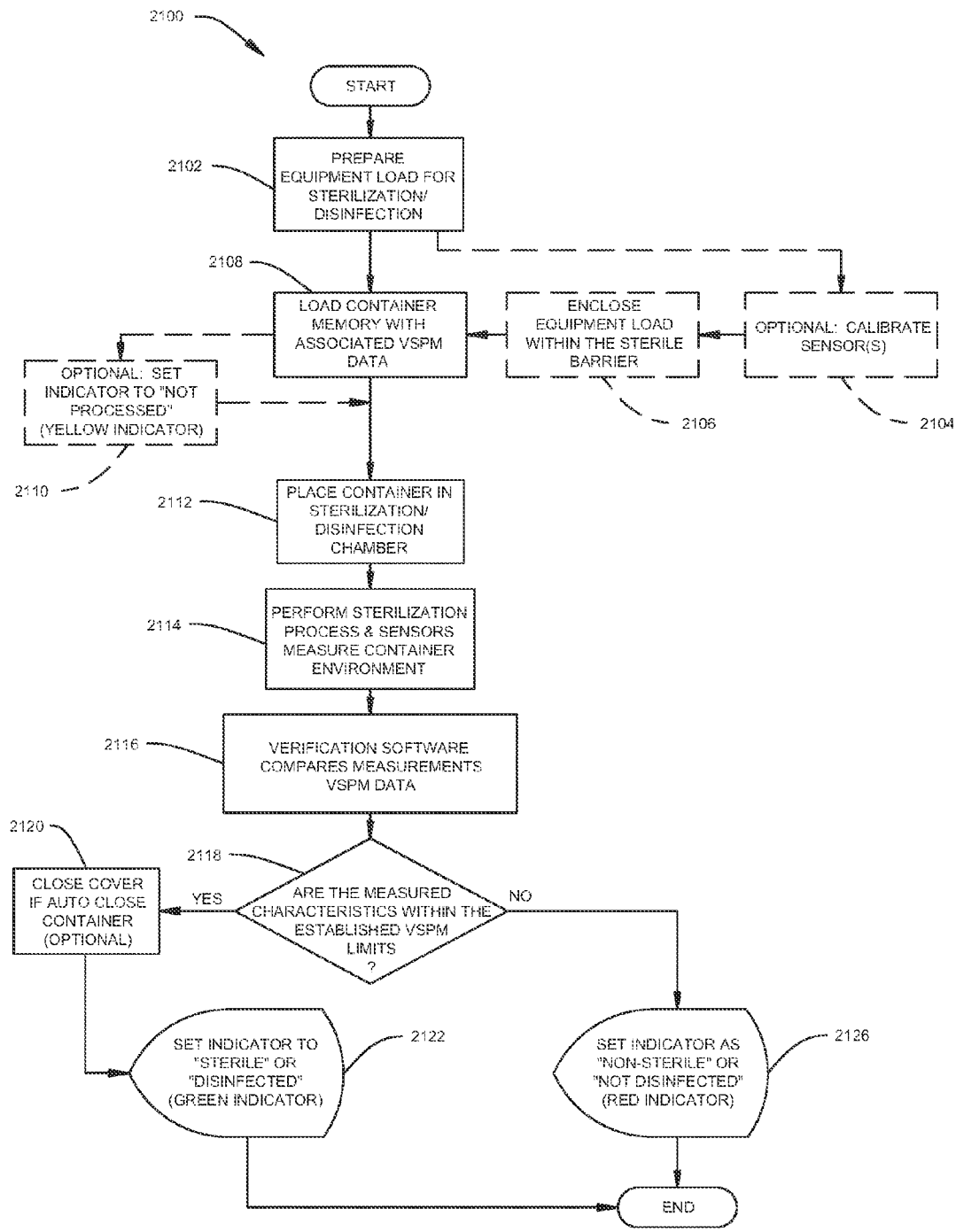
FIG. 21 is a flowchart of a method of determining if validated sterilization process measurements within a container have been achieved during a sterilization process in accordance with one embodiment.

XV. Operational Method to Determine if Validated Sterilization Process Measurements in a Container have been Verified During a Sterilization Process Referring to FIG. 21, a flowchart of a method 2100 of verifying if validated sterilization process measurements (VSPM) within a container have been achieved during a sterilization or disinfection process is shown. Method 2100 illustrates an exemplary method by which the container assemblies 90, 300, 400, 500, 600, 700 800, 2900 and 4600 (90-4600) and electronic sensor modules 200, 460, 560, 660, 760, 850, 950, 1000, 1050, 1080 and 3500 (200-3500) presented within the preceding figures perform different aspects of the processes that enable one or more embodiments of the disclosure. Method 2100 is described specifically as being performed using container assembly 400 (FIG. 7A) and sensor module 1050 (FIG. 12B). However, method 2100 can be performed using any of container assemblies 90-800 and electronic sensor modules 200-3500. The description of the method is provided with general reference to the specific components illustrated within the preceding figures. In the discussion of FIG. 21, reference will also be made to components from FIGS. 1-20.

Method 2100 begins at step 2102 where the equipment load of surgical instruments 180 is prepared for sterilization processing by an operator. Step 2102 includes the positioning of container 402 onto docking station 1200 or 1300 and if the container has a connector, connecting the corresponding connector 485, 1032 to the docking station. In an alternate embodiment, connecting the sensor module to the docking station can be made through a wireless communication system. At step 2102, handheld reader 1240 is used to scan the equipment load to be sterilized. In and alternate embodiment, equipment load or contents ID can be entered into the docking station or selected from a list or menu containing all equipment loads or content IDs that have associated VSPM data. Step 2102 further includes the placement of the equipment load into container 402 and enclosing the container with cover 450. During the loading of surgical instruments, 180, the operator refers to the display screen 1260 shown by docking station 1200 or 1300 to view the correct equipment load items and instrument loading orientation. This display can help the operator in setting up the same equipment load and orientation that was used when validating and associated VSPM data to the equipment load. In an optional step 2104, the sensors of electronic sensor module 460, 1050 are calibrated prior to use. Electronic sensor modules 460, 1050 are calibrated using docking station 1300. In another optional step 2106, the surgical instruments 180 and/or tray 160 and/or container 402 are wrapped in a sterile barrier material prior to sterilization processing.

At step 2108, sensor module memory 471, 1022 is programmed with validated sterilization process measurements (VSPM) data 1150 associated with the equipment load or content ID 1610. Container programming software 1461 (FIG. 17) acting on docking station processor 1410 (FIG. 17) identifies the specific VSPM 1150 associated with the container equipment load, using the data obtained from step 2102, and transmits the VSPM 1150 via the connector 485 for storage on the sensor module memory 471, 1022. As described earlier, the transmitted VSPM 1150 are specific to the equipment load (content ID) to be sterilized. In another embodiment, VSPM 1150 are transmitted via wireless means from the docking station to the container memory for storage. In another embodiment, step 2108 confirms that the current VSPM data residing in sensor memory is proper for the container equipment load and transmitting of new VSPM 1150 from docking station to sensor memory is not performed. This alternate embodiment may be used for sensor modules that are repeatedly used for the same equipment load for example sensor module 760 that is mounted to a customized instrument rack 720 or dedicated container assembly.

In an additional optional step at block 2110, sterilization verification software 1152 acting on processor 1020 turns on a yellow light emitting diode (LED) of LEDS 1030 (also shown as yellow LED 233 in FIG. 3) indicating to a user that the container assembly has not yet been processed through a sterilization process cycle.

The container 402 is placed into the sterilization chamber 52 (FIG. 1) at step 2112. The container and its contents are subjected to a sterilization process, step 2114. During the sterilization process, the chamber is heated, pressurized and a sterilant, such as steam or hydrogen peroxide vapor is into the sterilization chamber. By extension the environment inside the container is heated, pressurized and/or flooded with sterilant. The sterilization process may include a cool down phase, drying phase or drawing a vacuum on the chamber to remove any residual condensed sterilant. The sterilization chamber is set to operate using a set of nominal chamber process parameters (CPP) 66 (FIG. 1).

During the sterilization process of step 2114, sterilization verification software 1152 acting on processor 1020 monitors and collects measurements from the respective electronic sensors with which it is in communication during the sterilization process cycle. The sensors measure the characteristics of the environment in the container. The software 1152 running on processor 1020 receives the signals representative of these environmental characteristics. These measures are stored as data 1156 in memory 1022.

After the sterilization process is complete, software 1152, in step 2116, compares the measurement data 1156 collected during the sterilization process, to the VSPM data 1150. At decision step 2118, sterilization verification software 1152 acting on processor 1020 determines if the measurements data 1156 during the performed sterilization process meets or exceeds the VSPM data 1150 values within the VSPM data set to insure sterilization of the container contents. For example, if VSPM 1150 has a minimum temperature and time value of 250 degrees Fahrenheit for 20 minutes, sterilization verification software 1152 compares these values to the recorded time and temperate measurement values in data 1156.

The measured container characteristics may meet or exceed the VSPM data 1150. If this condition tests true, the process of this invention proceeds to step 2120 for containers that include closeable passages or vents. Step 2120 is the closing of the vent or passage. It should be understood that step 2120 is not executed immediately after the evaluation of step 2118 determines that the container environment met the requirements for a validated sterilization process. Instead, step 2120 is executed after the programmed time period, or detection of the set trigger event. This is ensure that between the completion of the actually sterilizing phases of the sterilization cycle and the closing of the vent there is sufficient time for the residual sterilant to vent from the container. For containers that do not contain closeable passages, step 2120 is of course, not executed. Method 2100 proceeds to step 2122.

Following the testing true evaluation of step 2118, the process proceeds to step 2122. In step 2122 processor 1020 indicates that the container contents were successfully sterilized by turning on a green LED such as LED 230 (FIG. 3) or a green LED of LEDS 1030 (FIG. 12B) at step 2122

The evaluation of step 2118 testing false is interpreted as indication that the contents of the container have not been sterilized to the desired levels. In response to this determination being made, the processor proceeds to a step 2126. In step 2126 the processor 1020 presents an indication the contents of the container were not successfully sterilized by turning on or flashing a red LED such as LED 232 (FIG. 3) or a red LED of LEDS 1030 (FIG. 12B). Not shown is the opening of the vent or port in versions of the invention with a cap that is selectively closed and open.

The completion of step 2122 or step 2126 is the end of a single sterilization cycle.

Figure 22:
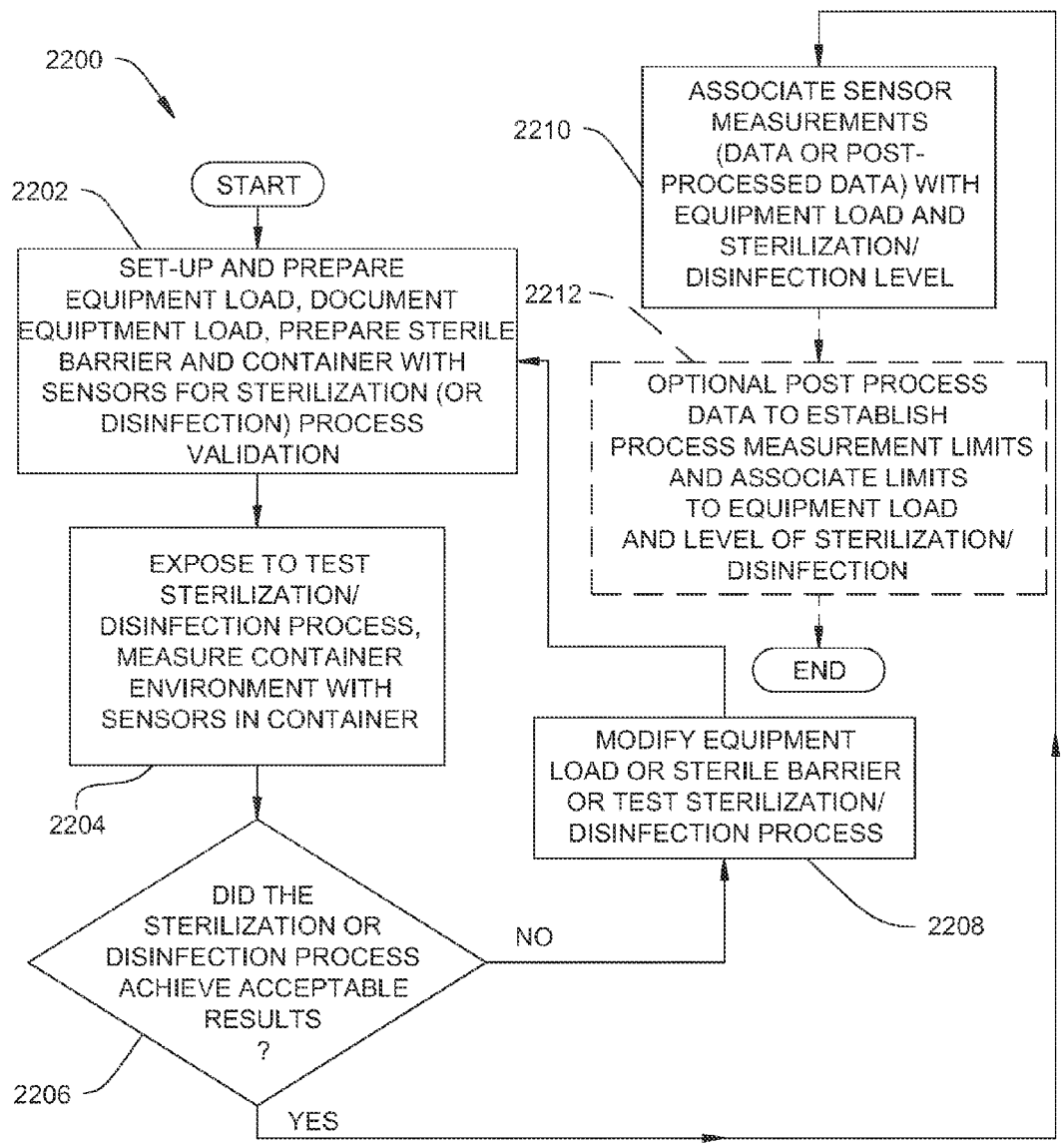
FIG. 22 is flowchart of a method of validating container environmental measurements in accordance with one embodiment.

XVI. Determining a Validated Sterilization Process Measurements for an Individual Container Load FIG. 22 is a flowchart of a method 2200 for determining a validated sterilization process measurements (VSPM) 1150 for a single, defined container load. This method can also be applied for determining a validated disinfection process measurements with the primary difference between sterilization and disinfection is the quantity of biological challenge organism reduction, that being an organisms reduction of $10^6$ for sterilization and an organism reduction of $10^3$ for disinfection. Method 2200 is specifically discussed as being performed using container assembly 400 (FIG. 7A) and sensor module 1050 (FIG. 12B). However, any of the preceding container assemblies 90-800 and electronic sensor modules 200-3500 can be used to perform method 2200. The description of the method is provided with general reference to the specific components illustrated within the preceding figures. In the discussion of FIG. 22, reference will also be made to components from FIGS. 1-20.

Method 2200 begins at step 2202 where an equipment load of surgical instruments 180 is prepared for a Sterilization Validation by an operator. At step 2202, the surgical equipment load is selected and prepared to be validated for a selected sterilization modality. The surgical equipment load includes all items inside of the sterile barrier that are desired to be validated for sterilization. The equipment load may include surgical instruments 180 and an instrument tray or rack 160 when desired. Step 2202 may further include the placement of the surgical equipment load into container 402. At step 2202, all contents of the container that make up the equipment load are documented. Documentation can include a written bill of materials, an electronic bill of material, descriptions and part numbers of the contents, photographs taken of the contents or a combination of these types of documentation. The documented equipment load can be assigned a content ID 1610 as described in FIG. 19. In another embodiment, Step 2202 also includes the placement of a biological challenge or inoculation of the equipment with biological challenge microorganisms in accordance with standard practices for sterilization assurance level validation or disinfection validation. One standard practice for inoculation of the equipment with microorganisms for steam sterilization can be found in ANSI/AAMI/ISO TIR17665-2:2009, Sterilization of health care products-Moist heat-Part 2: Guidance on the application of ANSI/AAMI/ISO 17665-1. Step 2202 includes completing the sterile barrier for the container which may be wrapping the container in a sterile barrier material, installing new filters, setting the container vents appropriately or other appropriate methods of completing the sterile barrier for the container, sterile barrier type and sterilization modality. For container assembly 400, installing new filters 440 and latching the lid assembly 450 to seal with container 402 completes the sterile barrier.

Also at step 2202, data recording software 1155 stored on memory 471, 1022 is triggered to operate on processor 1020. Data recording software 1155 monitors and records evaluation process measurements, as measured by the sensor module, during a test sterilization process cycle for storage on the sensor module memory 471, 1022.

The container 402 is placed into the sterilization chamber 52 (FIG. 1) and the test sterilization process cycle within sterilization chamber 52 is started (step 2204). The sterilization chamber is typically set to operate using a set of nominal chamber test process parameters. During the test sterilization process cycle, the sterilization chamber is heated, pressurized and a sterilant, such as steam or hydrogen peroxide vapor is introduced into the sterilization chamber. The sterilization process cycle typically includes a cool down phase or an evacuation phase to remove any residual and/or condensed sterilant.

Also, at step 2204, data recording software 1155 acting on processor 1020 monitors and collects measurement data from the respective electronic sensors with which it is in communication during the test sterilization process. The sensors record the evaluation process measurements and conditions within the sterile barrier. The collected measurement data is stored in memory 1022 as data 1156. For example, data recording software 1155 acting on processor 1020 collects water vapor data from water vapor sensor 1024, pressure data from pressure sensor 1026, temperature data from temperature sensor 1028 and hydrogen peroxide concentration data from hydrogen peroxide gas sensor 1052. In some embodiments, these data are simultaneously tracked and recorded as a function of time so as to capture the evaluation process measurements experienced inside of the sterile barrier on a time basis.

At step 2206, container 402 is removed from the sterilization chamber 52 and the equipment load is evaluated for the level of sterilization achieved. In one embodiment, an operator incubates and reads the biological challenge (or inoculated microorganisms) and determines if the survival rate of the microorganisms is below a pre-determined desired level. In another embodiment, a 0% survival rate of the microorganisms indicate that the evaluation process measurements are adequate to insure destruction of all pathogens during sterilization processing.

If the level of sterilization is not acceptable, the operator can modify the equipment load, the nominal sterilization process parameters or the sterile barrier. The operator can modify one or more of these items, or any other controllable items that can affect the test sterilization process results. For example, the modification of chamber (52) process parameters can include increasing one or more process parameters of the sterilization chamber 52. In one embodiment, the temperatures level and the lethal portion of the test sterilization process time are increased in step 2208. In another embodiment, step 2208 includes modifying the contents of container 402. For example, fewer surgical instruments 180 are placed inside the sterile barrier. Method 2200 then returns to step 2202 where the container 402 and equipment load is re-processed in sterilization chamber 52 repeating the steps until a desired level of sterilization is achieved at step 2206.

In response the sterilization level of the equipment load being acceptable, the recorded sensor measurements are collected from sensor module memory 1022 and the measurements become validated sterilization process measurements (VSPM) associated to the equipment load. VSPM 1150 are based on the received evaluation measurement data 1156 that were functionally confirmed to act on the contaminants within the equipment load wherein the evaluation measurements become validated measurements. In one embodiment, process measurement validation software 1466 acting on docking station processor 1410 reads the recorded evaluation measurement data 1156 from sensor module memory 1022 and stores the data on docking station memory 1412 at step 2210. Also in this embodiment at step 2210, an operator uses the evaluation measurement data 1156 recorded by the sensor module to determine and generate values for validated sterilization process measurements (VSPM) 1150. After the VSPM 1150 are determined, the operator inputs VSPM 1150 to docking station 1200, 1300 and directs VSPM 1150 to be stored to memory 1412.

In another embodiment, process measurement validation software 1466 acting on docking station processor 1410 automatically generates VSPM 1150 from evaluation measurement data 1156 and stores the data on docking station memory 1412 at step 2210. In all embodiments, correlation of the equipment load to the VSPM completes process step 2210 for the desired level of sterilization.

In an optional step 2212, the operator establishes measurement limits for VSPM 1150. Measurement limits could include upper and lower limit values for one or more sensor reading included in VSPM 1150 data set. Reading limits could include only an upper or only a lower limit. For example, in one embodiment, an operator can determine that a minimum or lower time limit experienced during the test sterilization processing is 20 minutes and a maximum or upper time limit is 40 minutes. In another embodiment, an operator can determine that a lower temperature limit experienced during the test sterilization process is 270° Fahrenheit. After the measurement limits are determined in this optional step, the operator sets the measurement limits for VSPM 1150 and directs the measurement limits to be stored to memory 1412. Optional step 2212 is completed when the measurement limits for VSPM 1150 are correlated to the equipment load for the desired sterilization level. Method 2200 then ends.

It should be understood that the definition of determining what constitutes whether or not a load of instruments was successfully sterilized in step 2206 is a function of the acceptable degree of sterilization for the instruments. Some instruments are considered adequately sterilized if they are only subjected to disinfection. Disinfection it is understood has a lower sterility assurance level than sterilization. Thus method 2200 as well as the sterilization process and equipment of this invention can be used to provide instruments that are sterile but not as sterile as typically required for instruments applied to tissue below the skin.

Once a set of validated sterilization process measurements are generated for a container load, these measurements are used to determine whether or not the load was sterilized even if the load was placed in a container different from the container used to generate the VSPM for the load. This is because changing form of the sterile barrier (the container) that surrounds the load essentially only changes the rate at which the environment around the load changes during the sterilization process.

For example, when the only difference between two containers is their porosities, the key difference in the environmental characteristics in the containers will be the rate at which these characteristics change. Thus, when sterilant is introduced into both containers, the concentration of the sterilant in the more porous container will rise at a faster rate than the concentration in the less porous container. Thus when the same load is subjected to sterilization process in the two different containers, the primary difference will be the time it takes for the concentration of sterilant adjacent the instruments forming the load to reach the desired, the validated levels. As long as the concentration of sterilant is at the validated concentration level for the validated time period, the instruments forming the load will reach the desired sterility level.

This feature of the invention frees the hospital from having to sterilize a specific load of instrument by always placing those instruments in a specific container. If a container a designed for a set of instruments is not available for use, the instruments can be placed in an alternate container. It is only necessary that sensing unit integral with this container be able to (1) measure the characteristics internal to the container and (2) compare the measured environmental characteristics to the VSPM for the load. When these conditions are met, the alternative container can hold instruments during sterilization and its sensing unit will provide an indication regarding whether or not the instruments were successfully sterilized.

Figure 23:
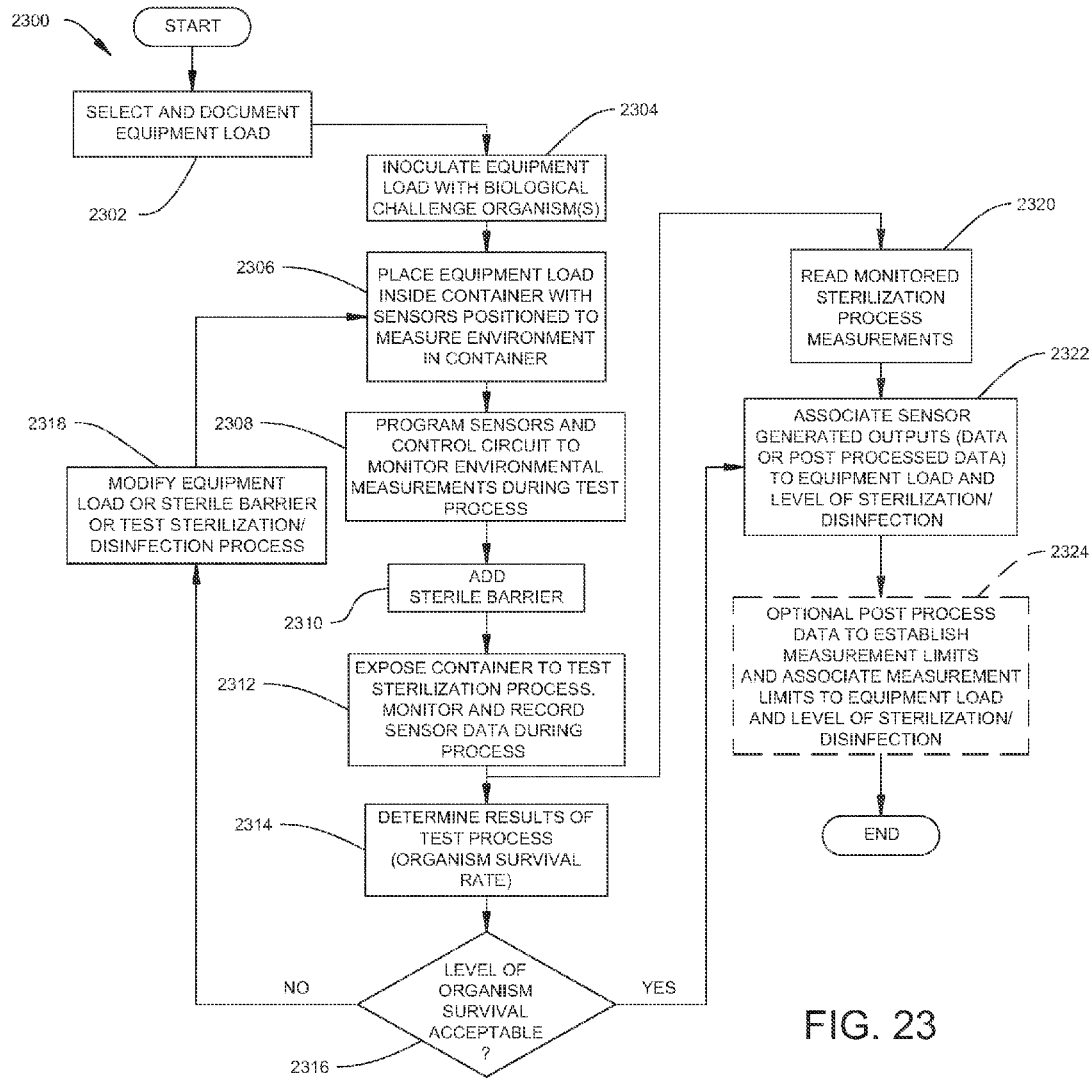
FIG. 23 is flowchart of another method of determining and validating sterilization process measurements in accordance with one embodiment.

XVII. Operational Method to Validate and Correlate Validated Sterilization Process Measurements Referring to FIG. 23, a flowchart of another method 2300 of determining, correlating and validating sterilization process measurements (VSPM) 1150 is shown. Method 2300 is discussed as being performed using container assembly 400 (FIG. 7A) and sensor module 1050 (FIG. 12B). However, any of the preceding container assemblies 90-800 and electronic sensor modules 200-1080 can be used to perform method 2300. The description of the method is provided with general reference to the specific components illustrated within the preceding figures. In the discussion of FIG. 23, reference will also be made to components from FIGS. 1-20.

Method 2300 describes the steps for an operator to validate and equipment load through a Sterilization Assurance Level Validation. At step 2302, the surgical equipment load is selected and prepared to be validated for a selected sterilization modality for example steam, chemical or hydrogen peroxide. The surgical equipment load includes all items inside of the sterile barrier that is desired to be validated for sterilization. Step 2302 includes the positioning of container 402 onto docking station 1200 or 1300 and if the container has a connector, connecting the corresponding connector 485, 1032 to the docking station. At step 2302, all contents of the container that make up the equipment load are documented. Documentation can include a written bill of materials, an electronic bill of material, descriptions and part numbers of the contents, photographs taken of the contents or a combination of these types of documentation. At step 2302, handheld reader 1240 can be used to scan container 402, tray 160 and the surgical instruments 180 to aid in the documentation of the equipment load.

At step 2304, a biological challenge device, biological indicator or a microorganism inoculation process is used to create a biological challenge for Sterilization Assurance Level Validation. These biological devices or processes include a known number of microorganisms that have a resistance to the mode of sterilization in use. These biological loads are used to determine if the proper sterilization level with a test sterilization process has been achieved for a given equipment load.

At step 2306, the equipment load is placed into container 402 that contains electronic sensor module 460 and is enclosed with cover 450 assembly including appropriate sterile barrier filters 440. At step 2308, data recording software 1155 stored on memory 471, 1022 is triggered to operate on processor 1020. Process measurement validation software 1466 (FIG. 17) acting on docking station processor 1410 (FIG. 17) transmits instructions for data recording software 1155 to monitor and record process measurements during a test sterilization process cycle for storage on the sensor module memory 471, 1022. Data recording software 1155 acting on processor 1020 monitors and records the process measurements during the test sterilization process cycle. At optional step 2310, the sterile barrier appropriate for the type of container and sterilization process is completed prior to placing the container into the sterilizer chamber 52.

The container 402 is placed into the sterilization chamber 52 (FIG. 1) and the test sterilization process cycle within sterilization chamber 52 is started (step 2312). During the sterilization process cycle, the sterilization chamber is heated, pressurized and a sterilant, such as steam or hydrogen peroxide vapor are introduced into the sterilization chamber. The sterilization process cycle typically includes a cool down phase and drawing a vacuum on the chamber to remove any residual and/or condensed sterilant. The sterilization chamber is set to operate using a nominal set of test process parameters.

Also, at step 2312, software 1155 monitors and collects time based data from the respective electronic sensors with which it is in communication during the sterilization process cycle. The sensors measure the environmental characteristics inside the sterile barrier. The collected measurements are stored as data 1156. For example, data recording software 1155 acting on processor 1020 collects water vapor or humidity data from humidity sensor 1024, pressure data from pressure sensor 1026, temperature data from temperature sensor 1028 and hydrogen peroxide concentration data from hydrogen peroxide vapor sensor 1052. Measurement data can be stored into memory 1022 until transferred to docking station memory at step 2320.

After the test sterilization process is complete, the in step 2314 the appropriate tests are executed to determine whether or not the instruments forming the load are sterile to the acceptable level. The means by which theses are performed are not part of the invention.

At decision step 2316, an operator determines the results of the test of step 2314 indicate whether or not the instruments forming the load were acceptably sterilized. If the evaluation of step 2316 tests false, the instruments are subjected to a subsequent test sterilization process, steps 2306-2312 are reelected. the subsequent sterilization process is, prior to the execution of this process, in a step 2318, modified so there is at least one difference between the just executed test sterilization process and the subsequent test sterilization process. This modification to the sterilization process can include increasing one or more process parameters of the sterilization chamber 52. In one embodiment, the temperature level or the process cycle time are increased in step 2318. In another embodiment, step 2318 includes modifying the contents of container 402. For example, fewer surgical instruments 180 are use for the equipment load or a different type of sterile barrier design can be used.

After the execution of the subsequent sterilization process, the instrument load is subjected to the previously described, sterilization testing, step 2314. Step 2316 is reexcuted to determine whether or not the results of the test indicate that the instruments forming the container load were successfully sterilized.

After a sterilization process, the results of the evaluation of step 2316 can test true. When this event occurs, the operator designates the data 1156 recorded by the sensors to determine values as the validated sterilization process measurements (VSPM) 1150 for the load. The VSPM 1150 data are associated to the load in step 2302. After the VSPM 1150 are determined, the operator inputs VSPM 1150 and associated equipment load to docking station 1200, 1300 using keyboard 1426 or an electronic data transfer method and directs VSPM 1150 to be stored to memory 1412 in association with the equipment load.

In another embodiment, process measurement validation software 1466 acting on docking station processor 1410 automatically generates VSPM 1150 from real time measurement data and stores the data on docking station memory 1412 at step 2322. In all embodiments, correlation of the equipment load to the VSPM completes process step 2322 for the desired level of sterilization.

In an optional step 2324, the operator establishes measurement limits for VSPM 1150. Measurement limits include upper and/or lower limit values for one or more process measurements to be included in VSPM 1150. For example, in one embodiment, an operator can determine that a minimum or lower temperature limit for the desired sterilization level is 270° F. for the first 2 minutes and another minimum temperature limit 272° F. for the next 3 minutes. The determination of process limits is performed using data collected from one or more sterilization process validation cycles each with different sterilization processing measurements and conditions. After the process measurement limits are determined, the operator sets the process measurement limits for VSPM 1150 and correlates them to the equipment load using keyboard 1426 or electronic data transfer and directs the process measurement limits to be stored to memory 1412. Additionally, the correlation of VSPM data set to the equipment load is stored to memory 1412. Method 2300 then ends.

Figure 24:
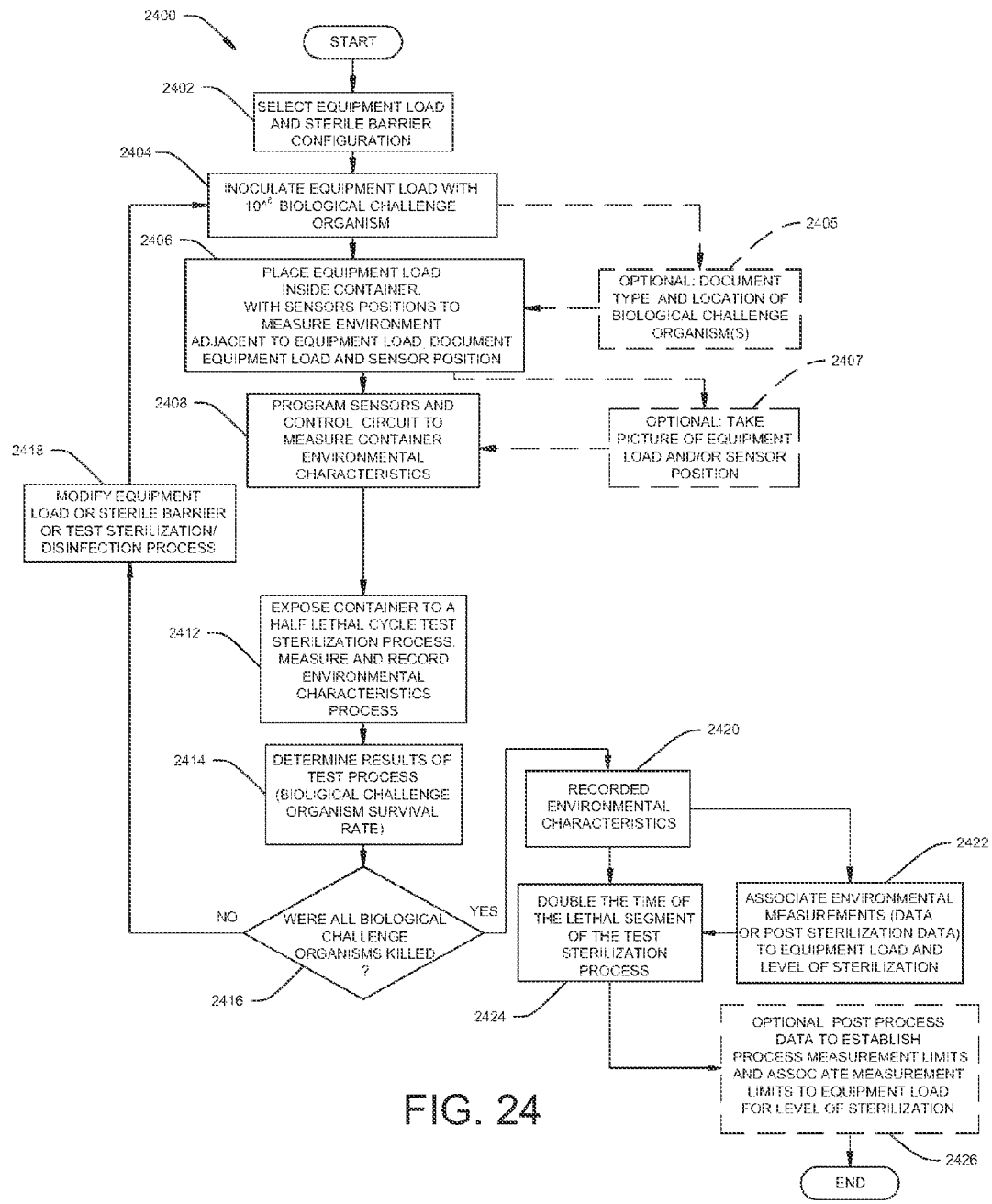
FIG. 24 is flowchart of an additional method of determining and validating sterilization process measurements in accordance with one embodiment.

XVIII. Operational Method to Determine and Correlate Validated Sterilization Process Measurement Using Overkill Methods Referring to FIG. 24, a flowchart of an additional method 2400 of determining and correlating validated sterilization process measurements (VSPM) 1150 is shown. Method 2400 is discussed as being performed using container assembly 400 (FIG. 7A) and sensor module 1050 (FIG. 12B). However, any of the preceding container assemblies 90-800 and electronic sensor modules 200-1080 can be used to perform method 2400. The description of the method is provided with general reference to the specific components illustrated within the preceding figures. In the discussion of FIG. 24, reference will also be made to components from FIGS. 1-20.

Method 2400 starts at step 2402 where the equipment load of surgical instruments 180 is selected for sterilization. The equipment load is defined as all items inside of the sterile barrier which can include not only the surgical instruments 180 but also an instrument rack 160 when present. Instrument racks can aid in affecting sterilization by positioning instruments with difficult to reach locations in preferential orientations for the steriliant to penetrate and perform sterilization. At step 2404, a biological test device or biological challenge organisms are placed within the equipment load typically at a difficult to sterilize location(s). For example, if the equipment load has a instrument with a small diameter and a long closed end lumen, a biological challenge can be placed into the hardest to reach location at the closed end. The biological challenge is processed through the test sterilization process cycle along with the surgical instruments.

The biological challenge carries a biological agent. During a successful sterilization process cycle, the biological agent is typically killed. The biological challenge includes a known number of microorganisms that have a know resistance to the mode of sterilization in use. For validation of a disinfection process, a minimum of 3 log reduction in the number of surviving microorganisms is required. For a biological challenge starting with $10^6$ organisms, a 3 log reduction would result in at least $10^3$ organisms killed. For validation of a sterilization process for an equipment load, a minimum of 6 log reduction in the number of surviving microorganisms is required.

In an optional step 2405, an operator documents the type of biological challenge used and the location of the biological challenge within the equipment load. The operator may enter this information into the docking station using keyboard 1426 or electronic data transfer (i.e. importing scans or documents). In another embodiment, step 2405 includes using a camera to take a picture of the biological challenge locations on the equipment load in container 402 and saving the image captured to docking station memory 1412.

The equipment load is documented and then is placed into container 402 that contains electronic sensor module 460 and is enclosed with cover 450, completing the sterile barrier at step 2406. To document the equipment load, the operator inputs the type and quantity of surgical instruments, the type of tray and other items within the sterile barrier. Container 402 is placed on docking station 1200 or 1300 and connected to the docking station using connector 485.

In another optional step 2407, the operator documents the equipment load of surgical instruments to be sterilized and the location of the sensors within container 402 with a photograph. The photograph can capture the equipment load, the orientation of the instruments and equipment within the load and the type and location of the sensors within the container. Step 2407 includes using a camera to take a picture of the contents and sensors within container 402 and saving the image captured to docking station memory 1412.

At step 2408, data recording software 1155 stored on memory 471, 1022 is triggered to operate on processor 1020. Process measurement validation software 1466 (FIG. 17) acting on docking station processor 1410 (FIG. 17) transmits instructions for data recording software 1155 to monitor and record process measurements during a test sterilization process cycle for storage on the sensor module memory 471, 1022. Data recording software 1155 acting on processor 1020 monitors and records the process measurements during the test sterilization process cycle.

The container 402 is placed into the sterilization chamber 52 by an operator (FIG. 1) and the test sterilization process cycle within sterilization chamber 52 is started (step 2412). The test sterilization process cycle at step 2412 is performed using a one-half test sterilization process within the sterilization chamber 52. For example, a one-half test sterilization process for a standard 4 minute autoclave steam cycle at 270° F. would be a 2 minute autoclave steam cycle at 270° F. In another example, a one-half test sterilization cycle for Hydrogen Peroxide 4 pulse cycle would be a 2 pulse cycle. During the sterilization process cycle, the sterilization chamber 52 is heated, pressurized and a sterilant, such as steam or hydrogen peroxide vapor is introduced into the sterilization chamber according to the half lethal chamber process parameter values.

Also, at step 2412, data recording software 1155 acting on processor 1020 monitors and collects time based data from the respective electronic sensors with which it is in communication during the sterilization process cycle. The sensors monitor the operating process measurements and conditions within the respective container they are mounted. The collected time based measurement data are stored in memory 1022 as data 1156. For example, data recording software 1155 acting on processor 1020 collects humidity data from humidity sensor 1024, pressure data from pressure sensor 1026, temperature data from temperature sensor 1028 and hydrogen peroxide concentration data from hydrogen peroxide gas sensor 1052. These measurements are typically taken simultaneously as a function of time.

After the one-half test sterilization process is completed, the biological challenge is extracted, placed in a growth medium and cultivated for a period of time and then analyzed for microorganism growth. A level of microorganism survival is determined in step 2414. In one embodiment, step 2414 includes determining if a greater than a 6 log reduction in the number of surviving microorganisms has occurred.

At step 2416, an operator determines if 100 percent or the desired quantity of the biological challenge microorganisms have been killed. In response to not all of the microorganisms being killed in step 2414, (i.e. some quantity survived and the level of sterilization is not acceptable), the set of test chamber process parameters can be modified at step 2418 by an operator. The modification of test chamber process measurements can include increasing one or more process parameters of the sterilization chamber 52. In one embodiment, the temperature level or the process cycle time are increased in step 2418. In another embodiment, step 2418 includes modifying the contents of container 402. For example, fewer surgical instruments 180 are placed in tray 160 or a different type of sterile barrier material can be used.

A new biological challenge is placed within the load and method 2400 returns to step 2404 as shown in FIG. 24, where the container 402 is re-processed in sterilization chamber 52 using the new one-half test sterilization chamber process.

In response to all of the microorganisms being killed in step 2414, (i.e. zero percent survival), container 402 is placed on docking station 1200, 1300 and the docking station is connected to container connector 485. Process measurement validation software 1466 acting on docking station processor 1410 reads the recorded measurement data from container memory 1022 and stores the data 1156 on docking station memory 1412 at step 2420.

At step 2422, an operator uses the data 1156 recorded by the sensors and correlates it to the equipment load and level of sterilization. This correlation is based on the received measurement data that were functionally confirmed to act on the biological challenge resulting in the desired level of sterilization.

In another embodiment, process measurement validation software 1466 acting on processor 1410 automatically generates one-half test sterilization values from the time based measurement data.

At step 2424, the lethal portion of the test sterilization process cycle is doubled to generate VSPM 1150. As shown in the previous examples, for an autoclave steam cycle at 270° F. the test cycle time above 270° F. portion of the test sterilization process cycle would be doubled. In another example, the lethal portion of the one-half test sterilization cycle for Hydrogen Peroxide, namely the number of hydrogen peroxide pulses, would be doubled from 2 pulses to 4 pulses. VSPM 1150 could be generated by process measurement validation software 1466. Process measurement validation software 1466 acting on processor 1410 increases the lethal portion of the test process operating time by a factor of two. In an example embodiment, if all of the biological organisms are killed after a lethal process cycle time of 20 minutes, the process cycle time is increased to 40 minutes by process measurement validation software 1466. The new VSPM 1150 with the increased cycle time is then stored to memory 1412. After the VSPM 1150 are determined, the operator inputs VSPM 1150 and correlated equipment load to docking station 1200, 1300 using keyboard 1426 or an electronic data transfer method and directs VSPM 1150 to be stored to memory 1412 in association with the equipment load.

In an optional step 2426, the operator establishes process limits for VSPM 1150. Process limits could include upper and/or lower limit values for one or more process measurements included in VSPM 1150. For example, in one embodiment, an operator can determine that a minimum or lower hydrogen peroxide concentration limit for sterilization processing is 8 mg/L and a maximum or upper hydrogen peroxide concentration limit is 10 mg/L. The determination of process limits could be performed using data collected from multiple sterilization process cycles each with different sterilization processing measurements and conditions. After the process limits are determined, the operator sets the process limits for VSPM 1150 using keyboard 1426 or the process measurement validation software 1466 transfers and directs the process limits to be stored to memory 1412. Additionally, the correlation of VSPM to the equipment load is stored to memory 1412. Method 2400 then ends.

XIX. Operational Method of Monitoring Sterility of Container Contents

Figure 25:
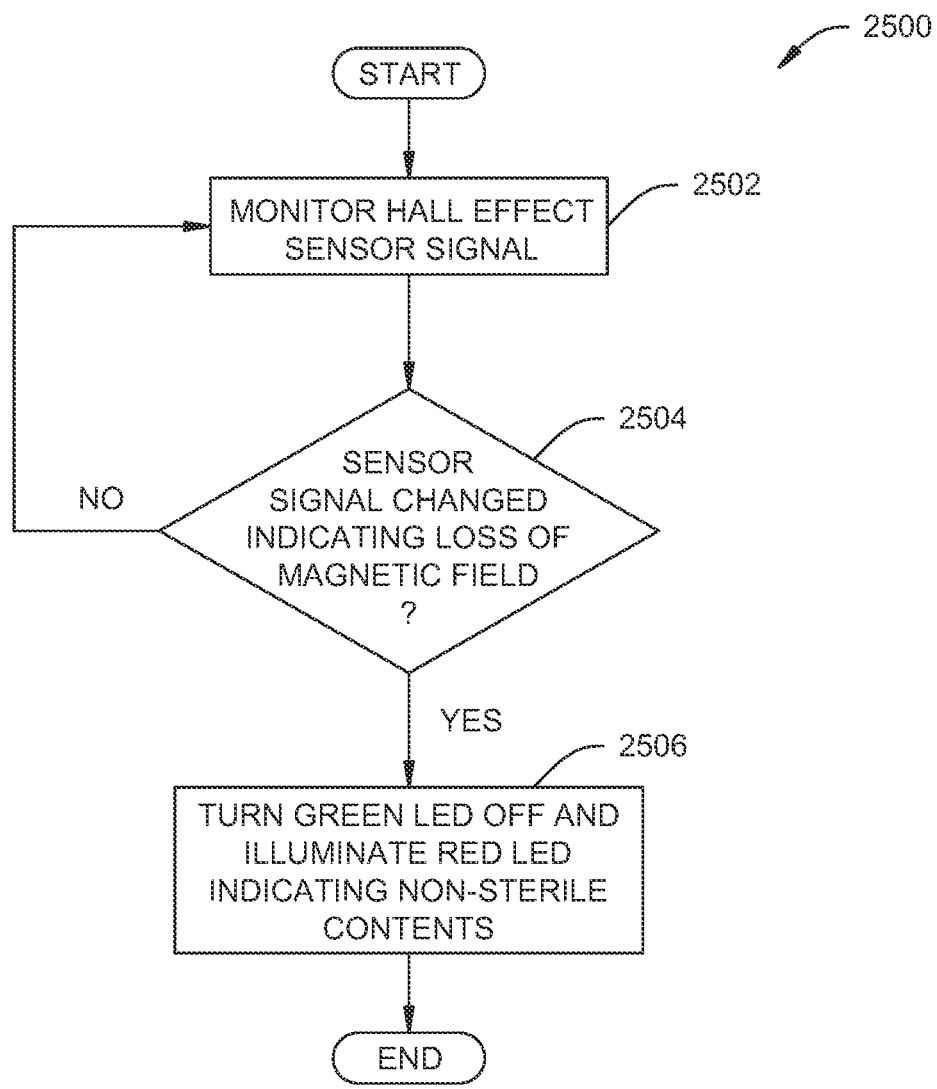
FIG. 25 is flowchart of a method of monitoring sterility of a container assembly in accordance with one embodiment.

Referring to FIG. 25 a flowchart of a method 2500 of monitoring sterility of the contents of container is illustrated. Method 2500 is particularly described as being performed using container assembly 400 (FIG. 7A). However, method 2500 can be utilized with any of the previously described container assemblies. The description of the method is provided with general reference to the specific components illustrated within the preceding figures. In the discussion of FIG. 25, reference will also be made to components from FIGS. 7A-7D, and 14 and sensor modules 200.

Method 2500 starts at step 2502 where sterile monitor software 1158 acting on processor 1020 monitors the electrical signals transmitted from Hall effect sensors 480. At step 2504, sterile monitor software 1158 determines if the Hall effect sensor signal has changed to indicate that the magnetic field is no longer detected.

In response to no change in the Hall effect sensor signal, sterile monitor software 1158 acting on processor 1020 continues to monitor the electrical signals transmitted from Hall effect sensors 480 (step 2502). In response to a change in or loss of the Hall effect sensor signal, sterile monitor software 1158 acting on processor 1020 causes the green LED of LEDS 487 to turn off and causes the red LED of LEDS 487 to be illuminated at step 2506 indicating the container latch was changed potentially allowing a breach to sterilization inside container. The Hall effect sensor signal changes with latch 446 movement or cover 450 movement like lifting away from container 402 or is removed from container 402. When the magnets 448 are moved away from Hall effect sensors 480 causing a loss of magnetic field to sensors 480. The lighting of the red LED indicates that the contents of container 402, such as surgical instruments 180, are at an increased risk of a sterile breach or are no longer sterile. Method 2500 then terminates.

XX. Operational Method of Loading Surgical Instruments into a Container

Figure 26:
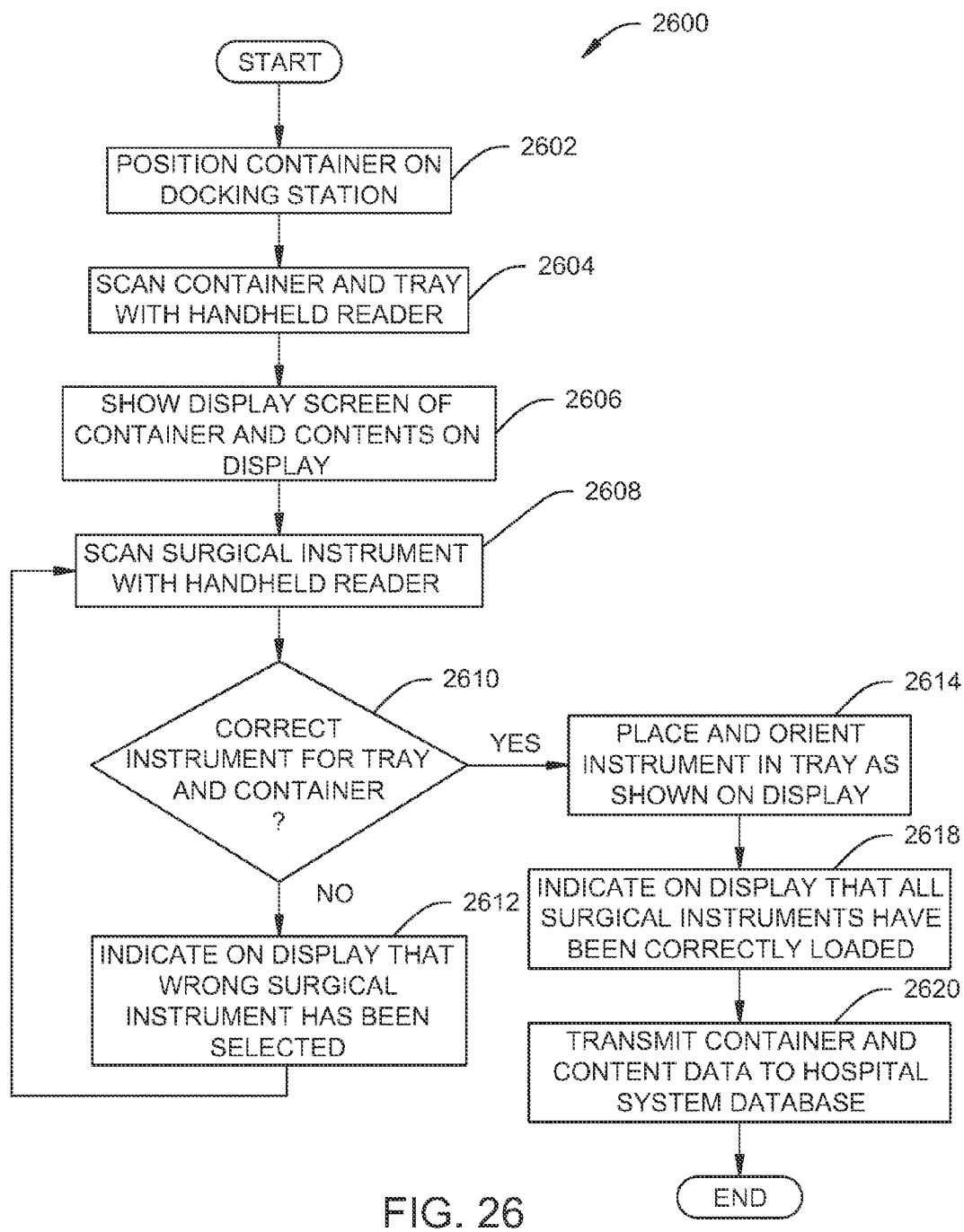
FIG. 26 is flowchart of a method of loading surgical instruments into a container assembly prior to sterilization in accordance with one embodiment.

Referring to FIG. 26 a flowchart of a method 2600 of loading surgical instruments into a container prior to sterilization processing is shown. Method 2600 is explained as being performed using container assembly 100 (FIGS. 2-4C) and docking station 1200 (FIG. 15). However, method 2500 can be utilized with any of the described container assemblies with sensor modules or docking stations. The description of the method is provided with general reference to the specific components illustrated within the preceding figures. In the discussion of FIG. 26, reference will also be made to components from FIGS. 2-4C, 15 and 17.

Method 2600 begins at step 2602 where an operator positions container 100 to rest on docking station shelf 1212. In an optional step, electronic sensor module 200 is connected to docking station 1200 for communication via cable 146.

At step 2604, the operator scans the bar code or RFID tag 135 on container 100 and the bar code or RFID tag 167 on tray 160 using handheld reader 1240. At step 2606, container loading software 1464 acting on processor 1410, searches container/tray configuration data 1465, selects a display screen 1260 from data 1465 corresponding to the respective scanned bar codes and RFID tags and causes the display screen 1260 to be shown on display 1230. The display screen 1260 illustrates the surgical instruments 180 to be loaded into tray 160 and the correct position and orientation of the surgical instruments 180 to be loaded.

The operator scans a first surgical instrument bar code or RFID tag 181 at step 2608 using handheld reader 1240. At decision step 2610, container loading software 1464 acting on processor 1410, determines if the scanned surgical instrument 180 is a correct surgical instrument to be loaded into tray 160 using container/tray data 1465.

In response to the scanned surgical instrument 180 being incorrect to load into tray 160, container loading software 1464 acting on processor 1410, indicates that the wrong surgical instrument has been selected for loading by changing the video screen 1260 at step 2612. In one embodiment, a red warning sign is flashed on display 1230 and an alarm sounded instructing the operator that they have selected an incorrect instrument. Method 2600 then returns to step 2608 where the next surgical instrument 180 to be loaded is scanned by the operator.

In response to the scanned surgical instrument 180 in step 2608 being correct to load into tray 160, the operator places the surgical instrument 180 into tray 160 with reference to the position and orientation information illustrated on display screen 1260 (step 2614). Display screen 1260 guides the operator during placement of surgical instruments into tray 160.

While not shown as a separate step, the container loading software 1464 running on processor 1410 determines if the tray 160 is fully loaded with surgical instruments 180. If this evaluation tests negative, the operator in a reexecution of step 2608 scans the next instrument 180 to be loaded. When the evaluation determines the tray is full the processor 1410 at step 2618 causes a display screen 1260 to indicate all of the surgical instruments are loaded into tray 160 and that container 100 is ready for further processing.

At step 2616, container loading software 1464 acting on processor 1410, transmits container/tray data 1465 to hospital computer system 1454 to update database 1456 with the current location and status of the loaded container, tray and surgical instruments. In an example embodiment, container/tray data 1465 updates database 1456 with the location of container 100, the specific surgical instruments 180 contained in tray 160 and that the container and contents are currently not sterile.

XXI. Operational Method of Calibrating Sensors

Figure 27:
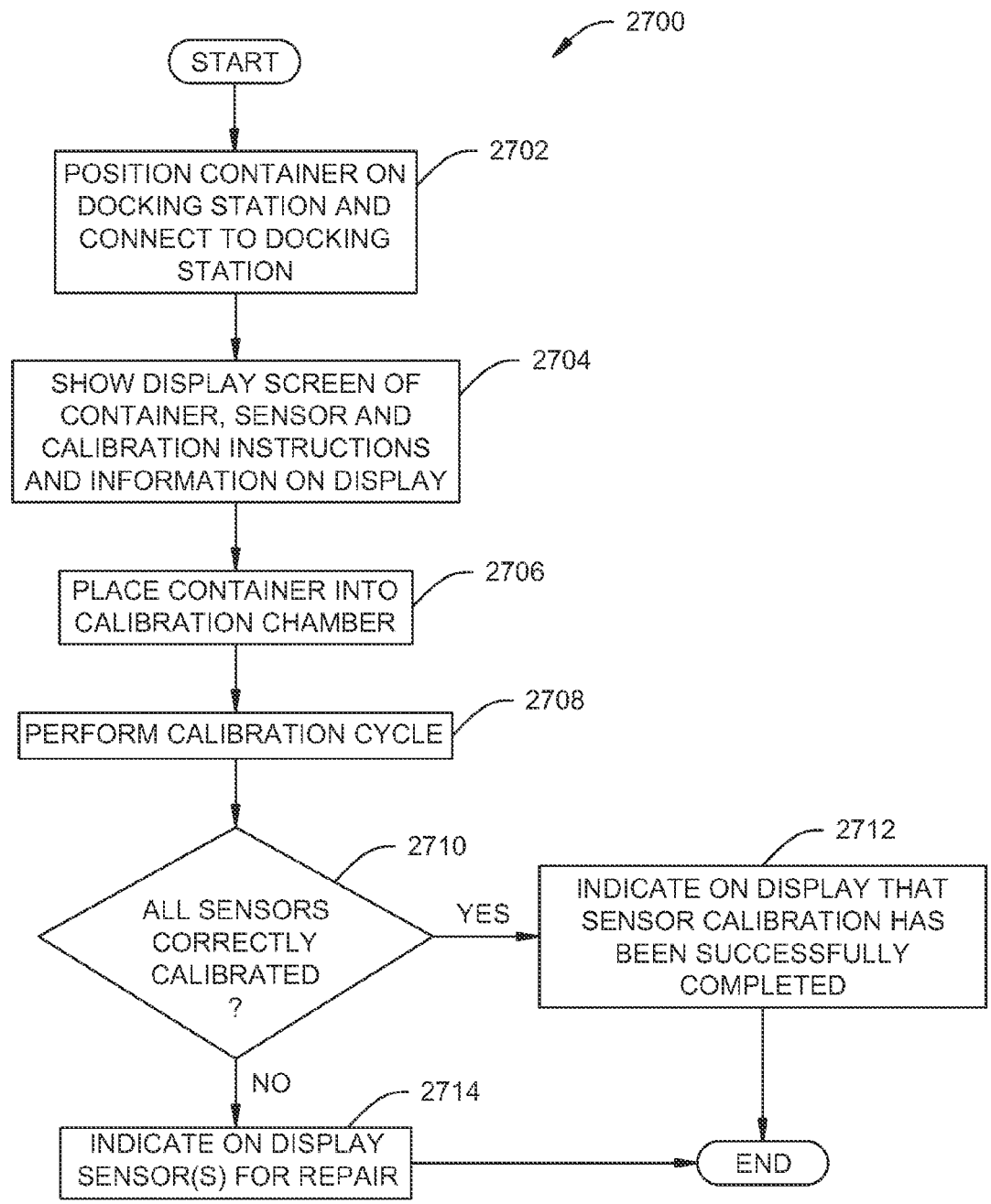
FIG. 27 is flowchart of a method of calibrating sensors in accordance with one embodiment.

Referring to FIG. 27, a flowchart of a method 2700 of calibrating sensors or verifying sensor accuracy and electronic sensor modules is shown. Calibration and sensor accuracy verification is used to check (verify) and/or adjust (calibration) the sensor response to a known set of simulated or generated environment conditions. Calibration and sensor accuracy verification methods are used to insure sensor measurements are accurate when used to generate VSPM data or verify VSPM data with sensor modules. Method 2700 is explained as being performed using container assembly 400 (FIGS. 7A-7C), sensor module 1050 (FIGS. 12B, 14) and docking station 1300 (FIGS. 16, 17). However, method 2700 can be utilized with any of the sensor modules described herein. The description of the method is provided with general reference to the specific components illustrated within the preceding figures.

Method 2700 begins at step 2702 where an operator positions container assembly 400 to rest on docking station shelf 1342 or into calibration chamber 1320 and connects docking station cable 1340 to container connector 485. The operator also connects docking station connectors 1336 and 1338 together such that docking station 1300 is in communication with container assembly 400 for sensor calibration. More specifically, docking station controller 1402 is in communication with electronic sensor module controller 1120.

At step 2704, sensor calibration software 1460 acting on processor 1410, causes a display screen 1260 to be shown on display 1230. If the sensor module has sensors that require calibration or require sensor performance verification, the display screen 1260 illustrates the container 402 and sensors to be calibrated and operator instructions to affect a proper calibration or sensor verification. If not already positioned, the operator places container assembly 400 into calibration chamber 1320 and closes door 1326.

For example at step 2708, sensor calibration software 1460 acting on processor 1410, causes calibration chamber 1320 and electronic sensor module 1050 to execute a sensor calibration process or sensor verification cycle. Depending on the type of sensors that require calibration or verification, various systems within the docking station are be used independently or in combination to calibrate or verify sensor accuracy. Sensor calibration process at step 2708 may include turning on and operating steam generator 1430, hydrogen peroxide generator 1432, pressure pump 1434, vacuum pump 1436 and heater 1438. Steam generator 1430, hydrogen peroxide generator 1432, pressure pump 1434, vacuum pump 1436 and heater 1438 all operate according to a pre-defined set of calibration operating parameters generated by sensor calibration software 1460 acting on processor 1410 and transmitted via input/output interface circuit 1414.

During the sensor calibration cycle at step 2708, steam generator 1430 supplies a standard concentration of steam to calibration chamber 1320 and hydrogen peroxide generator 1432 supplies a standard concentration of hydrogen peroxide gas to calibration chamber 1320. Pressure pump 1434 increases the pressure in calibration chamber 1320 to a standard pressure during the first part of the calibration cycle. Vacuum pump 1436 draws a standard vacuum level in calibration chamber 1320 during the later part of the calibration cycle. Heater 1438 heats calibration chamber 1320 to a pre-determined standard temperature. One or more states of each generator system can be generated in order to affect a known single point, two point or multiple point parameter state to calibrate or verify the sensor response.

In another embodiment at step 2708, sensor calibration software 1460 acting on processor 1410, triggers sensor calibration software 1154 acting on processor 1020 to operate one or more generator systems to calibrate water vapor sensor 1024, pressure sensor 1026, temperature sensor 1028 and hydrogen peroxide sensor 1052.

At step 2710, sensor calibration software 1460 acting on processor 1410, queries and receives feedback from calibration software 1154 acting on processor 1020 as to the success or failure of the calibration process on each sensor. Calibration software 1460 acting on processor 1410, determines if all of the sensors have been correctly calibrated or verified to the within specified accuracy.

In response to one or more of the sensors 1024-1052 not being correctly calibrated to the specified calibration measurements, the specific sensor(s) are identified and flagged for inspection and repair at step 2714. Calibration software 1460 acting on processor 1410, causes a display screen 1260 to be shown on docking station 1300 indicating the defective sensor(s). In another embodiment, calibration software can instruct sensor module to provide a visual indication, for example using flashing LEDs, to the operator that a calibration failure occurred. Method 2700 then ends.

In response to the sensors 1024-1052 being correctly calibrated and/or verified to the specified measurements, the sensors are indicated as being successfully calibrated at step 2712. Calibration software 1460 acting on processor 1410, causes a display screen 1260 to be shown on docking station 1300 indicating that all of the sensors 1024-1052 in container assembly 400 have been correctly calibrated or verified and are ready to be used in their appropriate sterilization process. Method 2700 then terminates.

In alternative versions of the invention, sensor calibration software 1460 is set to require the calibration of the sensors based on the number of times the sensors are used.

XXII. Method of Monitoring Container Usage and Billing on a Fee Per Use Basis

Figure 28:
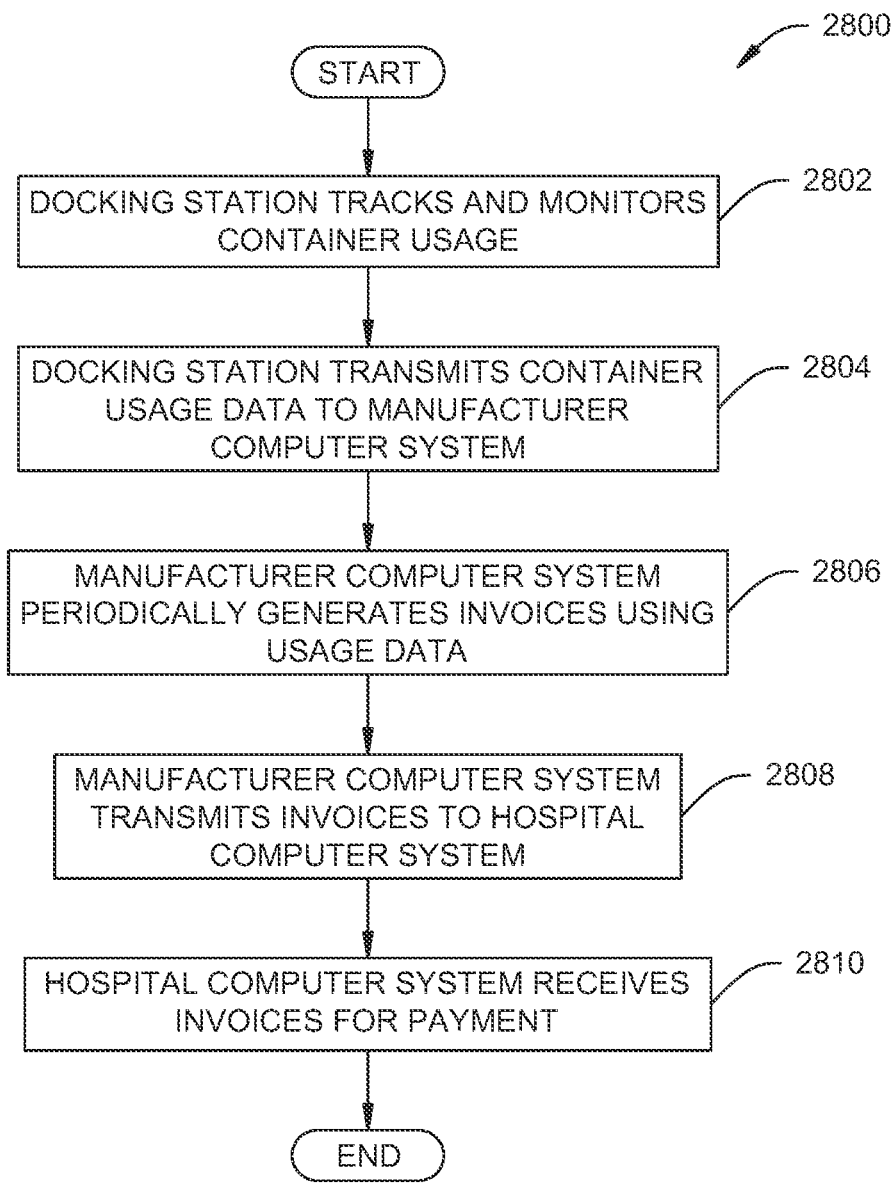
FIG. 28 is flowchart of a method of monitoring container usage and billing on a fee per use basis in accordance with one embodiment.

Turning to FIG. 28, a flowchart of a method 2800 of monitoring container usage and billing on a fee per use basis is shown. Method 2800 is explained as being performed using docking station 1200 (FIG. 18), manufacturer computer system 1510 (FIG. 18) and hospital computer system 1454 (FIG. 18). Method 2800 is used with any of the previously described containers 90-800. Method 2800 is described with reference to FIG. 18 and FIG. 28.

Method 2800 begins at step 2802 where usage software 1470 operating on processor 1410 monitors and tracks the usage of containers or sensor modules within a medical facility. When docking station 1200 is used during container loading and/or sensor programming typically prior to sterilization, usage software 1470 tracks the frequency of use of the containers or sensors, generates usage data 1472 and stores the usage data to memory 1412. In another embodiment, usage software 1472 reads the sensor module memory and extracts usage data for processing. In yet another embodiment, usage software 1472 clears or resets usage data in sensor module memory. Usage software 1470 operating on processor 1410 periodically transmits usage data 1472 to manufacturer computer system 1510 at step 2804. In one embodiment, usage data 1410 is transmitted on a weekly basis from docking station 1200 to manufacturer computer system 1510.

At step 2806, invoice software 1530 acting on manufacturer computer system processor 1520 periodically generates invoices 1532 based on usage data 1472. The invoices are stored to memory 1522. Invoice software 1530 operating on processor 1520 periodically transmits invoices 1532 to hospital computer system 1454 at step 2808. In one embodiment, invoices 1532 are generated and transmitted on a weekly basis from manufacturer computer system 1510 to hospital computer system 1454. At step 2810, hospital computer system 1454 receives invoices 1532 and stores the invoices to memory 1572 for payment processing. Method 2800 then ends.

Method 2800 is used in conjunction with a business model where docking station 1200, sensor modules or containers 90-800 are leased or rented to a medical facility or hospital. The medical facility or hospital pays for using the docking stations, sensor modules and containers on a fee per use basis as determined by usage software 1470 and invoice software 1530.

XXIII. Container with Removable Sensors

FIGS. 29-39 illustrate a container assembly 2900 with removable sensors. With specific reference to FIGS. 29 and 30, container assembly 2900 comprises container 2902 and a removable sensor apparatus 3000. Removable sensor apparatus 3000 is described below including an optional embodiment that contains a tamper evident sterile barrier monitoring system. This optional embodiment temper evident sterile barrier monitoring system is described below using one or more magnets and hall effect sensors. Other tamper evident systems, like breakable plastic mechanical locks, can be used to notify operators that the sterile barrier has been tampered with and these other tamper evident systems can be combined with removable sensor apparatus 3000.

Figure 29:
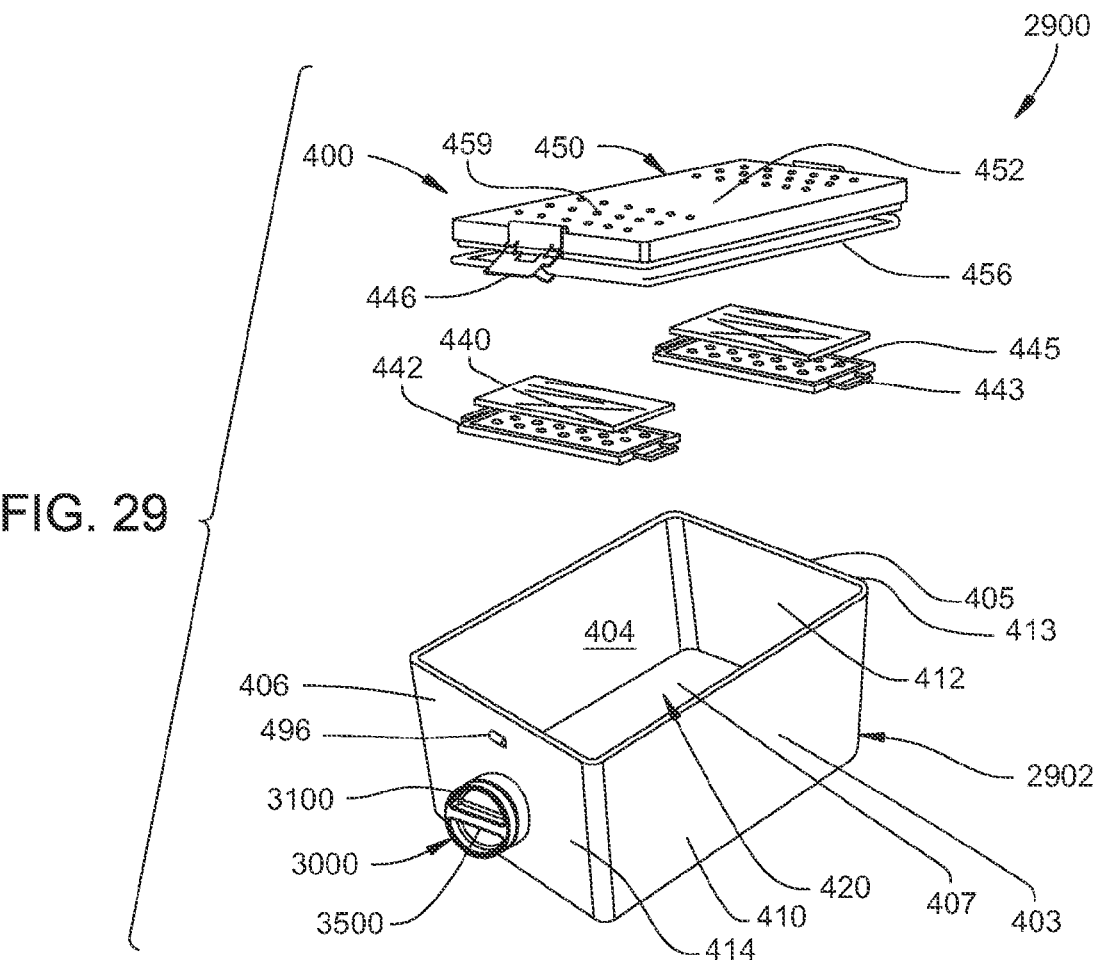
FIG. 29 is top perspective view of a container and cover for sterilization of medical/surgical instruments that includes a removable sensor assembly in accordance with one embodiment.
Figure 30:
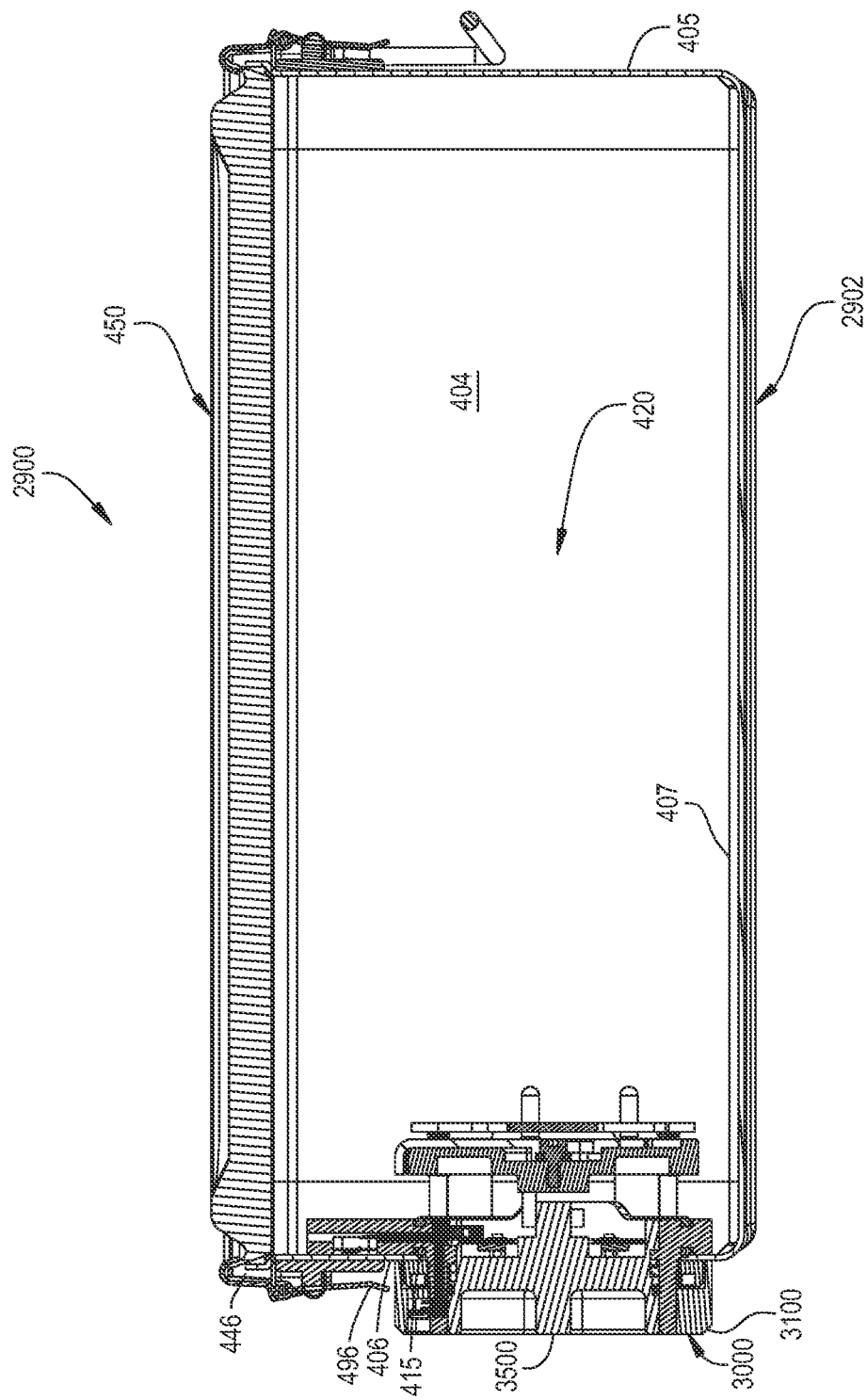
FIG. 30 is a cross sectional view of the container of FIG. 29 illustrating the removable sensor assembly mounted to the container.

Container 2902 of FIGS. 29 and 30 is the same as the previously described container 402 of FIG. 7A except that rectangular shaped openings 414 and 418 in side panel 406 have been omitted and a circular shaped opening 415 has been added in side panel 406. Cover 450 of FIGS. 29 and 30 is the same as the previously described cover 450 of FIG. 7A except that magnet 488 has been removed from cover 450 and mounted to the interior facing surface of container lid latch 496 (see FIG. 41). Cover 450 includes disposable filters 440 that are retained to cover 450 by filter support members 442.

Filters 440 are formed from a microbial barrier material that is permeable to sterilant. Filter 440 allows sterilant to pass from the outside of cover 450, through holes 459, through filter 440, through apertures 445 and into interior cavity 420 of container 2902 where the sterilant contacts surgical instruments contained therein. Filters 440 also form a microbial barrier preventing microorganisms from entering into container assembly 2900 after processing through a sterilization process. Filters can be present on one or more other container panels in replacement of or in addition to lid filter shown in container assembly 2900. This allows one or more filtered paths for sterilization agents to enter and exit container assembly while maintaining a microbial barrier.

A tray 160 (FIG. 2) containing surgical instruments 180 (FIG. 2) to be sterilized is placed into container 2902 so that tray 160 rests on bottom panel 407. Cover 450 is retained to container 2902 using locking lid latch 496. Locking lid latch 496 is rotated by a user upwardly over cover steps 446 and then downwardly to a locked position where cover 450 is retained to and locked to container 2902.

Figure 31:
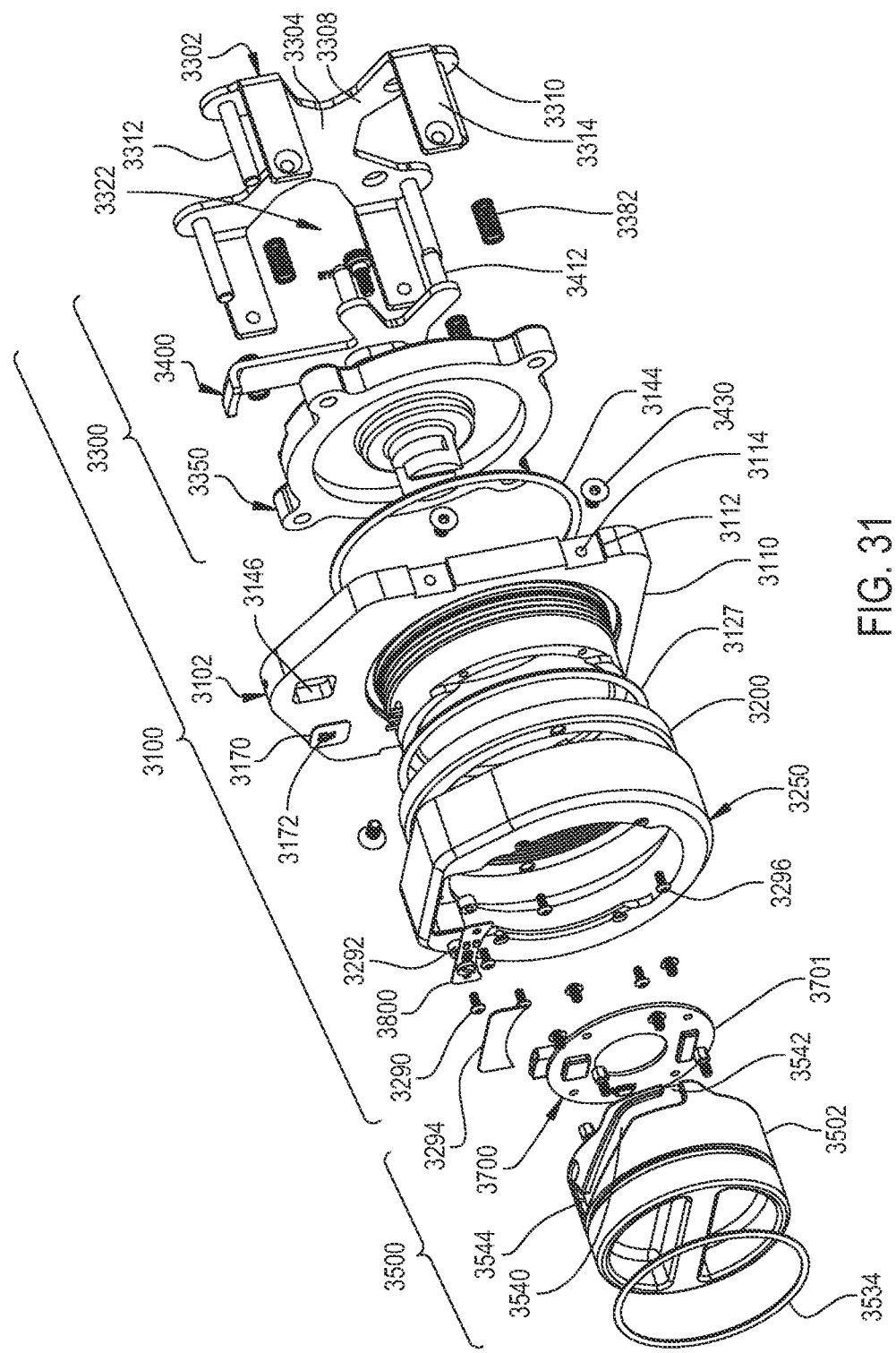
FIG. 31 is an exploded perspective view of the removable sensor assembly of FIG. 29.
Figure 32:
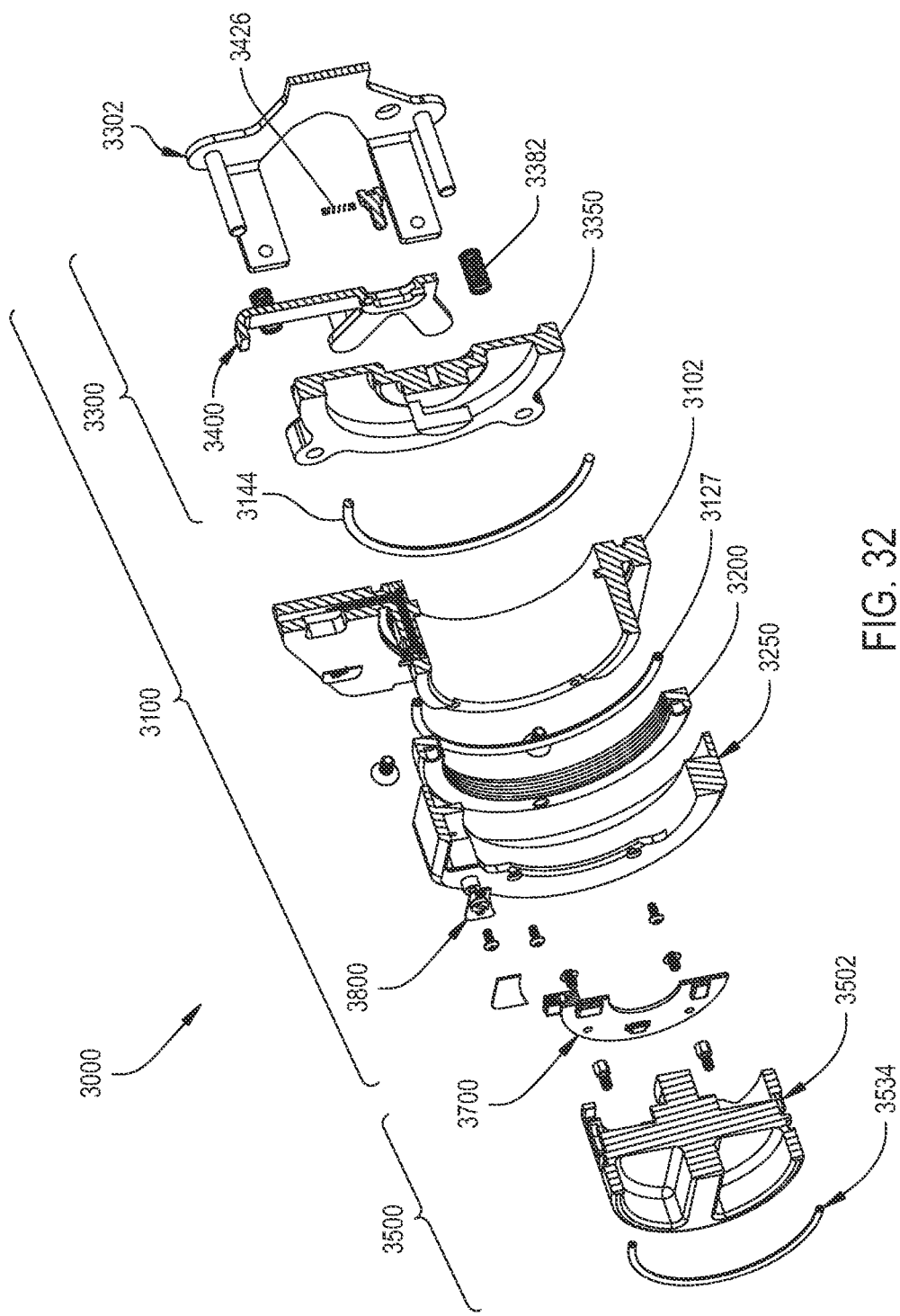
FIG. 32 is an exploded cross-sectional perspective view of the removable sensor assembly of FIG. 29.
Figure 33:
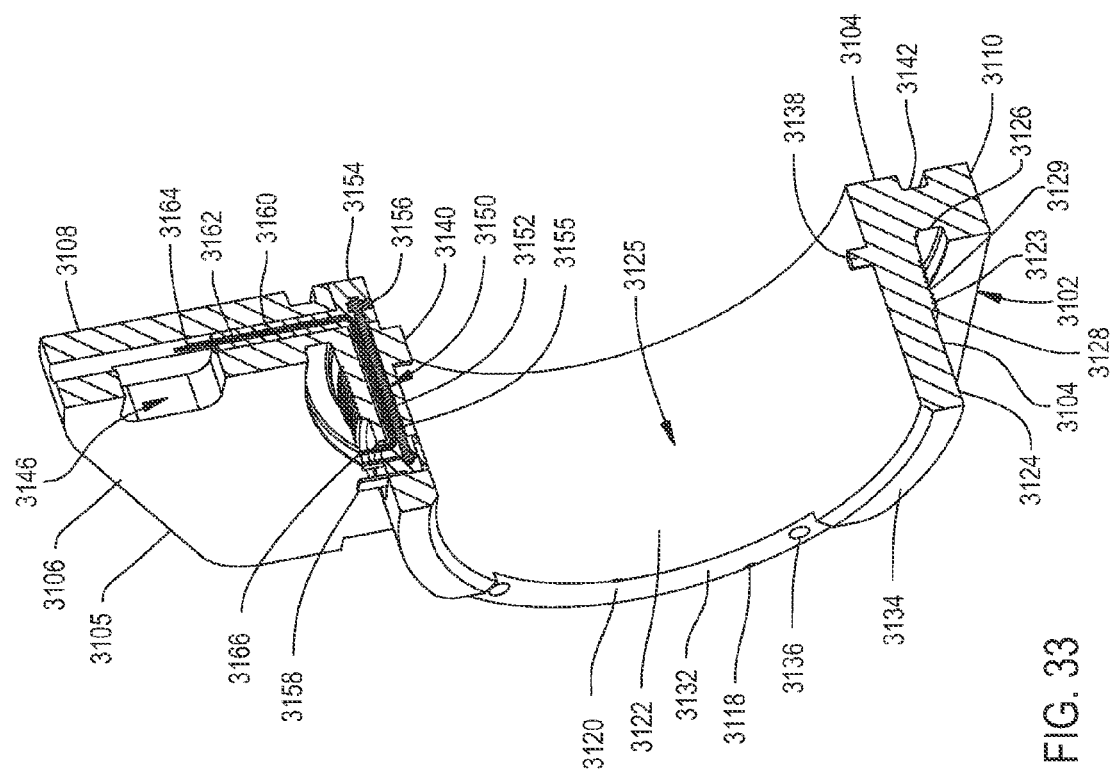
FIG. 33 is an enlarged cross sectional view of the receiver housing.

Referring to FIGS. 31, 32 and 33, details of removable sensor apparatus 3000 are shown. Removable sensor apparatus 3000 comprises a sensor module receiver 3100 and a removable sensor unit, device or module 3500. Removable sensor unit or module 3500 can be inserted into and removed from sensor module receiver 3100.

Sensor module receiver 3100 includes receiver housing 3102, retaining ring 3200, housing cover 3250, carriage assembly 3300 and lock mechanism 3400 all of which can be formed from injection molded plastic or metals. Receiver housing 3102 has a generally square shaped central body 3104 with an integral attached triangular shaped extension 3105. Body 3104 has a front surface 3106, rear surface 3108 and five sides 3110. Two slots 3112 are defined in two of the sides 3110. The sides 3110 with the slots are parallel and diametrically opposed to each other on opposite sides of body 3104. The length of slots 3112 are defined by the thickness of body 3104. Threaded bores 3114 are defined at the base of each slot 3112. Bores 3114 extend perpendicularly from the base of each slot 3112 partially into body 3104.

With specific reference to FIG. 33, a cylindrical sleeve 3118 extends perpendicularly away from front surface 3106 and terminates at a distal end 3120. A step 3128 is located on the sleeve outer surface and is positioned approximately half way between distal end 3120 and a groove 3126. Step 3128 separates a proximal annular outer surface 3123 and a distal annular outer surface 3124. Proximal annular outer surface 3124 has a larger diameter than distal annular outer surface 3124. Threads 3129 are defined on outer surface 3123. Sleeve 3118 further includes an inner annular surface 3122 that defines a thru bore 3125. Annular groove 3126 is located in body front surface 3106 surrounding sleeve 3118 at the base or proximal end of sleeve 3118. Groove 3126 is dimensioned to receive container O-ring 3127 (FIG. 32). O-ring 3127 is seated in groove 3126. After assembly, container O-ring 3127 forms a seal between receiver housing 3102 and container panel 406 by compressing seal 3127 between interior panel surface 412 of pane 406 through threaded compression with retaining ring 3200.

Two diametrically opposed portions of distal end 3120 are removed to define diametrically opposed arcuate shaped recesses 3132. The remaining portions of distal end 3120 form two diametrically opposed arcuate shaped shoulders 3134. The inner most edges of shoulders 3134 adjacent inner annular surface 3122 are beveled. Two threaded bores 3136 are defined in the base of each recess 3132. Bores 3136 extend perpendicularly from the base of each recess 3132 partially into sleeve 3118.

Fingers 3138 and 3140 extend perpendicularly away from inner annular surface 3122 partially into thru bore 3125. Fingers 3138 and 3140 are diametrically opposed to each other on opposite sides of bore 3125 and are located toward the proximal end of bore 3125. Finger 3140 has a larger width than finger 3138.

Annular groove 3142 is located in body rear surface 3108 spaced from and surrounding the opening of thru bore 3125. Groove 3142 is dimensioned to receive O-ring 3144 (FIG. 32). The O-ring 3144 is seated in groove 3142. The O-ring 3144 forms a seal between receiver housing 3102 and plate 3350. In some versions of the invention an adhesive is used to hold O-ring 3144 in groove 3412. A rectangular shaped chamber 3146 is defined in triangular extension 3105 and has an opening towards front surface 3106. Chamber 3146 is dimensioned to receive a printed circuit board as will be described later.

A terminal assembly 3150 is mounted in receiver housing 3102. Terminal assembly 3150 includes several elongated electrically conductive terminals 3152 that are electrically separated by an insulator 3154. Terminals 3152 are formed from a conductor material such as a copper alloy. Insulator 3154 is a material such as polyimide that is molded around terminals 3152 to form terminal assembly 3150.

In one embodiment, terminal assembly 3150 is placed in the same mold that is used to injection mold receiver housing 3102 from plastic. In another embodiment, terminal assembly 3150 is hermetically sealed to receiver housing 3102. After molding or sealing, terminal assembly 3150 is an integral part of receiver housing 3102. Terminal assembly 3150 defines an internal passage 3155 within sleeve 3118 through which terminals 3152 extend.

In another embodiment, terminal assembly 3150 is a flexible circuit that is inserted into internal passage 3155 within sleeve 3118. The flexible circuit is then held in place using a silicone adhesive or other appropriate curable adhesive or sealant.

Terminals 3152 further have flush proximal contact ends 3156 that face towards bore 3125. Terminals 3152 also have distal contact ends 3158 that extend perpendicularly away from the sleeve outer surface 3124. Contact ends 3156 and 3158 are electrically connected to other electrical components as will be described later. In another embodiment, another set of terminals 3160 may extend through passage 3155 and through another passage 3162 defined in extension 3105. Terminals 3160 have ends 3164 that terminates in chamber 3146 and ends 3166 that extends perpendicularly away from sleeve outer surface 3124 and are adjacent to contact ends 3158.

With additional reference to FIG. 31, an optional embodiment may contain an electronic sterile barrier monitoring system with Hall Effect printed circuit board 3170 which has an attached Hall Effect sensor 3172. Hall Effect printed circuit board 3170 is mounted in chamber 3146 and is electrically connected to terminal ends 3164 by suitable methods such as soldering or wire bonding. Hall Effect sensor 3172 detects the presence or absence of magnet 448 (FIG. 29). When cover 450 is mounted and latched to container 2902, Hall Effect sensor 3172 detects the magnetic field generated by magnet 448 and transmits an electrical signal indicating a detected magnetic field. When cover 450 is removed from container 2902, lid latch 496 is pivoted away from Hall Effect sensor 3172 causing sensor 3172 to detect the absence of a magnetic field and transmits an electrical signal indicating no magnetic field.

Figure 34:
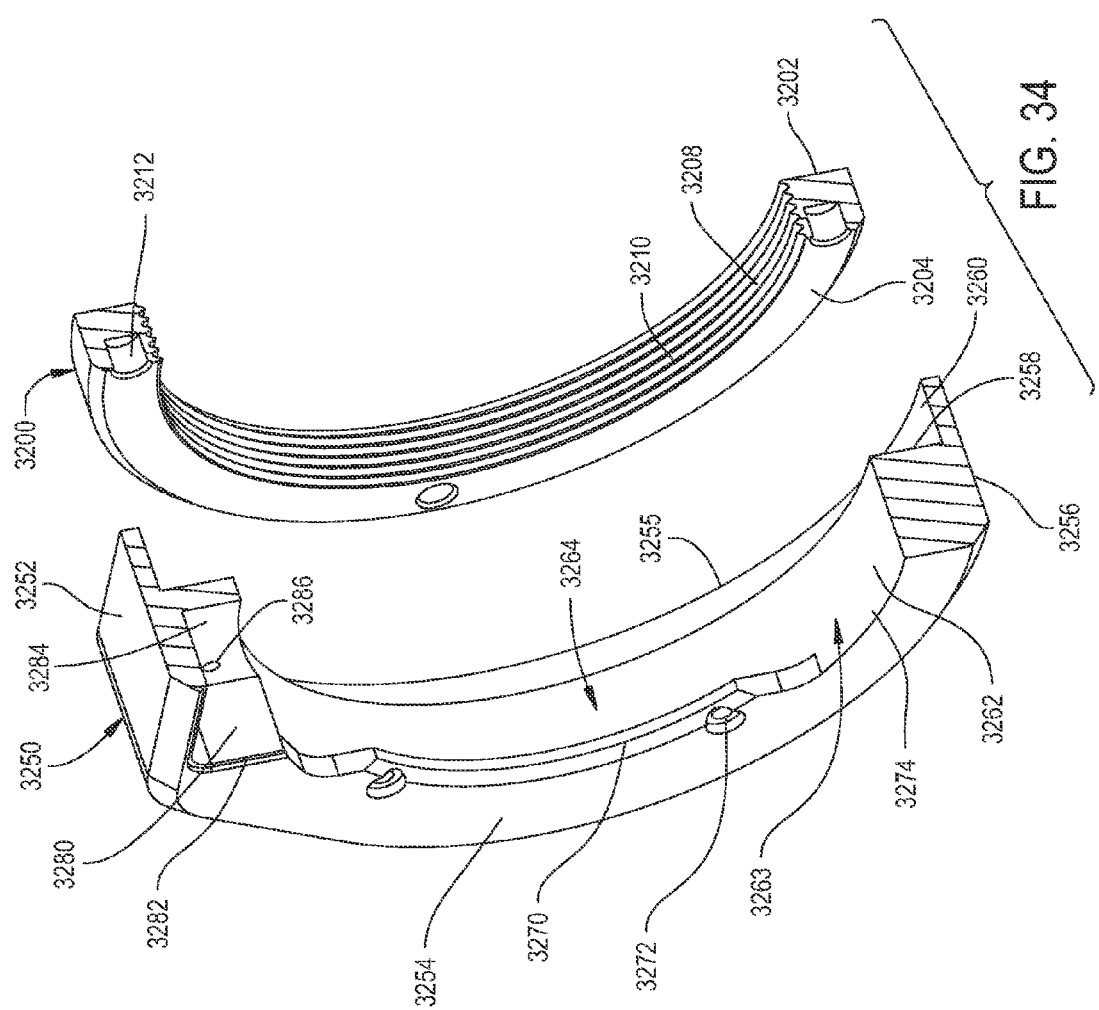
FIG. 34 is an enlarged cross sectional view of the receiver cover and retaining ring.

Turning to FIG. 34, details of retainer ring 3200 and cover 3250 are shown. Retainer ring 3200 is generally round in shape and has a proximal face 3202, a distal face 3204, an outer annular surface 3206 and an inner annular surface 3208. The outer peripheral edge of distal face 3204 is beveled. Threads 3210 are defined in inner annular surface 3208. Retainer ring threads 3210 mate with receiver housing threads 3129 in order to secure and seal sensor module receiver 3100 to container 2902. Threaded bores 3212 extend perpendicularly from distal face 3204 partially into retainer ring 3200.

Cover 3250 is generally round in shape with an extended section 3252. Cover 3250 has a distal face 3254, a proximal rim 3255, an outer annular surface 3256 and an inner step 3258. Inner step 3258 defines inner annular surface 3262. Inner annular surface 3262 terminates at proximal face 3254 and defines an opening 3263. A circular skirt 3260 extends in a proximal direction away from step 3258 and terminates at rim 3255. Skirt 3260 and annular surface 3262 defines thru bore 3264. The outer peripheral edge of distal face 3254 is beveled.

Two diametrically opposed arcuate ribs 3270 extend perpendicularly from inner annular surface 3262 into bore 3264. The inner edges of ribs 3270 are beveled. The distal facing surface of ribs 3270 is flush with proximal face 3254. Two holes 3272 are defined in each rib 3270. Holes 3272 extend entirely through rib 3270. Ribs 3270 define two diametrically opposed arcuate gaps 3274 located between each of ribs 3270.

Extended section 3252 is formed with a rectangular circuit board holder 3280. Holder 3280 includes a distal facing opening 3282 and a bottom wall 3284. Holder 3280 is open at distal face 3254. Apertures 3286 are defined in bottom wall 3284.

With additional reference to FIG. 31, a container printed circuit board (PCB) 3800 is mounted and retained in holder 3280. Opening 3282 is dimensioned to receive PCB 3800. Specifically, PCB 3800 is fastened to bottom wall 3284 by self tapping screws 3290 threaded into apertures 3286. Standoffs 3292 are positioned between bottom wall 3284 and PCB 3800 in order to space PCB 3800 from bottom wall 3284. Screws 3290 also extend through standoffs 3292. The components of container PCB 3800 will be described later. A transparent lens 3294 is mounted to distal face 3254 covering opening 3282. Lens 3294 allows a user to visually see light emitting diodes mounted to PCB 3800. Lens 3294 is attached to distal face 3254 using ultrasonic welding or is heat staked.

PCB 3800 is electrically connected to terminal assembly 3150 (FIG. 33). Specifically, PCB 3800 is connected to terminal ends 3158 and 3166 by suitable methods such as soldering or wire bonding. PCB 3800 is in communication with optional embodiment containing Hall Effect PCB 3170 via terminals 3160 (FIG. 33).

Retainer ring 3200 is attached to receiver housing 3102 by the mating of retainer ring threads 3210 with receiver housing threads 3129. Next, cover 3250 is mounted to retainer ring 3200. Cover 3250 is aligned with receiver housing 3102 and moved in the proximal direction so that cover ribs 3270 slide or fit into receiver housing gaps 3138 and receiver housing shoulders 3134 slide or fit into cover gaps 3274.

Cover 3250 contacts retainer ring 3200 such that cover step 3258 abuts ring distal face 3204 and cover skirt 3260 surrounds ring outer annular surface 3206. Fasteners such as screws 3296 extend through rib holes 3272 and are retained in threaded bores 3212 thereby attaching cover 3250 to retainer ring 3200.

Figure 35:
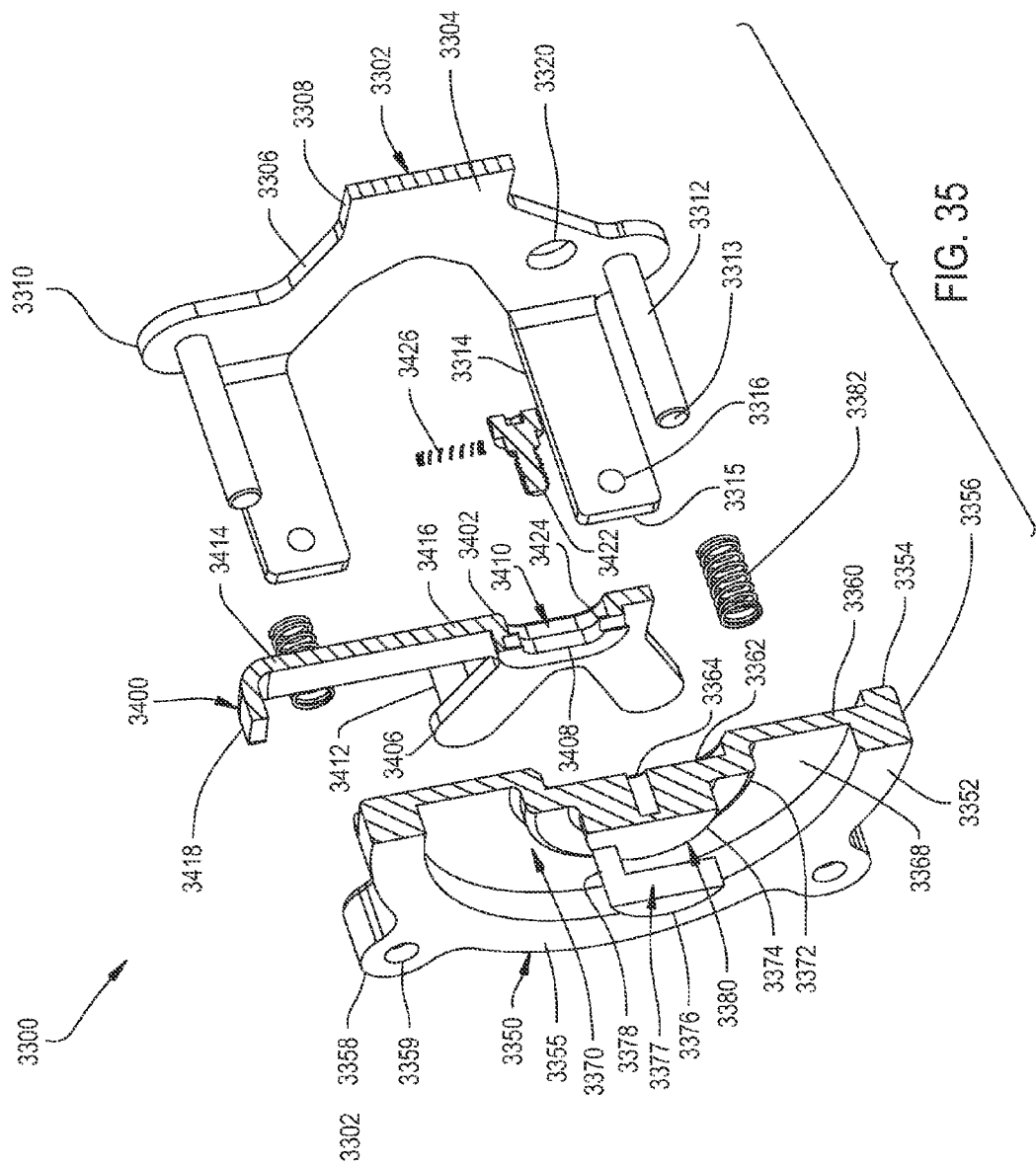
FIG. 35 is an enlarged cross sectional view of the carriage assembly.

Referring now to FIGS. 31 and 35, sensor module receiver 3100 further includes a carriage assembly 3300. Carriage assembly 3300 is attached to receiver housing 3102. Carriage assembly 3300 guides the movement of plate 3350 between the open and closed positions of the plate. Carriage assembly 3300 comprises support bracket 3302, plate 3350 and lock mechanism 3400.

Support bracket 3302 includes a base 3304 with four orthogonal arms 3306 extending away from base 3304. Arms 3306 form an X-shape. Each arm 3306 has an attached distal foot 3310 that is oriented at an approximate 45 degree angle to arm 3306. From the center of each foot 3310, a cylindrical shaped post 3312 extends perpendicularly away from foot 3310 and has a terminal end 3313. From an outer side of each foot 3310, a rectangular shaped leg 3314 extends perpendicularly away from foot 3310 and has a terminal end 3315. Posts 3312 are parallel to legs 3314. A hole 3316 is defined in each leg 3314 towards terminal end 3315. An aperture 3320 is defined in each of the lower most arms 3306. Support bracket 3302 surrounds an interior area 3322.

Plate 3350 is generally round in shape and is mounted to support bracket 3302 for sliding movement along posts 3312. Plate 3350 has a proximal side 3354, a distal side 3352 and an outer annular surface 3356. Four ears 3358 extend radially away from outer annular surface 3356. Ears 3358 are spaced 90 degrees apart from each other on outer annular surface 3356. A bore 3359 is formed in each ear 3358. Bore 3359 extends through the entire thickness of ear 3358. Bore 3359 is accurately formed to allow sliding movement of plate 3350 along post 3312.

Plate 3350 further has a first annular step 3360 defined in proximal side 3354 and a second annular step 3362 defined in proximal side 3354. Step 3360 has a larger diameter than step 3362 and encircles step 3362. A threaded bore 3364 is defined at the center of step 3362. Bore 3364 is perpendicular to step 3362.

A third annular step 3368 is formed in distal side 3352 and defines an annular channel 3370. The remaining portion of distal side 3352 forms a distally directed annular face 3355. After assembly, annular face 3355 is juxtaposed to face seal O-ring 3144 seated in groove 3142. Circular shaped drum 3372 extends in a distal direction perpendicularly away from the center of step 3368. A cylindrical boss 3374 extends from drum 3372 in a distal direction parallel to drum 3372. Boss 3374 has a smaller diameter than drum 3372. A pair of diametrically opposed shoes 3376 is attached to boss 3374 by spars 3378. Shoes 3376 are spaced from boss 3374 by spars 3378. A slot 3377 is defined between the opposed faces of shoes 3376. Receptacles 3380 are defined between the proximal facing portion of shoe 3376 and the distal facing portion of boss 3374. Slot 3377 and receptacles 3380 are dimensioned to receive a portion of case 3502 as will be described later.

Plate 3350 is coupled to posts 3312 such that plate 3350 slides along posts 3312. A plate return coil spring 3382 is mounted over and surrounds each post 3312. One end of coil spring 3382 abuts foot 3310 and the other end of coil spring 3382 abuts the proximal face of ear 3358. Bores 3359 are aligned with posts 3312 and plate 3350 is slid onto posts 3312 such that posts 3312 extend through bores 3359. In this position, plate return coil spring 3382 is compressed between foot 3310 and the proximal face of ear 3358. Plate return coil spring 3382 biases plate 3350 in a distal direction towards receiver housing 3102.

Carriage assembly 3300 also includes a lock mechanism 3400. Lock mechanism 3400 functions to prevent plate 3350 from being opened or moved to an open position when plate 3350 is in a closed position. Lock mechanism 3400 comprises a hub 3402 with four orthogonal arms 3406 extending away from hub 3402. The ends of arms 3406 are rounded. Hub 3402 has a distal facing oval shaped raised wall 3408 that surrounds and defines oval shaped central opening 3410.

A rod 3412 is mounted to a proximal facing surface of each of arms 3406. Rods 3412 extend in a proximal direction perpendicular to and away from arms 3406. The terminal ends of rods 3412 are rounded. Lever 3414 is connected to hub 3402. Specifically, lever end 3416 is attached to hub 3402. The other lever end 3418 is curved or hooked. Lever 3414 is configured to be manually grasped by an operator.

Lock mechanism 3400 is retained to plate 3350 in a manner that allows sliding movement by lock mechanism 3400 relative to plate 3250. A fastener such as threaded screw 3422 extends through opening 3410 and is received and retained in plate threaded bore 3364. Screw 3422 has a head that is dimensioned to have a larger diameter than the width of opening 3410. During installation, the head of screw 3422 is drawn against the proximal surface of hub 3402, thereby retaining lock mechanism 3400 to plate 3250.

A lumen 3424 is formed thru the bottom of oval shaped raised wall 3408 below opening 3410. A lock return coil spring 3426 is disposed in lumen 3424 such that one end of spring 3426 abuts screw 3422 and the other end abuts the outer circumferential wall of step 3362. Return coil spring 3426 biases lock mechanism 3400 in an upward direction towards cover 450 (FIG. 30).

Carriage assembly 3300 is assembled by sliding plate 3350 with attached lock mechanism 3400 over posts 3312 with coil springs 3382 such that posts 3312 extend through bores 3359. The carriage assembly 3300 is then mounted to receiver housing 3102. Each of the four support bracket legs 3314 are positioned in housing receiver slots 3112 such that leg holes 3316 are aligned with housing receiver bores 3114. Threaded fasteners 3430 extend thru leg holes 3316 and into bores 3114. Carriage assembly 3300 is thereby connected to receiver housing 3102.

With specific reference to FIGS. 31 and 36, details of removable sensor module 3500 are illustrated. Removable sensor module 3500 is inserted into and received by sensor receiver 3100. Removable sensor module 3500 contains one or more sensors for sensing the operating environment within container 2902 (FIG. 29). Removable sensor module 3500 comprises a circuit board assembly 3700 that is mounted to a sensor case 3502. Sensor case 3502 is generally cylindrical in shape and has a proximal end 3504 and a distal end 3506. Case 3502 has an outer annular surface 3508. Case 3502 further includes a central dividing wall 3510 that bisects case 3502 and is perpendicular to outer surface 3508. A first annular skirt 3512 extends in a distal direction from wall 3510 terminating at distal end 3506. A second annular skirt 3520 extends in a proximal direction from wall 3510 terminating at proximal end 3504. Second skirt 3520 and dividing wall 3510 define an annular cavity 3530.

First skirt 3512 is bisected by a grip 3514 that extends across the diameter of first skirt 3512. The base of grip 3514 is connected to the distal facing side of dividing wall 3510. Grip 3514 and first skirt 3512 define two finger cutouts 3516. An operator manually manipulates or rotates removable sensor module 3500 by inserting their fingers into cutouts 3516 and squeezing grip 3514 between their fingers.

A cylindrical shaped drum 3522 extends perpendicularly from the center of dividing wall 3510 in a proximal direction. An oval shaped head 3523 is attached to drum 3522 by a shaft 3526. Head 3523 is spaced away from drum 3522 in the proximal direction by shaft 3526. Head 3523 includes a pair of diametrically opposed fins 3524 that extend away from head 3523 in opposite directions. Fins 3524 are perpendicular to shaft 3526. Head 3524 and fins 3525 are dimensioned to mate with shoes 3376 (FIG. 35). A gap 3525 is defined between fins 3524 and the proximal facing side of drum 3522.

Fins 3524 mate with shoes 3376 (FIG. 35) in order to couple case 3502 to plate 3350. Head 3523 is dimensioned to fit into plate slot 3377 (FIG. 35) when case 3502 is oriented such that fins 3524 are parallel to shoes 3376 (FIG. 35). As case 3502 is manually inserted in a proximal direction into receiver housing 3102, head 3523 will eventually contact and abut the distal facing side of boss 3374. In this position, case 3502 is rotated 90 degrees causing fins 3524 to move into receptacles 3380. Receptacles 3380 are dimensioned to receive fins 3524. Case 3502 is now retained to plate 3350.

An annular groove 3532 is defined in outer annular surface 3508. Groove 3532 is dimensioned to receive a circular O-ring 3534. O-ring 3534 is seated in groove 3532. O-ring 3534 forms a seal with the inner annular surface 3122 (FIG. 33 of sleeve 3118 (FIG. 33).

Two channels 3540 and 3541 are defined in the case outer annular surface 3508. Channels 3540 and 3541 are diametrically opposed to each other on opposite portions of the circumference of case 3502. Channel 3540 has an entrance opening 3542 (FIG. 31) that is adjacent proximal end 3504. Channel 3541 has an entrance opening 3543 (not shown) that is adjacent proximal end 3504. Channel 3541 and entrance opening 3542 are formed to have a larger or wider width than channel 3540 and entrance opening 3542. Channel 3540 angles from opening 3542 in a distal direction along the circumference of surface 3508 and terminates in an L-shaped trap 3544. Channel 3541 angles from opening 3543 in a distal direction along the circumference of surface 3508 and terminates in another L-shaped trap 3544. Channel 3540 is dimensioned to mate with and receive finger 3138 during the loading of sensor case 3502 into receiver housing 3102. Channel 3541 receives and mates with finger 3140 during the loading of sensor case 3502 into receiver housing 3102. Fingers 3138, 3140 and channels 3540, 3541 act as a key and keyway respectively to properly align and index case 3502 with respect to receiver 3100.

Because opening 3542 is smaller than the width of finger 3140, if case 3502 is misaligned with receiver 3100, case 3502 is blocked from being inserted into receiver 3100. Case 3502 can only be inserted into receiver 3100 when finger 3138 is aligned with channel opening 3543 and finger 3140 is aligned with channel opening 3542.

Case 3502 also includes a connector passage 3550 that is located between one of the traps 3544 and proximal end 3504. Connector passage 3550 extends perpendicularly through second skirt 3520 into cavity 3530. Connector passage 3550 is dimensioned to receive a connector 3750 that is attached to circuit board assembly.

Threaded bores 3554 are defined in the proximal face of dividing wall 3510 located at the bottom of cavity 3530. Threaded bores 3554 extend perpendicularly into wall 3510 and are dimensioned to receive the external threaded distal end 3558 of PCB standoffs 3556. PCB standoffs 3556 also have an internal threaded proximal end or head 3560. PCB standoffs 3556 are screwed into bores 3554 forming a support for circuit board assembly 3700.

Turning to FIGS. 36, 37A and 37B, details of circuit board assembly 3700 are shown. Assembly 3700 has a printed circuit board (PCB) 3701 that is generally planar and doughnut shaped. PCB 3701 includes a proximal facing side 3702 and a distal facing side 3704 a circular opening 3706 is defined through the center of PCB 3701. PCB 3701 is mounted in case cavity 3530. Specifically, PCB distal side 3702 rests on and is supported by standoffs 3556 with side 3702 abutting head 3560. Skirt 3520 surrounds the outer circumferential edge of PCB 3700. In this position, head 3523 (FIG. 36) and drum 3522 (FIG. 36) extend through central opening 3706. Screws 3710 extend through PCB holes 3712 and are received by internally threaded heads 3560 retaining PCB 3701 to case 3502.

PCB 3701 is a multi-layer printed circuit board that includes numerous printed circuit lines 3716 for the interconnection of electrical components and sensors mounted on PCB 3701. A battery 3720, processor 1020, memory 1022, I/O interface 1124 and wireless transceiver 1138 are mounted to the distal facing side 3704 of PCB 3701. Battery 3720 supplies electrical power to the components of circuit board assembly 3700. Processor 1020, memory 1022, I/O interface 1124 and wireless transceiver 1138 are the same as previously described in FIGS. 12B and 13.

One or more sensors are mounted to the removable sensor module 3500 and connected to PCB 3701. In the embodiment shown, sensors are mounted to proximal facing side 3702 of PCB 3701. Water vapor 1024, pressure sensor 1026 and temperature sensor 1028 are mounted to side 3702. Water vapor sensor 1024, pressure sensor 1026 and temperature sensor 1028 are the same as previously described in FIGS. 12B and 13. In an optional embodiment, also mounted to side 3702 is an optical sensor 1052 that senses the amount of infrared (IR) or ultraviolet (UV) light transmitted through an optical path length 3770 within container 2902. In one embodiment, optical sensor 1052 detects and measures concentrations of hydrogen peroxide vapor ($H_2O_2$). In one embodiment, optical sensor 1052 detects water vapor or another gas or vapor where absorbance characteristics of the gas or vapor are known.

Optical sensor 1052 includes an IR or UV source or emitter 1056, an optical reflector or mirror 3764 and an IR or UV receiver or detector 1058 mounted to side 3702. Light filters (not shown) can be mounted around source 1056 or detector 1058 to remove any undesired light wavelengths. Mirror 3764 is positioned to reflect incident light energy towards detector 1058. Mirror 3764 is formed from a material that reflects emitter energy 1056 back to detector 1058 such as vacuum deposited aluminum on glass.

Mirror 3764 allows for a longer optical path length 3770 than would otherwise be possible without the use of mirror 3764. A longer optical path length 3770 improves the accuracy and precision of measurements of detected hydrogen peroxide vapor concentrations.

Because hydrogen peroxide vapor absorbs infrared or ultraviolet light at specific know wavelengths, the amount of light at that frequency transmitted through a known path length 3770 containing hydrogen peroxide vapor is proportional to the concentration of the hydrogen peroxide vapor. Other vapors or gases with known wavelength absorbance characteristics can be detected and measured by appropriately selected emitter 1056 and detector 1058.

Connector 3740 is mounted to PCB 3701. Specifically connector 3740 has an insulating body 3742 that contains several terminals 3744. Terminals 3744 are attached PCB 3701 by suitable methods such as soldering. The other end of terminals 3744 are connected to button contacts 3746. Button contacts 3746 face radially outward from body 3742. Button contacts 3746 mate with receiver housing proximal contact ends 3156 (FIG. 33) to form an electrical connection between removable sensor circuit board assembly 3700 and container printed circuit board 3800. When PCB 3701 is mounted in case 3502, connector 3740 is received by and disposed in connector opening 3550 (FIG. 36). Button contacts 3746 extend slightly beyond insulating body 3742 and extend slightly beyond the adjoining outer annular surface 3708 (FIG. 36). This extension of button contacts 3746 allows them to mate with proximal contact ends 3156 when removable sensor module 2500 is properly inserted into sensor receiver 3100.

Figure 38:
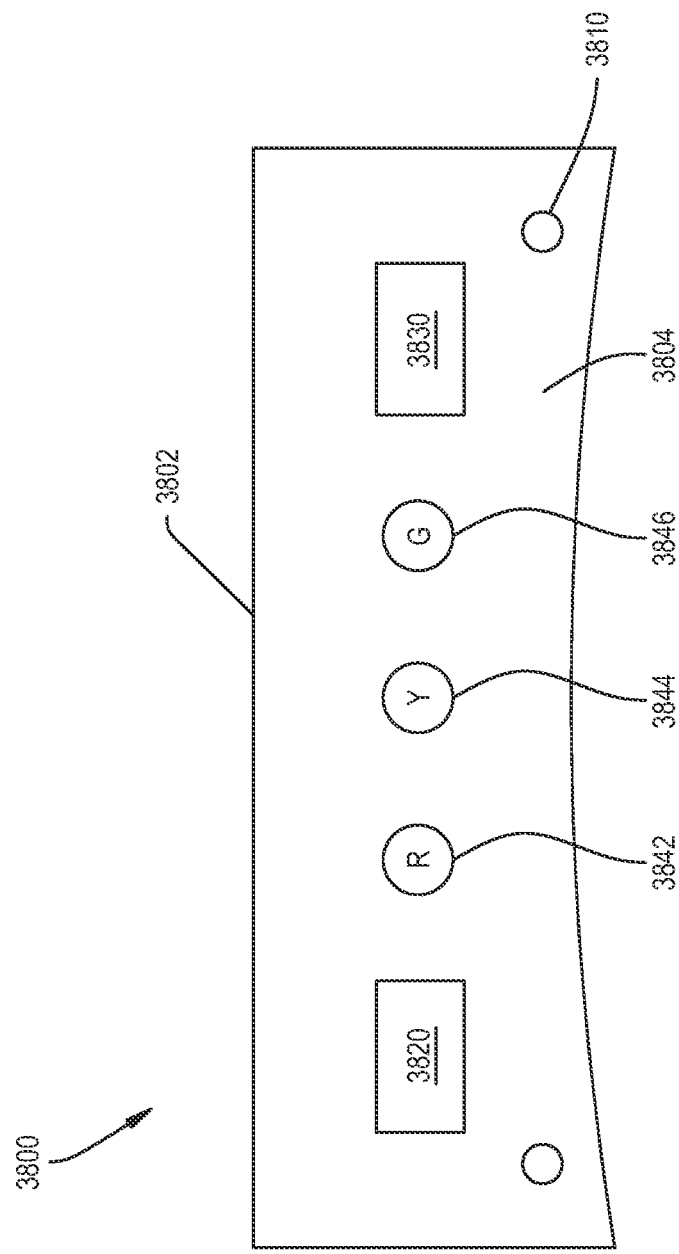
FIG. 38 is a front view of the container printed circuit board.
Figure 39:
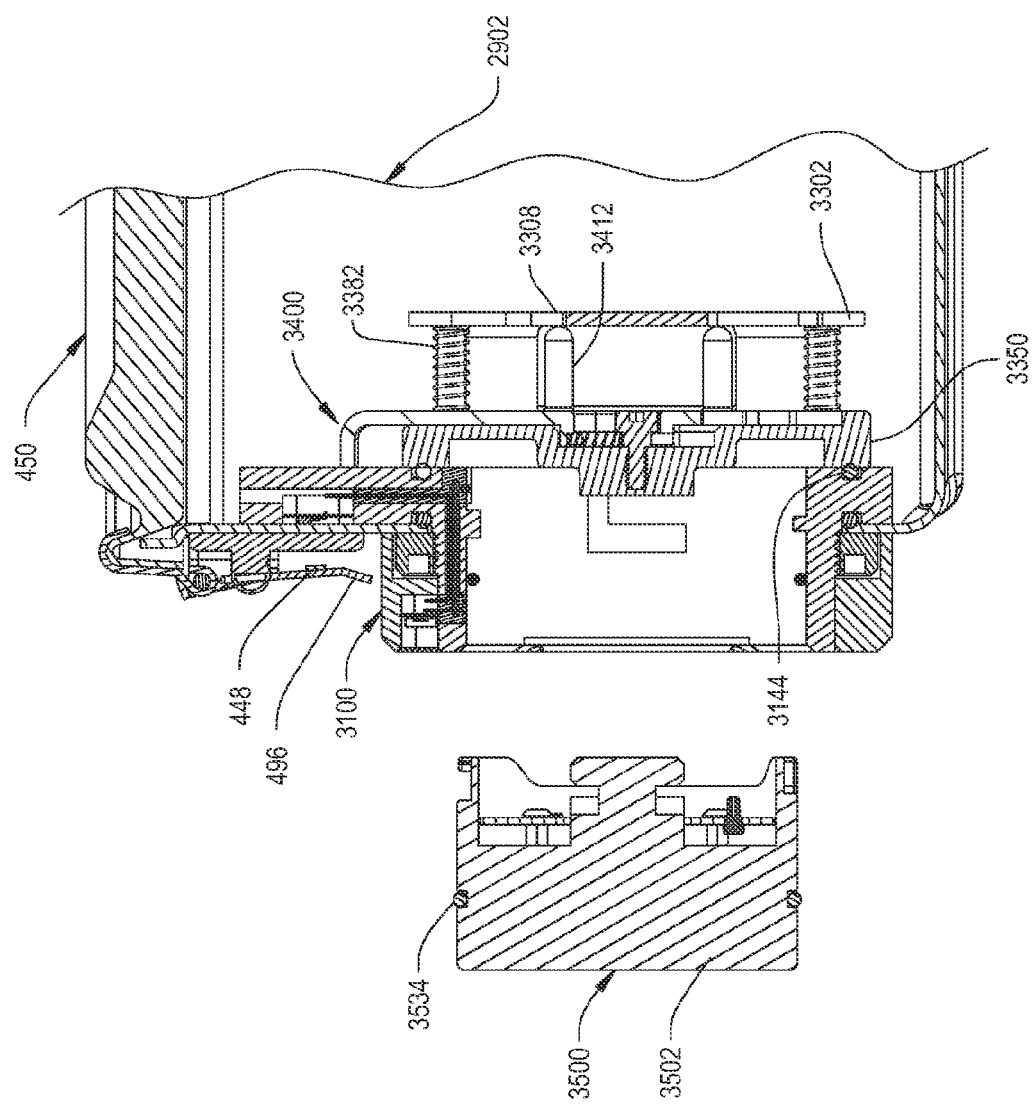
FIG. 39 is an assembled cross sectional view of the removable sensor assembly illustrating the removable sensor module separated from the receiver.

FIG. 38 illustrates details of container printed circuit board (PCB) 3800. PCB 3800 is mounted in cover circuit board holder 3280 (FIG. 34). PCB 3800 is generally planar and rectangular in shape. PCB 3800 includes a proximal facing side 3802 and a distal facing side 3804. PCB 3800 is a multi-layer printed circuit board that includes numerous printed circuit lines (not shown) for the interconnection of electrical components and in certain embodiments sensors mounted on PCB 3800. Holes 3810 are defined in PCB 3800. Screws 3290 (FIG. 31) pass through holes 3810 in order to retain PCB 3800 to cover 3250 (FIG. 31).

A battery 3820, controller 3830, one or more LEDs 3842, 3844 3846 are all mounted to the distal facing side 3804. Battery 3820 supplies electrical power to the components of PCB 3800. Controller 3830 is a micro-controller that includes an internal memory that stores sets of instruction or software. PCB 3800 may also include memory that can store data such as measurement data from sterilization process, VSPM data, usage data or other workflow process data for example the operator who programmed the sensor module with VSPM data or operator who assembled the equipment load into container or the time and date of the sterilization process. The PCB 3800 combined with the removable sensor PCB 3700 functions like steam sensor modules 1000, hydrogen peroxide sensor module 1050, combined steam and hydrogen peroxide sensor module, or other sensor modules 200, 460, 560, 660, 760, 850 described herein. PCB 3800 will have some additional electronic components, some redundant with removable sensor module PCB 3700 so after removable sensor module 3500 is removed, PCB 3800 memory may contain information tied to the specific sterilization process, equipment load, operator information, programming information and other information required to track, record or monitor business processes, regulation processes or quality control processes for sterilization events. Controller 3830 is in communication with optional Hall Effect circuit board 3170 (FIG. 31) via terminal 3162 (FIG. 33). When removable sensor module 3500 is coupled to sensor module receiver 3100 (FIG. 31), controller 3830 is in communication with processor 1020 via I/O interface 1024. Controller 3830 allows for data and instructions to be sent and received from processor 1020.

Red LED 3842, yellow LED 3844 and green LED 3846 provide visual information to a user of container assembly 2900. LEDS 3842, 3844 and 3846 are viewed by a user through transparent lens 3294 (FIG. 31). In one embodiment, red LED 3842 indicates that container 2902 and its contents have been processed through a sterilization cycle that was unsuccessful in meeting a pre-determined set of minimum validated sterilization process measurements such as previously described VSPM 1150 (FIG. 19). As such the contents of container 2902 are considered to be non-sterile.

In another embodiment, yellow LED 3842 indicates that container 2902 and its contents have not been processed through a sterilization cycle. In an additional embodiment, green LED 3846 indicates that container 2902 and its contents have been processed through a sterilization cycle that was successful in meeting a pre-determined set of minimum validated sterilization process measurements such as previously described VSPM 1150 (FIG. 19). As a result, the contents of container 2902 are considered to be sterile.

XXIV. Insertion and Removal of Removable Sensor Module

FIGS. 39-43 illustrate a sequence of steps in the insertion and removal of removable sensor module 3500 into and from sensor receiver 3100. With specific reference to FIGS. 31 and 39, removable sensor module apparatus 3000 is shown in an initial or first position where sensor module 3500 is separated from receiver 3100. In this position, plate 3350 is compressed by springs 3382 against face seal O-ring 3144 forming a seal between distally directed annular face 3355 (FIG. 35) and O-ring 3144. In some embodiments, this seal and plate form part of a sterile barrier enclosure with container assembly 2900. Also, in the first position, lock mechanism 3400 is in a locked state. In the locked state, lock mechanism 3400 prevents plate 3350 from being opened or moved away from receiver housing 3102 maintaining a sealed position. In the locked position, lock mechanism 3400 is in an uppermost location where raised wall 3408 (FIG. 35) abuts the upper side wall of step 3362 (FIG. 35) and rods 3412 are positioned adjacent to and in abutting relationship to bracket arms 3306 preventing movement of plate 3350 in the proximal direction away from receiver housing 3102.

Figure 40:
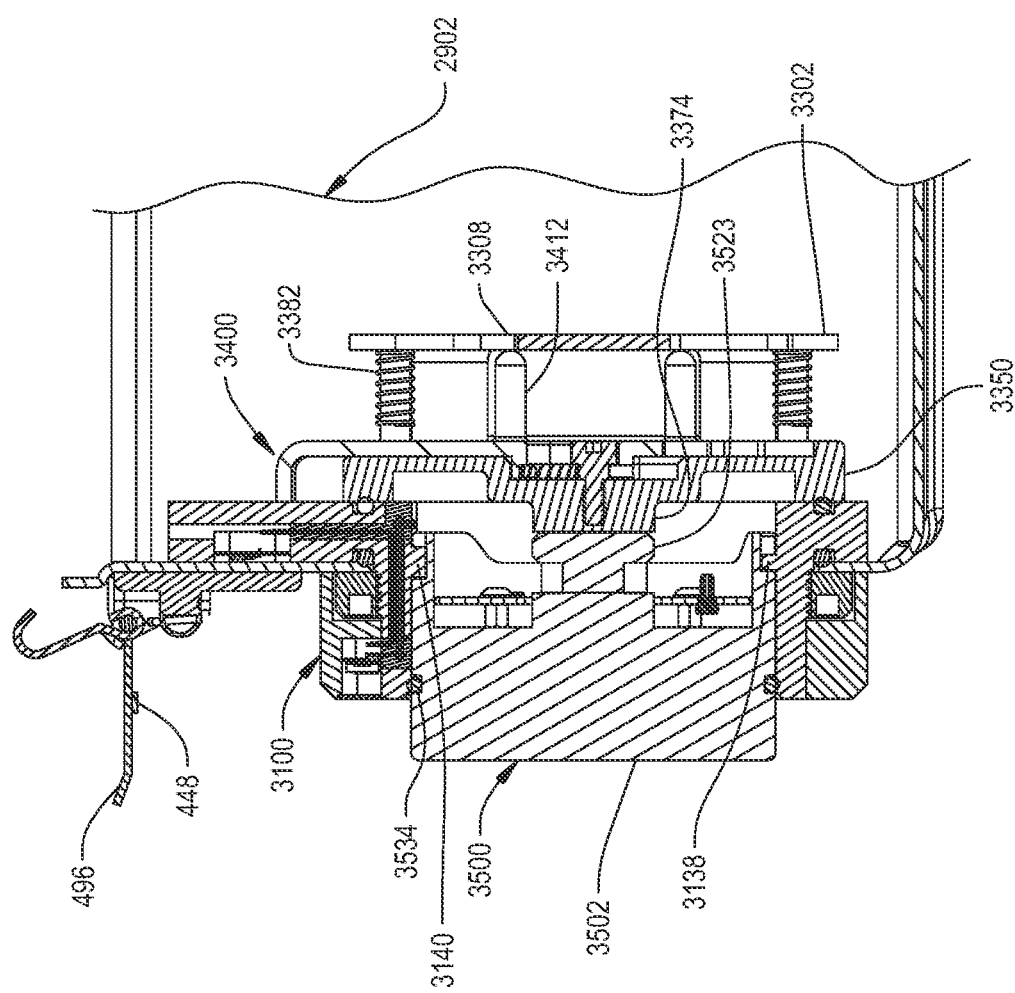
FIG. 40 is an assembled cross sectional view of the removable sensor assembly illustrating the removable sensor module seated in an initial position in the receiver.

Turning to FIGS. 31 and 40, sensor module 3500 is shown in a second position being loaded into receiver 3100. In this position, lid 450 has been removed from container 2902 and removable sensor module 3500 has been manually inserted into opening 3263 (FIG. 34) and bore 3125 (FIG. 34) of sleeve 3118 (FIG. 34). In the second position, O-ring 3534 forms a seal with the inner annular surface 3122 (FIG. 33) of sleeve 3118 (FIG. 33). As case 3502 is manually inserted in a proximal direction into receiver housing 3102, head 3523 will eventually contact and abut the distal facing side of boss 3374 limiting movement in the proximal direction. Also, in this location, fingers 3138 and 3140 are aligned with channel openings 3542 (FIG. 31). Plate 3350 is still in a sealed and locked position.

As part of the process of inserting sensor module, the lever 3414 is manually pressed downwardly. This places locking mechanism 3400 in the unlocked position. This repositioning of the locking mechanism frees plate 3350 to move inwardly. This freeing of the plate 3500 for movement allows the continued insertion of the sensor module 3500 into the container receiver 3100. As the sensor module is inserted in the receiver, the module pushes against and displaces plate 3350. This displacement of plate 3350 temporarily breaks the seal between the receiver housing 3102 and the plate.

In the unlocked position, lock mechanism 3400 is in a lowermost location where raised wall 3408 (FIG. 35) abuts the lower side wall of step 3362 (FIG. 35) and lever end 3418 abuts the outer surface of plate 3350. This prevents further downward movement of lever 3414. Also, in the unlocked position, the two upper rods 3412 are positioned below the upper bracket arms 3306 and the two lower rods are in axial alignment with holes 3320 (FIG. 35) allowing movement of plate 3350 in the proximal direction away from receiver housing 3102.

Next, the operator rotates case 3502 45°. This rotation results in fins 3524 moving into plate receptacles 3380 and adjacent shoes 3376 (FIG. 35). Receptacles 3380 are dimensioned to receive fins 3524. Case 3502 is now retained to plate 3350.

Case 3502 is then rotated an additional 45°. As a result of this rotation, fingers 3138 and 3140 track along channels 3540. Thus results in case 3502 being drawn in the proximal direction towards bracket 3302. Because case 3502 is coupled to plate 3350, the rotation of case 3502 also causes a like movement of plate 3350 in a proximal direction away from receiver housing 3102 opening plate 3350. As plate 3350 moves in the proximal direction, springs 3382 are compressed and rods 3412 also move in a proximal direction past bracket arms 3306 and through holes 3320 (FIG. 35). Plate 3350 moves away from O-ring 3144 creating a passage 4110 between plate 3350 and sensor circuit board assembly 3700. Passage 4110 allows sensors on circuit board assembly 3700 to be exposed to the operating environment and conditions within container 2902.

Figure 41:
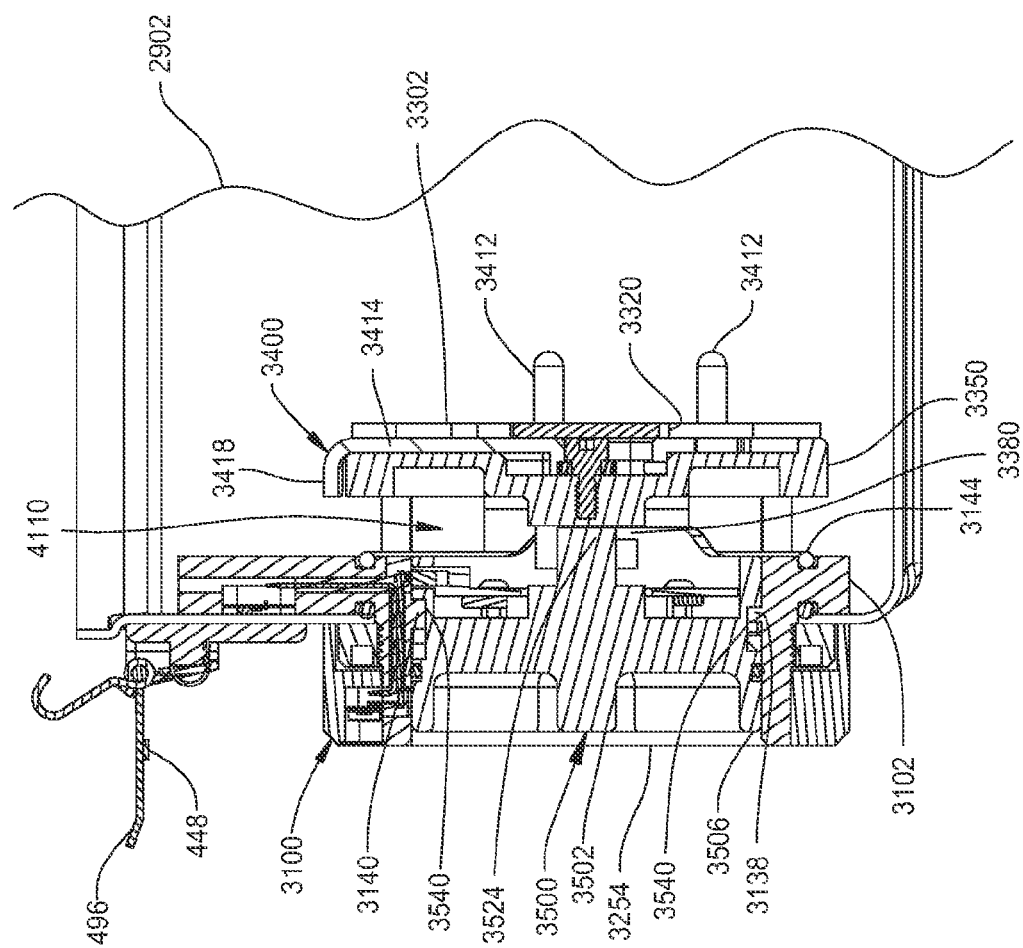
FIG. 41 is an assembled cross sectional view of the removable sensor assembly illustrating the internal locking mechanism being actuated and opening of the plate to expose the sensors to the internal container environment.

As shown in FIG. 41, case 3502 is now in a position where the distal end 3506 of case 3502 has moved slightly past distal face 3254 of cover 3250 and into bore 3264 (FIG. 34).

Figure 42:
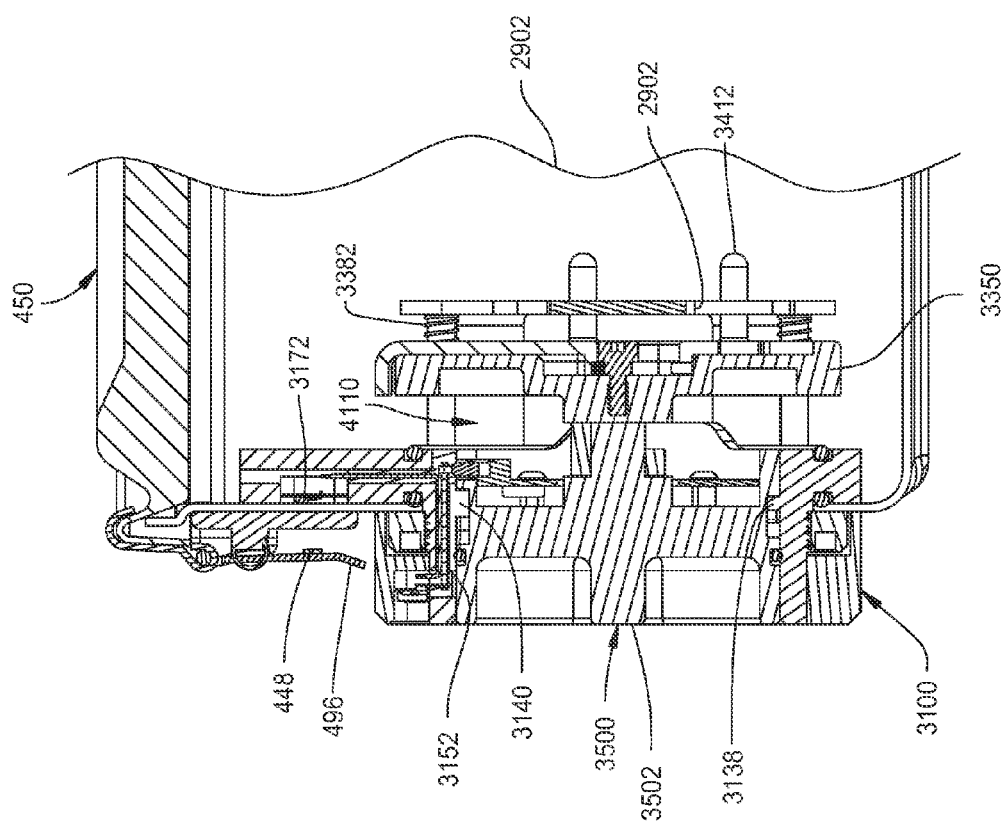
FIG. 42 is an assembled cross sectional view of the removable sensor assembly illustrating the removable sensor module in the locked position and ready to collect data during a sterilization process cycle.
Figure 43:
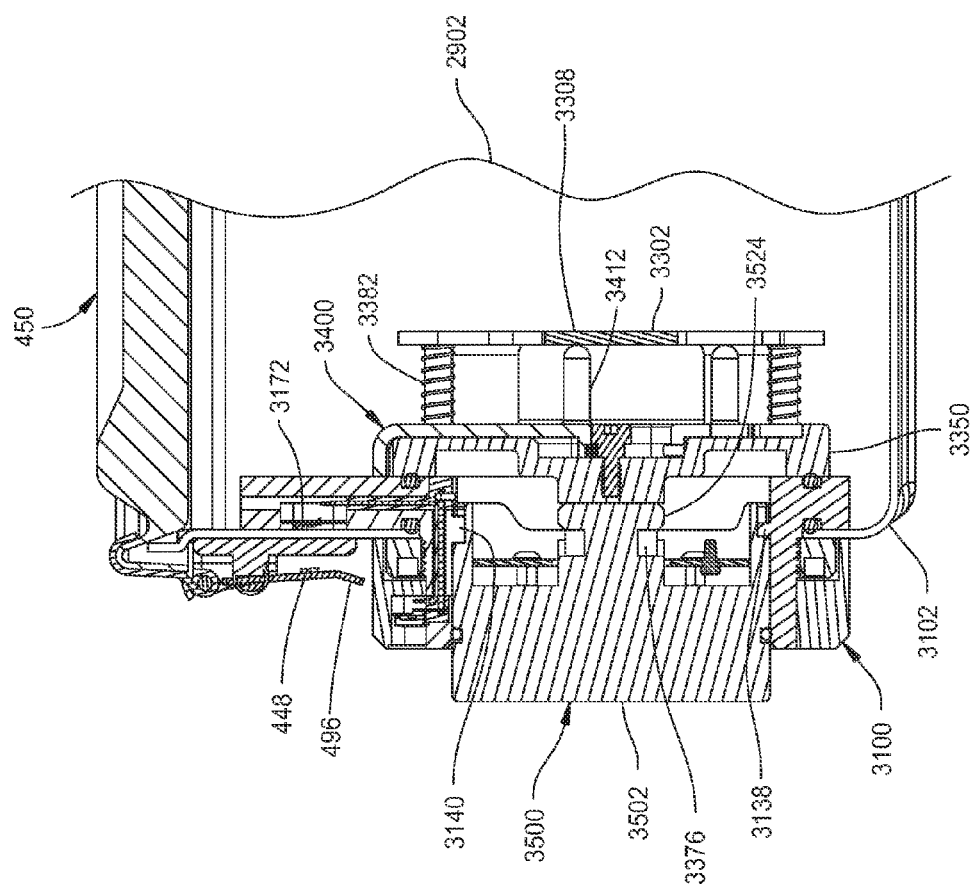
FIG. 43 is an assembled cross sectional view of the removable sensor assembly illustrating closing of the plate and removing the removable sensor module from the receiver.

With reference to FIGS. 31 and 42, removable sensor module 3500 is shown in a fourth operational position. When the operator manually releases case 3502, compressed coil springs 3382 cause plate 3350 and case 3502 to move in distal direction such that fingers 3138 and 3140 are seated in trap 3544 (best seen in FIG. 36). Case 3502 is now rotatably locked to receiver housing 3102. At the same time, distal movement of case 3502 causes contact buttons 3746 (FIG. 37B) to be engaged and seated against terminal ends 3156 (FIG. 33) creating an electrical connection between sensor PCB 3702 and container PCB 3800 via terminals 3152 (FIG. 34). The components of sensor PCB 3702 are now in communication with components of container PCB 3800

Surgical instruments 180 to be sterilized are manually loaded into container 2902 and cover 450 is placed over container 2902. Locking lid latch 496 is moved to a locked position retaining cover 450 to container 2902. In an optional embodiment, pivoting of lid latch 496 causes magnet 448 to be positioned in proximity to Hall Effect sensor 3172 such that Hall Effect sensor 3172 senses the magnetic field generated by magnet 448. Container assembly 2900 is now ready to be processed through a sterilization process cycle within sterilization chamber 52 (FIG. 1). During the sterilization process cycle, removable sensor module 3500 monitors and collects data in regards to the operating environment, conditions and process measurements within container 2902.

After the sterilization process cycle is completed, sensor module 3500 is removed from sensor receiver 3100 while maintaining the sterile state inside of the container assembly 2900. The sensor module is removed by pressing module case 3502 in the proximal direction while simultaneously rotating the case counterclockwise. The proximal movement of the case 3502 causes fingers 3138 and 3140 to move out of trap 3544. As case 3502 is rotated counterclockwise, fingers 3138 and 3140 track along channels 3540 causing case 3502 to be drawn in a distal direction away from receiver housing 3102. Plate 3350, it is understood is coupled to the case 3502 for axial movement. Consequently, the longitudinal displacement of case 3502 causes a like displacement of the plate 3350. The movement of case 3502 and plate 3350 in the distal direction is assisted by coil springs 3382. The counterclockwise rotation of case 3502 also causes the disconnection of contact buttons 3746 from terminals ends 3156. FIG. 41 sensor module 3500 is shown in this position Eventually, the distally directed annular face 3355 (FIG. 35) of plate 3350 contacts O-ring 3144. This establishes a seal between plate 3350 and receiver housing 3102. This seal closes passage 4110 (FIG. 42). After the seal is established, lock mechanism 3400 is biased by coil spring 3426 (FIG. 35) to move into the locked state. Coil spring 3426 causes lock mechanism 3400 to move to an uppermost location where raised wall 3408 (FIG. 35) abuts the upper side wall of step 3362 (FIG. 35) limiting upward movement of lock mechanism 3400 and rods 3412 are positioned adjacent to bracket arms 3306 preventing movement of plate 3350 in the proximal direction away from receiver housing 3102.

During this removal of the sensor module, plate 3350 is pulled outwardly. This results in the plate 3350 being pressed against O-ring 3144. This adds to the force springs 3382 apply to the plate so as to hold the plate in sealed and locked position.

As case 3502 is further rotated counterclockwise, fins 3524 will move out of engagement with shoes 3376 and out of plate receptacles 3380 allowing case 3502 to be separated from plate 3350. Continued manual movement by the operator of case 3502 in the distal direct causes removable sensor module 3500 to be removed and separated from receiver housing bore 3125 (FIG. 34) and opening 3263 (FIG. 34). Throughout the removal of removable sensor module from sensor receiver, the seals 3534 and 3144 act together so that at least one seal will always be sealing to adjacent surfaces, preventing air and microorganisms from entering the container throughout the removal process. This at least one seal maintained embodiment temporarily forms part of the sterile barrier enclosure during the removal process. Removable sensor module 3500 is now available to be reused with other containers 2902 during sterilization processing.

Sensor module 3000 is constructed so that a sterile seal is maintained between container 2902 and receiver 3100 regardless of the position of removable sensor module 3500. When sensor module 3500 is removed from receiver 3100, annular face 3355 (FIG. 35) of plate 3350 and face seal O-ring 3144 form a sterile seal preventing contaminants from moving thru receiver 3100 and into container 2902. When sensor module 3500 is inserted or removed, O-ring 3534 and inner annular surface 3122 (FIG. 33) maintain another sterile seal whenever plate 3350 is in a open position forming another sterile barrier.

When the container is subjected to sterilization, the surfaces of plate 3500 and the adjacent receiver as well the exposed surfaces of O ring 3534 are exposed to sterilant. Consequently, when these surface abut so as to form a seal upon the removal of the sensor module, there is little likelihood that contaminates will be trapped between these surfaces.

Lock mechanism 3400 is designed so that plate 3350 can only be opened after cover 450 is open or removed. Lock mechanism 3400 has to be manually actuated from within container 2902 in order to open. After container 2902 has been sterilized and after sensor module 3500 has been detached from receiver 3100, any subsequent attempts to reinsert another removable sensor module 3500 into receiver 3100 will be blocked by lock mechanism 3400 being in the locked state, thereby maintaining sterile conditions within container 2902. Fourth, because removable sensor module 3500 can be detached from container 2902, Removable sensor module 3500 is available to be reused with other additional containers 2902 during sterilization processing. If removable sensor module 3500 is a relatively high cost item, the use of a small number of removable sensor modules 3500 with a larger number of containers 2902 results in a more cost efficient solution for the monitoring of process measurements during sterilization processing. Also, sensors or electronics that are located on the removable sensor module 3500, will not be exposed to potential damage from cleaning, automated washing and rough handling that sensors or electronics permanently mounted to containers may experience.

In some of this embodiment of the invention, some of the components that form part of the sensing assembly are mounted to the container. Typically these components are mounted to the receiver. Components that may be so affixed to the receiver include the processor, the memory, the indicator lights or the battery. Also, owing some sensors may be permanently mounted to the container.

XXIV. Docking Station for Use with Removable Sensor Modules

Figure 44:
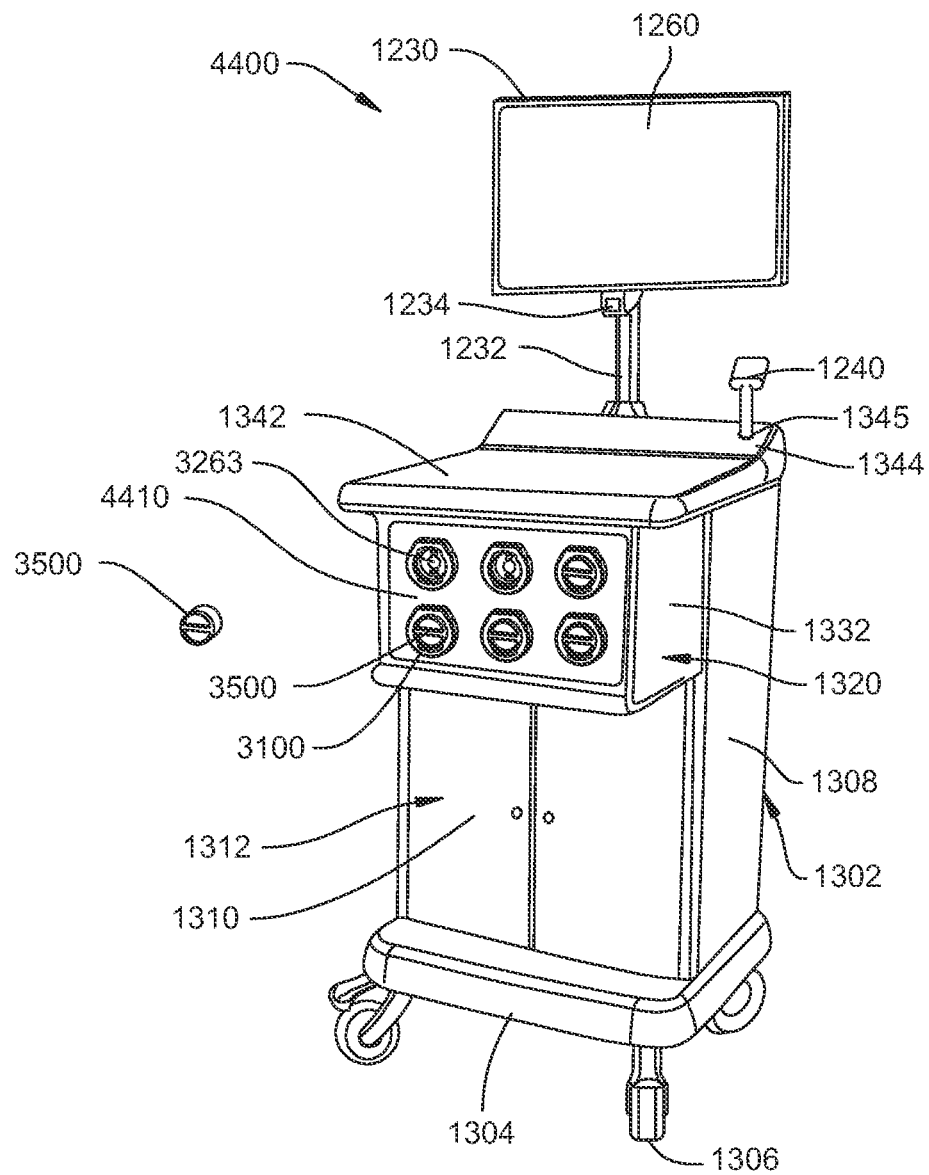
FIG. 44 is a perspective view of docking station that includes sensor calibration for use with the removable sensor assembly of FIG. 29 in accordance with one embodiment.

Referring to FIG. 44, another embodiment of a docking station 1300 is shown. Docking station 4400 is used in conjunction with removable sensor apparatus 3000. Docking station 4400 is used during the loading of surgical instruments into containers 2902, to calibrate the sensors of removable sensor module 3500 and to recharge batteries. Docking station 4400 has many features in common with docking station 1300 previously described with reference to FIG. 16. Docking station 4400 differs from docking station 1300 in that calibration chamber 1320 has been modified to eliminate door 1326 (FIG. 16) and to add a fixed front panel 4410. Several sensor receivers 3100 are mounted to front panel 4410. While six sensor receivers 3100 are shown mounted to calibration chamber 1320, more or fewer sensor receivers 3100 can be used.

Removable sensor modules 3500 are attachable and detachable with each of the sensor receivers 3100. The sensor receivers 3100 of docking station 4400 are connected to and in communication with docking station controller 1402 (FIG. 17). When sensor modules 3500 are inserted into receivers 3100, sensor processor 1020 (FIG. 37A) is in communication with docking station controller 1402 and docking station processor 1410 (FIG. 17).

Docking station 4400 contains steam generator 1430, hydrogen peroxide generator 1432, pressure pump 1434, vacuum pump 1436 and heater 1438 (FIG. 17) all of which can be used as needed to provide known concentrations and values within calibration chamber 1320 during a calibration procedure.

Docking station 4400 is used in conjunction with removable sensor apparatus 3000 in the same manner that docking station 1300 is used with container 402. Docking station 4400 is used to program removable sensor module 3500 with validated sterilization process measurements (VSPM) 1150 prior to sterilization processing as previously described in step 2108 of FIG. 21. Docking station 4400 is used to recharge battery 3720 (FIG. 37A) in removable sensor module 3500. Docking station 4400 is used to calibrate the sensors in removable sensor module 3500 in the same manner as previously described in steps 2704-2714 of FIG. 27. Sensor calibration software 1460 (FIG. 17) is used by docking station 4400 during the calibration of the sensors associated with a respective removable sensor module 3500. Sensor calibration software 1460 at least partially controls the operation of steam generator 1430, hydrogen peroxide generator 1432, pressure pump 1434, vacuum pump 1436 and heater 1438 during a calibration procedure.

It is noted that docking station 4400 can be used to program and calibrate a large number of removable sensor modules 3500 at the same time.

Figure 45:
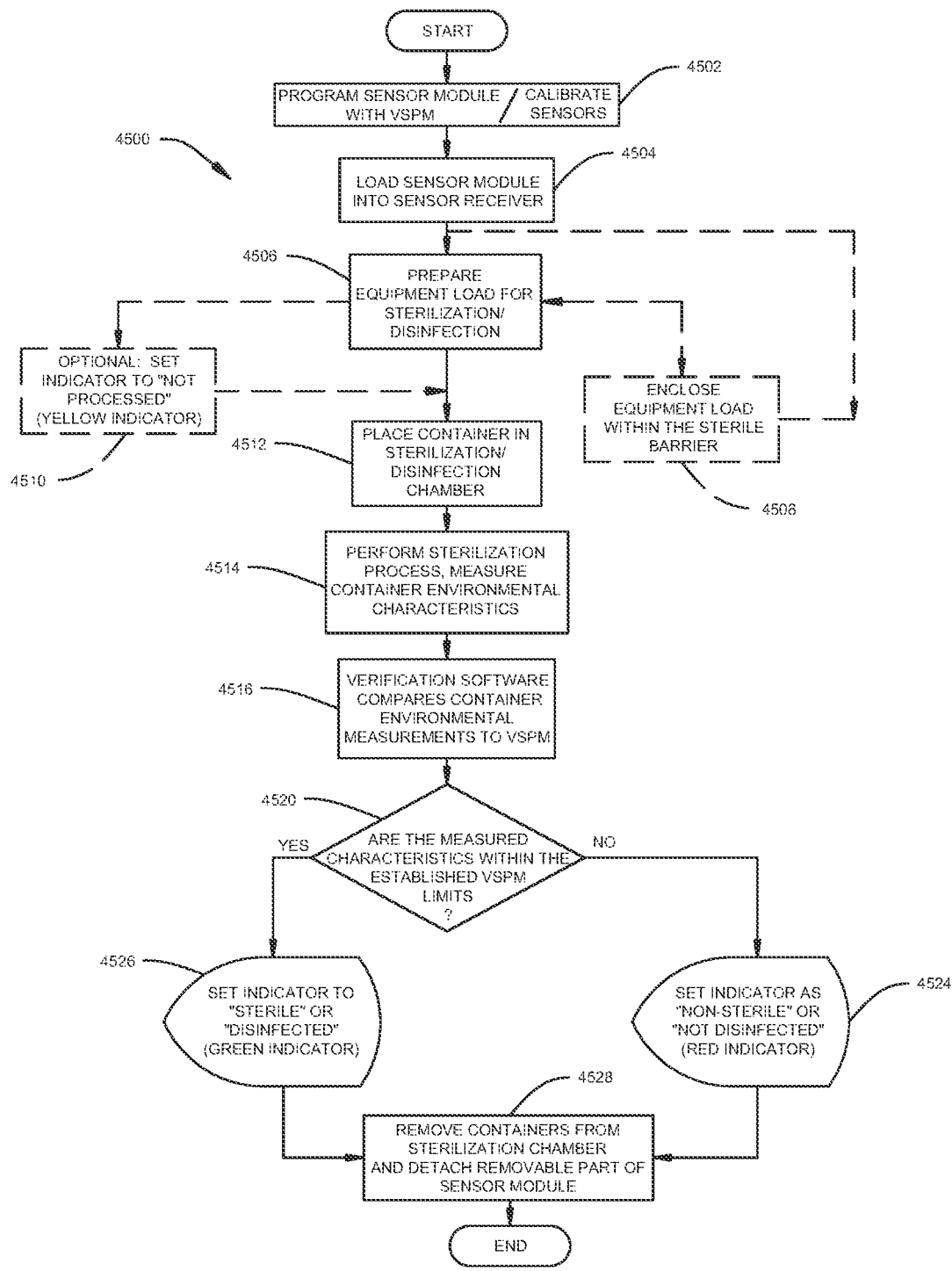
FIG. 45 is flowchart of a method of determining if validated sterilization process measurements within a container have been completed using the container and removable sensor assembly of FIG. 29 in accordance with one embodiment.

XXV. Operational Method to Determine if Validated Sterilization Process Measurements have been Achieved During a Sterilization Process Using Removable Sensor Modules Referring to FIG. 45, a flowchart of a method 4500 of determining if validated sterilization process measurements within a container have been achieved during a sterilization process using removable sensor modules 3500 is shown. Method 4500 illustrates an exemplary method by which container assemblies 3000 and removable sensor module 3500 presented within the preceding figures perform different aspects of the processes that enable one or more embodiments of the disclosure. In the discussion of FIG. 45, reference will also be made to components from FIGS. 29-44.

Method 4500 begins at step 4502 where removable sensor modules 3500 are programmed with VSPM 1150. Removable sensor modules 3500 are loaded into docking station 4400 (FIG. 44) for programming. At step 4502, memory 1022 (FIG. 37A) is programmed with specific validated sterilization process measurements (VSPM) 1150. Container programming software 1461 (FIG. 17) executing on docking station processor 1410 (FIG. 17) identifies the specific VSPM 1150 associated with the container equipment load, using the data obtained from handheld reader 1240 (FIG. 44), and transmits the VSPM 1150 for storage on memory 1022. The transmitted VSPM 1150 are specific to the equipment load to be sterilized.

Optionally at step 4502, the sensors of removable sensor module 3500 are calibrated prior to use. Removable sensor module 3500 is calibrated using docking station 4400.

Removable sensor module 3500 is removed from docking station 4400 and loaded into a sensor receiver 3100 (FIG. 40) attached to container 2902 (FIG. 40) at step 4504. Step 4504 includes manual depression of lock mechanism 3400 within container 2902 when the lid is open to allow insertion of case 3502. Sensor module 3500 processor 1020 (FIG. 37A) establishes communications with container controller 3830 at this time.

At step 4506, the equipment load of surgical instruments 180 (FIG. 2) is prepared for sterilization processing by an operator. At step 4506, the surgical instruments are placed into tray 160 (FIG. 2) and tray 160 is placed into container 2902. Cover 450 (FIG. 40) is attached and closed to container 2902.

In an optional step 4508, the surgical instruments 180 and/or tray 160 and/or container 2902 are wrapped in a sterile barrier material prior to sterilization processing.

In an additional optional step at block 4510, sterilization verification software 1152 (FIG. 14) executing on processor 1020 turns on container yellow LED 3844 (FIG. 38) indicating to a user that the container assembly has not yet been processed through a sterilization process cycle.

The container 402 is placed into the sterilization chamber 52 (FIG. 1) at step 4512 and the sterilization process cycle within sterilization chamber 52 is started (block 4514).

During the sterilization process cycle, the sterilization chamber is heated, pressurized and a sterilant, such as steam or hydrogen peroxide gas are pumped into the sterilization chamber. The sterilization process cycle also includes a cool down phase and drawing a vacuum on the chamber. These sub-steps remove residual condensed sterilant from the container. The sterilization chamber is set to operate using a set of chamber process parameters (CPP) 66 (FIG. 1). CPP 66 are the set of nominal process parameter settings within the sterilization chamber. The sterilization chamber is set to operate using CPP 66.

Also, at step 4514, sterilization verification software 1152 executing on processor 1020 monitors and collects real time data from the respective electronic sensors in sensor module 3500 during the sterilization process. The sensors monitor the environmental characteristics within their respective containers. The collected real time operating data is stored in memory 1022 as data 1156 (FIG. 14). For example, sterilization verification software 1152 executing on processor 1020 collects water vapor data from water vapor sensor 1024, pressure data from pressure sensor 1026, temperature data from temperature sensor 1028 and hydrogen peroxide concentration data from hydrogen peroxide gas sensor 1052. All of the data recorded during the sterilization process is stored as data 1156 in memory 1022.

In step 4516, the processor 1020 compares the observed environmental measurements to the VSPM 1150. At decision step 4520, sterilization verification software 1152 operating on processor 1020 determines if the real time measured data 1156 during the performed sterilization process meets or exceeds the minimum VSPM 1150 values for each operating parameter to insure sterilization of the container contents. For example, if VSPM 1150 has a minimum temperature and time value of 250 degrees Fahrenheit for 20 minutes, sterilization verification software 1152 compares these values to the recorded time and temperature values in data 1156.

In response to the recorded data 1156 values meeting or exceeding the minimum VSPM 1150 values for each sterilization operating measurement, Method 4500 proceeds to step 4526 where sterilization verification software 1152 executing on processor 1020 indicates that the container contents have been successfully sterilized by turning on green container LED 3846. (FIG. 38). In one embodiment additional data related to the sterilization process may be transferred to container memory of PCB 3800 for storage, workflow process or quality control practices. For example in one embodiment, measurement data, VSPM programmed data set, sterilization verification results, sterilization date and VSPM programming operator can be stored on container memory on PCB 3800. The container assembly is removed from the sterilization chamber and the removable sensor module 3500 is detached from container 2902 at step 4528. The contents of container 2902 remain in a sealed sterile state during and after sensor module 3500 has been disconnected from container 2902. Method 4500 then ends.

In response to the recorded data 1156 values not meeting or exceeding the minimum VSPM 1150, processor 1020 proceeds to step 4524, Step 4524 is identical to previously described step 2126.

The container is removed from the sterilization chamber and the removable sensor module 3500 is detached from container 2902 at step 4528. The contents of container 2902 should be reprocessed prior to use. Method 4500 then terminates.

During storage, controller 3830 (FIG. 38) executes a set of instructions similar to sterile monitor software 1158 (FIG. 14) that causes controller 3830 to monitor the electrical signal received from optional embodiment with Hall Effect sensor 3172 (FIG. 31) during storage. If cover 450 is opened, the electrical signal from Hall Effect sensor 3172 changes triggering controller 3830 to turn off green LED 3846 (FIG. 38) and to turn on red LED 3842 (FIG. 38). The illumination of red LED 3842 provides a visual indication to an operator that the contents of container 2902 are no longer considered sterile.

XXVI. Automatic Closing Container with Scissor Lifting and Lowering Mechanism Turning to FIGS. 46 and 47, another automatic closing container assembly 4600 is illustrated. Container assembly 4600 uses a scissors mechanism 4700 to close a moveable frame 4750. The frame is closed after the sterilization process is executed and residual sterilant withdrawn from the container.

Figure 46:
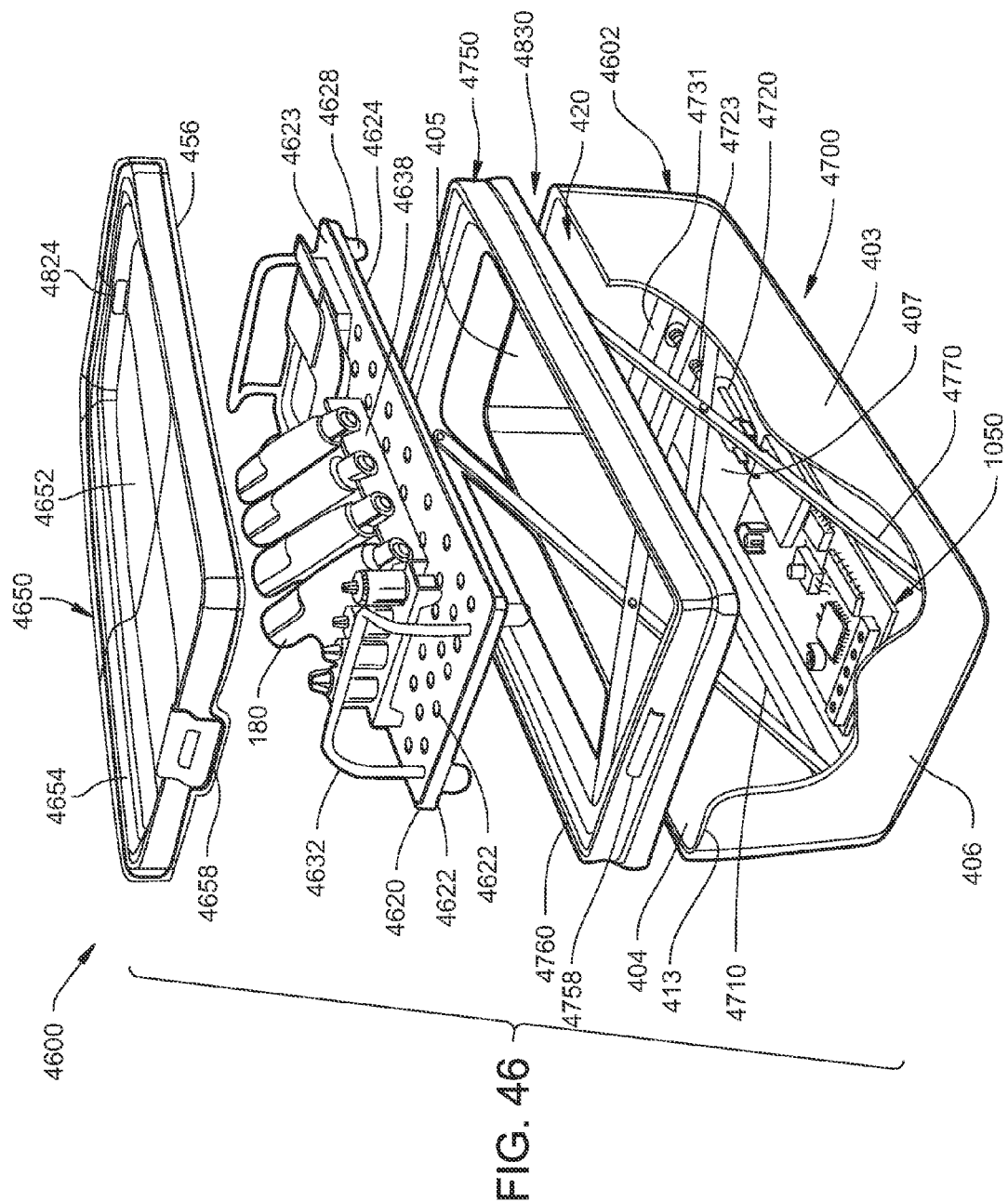
FIG. 46 is an exploded top perspective view of an automatic closing container assembly used for sterilization of medical/surgical instruments in accordance with one embodiment.
Figure 47:
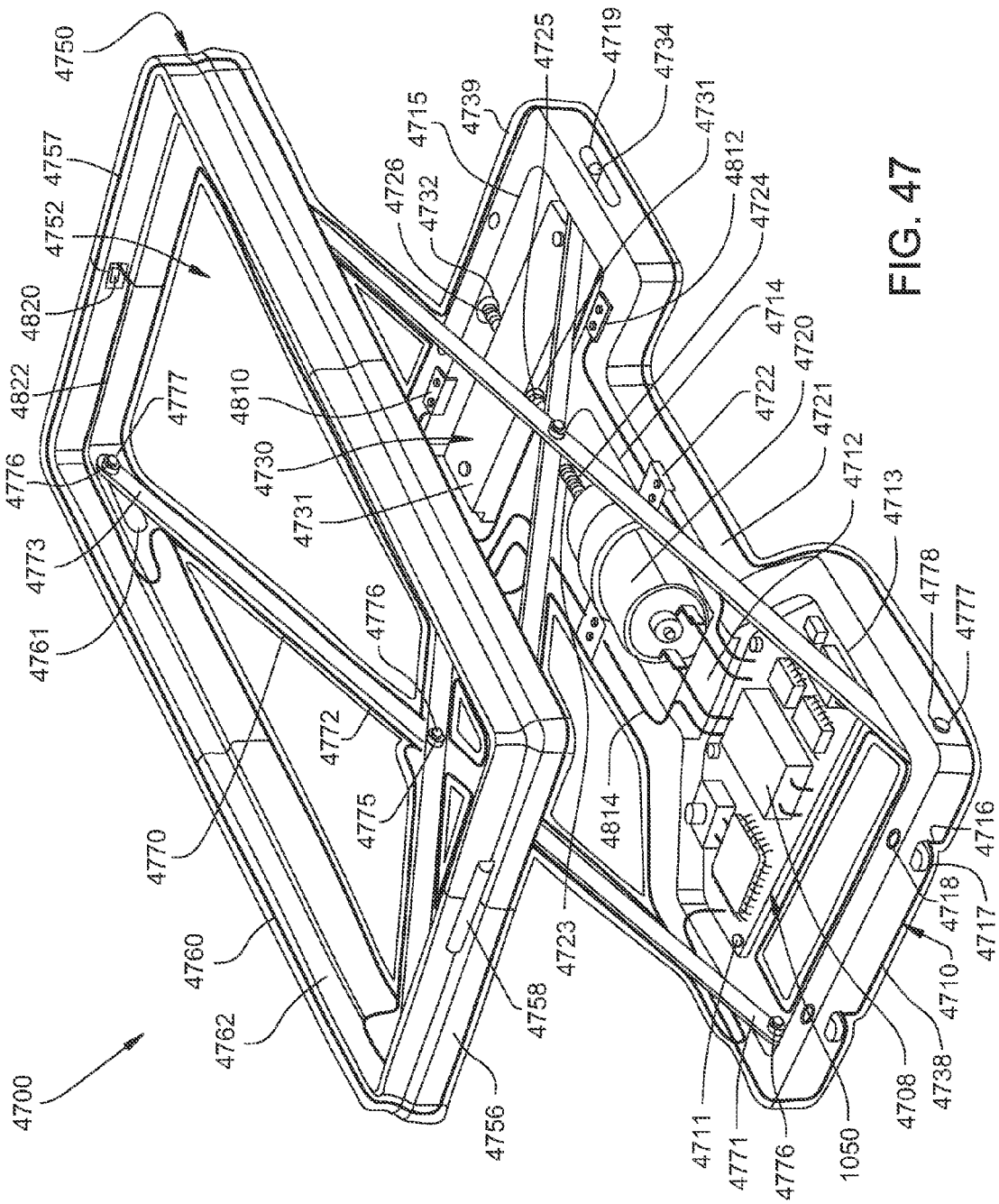
FIG. 47 is an enlarged top perspective view of a scissors lift mechanism within the automatic closing container assembly of FIG. 46.

Container assembly 4600 comprises a container 4602. Container 4602 of FIG. 46 is the same the previously described container 402 of FIG. 7A except that opening 414 and lid latches 496 have been omitted from container 402. For the description of container assembly 4600, container 4602 will be referred to using common reference numbers from FIG. 7A.

Container assembly 4600 further includes a rack or tray 4620. Tray 4620 can be formed from suitable materials such as stainless steel or aluminum. Tray 4620 comprises a generally planar rectangular shaped base 4622 that is perforated with an array of holes 4626. Holes 4626 allow sterilant to circulate below base 4622. Base 4622 has an upper surface 4623 and a bottom surface 4624. Four support feet 4628 are mounted to base 4622 and extend perpendicularly downward from the bottom surface 4624. Feet 4628 rest on the upper surface of support skeleton 4710 when tray 4620 is placed into container 4602.

Tray 4620 is used to hold medical/surgical instruments 180 within container 4602 during sterile processing. Tray 4620 includes a pair of spaced apart handles 4632 that are mounted to opposite ends of base 4622. Handles 4632 allow a user to grasp and lift tray 4620.

Tray 4620 is formed with several support members 4638 that extend upwardly from base 4622. Medical/surgical instruments 180 rest on and are supported by support members 4638. Support members 4638 are dimensioned and shaped so that medical/surgical instruments 180 are held and retained in a preferred orientation for sterile processing. It is important for some medical/surgical instruments 180 to be oriented in certain geometric orientations during sterile processing such that sterilant can readily enter and exit from the surgical instruments.

Cover 4650 is used to cover and enclose container 4602. Cover 4650 includes a generally rectangular shaped panel 4652 that is surrounded by a raised peripheral flange 4654. Cover 4650 is formed from materials such as stamped aluminum or other suitable materials. Two latches 4658 are mounted to opposite sides of cover 4650. Each latch 4658 is diametrically opposed to the other and is attached to flange 4654. Latch 4658 mates with a clip 4758 that extends outwardly from two ends of moveable frame 4750. When cover 4650 is moved downwardly into contact with moveable frame 4750, latch 4658 slightly pivots and engages clip 4758 resulting in the retention of cover 4650 to frame 4750. Cover 4650 has an elastomeric gasket 456 (see FIG. 7B) that is retained in a groove 455 (see FIG. 7B). Gasket 456 mates with peripheral lip 4760 of frame 4750 to form a seal between cover 4650 and moveable frame 4750. Other latches can be used that secure and seal cover to moveable frame as long as these latches allow the operator to unlatch, remove the cover and access contents inside container.

Container assembly 4600 further includes a scissor mechanism 4700. Scissor mechanism 4700 is received by interior cavity 420 of container 4602 and rests on bottom panel 407. Scissor mechanism 4700 is used to raise and lower frame 4750 during sterilization processing of container assembly 4600. Scissor mechanism 4700 comprises a dog bone shaped skeleton 4710 that is linked by a pair of central cross-members 4712. Skeleton 4710 has opposed ends 4738 and 4739. Skeleton 4710 and cross members 4712 define three cavities 4713, 4714 and 4715 within skeleton 4710. Four openings 4716 are defined in opposite ends of skeleton 4710. Openings 4716 receive locking fingers 4717 that have an attached slotted head 4718 that faces upwardly from the top surface of skeleton 4710. With skeleton 4710 resting on container bottom panel 407, slotted heads 4718 are rotated using a tool such as a screwdriver forcing locking fingers 4717 into engagement with a retention feature (not shown) on the inside surface of sides walls 405 and 406. The engagement of locking fingers 4717 with the retention features fixes skeleton 4710 to container 4602 and retains scissor mechanism 4700 to container 4602. In one embodiment, skeleton is realesably secured to the bottom of container. In yet another embodiment, skeleton is fastened to bottom of container. In all embodiments, skeleton is coupled to container in a manner that allows the skeleton and actuator system to create enough sealing force between the moveable frame and container to prevent ingress of microorganisms.

Sensor module 1050 is mounted in cavity 4713 and retained to skeleton 4710 by retention means 4711. Sensor module 1050 is the same as previously described in FIG. 12B except that an actuator driver circuit 4708 is incorporated into module 1050.

Rotary actuator 4720 is mounted in cavity 4714. Rotary actuator 4720 is attached to side sections 4721 of skeleton 4710 by a C-shaped clamp 4722. A threaded shaft 4723 extends perpendicularly away from one end of rotary actuator 4720. Rotary actuator 4720 can be rotated in either a clockwise or counterclockwise rotation causing a like a clockwise or counterclockwise rotation of threaded shaft 4723. Threaded shaft 4723 has a proximal end 4724 closest to actuator 4720, a center section 4725 and a distal end 4726.

A moveable carriage 4730 is mounted in cavity 4715. Moveable carriage 4730 includes a rectangular shaped block 4731 that is positioned in cavity 4715. Block 4731 has a threaded center bore 4731 that extends entirely through block 4731 and is perpendicular to shaft 4723. Threaded shaft 4723 is screwed into threaded bore 4731 and extends out the distal side of block 4731. The distal end 4726 of shaft 4723 is received in a bearing 4732 that is mounted in end 4739 of skeleton 4710.

Two diametrically opposed rods 4734 are fixed to and extend away from two ends of block 4731 in a perpendicular manner. Rods 4734 are received by diametrically opposed slots 4719 that are defined in sides of skeleton 4710 toward end 4739. The travel of moveable carriage 4730 in either direction is limited by the abutment of rods 4734 against the ends of slots 4731.

Because rotary actuator 4720 is fixed to skeleton 4710, clockwise rotation of threaded shaft 4723 causes block 4731 to move away from actuator 4720. The counterclockwise rotation of threaded shaft 4723 causes block 4731 to move toward actuator 4720.

Scissor mechanism 4700 further includes four elongated arms 4770. Each arm 4770 has a proximal end 4771, a center section 4772 and a distal end 4773. Apertures 4775 are defined through each respective proximal end 4771, center section 4772 and distal end 4773. Each aperture 4775 receives a retaining member 4776.

At skeleton end 4738, the lower arms proximal end 4771 retaining member 4776 has a pin 4777 that extends into a hole 4778 in skeleton 4710. Pin 4777 allows the lower arm proximal ends 4771 to rotate with respect to skeleton 4710.

At frame end 4756, the upper arms proximal end 4771 retaining members 4776 are received into holes (not shown) that extend into frame 4750. Retaining members 4776 allow the upper arm proximal ends 4772 to rotate with respect to frame 4750. In center section 4772, retaining member 4776 pivotally attaches the two crossing arms 4770. Retaining member 4776 allows the two arms 4470 to rotate with respect to each other.

At skeleton end 4739, the lower arms distal ends 4773 have apertures 4775 through which rods 4734 extend. Rods 4734 extend through distal ends 4773 and terminate in slots 4719. Apertures 4775 are dimensioned to be slightly larger than rods 4734 to allow the lower arm distal ends 4773 to rotate with respect to skeleton 4710.

At frame end 4757, the upper arm distal ends 4773 retaining members 4776 have pins 4777 that are received by slots 4761 that extend into frame 4750. Pins 477 extend perpendicularly away from distal arm ends 4773. Slots 4761 are dimensioned to be slightly larger than pins 4777 to allow pins 4777 to slide in slots 4761. Also, apertures 4775 are dimensioned to be slightly larger than pins 4777 to allow the upper arm distal ends 4773 to rotate with respect to skeleton frame 4750.

Figure 48:
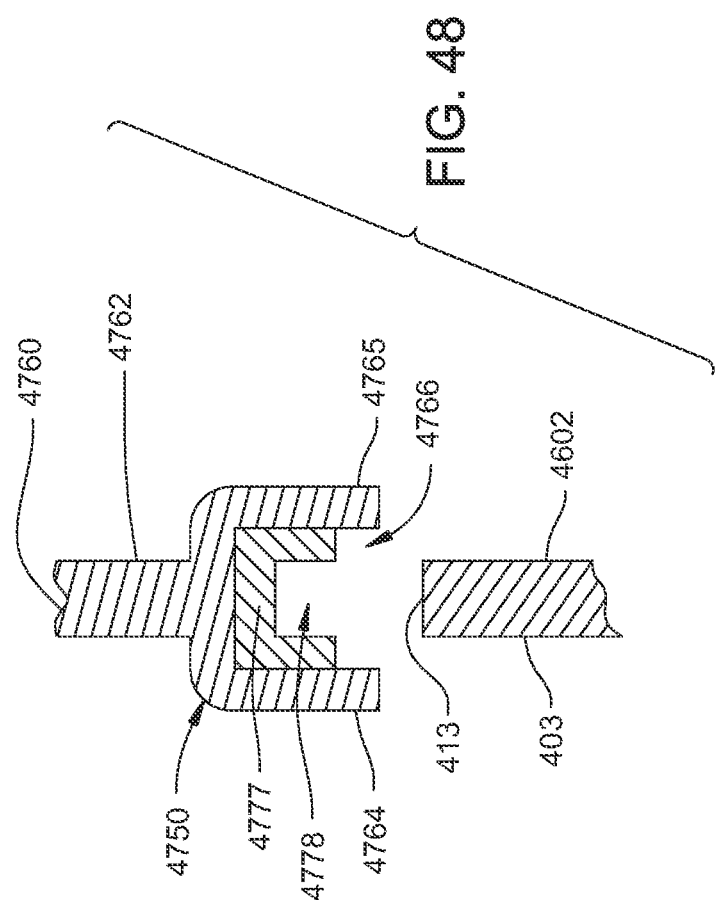
FIG. 48 is an enlarged cross-sectional view of a moveable frame and container.

The perimeter of moveable frame 4750 defines a central opening 4752. With additional reference to FIG. 48, a cross-sectional view of moveable frame 4750 is shown. Moveable frame 4750 includes an upwardly extending wall 4762 that terminates in lip 4760. Two spaced apart walls 4764 and 4765 extend downward from frame 4750 defining a channel 4766 there between. Channel 4766 receives an elastomeric split lip gasket or seal 4777. Gasket or seal 4777 is split into two lips that define a groove 4778. When moveable frame 4750 is lowered by scissors mechanism 4700 onto container 4602, gasket 4777 receives and engages rim 413 in groove 4778 forming a seal between frame 4750 and container 4602.

Container assembly 4600 further includes several sensors to detect the opening and closing of moveable frame 4750 or the insertion and removal of cover 4650. A close position micro-switch or limit switch 4810 is mounted to skeleton end 4739 facing into cavity 4715. An open position micro-switch or limit switch 4812 is mounted to cross-member 4712 facing into cavity 4715. Micro-switches 4810 and 4812 are in communication with electronic sensor module 1050 via an electrical cable 4814.

When moveable frame 4750 moves to a closed position, one side of block 4731 contacts and closes micro-switch 4810. When moveable frame 4750 moves to an open position, another side of block 4731 contacts and closes micro-switch 4812. When moveable frame 4750 is in the open position, a passage 4830 is created between container 4602 and frame 4750. Processor 1020 (FIG. 13) can interpret the signals from micro-switches 4810 and 4812 to determine the position of moveable frame 4750.

A Hall Effect sensor 4820 is mounted to the inner surface of frame wall 4762 facing opening 4752. Hall Effect sensor 4820 is in communication with electronic sensor module 1050 via an electrical cable 4822. A magnet 4824 (FIG. 46) is attached to the raised flange 4654 of cover 4650 opposite latch 4658.

When cover 4650 is placed over and attached to moveable frame 4750, magnet 4824 is positioned in proximity to Hall Effect sensor 4820. Hall Effect sensor 4820 detects the magnetic field generated by magnet 4824 and transmits an electrical signal indicating a detected magnetic field to processor 1020 (FIG. 13). When cover 4650 is removed from moveable frame 4750, magnet 4824 is positioned away from Hall Effect sensor 4820. Hall Effect sensor 4820 detects the absence of a magnetic field and transmits an electrical signal indicating no detected magnetic field to processor 1020. Processor 1020 uses the electrical signal to determine the position of cover 4650.

Figure 49:
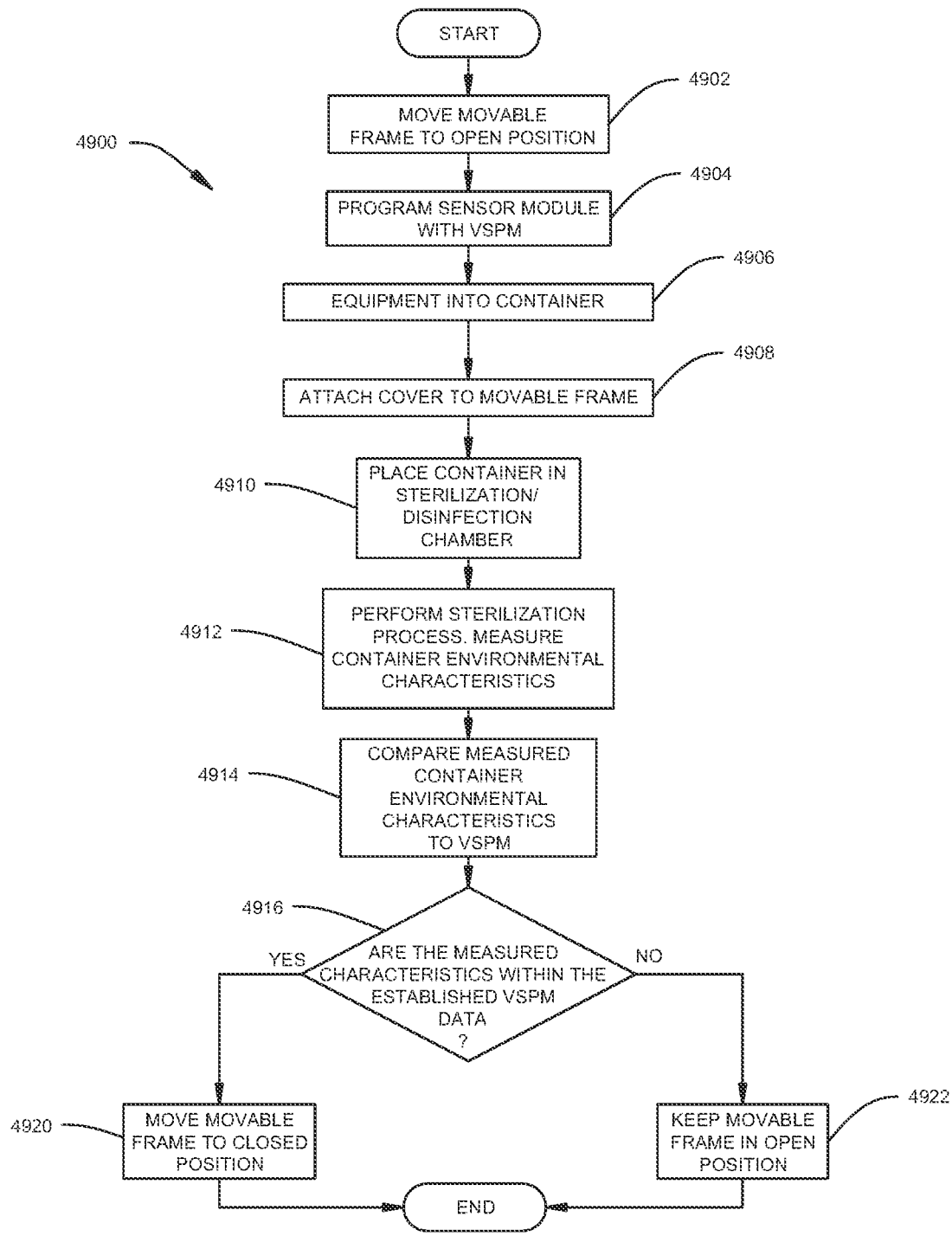
FIG. 49 is flowchart of a method of determining if validated sterilization process measurements taken within a container have been met or exceeded using the automatic closing container assembly of FIG. 46 in accordance with one embodiment.

XXVII. Operational Method to Determine if Validated Sterilization Process Measurements have been Achieved During a Sterilization Process Using an Automatic Closing Container with Scissor Lifting and Lowering Mechanism Referring to FIG. 49, a flowchart of a method 4900 of determining if validated sterilization process measurements within a container have been achieved during a sterilization process using automatic closing container assembly 4600 is shown. Method 4900 illustrates an exemplary method by which container assembly 4600 and electronic sensor module 1050 presented within the preceding figures perform different aspects of the processes that enable one or more embodiments of the disclosure. In the discussion of FIG. 49, reference will also be made to components from FIGS. 46-48.

Method 4900 begins at step 4902, where if the moveable frame 4750 is not in the open position, processor 1020 is triggered to move frame 4750 to the open position. In one embodiment, container assembly 4600 is placed on docking station 1300 (FIG. 16) and communicatively coupled to docking station 1300 using connector 1338 (FIG. 16) and cable 1340 (FIG. 16) that are connected to connector 1032 of electronic sensor unit 1050. Docking station processor 1410 (FIG. 17) in communication with container processor 1020, queries container processor 1020 as to the position of moveable frame 4750. If the moveable frame 4750 is not in the open position, processor 1410 transmits a signal triggering processor 1020 to cause rotary actuator 4720 to rotate threaded shaft 4723 in a counterclockwise manner.

The rotation of threaded shaft 4723 in a counterclockwise manner causes a linear movement of block 4731 in a proximal direction toward actuator 4720, which in turn causes scissor arms 4770 to move moveable frame 4750 upwardly away from the rim 413 of container 4602. In one embodiment, the contact of the proximal side of block 4731 with open position micro-switch 4812 triggers processor 1020 to turn off rotary actuator 4720. Frame 4720 is now in an open position where sterilant can enter container 4602 through passage 4830 during sterilization processing. In an alternate embodiment, container assembly is placed in sterilizer chamber with moveable frame in a closed state. In this embodiment a signal from controller 1020 lifts and opens frame during the sterilization process occurring within sterilizer 52.

At step 4904, sensor module 1050 is programmed with validated sterilization process measurements (VSPM) 1150. Memory 1022 (FIG. 14) is programmed with specific validated sterilization process measurements (VSPM) 1150. Container programming software 1461 (FIG. 17) executing on docking station processor 1410 (FIG. 17) identifies the specific VSPM 1150 associated with the container equipment load, optionally using the data obtained from handheld reader 1240 (FIG. 44), and transmits the VSPM 1150 for storage on container memory 1022. The transmitted VSPM 1150 are specific to the equipment load to be sterilized. The connector 1338 and cable 1340 are then disconnected from connector 1032.

The equipment load of surgical instruments 180 is prepared for sterilization processing by an operator. At step 4906, the surgical instruments 180 are placed into tray 4620 and tray 4620 is placed into container 4602. If no instrument rack is required per the content ID, instruments are placed inside container without a instrument rack. Cover 4650 is attached and closed to moveable frame 4750 via the latching of latch 4658 to clip 4758 (step 4908). Cover 4650 is now sealed to moveable frame 4750.

The container 4602 is placed into the sterilization chamber 52 (FIG. 1) at step 4910 and the sterilization process cycle within sterilization chamber 52 is started (block 4912). During the sterilization process cycle, the sterilization chamber runs the nominal sterilization process by introducing a sterilization agent, such as steam or hydrogen peroxide gas into the sterilization chamber. The sterilization agent enters and exits through passage 4830 created when moveable frame is not in the closed and sealed position. The sterilization process cycle may also include a cool down phase and drawing a vacuum on the chamber to remove any residual condensed sterilant. In one embodiment, the sterilization agent is removed from the contents of the container through passage 4830 by maintaining the moveable frame in a open position during this phase of the sterilization process. The sterilization chamber is set to operate using a set of chamber process parameters (CPP) 66 (FIG. 1). CPP 66 are the set of nominal process parameter settings for the sterilization chamber to operate using CPP 66.

Also, at step 4912, sterilization verification software 1152 (FIG. 14) executing on processor 1020 monitors and collects real time data from the respective electronic sensors in sensor module 1050 during the sterilization process cycle. The sensors monitor the operating process measurements and conditions within their respective container. The collected real time operating data is stored in memory 1022 as data 1156 (FIG. 14). For example, sterilization verification software 1152 executing on processor 1020 collects water vapor data from water vapor sensor 1024, pressure data from pressure sensor 1026, temperature data from temperature sensor 1028 and hydrogen peroxide concentration data from hydrogen peroxide gas sensor 1052. All of the data recorded during the sterilization process is stored as data 1156 in memory 1022.

Sterilization verification software 1152 executing on processor 1020 at step 4914 compares the observed real time data 1156, collected during the sterilization process cycle, to VSPM 1150. At decision step 4916, sterilization verification software 1152 operating on processor 1020 determines if the measured data 1156 during the performed sterilization process meets or exceeds the minimum or threshold VSPM 1150 values for each operating parameter to insure sterilization of the container contents. For example, if VSPM 1150 has a minimum temperature and time value of 250 degrees Fahrenheit for 20 minutes, sterilization verification software 1152 compares these values to the recorded time and temperature values in data 1156.

In response to the recorded data 1156 values meeting or exceeding the minimum or threshold VSPM 1150 values for each sterilization operating parameter indicating sterilization of the container contents, method 4900 proceeds to step 4920. At step 4920, processor 1020 triggers rotary actuator 4720 to rotate threaded shaft 4723 in a clockwise manner. In an alternate embodiment after VSPM data have been verified, sterilization verification software keeps passage 4830 open to affect sterilization agent removal from the container contents prior to closing passage with moveable frame. In this embodiment, closing signal can be sent from controller based on a specific time interval following the lethal sterilization part of the cycle or after a certain sensor monitored signal indicating sterilization agent removal is complete.

The clockwise rotation of threaded shaft 4723 causes a linear movement of block 4731 in a distal direction toward skeleton end 4739, which in turn causes scissor arms 4770 to move moveable frame 4750 downwardly into engagement with rim 413 of container 4602. In one embodiment, the contact of the distal side of block 4731 with closed position micro-switch 4810 triggers processor 1020 to turn off rotary actuator 4720.

Moveable frame 4720 is now sealed to container 4602 and is in the closed position. The lid being in the closed state functions as indication that the load in the container is properly sterilized. The contents of container assembly 4600 are now in a sealed sterile state and are ready for storage. In this basic execution of method 4900, residual sterilant vents from the container, through microbial barriers into the ambient environment.

In response to the recorded data 1156 indicating that the environmental measurements did not meet the VSPM 1150, the processor, as represented by step 4922, holds the frame in the open position. The frame 4750 being in the open state, serves as an indication that the contents of the container were not properly sterilized.

During storage, processor 1020 executes a set of instructions such as sterile monitor software 1158 (FIG. 14) that causes processor 1020 to monitor the electrical signal received from Hall Effect sensor 4820 (FIG. 47) during storage. If cover 4650 is opened, the electrical signal from Hall Effect sensor 4820 changes, triggering processor 1020 to move the moveable frame 4750 to the open position. In an alternate embodiment, sterile monitor software flashes an LED instead of opening the moveable frame. The moveable frame 4750, in the open position, indicates to a technician that the contents of the container 2602 are no longer considered to be sterile.

In one alternative version of this embodiment, after the sensor module measures the environmental characteristics in the container after the sterilizing portion of the sterilization process is executed. This monitoring occurs after the evaluation of step 4916 indicates that the load in the container is properly sterilized. During this phase of operation, the sensors measure the extent to which residual sterilant is still present in the container. The processor, based on these measurements, determines it the residual sterilant is at or below an acceptable level. When the processor determines that the container is in this state, the processor then executes step 4920 so as cause the frame to close so as to seal the container.

Figure 50:
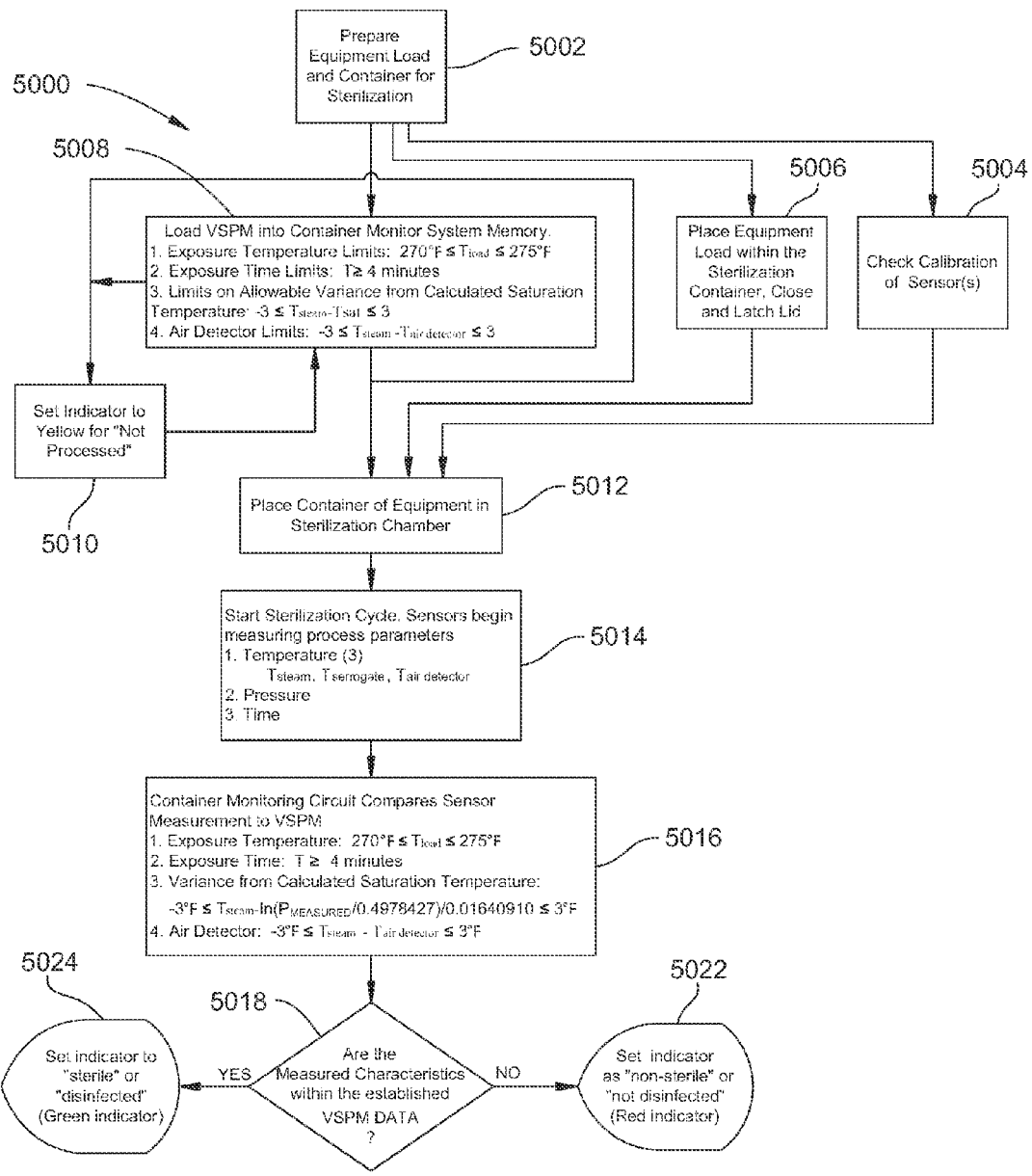
FIG. 50 is flowchart of a method of determining if verified sterilization process parameters within a container have been met during a steam sterilization process in accordance with one embodiment.

XXVIII. Operational Method to Verify Sterilization Process Parameters in a Container During a Steam Sterilization Process Referring to FIG. 50, a flowchart of a method 5000 of determining if verified sterilization process measurements within a container have been achieved during a steam sterilization process is shown. Method 5000 illustrates an exemplary method by which any of the container assemblies 90, 300, 400, 500, 600, 700 and 800 (90-800) and electronic sensor modules 200, 460, 560, 660, 760, 850, 950, 1000, 1050 and 1080 (200-1080) presented within the preceding figures perform different aspects of the processes that enable one or more embodiments of the disclosure. Method 5000 is described specifically as being performed using container assembly 400 (FIG. 7A) and sensor module 1050 (FIG. 12B). However, method 5000 can be performed using any of container assemblies 90-800 and electronic sensor modules 200-1080. The description of the method is provided with general reference to the specific components illustrated within the preceding figures. In the discussion of FIG. 50, reference will also be made to components from FIGS. 7A, 12B and 15.

Generally method 5000 is described as being implemented via container processor 1020 and particularly the execution of code provided by software/firmware modules acting within processor 1020. It is however appreciated that certain aspects of the described methods may be implemented via other processing devices and/or execution of other code.

Method 5000 begins at step 5002 where the equipment load of surgical instruments 180 is prepared for sterilization processing by an operator. Step 5002 includes the positioning of container 402 onto docking station 1200 or 1300 and if the container has a connector, connecting the corresponding connector 485, 1032 to the docking station. At step 5002, the handheld reader 1240 is used to scan container 402, tray 160 and the surgical instruments 180 to be sterilized. At step 5006, the surgical instruments are placed into tray 160, tray 160 is placed into container 402 and the cover 450 is attached and latched closed. During the loading of surgical instruments, 180, the operator refers to the display screen 1260 shown by docking station 1200 or 1300 to view the correct equipment load and orientation.

In an optional step 5004, the sensors of electronic sensor module 1050 are calibrated prior to use. Electronic sensor modules 1050 is calibrated using docking station 1300.

At step 5008, the memory 1022 within container 402 is programmed with specific verified steam sterilization process parameters (VSPP) 1150. Container programming software 1461 (FIG. 17) executing on docking station processor 1410 (FIG. 17) identifies the specific VSPP 1150 associated with the container equipment load, using the data obtained from handheld reader 1240, and transmits the VSPP 1150 via the connector 485 for storage on the container memory 1022. The transmitted VSPP 1150 are specific to the equipment load within the container to be sterilized.

In the steam sterilization example of FIG. 50, the VSPM 1150 include:
1. Temperature Range Indicative Of Saturated Steam: 132° C.≤Tsat≤135° C.
2. Time Period Exposed Saturated Steam: t≥4 minutes
3. Acceptable Range of Temperature Differences Between Calculated Temperature of Saturated Steam And Measured Temperature±1.6° C.
4. Range of Temperature Differences Between Measured Temperatures At Spaced Apart Locations In The Container That Indicates The Load Is Surrounded By Saturated Steam±1.6° C.

In an additional optional step at block 5010, is the processor 1020 turning on a yellow light emitting diode (LED) of LEDS 1030. This is to indicate the container assembly has not cycled through the sterilization process.

In step 5102 the container 402 is placed into the sterilization chamber 52. Step 5014 is the starting of the sterilization process. During the sterilization process, the sterilization chamber is heated, pressurized and a steam sterilant is introduced into the sterilization chamber. The sterilization process cycle also includes a cool down phase and drawing a vacuum on the chamber to remove any residual condensed sterilant. The sterilization chamber is set to operate using a set of chamber process parameters (CPP) 66 (FIG. 1). CPP 66 are the set of process parameter settings within the sterilization chamber. The sterilization chamber is set to operate using the CPP 66.

Also, at step 5014, processor 1020 running sterilization verification software 1152 monitors and collects real time data from the respective electronic sensors with which it is in communication during the sterilization process cycle. The sensors monitor the characteristics of the environment in the container in which the sensors are mounted. The collected measurements, which are time based are stored in memory 1022 as data 1156. For example, processor 1020 collects humidity data from humidity sensor 1024, pressure data from pressure sensor 1026, temperature data from temperature sensor 1028 and time data. The temperature data includes recording the temperature during the incoming steam phase (Tsteam), the temperature of the load (Tsurrogate) and the temperature of the steam laden atmosphere within the air detection lumen (lair detector). The temperature of the load is referred to as a surrogate temperature because it can be difficult to provide sensors that monitor the temperature of the load. Instead, the sensors monitor the void near the load. The surrogate temperature should thus be considered substantially equal to if not identical to the actual temperature of the load. The temperature of this void is considered a surrogate for the temperature of the load. All of the data recorded during the sterilization process is stored as data 1156 in memory 1022.

At step 5016, processor 1020 running sterilization verification software 1152 compares the observed real time data 1156, collected during the sterilization process cycle, to VSPM 1150 limits.

At decision step 5018, processor 1020 determines if the real time measured data 1156 during the performed steam sterilization process are within the VSPP 1150 limits for each operating parameter to insure sterilization of the container contents.

If the measured environmental characteristics meet or the VSPM, the processor executes step 5024. Step 5024 is identical to previously described step 2122.

The measured environmental characteristics may not meet the VSPM for the load. If this condition exists, the processor executes step 5022. Step 5022 is understood is identical to step 2126.

In response to the sterilization process cycle not being completed at step 5020, method 5000 returns to step 5016 where processor 1020 continues monitoring and recording sterilization process operating parameters during the sterilization process cycle.

In response to the sterilization process cycle being complete at step 5020, processor 1020 indicates that the container contents have not successfully completed sterilization processing and are not sterile by turning on a red LED such as red LED of LEDS 1030 at step 5022. Method 5000 then ends.

Figure 51:
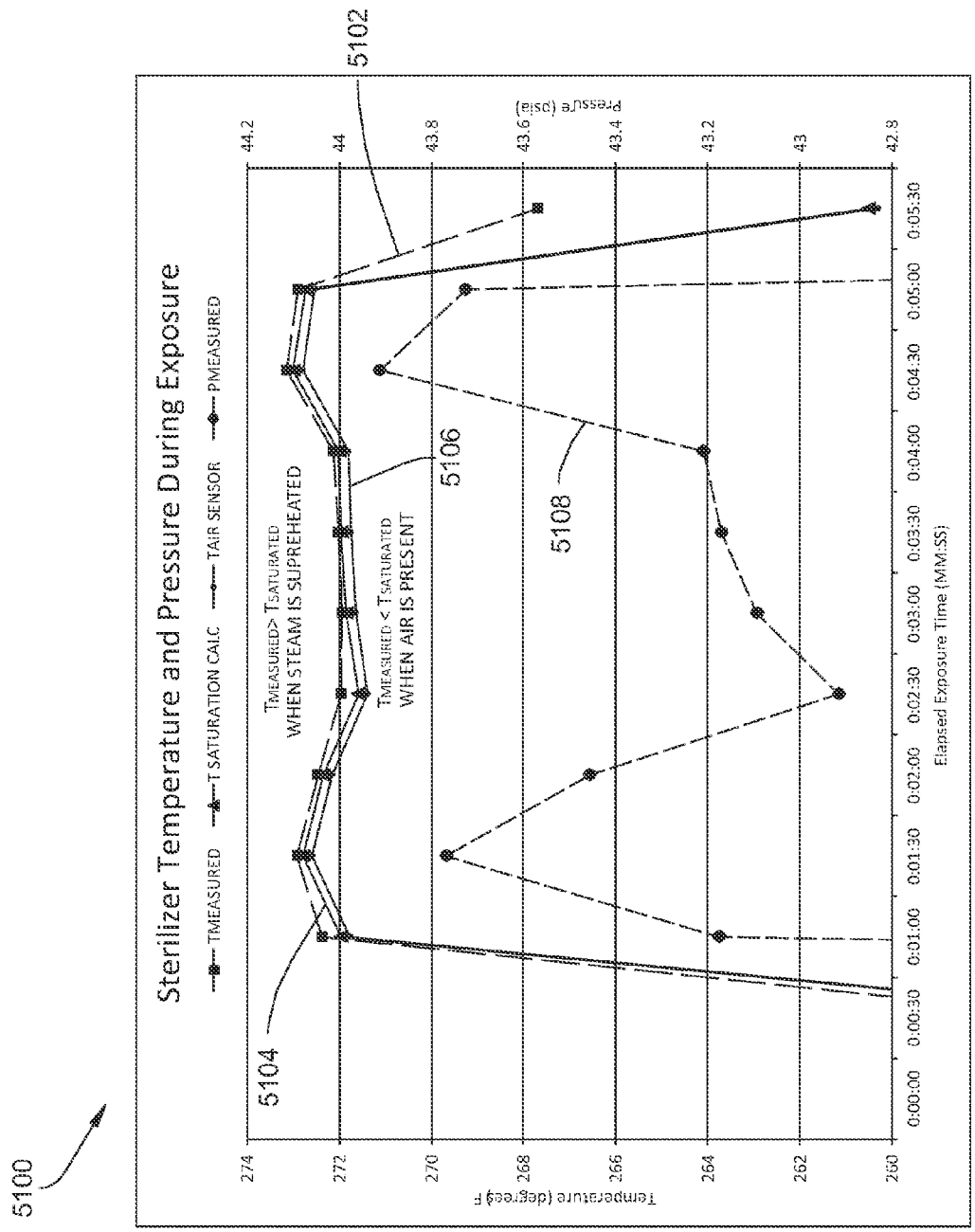
FIG. 51 is a graph of an example of measured steam process measurements versus time for the method of FIG. 50.

FIG. 51 illustrates an example graph 5100 of process parameter measurements taken by sensor module 1050 inside container 402 of instruments that were processed using a steam sterilization process. Only the exposure phase measurements are shown in the graph. FIG. 51 shows a graph 5100 of temperature and pressure versus time. The measurements include Tsteam (Tmeasured) or Tload 5102, Tair detector 5106 and pressure 5108. The graph also includes a superimposed graph of the calculated temperature for saturated steam (Tsat 5104) based upon the pressure measurement within the container.

Figure 52:
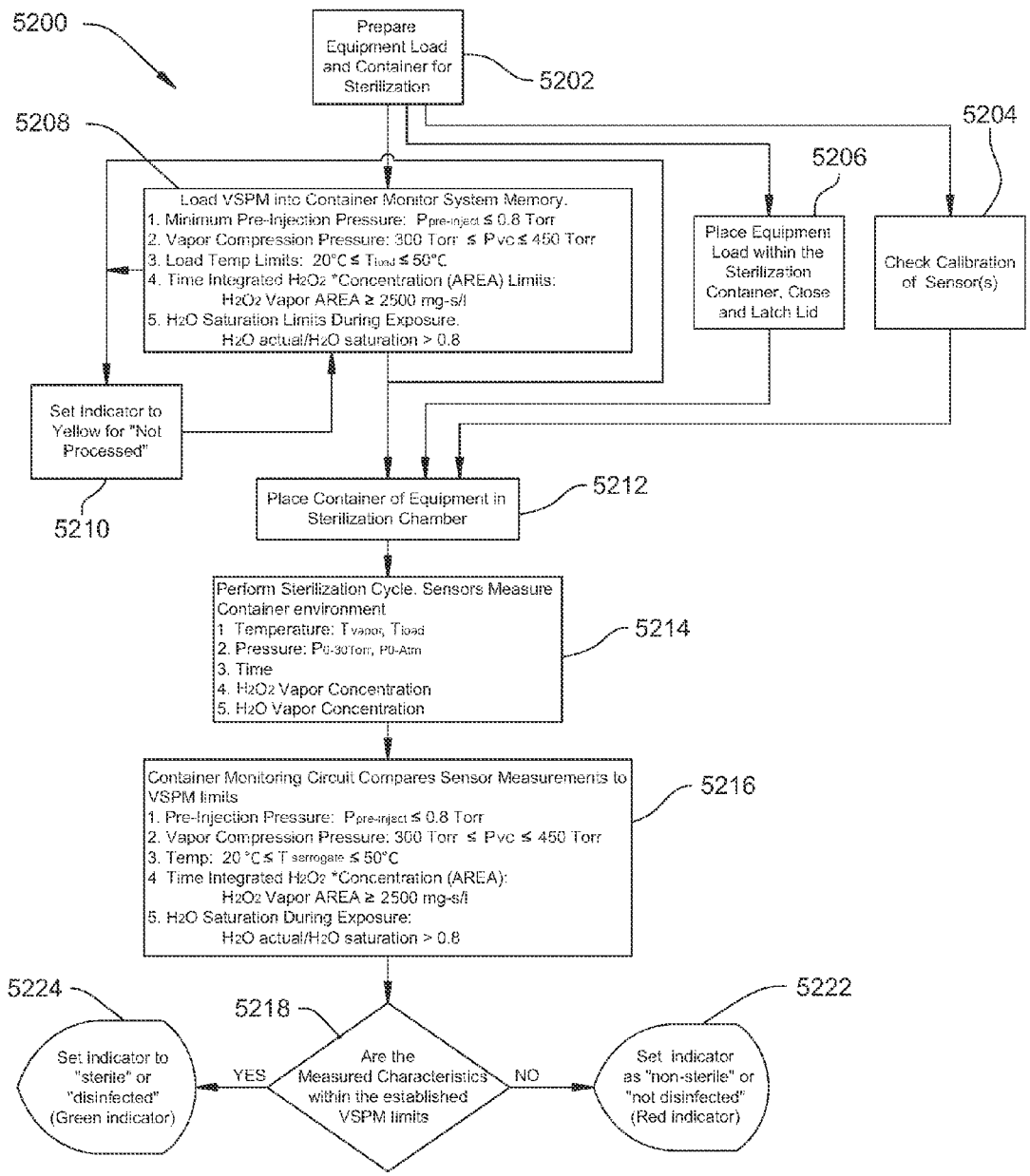
FIG. 52 is flowchart of a method of determining if verified sterilization process parameters within a container have been met during a hydrogen peroxide sterilization process in accordance with one embodiment.

XXIX. Operational Method to Verify Sterilization Process Parameters in a Container During a Hydrogen Peroxide Sterilization Process FIG. 52 is a flowchart of a method 5200 for determining validated sterilization process measurements for a load sterilized using vaporized hydrogen peroxide sterilization process is shown. Method 5200 illustrates an exemplary method by which the container assemblies 400, 500, 600, 700 and 800 (400-800) and electronic sensor modules 460, 560, 660, 760, 850, 950, 1000, 1050 and 1080 (460-1080) presented within the preceding figures perform different aspects of the processes that enable one or more embodiments of the disclosure. Method 5200 is described specifically as being performed using container assembly 400 (FIG. 7A) and sensor module 1050 (FIG. 12B). However, method 5200 can be performed using any of container assemblies 400-800 and electronic sensor modules 460-1080. The description of the method is provided with general reference to the specific components illustrated within the preceding figures. In the discussion of FIG. 52, reference will also be made to components from FIGS. 7A, 12B and 15.

Generally method 5200 is described as being implemented via container processor 1020 and particularly the execution of code provided by software/firmware modules acting within processor 1020. It is however appreciated that certain aspects of the described methods may be implemented via other processing devices and/or execution of other code.

Method 5200 begins at step 5202 where the equipment load of surgical instruments 180 is prepared for sterilization processing by an operator. Step 5202 includes the positioning of container 402 onto docking station 1200 or 1300 and if the container has a connector, connecting the corresponding connector 485, 1032 to the docking station. At step 5202, the handheld reader 1240 is used to scan container 402, tray 160 and the surgical instruments 180 to be sterilized. At step 5206, the surgical instruments are placed into tray 160, tray 160 is placed into container 402 and the cover 450 is attached and latched closed. During the loading of surgical instruments, 180, the operator refers to the display screen 1260 shown by docking station 1200 or 1300 to view the correct equipment load and orientation.

In an optional step 5204, the sensors of electronic sensor module 1050 are calibrated prior to use. Electronic sensor module 1050 is calibrated using docking station 1300.

At step 5208, the memory 1022 is loaded with verified hydrogen peroxide sterilization process measurements (VSPM) 1150. Container programming software 1461 (FIG. 17) executing on docking station processor 1410 (FIG. 17) identifies the specific VSPP 1150 associated with the container equipment load, using the data obtained from handheld reader 1240, and transmits the VSPP 1150 via the connector 485 for storage on the container memory 1022. The transmitted VSPP 1150 are specific to the equipment load within the container to be sterilized.

In the hydrogen peroxide sterilization example of FIG. 52, the VSPM 1150 include:
1. Minimum Pre-Injection Pressure: Ppre-inject ≤0.8 Torr
2. Vapor Compression Pressure: 300 Torr≤PVC≤450 Torr 3. Vapor Temp Limits: 20° C.≤Tvapor≤50° C.
4. Time Integrated H2O2*Concentration (AREA) Limits: H2O2 Vapor AREA≥2500 mg-s/l
5. H2O Saturation Limits during Exposure: H2O actual/H2O saturation >0.8

In an additional optional step at block 5210, sterilization verification software 1152 executing on processor 1020 turns on a yellow light emitting diode (LED) of LEDS 1030 indicating to a user that the container assembly has not yet been processed through a sterilization process cycle.

Next, the container 402 is placed into the sterilization chamber 52 (FIG. 1) at step 5212 and the sterilization process cycle within sterilization chamber 52 is started (block 5214). During the sterilization process cycle, the sterilization chamber is heated, pressurized and a hydrogen peroxide sterilant is pumped into the sterilization chamber. The sterilization process cycle also includes a cool down phase and drawing a vacuum on the chamber to remove any residual condensed sterilant. The sterilization chamber is set to operate using a set of chamber process parameters (CPP) 66.

Also, at step 5214, processor 1020 records the time based measurements of the environmental characteristics received from the sensors.

The recorded temperature measurements are understood to include the temperature of the hydrogen peroxide vapor (Tvapor). All of the data recorded during the sterilization process is stored as data 1156 in memory 1022.

At step 5216, processor 1020 running sterilization verification software 1152 compares the measured environmental characteristics to the VSPM 1150. An exemplary set of VSPM 1150 for a load that sterilized with vaporized hydrogen peroxide process is:
1. Pre-Injection Pressure: Ppre-inject ≤0.8 Torr
2. Vapor Compression Pressure: 300 Torr≤PVC≤450 Torr
3. Load Temp: 20° C.≤Tvapor≤50° C.
4. Time Integrated H2O2*Concentration (AREA): H2O2 Vapor AREA≥2500 mg-s/l
5. H2O Saturation during Exposure: H2O actual/H2O saturation >0.8

At decision step 5218, processor 1020 determines if the measured environmental characteristics meet or exceed the VSPM 1150 for the load. The third validated measurement above is an area under a time based curve of concentration. Part of step 5218 includes integrating the individual H2O2 concentrations taken over a time period to determine the integrated value of these measurements.

In response to the measured environmental characteristics meeting the VSPM, processor 1020 executes step 5224 which is identical to previously described step 2122.

Alternatively in step 5216 it may be determined that the measured environmental characteristics did not meet the VSPM 115 for the load If this condition exists, the processor executes step 5222 which is identical to previously described step 2128.

Figure 53:
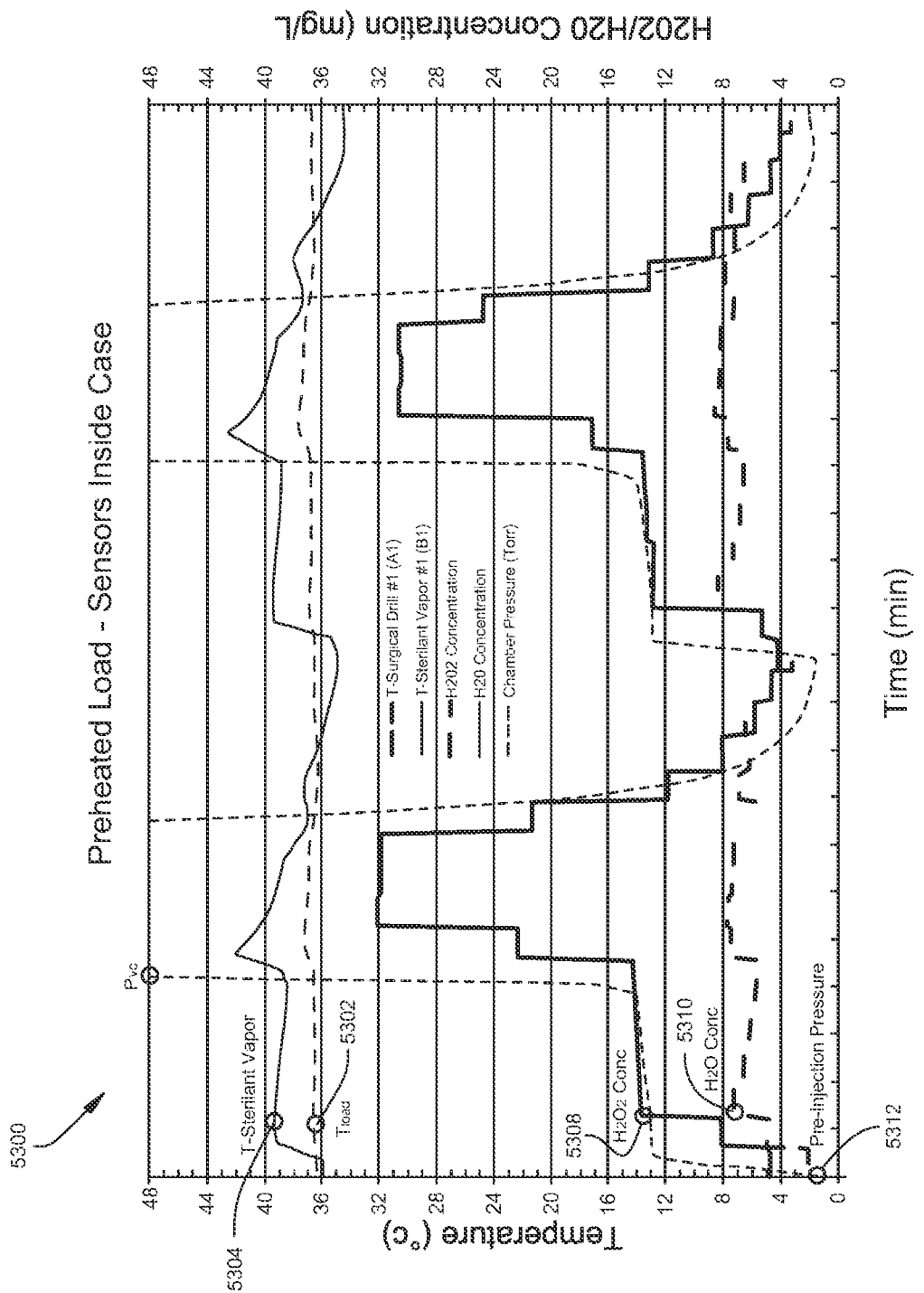
FIG. 53 is a graph of an example of measured hydrogen peroxide process measurements versus time for the method of FIG. 52.

FIG. 53 illustrates an example graph 5300 of process parameter measurements taken by sensor module 1050 inside container 402 of instruments that sterilized with hydrogen peroxide. The pressure measurements are graphed using a scale that places the pressure measurements during the vapor compression phase (which are around 400 Torr) off the visible part of the graph. In the graph 5300 of temperature and pressure (left axis) versus time and hydrogen peroxide and water vapor concentration (right axis) versus time. The measurements include the temperature of the hydrogen peroxide vapor (Tsertilant vapor) 5304, the pressure in the container prior to vapor injection (Pre-injection pressure) 5312, the hydrogen peroxide concentration 5308 and the water vapor concentration 5310.

The measurements of a number of the environmental characteristics are shown as being made repeatedly over the time period of the sterilization process. These are the measurements used in step 5216 to determine the integrated area under the hydrogen peroxide curve. These measurements are also used to determine the presence of the saturated water vapor.

The environmental measurements of FIG. 53 are the measurements that are compared to the VSPM 1150. As a result of this comparison, the processor determines that four of the measured environmental characteristics met the validated measurements associated with these characteristics. Specifically the vaporized hydrogen peroxide was compressed to a pressure of 400 Torr when the validate measurement for this compression is the range of 300 to 450 Torr. The vapor state hydrogen peroxide was at measured to fluctuate at a temperatures between 36 and 38° C. when the validate measurement for this temperature is the range of 20 to 50° C. The integrated vaporized hydrogen peroxide over time was 2846 mg-s/l. The validated measurement for this characteristic is a value of at least 2500 mg-s/l. The fifth measured environmental characteristic is the ratio of total water vapor present to water saturation was calculated at 1.63. The test sterilization processes for this load showed that the minimal validated measurement for this characteristic is 0.8.

However, the pre-injection pressure measured during the process was 1.5 Torr. The VSPM for this load indicated that the maximum level of this pressure is 0.8 Torr. Consequently when evaluating these data, in step 5218 the processor determines that not all the required validated sterilization measurements were met. The processor 1020 thus would execute step 5222 to provide an indication that the load was not satisfactorily sterilized.

The containers may have other structural features. For example the control buttons may be mounted to the sensor module. Conductors that extend from the module connect the buttons to the on container electrical devices controlled by the buttons.

In some versions of the invention breakable, frangible single use tamper evident devices may be fitted to the containers of this invention. The states of these devices provide visual indicia of the unbroken/broken state of the seal around the container. These devices may be used in addition to or a substitute for the electronic devices described above that provide indicia of the unbroken/broken seal state.

Sensors other than Hall sensors may be used to detect the open/closed state of a container lid. These sensors include mechanical switches and magnetoresistive transducers.

Likewise the sensor containers that measure the concentration of gas are a function of the type of sterilizer with which the containers are used. Some sensors thus monitor the concentration of sterilizing gases such as ozone or ethylene oxide. If a sterilizing process involves introducing plural gases into a container the container will have one or more sensors capable of monitoring the concentrations of each of the gases. A single sensor assembly is all that is required if the sensor assembly is able to measure and output signals representative of the concentrations of the plural gases employed in the sterilization process.

It should thus be appreciated that the sensors that monitor gas concentration are not limited to sensors that function by monitoring the absorption of light at a selected wavelength. Alternative sensors that output signals that vary as a function of the concentration of the gas measured by the sensor may be integrated into alternative versions of this invention. These include, for example, transducers that change in either resistance or capacitance as a function of the concentration of target gas.

In a version of the invention with a removable sensor module the sensor module may include components such as switches that are tripped when the module is correctly installed. The tripping of the switch causes a light to be illuminated that indicates the unit is correctly installed.

Likewise, the removable sensor modules of this invention can be placed in a calibration chamber without having to first place the sensor modules in containers.

Therefore, it is an object of the appended claims to cover all such variations and modifications that come within the true spirit and scope of this invention.

What is claimed is:

1. A sterile barrier assembly, said assembly including:
a sterile barrier for holding at least one surgical instrument to be sterilized, said sterile barrier adapted for removable insertion in the interior chamber of a sterilizer, said sterile barrier formed from material through which sterilant can pass through during a sterilization process and contact the surgical instrument and that serves as a microbial barrier that prevents microorganisms from entering into said sterile barrier after the sterilization process;
at least one sensor mounted to said sterile barrier for measuring at least one characteristic of the environment inside said sterile barrier during the sterilization process and generating signals representative of the measured environmental characteristic;
a processor mounted to said sterile barrier and connected to said at least one sensor for receiving from said at least one sensor the signals representative of the measurements of the at least one characteristic of the environment inside said sterile barrier during the sterilization process wherein, said processor includes a memory that contains validated sterilization process measurement data, the validated sterilization process measurement data indicating the environmental characteristics associated with a validated sterilization process associated with the at least one surgical instrument inside said sterile barrier and said processor is configured to:
compare the environmental characteristics as measured by said at least one sensor to the validated sterilization process measurement data; and
based on the comparison, assert a signal indicating whether or not the instrument was subjected to the validated sterilization process; and
a battery mounted to said sterile barrier for providing power to said processor.

2. The sterile barrier assembly of claim 1, wherein:
at least one light or a display is mounted to said sterile barrier to be seen outside of said sterile barrier; and
the signal asserted by the processor indicating whether or not the instrument was subjected to the validated sterilization process is sent to said at least one light or said display so as to cause said light or said display to present a visual indication regarding whether or not the instrument was subjected to the validated sterilization process.

3. The sterile barrier assembly of claim 1, wherein said at least one sensor is mounted in said sterile barrier.

4. The sterile barrier assembly of claim 1, wherein said processor is mounted in said sterile barrier.

5. The sterile barrier assembly of claim 1, wherein said battery is mounted in said sterile barrier.

6. The sterile barrier assembly of claim 1, wherein:
plural said sensors are mounted to said sterile barrier, wherein at least two said sensors are adapted to measure different characteristics of the environment in said sterile barrier and each said sensor generates signals representative of the environmental characteristic measured by said sensor;
the validated state process measurement data contained in said processor memory are data describing plural different environment characteristics that are associated with the validated sterilization process for the at least one surgical instrument inside said sterile barrier; and
said processor is connected to the said plural said sensors for receiving the plural signals representative of the measurements of the different environmental characteristics in said sterile barrier and is further configured to compare the measurements of the different environmental characteristics to the validated state process measurement data to determine if the at least one surgical instrument was subjected to the validated sterilization process.

7. The sterile barrier assembly of claim 1, wherein said at least one sensor is configured to measure one of the following environmental characteristics inside said sterile barrier: the concentration of water vapor (steam); temperature; pressure; or the concentration of a gas other than steam.

8. The sterile barrier assembly of claim 1, wherein a connector is mounted to said sterile barrier and is connected to said memory so that validated sterilization process measurement data for a specific at least one surgical instrument can be loaded through said connector into said memory.

9. The sterile barrier assembly of claim 1, wherein said sterile barrier includes a container assembly that includes a container and a cover that encloses said container.

10. The sterile barrier assembly of claim 1, further including a wireless transceiver that is connected to said processor that is capable of transmitting the signal asserted by said processor.

11. The sterile barrier assembly of claim 1, wherein:
said at least one sensor is contained in a module;
said sterile barrier includes a receiver configured to releasably hold said module; and
a seal assembly attached to said module and said receiver prevents microorganisms from entering into said sterile barrier during the removal of said module from said receiver.

12. The sterile barrier assembly of claim 11, wherein said module comprises a switch that is tripped when said module is correctly installed in said receiver.

13. A method of sterilizing at least one surgical instrument, said method including the steps of:
placing at least one surgical instrument in a sterile barrier, the sterile barrier being formed from material through which sterilant can pass through and contact the surgical instrument and that serves as a microbial barrier that prevents microorganisms from entering into said sterile barrier after a sterilization process and the sterile barrier includes:
at least one sensor capable of measuring at least one characteristic of the environment inside the sterile barrier during a sterilization process and generating a signals representative of the measured environmental characteristic;
a processor that is connected to the at least one sensor for receiving from the at least one sensor the signals representative of the measurements of the at least one characteristic of the environment inside the sterile barrier during the sterilization process, the processor includes a memory that contains validated sterilization process measurement data, the validated sterilization process measurement data indicating the environmental characteristics associated with a validated sterilization process associated with the at least one surgical instrument placed inside the sterile barrier; and a battery;

placing the instrument-containing sterile barrier container in the chamber of a sterilizer;

actuating the sterilizer to subject said sterile barrier and the at least one surgical instrument to a sterilization process in which the environment inside said sterile barrier is modified;

with the at least one sensor, measuring at least one characteristic of the environment in said sterile barrier during the sterilization process;

powering the processor with the battery;

during said sterilization process, providing signals from the sensor to the processor that indicate the measured environmental characteristics in the sterile barrier during the sterilization process;

with the processor, comparing the environmental characteristics as measured by the at least one sensor to the validated sterilization process measurement data stored in the processor memory;

having the processor, based on said comparison, assert signal indicating whether or not the instrument was subjected to the validated sterilization process for the at least one surgical instrument; and based on the signal asserted by the processor, providing an indication obtainable outside the sterile barrier whether or not the at least one surgical instrument was subjected to the validated sterilization process.

14. The method of sterilizing at least one surgical instrument of claim 13, wherein, the processor performs said step of asserting a signal indicating whether or not the instrument was subjected to the validated sterilization process for the at least one surgical instrument by selectively actuating a light or a display attached to the sterile barrier.

15. The method of sterilizing at least one surgical instrument of claim 13, wherein, in said step of placing the at least one surgical instrument in the sterile barrier, the at least one surgical instrument is placed in a sterile barrier in which the at least one sensor is mounted in the sterile barrier.

16. The method of sterilizing at least one surgical instrument of claim 13, wherein, in said step of placing the at least one surgical instrument in the sterile barrier, the at least one surgical instrument is placed in a sterile barrier in which the processor is mounted in the sterile barrier.

17. The method of sterilizing at least one surgical instrument of claim 13, wherein:

in said step of placing the at least one surgical instrument in the sterile barrier, the at least one surgical instrument is placed in a sterile barrier to which plural sensors are mounted, at least two of the sensors being adapted to measure different characteristics of the environment in the sterile barrier and each sensor generates signals representative of the environmental characteristic measured by said sensor;

during said sterilization process, the plural sensors provide the processor with the signals representative of the different environmental characteristics measured inside the sterile barrier; and in said step of comparing the environmental characteristics as measured by the at least one sensor to the validated sterilization process measurement data stored in the memory, comparing the environmental characteristics measured by the plural sensors to the validated state process measurement data to determine if the at least one surgical instrument was subjected to the validated sterilization process.

18. The method of sterilizing at least one surgical instrument of claim 13, wherein, in said step of placing the at least one surgical instrument in the sterile barrier, the at least one surgical instrument is placed in a sterile barrier in which the at least one sensor is configured to measure one of the following environmental characteristics inside the sterile barrier: the concentration of water vapor (steam); temperature; pressure; or the concentration of a gas other than steam.

19. The method of sterilizing at least one surgical instrument of claim 13, wherein, prior to performing said sterilization process, the processor memory is loaded with validated sterilization process measurement data that is specific for the instrument container in the sterile barrier.

20. The method of sterilizing at least one surgical instrument of claim 13, wherein, in said step of placing the at least one surgical instrument in the sterile barrier, the at least one surgical instrument is placed in a sterile barrier that includes a container and a cover that encloses the container.

21. The method of sterilizing at least one surgical instrument of claim 13, wherein, in said step of placing the at least one surgical instrument in the sterile barrier, the at least one surgical instrument is placed in a sterile barrier that includes a wireless transceiver that is capable of transmitting the signal asserted by said processor.

22. The method of sterilizing at least one surgical instrument of claim 13, wherein:

in said step of placing the at least one surgical instrument in the sterile barrier, the at least one surgical instrument is placed in a sterile barrier that includes a receiver configured to releasably hold a module; and prior to performing said sterilization process, a module is attached to the receiver, the module including the at least one sensor.

* * * * *